United States Patent [19]

Yanagisawa et al.

[11] Patent Number: 5,780,490
[45] Date of Patent: Jul. 14, 1998

[54] OXIME DERIVATIVES, THEIR PREPARATION AND THEIR THERAPEUTIC USE

[75] Inventors: Hiroaki Yanagisawa; Takashi Fujita; Koichi Fujimoto; Takao Yoshioka; Kunio Wada; Minoru Oguchi; Toshihiko Fujiwara; Hiroyoshi Horikoshi, all of Tokyo, Japan

[73] Assignee: Sankyo Company, Limited, Tokyo, Japan

[21] Appl. No.: 878,219

[22] Filed: Jun. 18, 1997

Related U.S. Application Data

[62] Division of Ser. No. 539,541, Oct. 5, 1995, Pat. No. 5,703,096.

[30] Foreign Application Priority Data

Oct. 7, 1994 [JP] Japan ................ 6-243876
Jun. 2, 1995 [JP] Japan ................ 7-136788

[51] Int. Cl.$^6$ .................. A61K 31/425; C07D 277/04
[52] U.S. Cl. .................. 514/369; 548/183; 548/227; 548/144; 514/364; 514/376
[58] Field of Search .................. 548/144, 183, 548/227; 514/364, 369, 376

[56] References Cited

U.S. PATENT DOCUMENTS

| | | | |
|---|---|---|---|
| 4,728,739 | 3/1988 | Kees et al. | 548/183 |
| 5,002,953 | 3/1991 | Hindley | 514/275 |
| 5,391,565 | 2/1995 | Hindley | 514/375 |

FOREIGN PATENT DOCUMENTS

| | | |
|---|---|---|
| 0 008 203 | 2/1980 | European Pat. Off. |
| 0 139 421 | 5/1985 | European Pat. Off. |
| 0 177 353 | 4/1986 | European Pat. Off. |
| 0 208 420 | 1/1987 | European Pat. Off. |
| 0 295 828 | 12/1988 | European Pat. Off. |
| 0 306 228 | 3/1989 | European Pat. Off. |
| 0 356 214 | 2/1990 | European Pat. Off. |
| 0 441 605 | 8/1991 | European Pat. Off. |
| 0 528 734 | 2/1993 | European Pat. Off. |
| WO 91/07107 | 5/1991 | WIPO |
| WO 92/02520 | 2/1992 | WIPO |
| WO 92/03425 | 3/1992 | WIPO |
| WO 92/07838 | 5/1992 | WIPO |
| WO 92/07839 | 5/1992 | WIPO |
| WO 92/97850 | 5/1992 | WIPO |

OTHER PUBLICATIONS

Takashi Shohda et al, "Studies on Antidiabetic Agents II.[1]) Synthesis of 4-[4-(1-Methylcyclohexylmethoxy)-benzyl] thiazolidine-2,4-dione (ADD-3878) and Its Derivatives," Chem. Pharm. Bull. 30, 1982, pp. 3580-3600.

*Primary Examiner*—C. Warren Ivy
*Assistant Examiner*—Charanjit S. Aulakm
*Attorney, Agent, or Firm*—Frishauf, Holtz, Goodman, Langer & Chick, P.C.

[57] ABSTRACT

Compounds of formula (I):

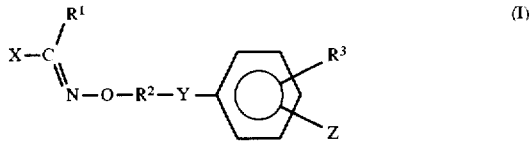

wherein: $R^1$ is hydrogen or alkyl; $R^2$ is alkylene; $R^3$ is hydrogen, alkyl, alkoxy, alkylthio, halogen, nitro group, amino group, monoalkylamino, dialkylamino, aryl, or aralkyl; X is aryl, or aromatic heterocyclic; Y is oxygen, sulfur or a group of formula $>N-R^4$, in which $R^4$ is hydrogen, alkyl or acyl; and Z is a group of formula (Za), (Zb), (Zc) or (Zd):

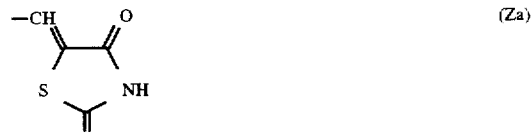

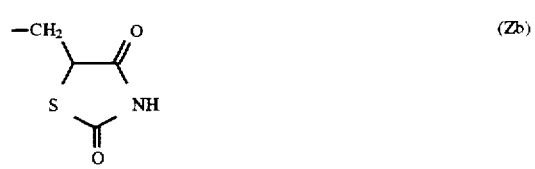

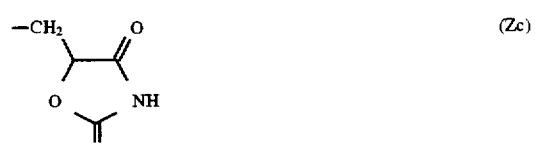

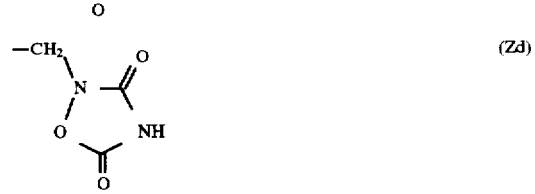

and salts thereof can be used to treat or prevent are included those arising from hyperlipidemia, hyperglycemia, obesity, impaired glucose tolerance (IGT), insulin resistant non-IGT (NGT), non-diagnostic glucose tolerance, insulin resistance, diabetic complications, fatty liver, polycystic ovary syndrome (PCOS) and gestational diabetes mellitus (GDM); in addition the compounds of the present invention have aldose reductase inhibitory activity.

50 Claims, No Drawings

OXIME DERIVATIVES, THEIR PREPARATION AND THEIR THERAPEUTIC USE

This application is a divisional of Ser. No. 08/539,541, filed on Oct. 5, 1995, which is now published as U.S. Pat. No. 5,703,096.

BACKGROUND OF THE INVENTION

The present invention relates to a series of new oxime derivatives which contain inter alia, a thiazolidinedione or oxazolidinedione group attached, via a methylene or methylidene group, to a benzene ring and which have a variety of therapeutic uses, and provides processes for preparing them as well as methods and compositions using them. Among the disorders which these compounds can be used to treat or prevent are included those arising from hyperlipidemia, hyperglycemia, obesity, impaired glucose tolerance (IGT), insulin resistant non-IGT (NGT), non-diagnostic glucose tolerance, insulin resistance, diabetic complications, fatty liver, polycystic ovary syndrome (PCOS) and gestational diabetes mellitus (GDM); in addition the compounds of the present invention have aldose reductase inhibitory activity.

It is known that compounds which, like those of the present invention, contain a thiazolidinedione or oxazolidinedione group attached, via a methylene or methylidene group, to a benzene ring have this type of activity. Compounds of this general type are disclosed, for example, in Chem. Pharm. Bull., 30, 3590 (1982), in European Patent Publications No. 008 203, 139 421, 177 353, 208 420, 306 228, 356 214, 441 605 and 528 734, in WO 92/07839, 91/07107, 92/02520 and 92/03425, and in U.S. Pat. No. 4,728,739. However, none of the prior art of which we are aware, including the above prior art, discloses compounds having an oxime (—C=N—O—) group in a side chain attached to the benzene ring, which is characteristic of the compounds of the present invention. U.S. Pat. No. 4,728,739 discloses compounds in which an oxime group is present as a substituent on a cyclohexyl group, but the location of the oxime group and the remaining structure of the compound are substantially different from those of the compounds of the present invention. Surprisingly, the compounds of the present invention have a much improved activity and greatly reduced toxicity compared to these prior art compounds.

BRIEF SUMMARY OF THE INVENTION

Thus, it is an object of the present invention to provide a series of new chemical compounds which are thiazolidine and oxazolidine derivatives.

It is a further, and more specific, object of the invention to provide such compounds, at least some of which may be useful for the treatment and/or prophylaxis of a variety of disorders, including one or more of: hyperlipemia, hyperglycemia, obesity, impaired glucose tolerance (IGT), insulin resistant non-IGT (NGT), non-diagnostic glucose tolerance, insulin resistance, diabetic complications, fatty liver, polycystic ovary syndrome (PCOS) and gestational diabetes mellitus (GDM).

Other objects and advantages of the present invention will become apparent as the description proceeds.

Thus, the present invention provides compounds of formula (I):

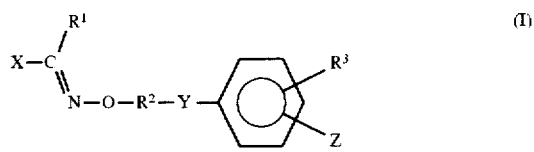

wherein:
$R^1$ represents a hydrogen atom or an alkyl group having from 1 to 6 carbon atoms;
$R^2$ represents an alkylene group having from 2 to 6 carbon atoms;
$R^3$ represents a hydrogen atom, an alkyl group having from 1 to 6 carbon atoms, an alkoxy group having from 1 to 4 carbon atoms, an alkylthio group having from 1 to 4 carbon atoms, a halogen atom, a nitro group, an amino group, a monoalkylamino group having from 1 to 4 carbon atoms, a dialkylamino group whose alkyl groups are the same or different and each has from 1 to 4 carbon atoms, an aryl group having from 6 to 10 carbon atoms in a carbocyclic ring which is unsubstituted or is substituted by at least one of the following substituents α, or an aralkyl group in which an alkyl group having from 1 to 4 carbon atoms is substituted by an aryl group as defined above;
X represents an aryl group having from 6 to 10 carbon atoms in a carbocyclic ring which is unsubstituted or is substituted by at least one of the following substituents α, or an aromatic heterocyclic group having one or two rings, of which at least one is heterocyclic, said group being unsubstituted or being substituted by at least one of the following substituents α;
said substituents a are preferably selected from the group consisting of: 1) alkyl groups having from 1 to 6 carbon atoms; 2) halogenated alkyl groups having from 1 to 4 carbon atoms; 3) hydroxy groups; 4) acyloxy groups having from 1 to 4 carbon atoms; 5) alkoxy groups having from 1 to 4 carbon atoms; 6) alkylene-dioxy groups having from 1 to 4 carbon atoms; 7) aralkyloxy groups in which an alkoxy group having from 1 to 4 carbon atoms is substituted by an aryl group as defined in 16 below; 8) alkylthio groups having from 1 to 4 carbon atoms; 9) alkylsulfonyl groups having from 1 to 4 carbon atoms; 10) halogen atoms; 11) nitro groups; 12) amino groups; 13) monoalkylamino groups having from 1 to 4 carbon atoms; 14) dialkylamino groups, whose alkyl groups are the same or different and each is an alkyl group having from 1 to 4 carbon atoms; 15) aralkyl groups in which an alkyl group having from 1 to 4 carbon atoms is substituted by an aryl group as defined in 16 below; 16) aryl groups having from 6 to 10 carbon atoms in a carbocyclic ring which is unsubstituted or is substituted by at least one of the following substituents β; 17) aryloxy groups in which the aryl part is as defined in 16 above; 18) arylthio groups in which the aryl part is as defined in 16 above; 19) arylsulfonyl groups in which the aryl part is as defined in 16 above; 20) arylsulfonylamino groups in which the aryl part is as defined in 16 above and in which the nitrogen atom is unsubstituted or is substituted by an alkyl group having from 1 to 6 carbon atoms; 21) groups of formula —$R^x$; 22) groups of formula —$OR^x$; 23) groups of formula —$SR^x$; 24) groups of formula —$SO_2R^x$; and 25) groups of formula —$N(R^z)SO_2R^x$; in which $R^x$ represents an aromatic heterocyclic ring having 5 or 6 ring atoms of which from 1 to 3 are selected from the group consisting of nitrogen, oxygen and sulfur atoms or a fused ring system in which such an aromatic heterocyclic ring is fused to an aryl group having from 6 to 10 carbon atoms in a carbocyclic ring or to such an aromatic heterocyclic ring; and R⁵ represents an alkyl group having from 1 to 6 carbon atoms;

said substituents p are selected from the group consisting of alkyl groups having from 1 to 6 carbon atoms, halogenated alkyl groups having from 1 to 4 carbon atoms, alkoxy groups having from 1 to 4 carbon atoms, halogen atoms, and alkylenedioxy groups having from 1 to 4 carbon atoms;

Y represents an oxygen atom, a sulfur atom or a group of formula >N—R⁴, in which R⁴ represents a hydrogen atom, an alkyl group having from 1 to 6 carbon atoms or an acyl group having from 1 to 8 carbon atoms; and Z represents a group of formula (Za), (Zb), (Zc) or (Zd):

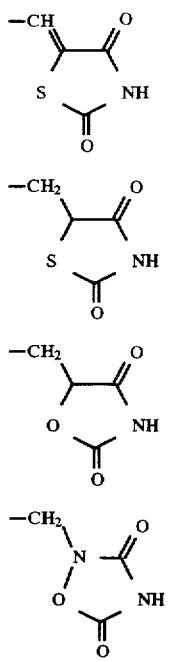

and salts thereof.

The invention also provides a pharmaceutical composition for the treatment or prophylaxis of diabetes, hyperlipemia, hyperglycemia, obesity, arteriosclerosis, essential hypertension, cachexia, psoriasis, osteoporosis, impaired glucose tolerance (IGT), insulin resistant non-IGT (NGT), non-diagnostic glucose tolerance, insulin resistance, diabetic complications, fatty liver, polycystic ovary syndrome (PCOS) and gestational diabetes mellitus (GDM), and complications thereof, which composition comprises an effective amount of an active compound in admixture with a pharmaceutically acceptable carrier or diluent, wherein said active compound is selected from the group consisting of compounds of formula (I), defined above, and salts thereof.

The invention still further provides a method for the treatment or prophylaxis of diabetes, hyperlipemia, hyperglycemia, obesity, arteriosclerosis, essential hypertension, cachexia, psoriasis, osteoporosis, impaired glucose tolerance (IGT), insulin resistant non-IGT (NGT), non-diagnostic glucose tolerance, insulin resistance, diabetic complications, fatty liver, polycystic ovary syndrome (PCOS) and gestational diabetes mellitus (GDM), and complications thereof in a mammal, which may be human, which method comprises administering to said mammal an effective amount of an active compound, wherein said active compound is selected from the group consisting of compounds of formula (I), defined above, and salts thereof.

The invention also provides processes for the preparation of the compounds of the present invention, which processes are described in more detail hereafter.

DETAILED DESCRIPTION OF INVENTION

In the compounds of the present invention, where $R^1$, $R^3$ or $R^4$ represents an alkyl group, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl and 1,2,2-trimethylpropyl groups. Of these, we prefer those alkyl groups having from 1 to 4 carbon atoms, preferably the methyl, ethyl, propyl, isopropyl, butyl and isobutyl groups, and most preferably the methyl and ethyl groups.

Preferably, $R^1$ represents a hydrogen atom or an alkyl group having from 1 to 4 carbon atoms.

Where $R^2$ represents an alkylene group, this may be a straight or branched chain group having from 2 to 6 carbon atoms, and examples of such alkylene groups include the ethylene, methylethylene, ethylethylene, 1,1-dimethylethylene, 1,2-dimethylethylene, trimethylene, 1-methyltrimethylene, 1-ethyltrimethylene, 2-methyltrimethylene, 1,1-dimethyltrimethylene, tetramethylene, pentamethylene and hexamethylene groups, of which we prefer the straight or branched chain alkylene groups having from 2 to 5 carbon atoms, and most prefer straight and branched chain alkylene groups having from 2 or 3 carbon atoms. Particularly preferred such groups include the ethylene, methylethylene, ethylethylene, trimethylene, 1-methyltrimethylene, 1-ethyltrimethylene and 2-methyltrimethylene groups.

Where $R^3$ represents an alkoxy group, this may be a straight or branched chain group having from 1 to 4 carbon atoms, and examples of such alkoxy groups include the methoxy, ethoxy, propoxy, isopropoxy, butoxy, sec-butoxy, t-butoxy and isobutoxy groups, of which we prefer the methoxy group.

Where $R^3$ represents an alkylthio group, this may be a straight or branched chain group having from 1 to 4 carbon atoms, and examples of such alkylthio groups include the methylthio, ethylthio, propylthio, isopropylthio, butylthio, sec-butylthio, t-butylthio and isobutylthio groups, of which we prefer the methylthio group.

Where $R^3$ represents a halogen atom, this may be, for example, a fluorine, chlorine, bromine or iodine atom, preferably a fluorine, chlorine or bromine atom, and most preferably a fluorine or chlorine atom.

Where $R^3$ represents a monoalkylamino group, the alkyl part has from 1 to 4 carbon atoms and may be a straight or branched chain group. Examples of such monoalkylamino groups include the methylamino, ethyl-amino, propylamino, isopropylamino, butylamino, sec-butylamino, t-butylamino and isobutylamino groups, of which we prefer the methylamino and ethylamino groups.

Where $R^3$ represents a dialkylamino group, the two alkyl groups are the same as or different from each other, and each may be a straight or branched chain alkyl group having from 1 to 4 carbon atoms. Examples of such dialkylamino groups include the dimethylamino, diethylamino, dipropylamino, diisopropylamino, dibutyl-amino, N-methyl-N-ethylamino and N-ethyl-N-isopropyl-amino groups, of which we prefer the dimethylamino and diethylamino groups.

Where $R^3$ represents an aryl group having from 6 to 10 carbon atoms, this is a carbocyclic group having from 6 to 10 carbon atoms in one or more aromatic rings. Examples of such aryl groups include the phenyl and naphthyl groups, preferably the phenyl group. The group may be unsubstituted or it may be substituted by one or more of substituents α, as defined above and exemplified below.

Where $R^3$ represents an aralkyl group, this is a group in which an alkyl group having from 1 to 4 carbon atoms is substituted by an aryl group as defined above. The group preferably has from 7 to 12 carbon atoms in total, and examples of such aralkyl groups include the benzyl, phenethyl, 3-phenylpropyl, 4-phenylbutyl, 1-naphthylmethyl and 2-naphthylmethyl groups, of which we prefer the benzyl and phenethyl groups, more preferably the benzyl group. The aryl part of the group may be unsubstituted or it may be substituted by one or more of substituents α, as defined above and exemplified below.

Preferably, $R^3$ represents a hydrogen atom, an alkyl group having from 1 to 4 carbon atoms, an alkoxy group having 1 or 2 carbon atoms, an alkylthio group having 1 or 2 carbon atoms or a halogen atom.

Where $R^4$ represents an acyl group, this is preferably a carboxylic acyl group having from 1 to 8 carbon atoms, and it may be, for example: an aliphatic carboxylic acyl group, including an alkanoyl group, such as a formyl, acetyl, propionyl, butyryl, pentanoyl, hexanoyl, heptanoyl or octanoyl group; or an aromatic carboxylic acyl group, i.e. an arylcarbonyl group (in which the aryl part is as defined and exemplified below in relation to $R^4$), such as a benzoyl or p-toluoyl group. Of these, we prefer the alkanoyl groups, especially those containing from 2 to 5 carbon atoms, and most preferably the acetyl group.

Where X represents an aryl group having from 6 to 10 carbon atoms, this is a carbocyclic group having from 6 to 10 carbon atoms in one or more aromatic rings. Examples of such aryl groups include the phenyl and naphthyl groups, preferably the phenyl group. The group may be unsubstituted or it may be substituted by one or more of substituents a, as defined above and exemplified below.

Where X represents an aromatic heterocyclic group, this preferably has from 5 to 10 ring atoms arranged in one or two rings, of which at least one is heterocyclic. In the case of a bicyclic system consisting of two fused rings, one of these may be heterocyclic and the other carbocyclic, or both may be heterocyclic. The or each heterocyclic ring preferably has 5 or 6 ring atoms, of which from 1 to 4 are hetero-atoms selected from the group consisting of oxygen, sulfur and nitrogen atoms. In the case of those groups having 4 ring hetero-atoms, we prefer that all four are nitrogen atoms, and correspondingly none are oxygen and/or sulfur atoms. In the case of those groups having 3 ring hetero-atoms, we prefer that all three, two or one are nitrogen atoms, and correspondingly none, one or two are oxygen and/or sulfur atoms. In the case of those groups having 2 ring hetero-atoms, we prefer that two, one or none are nitrogen atoms, and correspondingly none, one or two are oxygen and/or sulfur atoms. These groups may be substituted or unsubstituted and, if substituted, the substituents are selected from the group consisting of substituents α, defined above and exemplified below. Although there is no restriction on the number of substituents except that imposed by the number of substitutable positions and possibly by steric constraints, we generally prefer from 1 to 3 substituents, more preferably 1 or 2 substituents and most preferably 1 substituent.

Examples of such monocyclic aromatic heterocyclic groups which may be represented by X include: pyrrolyl groups, such as the 2-pyrrolyl or 3-pyrrolyl group; furyl groups, such as the 2-furyl or 3-furyl group; thienyl groups, such as the 2-thienyl or 3-thienyl group; pyridyl groups, such as the 2-pyridyl, 3-pyridyl or 4-pyridyl group; imidazolyl groups, such as the 2-imidazolyl or 4-imidazolyl group; pyrazolyl groups, such as the 3-pyrazolyl or 4-pyrazolyl group; oxazolyl groups, such as the 2-oxazolyl, 4-oxazolyl or 5-oxazolyl group; isoxazolyl gruops, such as the 3-isoxazolyl, 4-isoxazolyl or 5-isoxazolyl group; thiazolyl groups, such as the 2-thiazolyl, 4-thiazolyl or 5-thiazolyl group; isothiazolyl groups, such as the 3-isothiazolyl, 4-isothiazolyl or 5-isothiazolyl group; triazolyl groups, such as the 1,2,3-triazol-4-yl or 1,2,4-triazol-3-yl group; thiadiazolyl groups, such as the 1,3,4-thiadiazol-2-yl group; oxadiazolyl groups, such as the 1,3,4-oxadiazol-2-yl group; tetrazolyl groups, such as the 5-tetrazolyl group; pyridazinyl groups, such as the 3-pyridazinyl or 4-pyridazinyl group; pyrimidinyl groups, such as the 2-pyrimidinyl, 4-pyrimidinyl or 5-pyrimidinyl group; the pyrazinyl group; oxazinyl groups, such as the 1,4-oxazin-2-yl or 1,4-oxazin-3-yl group; and thiazinyl groups, such as the 1,4-thiazin-2-yl or 1,4-thiazin-3-yl group.

Examples of such condensed ring aromatic heterocyclic groups which may be represented by X include: indolyl groups, such as the indol-2-yl, indol-3-yl, indol-4-yl, indol-5-yl, indol-6-yl or indol-7-yl group; indazolyl groups, such as the indazol-2-yl, indazol-3-yl, indazol-4-yl, indazol-5-yl, indazol-6-yl or indazol-7-yl group; benzofuranyl groups, such as the benzofuran-2-yl, benzofuran-3-yl, benzofuran-4-yl, benzofuran-5-yl, benzofuran-6-yl or benzoturan-7-yl group; benzothiophenyl groups, such as the benzo-thiophen-2-yl, benzothiophen-3-yl, benzothiophen-4-yl, benzothiophen-5-yl, benzothiophen-6-yl, or benzothiophen-7-yl group; benzimidazolyl groups, such as the benzimidazol-2-yl, benzimidazol-4-yl, benzimidazol-5-yl, benzimidazol-6-yl or benzimidazol-7-yl group; benzoxazolyl groups, such as the benzoxazol-2-yl, benzoxazol-4-yl, benzoxazol-5-yl, benzoxazol-6-yl or benzoxazol-7-yl group; benzothiazolyl groups, such as the benzothiazol-2-yl, benzothiazol-4-yl, benzothiazol-5-yl, benzothiazol-6-yl or benzothiazol-7-yl group; quinolyl groups, such as the 2-quinolyl, 3-quinolyl, 4-quinolyl, 5-quinolyl, 6-quinolyl, 7-quinolyl or 8-quinolyl group; isoquinolyl groups, such as the 1-isoquinolyl, 3-isoquinolyl, 4-isoquinolyl or 8-isoquinolyl group; benzoxazinyl groups, such as the 1,4-benzoxazin-2-yl or 1,4-benzoxazin-3-yl group; benzothiazinyl groups, such as the 1,4-benzothiazin-2-yl or 1,4-benzothiazin-3-yl group; pyrrolo[2,3-b]pyridyl groups, such as the pyrrolo[2,3-b]pyrid-2-yl or pyrrolo-[2,3-b]pyrid-3-yl group; furo[2,3-b]pyridyl groups, such as the furo[2,3-b]pyrid-2-yl or furo[2,3-b]pyrid-3-yl group; thieno[2,3-b]pyridyl groups, such as the thieno-[2,3-b]pyrid-2-yl or thieno[2,3-b]pyrid-3-yl group; naphthyridinyl groups, such as the 1,8-naphthyridin-2-yl, 1,8-naphthyridin-3-yl, 1,5-naphthyridin-2-yl or 1,5-naphthyridin-3-yl group; imidazopyridyl groups, such as the imidazo[4,5-b]pyrid-2-yl or imidazo[4,5-b]pyrid-5-yl group; oxazolopyridyl groups, such as the oxazolo-[4,5-b]pyrid-2-yl or oxazolo[5,4-b]pyrid-2-yl group; thiazolopyridyl groups, such as the thiazolo[4,5-b]pyrid-2-yl or thiazolo[4,5-c]pyrid-2-yl group.

Preferred monocyclic aromatic heterocyclic groups which may be represented by X are groups containing 5 or 6 ring atoms, of which from 1 to 3 are hetero-atoms selected from the group consisting of nitrogen, oxygen and sulfur atoms, and particularly the pyrrolyl, furyl, thienyl, pyridyl, imidazolyl, pyrazolyl, oxazolyl, isoxazolyl, thiazolyl, triazolyl, thiadiazolyl, oxadiazolyl, pyridazinyl, pyrimidinyl and pyrazinyl groups as illustrated above. Preferred condensed ring aromatic heterocyclic groups consist of a benzene ring fused to one of the monocyclic aromatic heterocyclic groups defined above, and preferred such groups are the indolyl, benzofuranyl, benzothiophenyl, benzimidazolyl, benzoxazolyl, benzothiazolyl, quinolyl and isoquinolyl groups as illustrated above.

Most preferred monocyclic aromatic heterocyclic groups which may be represented by X are the imidazolyl, oxazolyl and pyridyl groups, and most preferred condensed ring aromatic heterocyclic groups are the indolyl, quinolyl and isoquinolyl groups.

Where X represents an aryl group or an aromatic heterocyclic group, these groups may be unsubstituted or they may be substituted as defined above, preferably with from 1 to 3 substituents selected from the group consisting of substituents a, as defined above, for example as follows.

Where the substituent a is an alkyl group having from 1 to 6 carbon atoms, an alkoxy group having from 1 to 4 carbon atoms, an alkylthio group having from 1 to 4 carbon atoms, a halogen atom, a straight or branched chain monoalkylamino group having from 1 to 4 carbon atoms, a dialkylamino group, whose alkyl groups are the same or different and each has from 1 to 4 carbon atoms, or an aralkyl group having from 7 to 12 carbon atoms, it may be, for example, as exemplified in relation to $R^3$ above.

Where the substituent a is a straight or branched chain halogenated alkyl group having from 1 to 4 carbon atoms, the alkyl part may be any of those alkyl groups having from 1 to 4 carbon atoms included in the groups represented by $R^3$, and examples of such halogenated alkyl groups include the chloromethyl, bromomethyl, fluoromethyl, iodomethyl, difluoromethyl, trifluoromethyl, pentafluoroethyl, 2,2,2-trifluoroethyl, 2,2,2-trichloroethyl and trichloromethyl groups, of which the fluoromethyl, difluoromethyl and trifluoromethyl groups are preferred.

Where the substituent a represents an acyloxy group having from 1 to 4 carbon atoms, this is a carboxylic acyloxy group and is preferably an alkanoyl or alkenoyl group, more preferably an alkanoyl group, and examples of such acyloxy groups include the formyloxy, acetoxy, propionyloxy and butyryloxy groups, of which the acetoxy group is preferred.

Where the substituent α is a straight or branched chain alkylenedioxy group having from 1 to 4 carbon atoms, examples of such alkylenedioxy groups include the methylenedioxy, ethylenedioxy, trimethylenedioxy, tetramethylenedioxy and propylenedioxy groups, of which the methylenedioxy and ethylenedioxy groups are preferred.

Where the substituent c represents an aralkyloxy group having from 7 to 12 carbon atoms, the aralkyl part may be as defined and exemplified above in relation to $R^3$, and examples of such aralkyloxy groups include the benzyloxy, phenethyloxy, 3-phenylpropoxy, 4-phenyl-butoxy, 1-naphthylmethoxy and 2-naphthylmethoxy groups, of which we prefer the benzyloxy, phenethyloxy, 1-naphthylmethoxy and 2-naphthylmethoxy groups.

Where the substituent a is an alkylsulfonyl group, the alkyl part has from 1 to 4 carbon atoms and may be any of those alkyl groups having from 1 to 4 carbon atoms included in the groups represented by $R^3$. Examples of such alkylsulfonyl groups include the methylsulfonyl, ethylsulfonyl, propylsulfonyl, isopropylsulfonyl, butylsulfonyl, isobutylsulfonyl, sec-butylsulfonyl and t-butylsulfonyl groups, of which we prefer the methylsulfonyl, ethylsulfonyl and isopropylsulfonyl groups.

Where the substituent α is an aryl group, this has from 6 to 10 carbon atoms in a carbocyclic ring, which is unsubstituted or has at least one substituent selected from the group consisting of substituents β:

alkyl groups having from 1 to 6 carbon atoms, such as defined and exemplified above in relation to $R^3$;

straight or branched chain halogenated alkyl groups having from 1 to 4 carbon atoms, such as defined and exemplified above in relation to substituents α;

alkoxy groups having from 1 to 4 carbon atoms, such as defined and exemplified above in relation to $R^3$;

halogen atoms, such as defined and exemplified above in relation to $R^3$; and alkylenedioxy groups having from 1 to 4 carbon atoms, such as defined and exemplified above in relation to $R^3$.

Examples of such substituted and unsubstituted aryl groups include the phenyl, 1-naphthyl, 2-naphthyl, 4-methylphenyl, 4-trifluoromethylphenyl, 4-methoxyphenyl, 3-ethoxyphenyl, 4-fluorophenyl, 4-chlorophenyl, 3-bromophenyl and 3,4-methylenedioxyphenyl groups, of which we prefer the phenyl, 4-methoxyphenyl and 3,4-methylenedioxyphenyl groups.

Where the substituent a is an aryloxy group, this has from 6 to 10 carbon atoms in a carbocyclic ring, which is unsubstituted or has at least one substituent selected from the group consisting of substituents β, which are defined and exemplified above. Examples of such aryloxy groups include the phenoxy, 1-naphthoxy, 2-naphthoxy, 4-methylphenoxy, 4-trifluoromethyl-phenoxy, 4-methoxyphenoxy, 3-ethoxyphenoxy, 4-chloro-phenoxy, 3-bromophenoxy and 3,4-methylenedioxyphenoxy groups, of which we prefer the phenoxy group.

Where the substituent α is an arylthio group, this has from 6 to 10 carbon atoms in a carbocyclic ring, which is unsubstituted or has at least one substituent selected from the group consisting of substituents β, which are defined and exemplified above. Examples of such arylthio groups include the phenylthio, 4-methyl-phenylthio, 4-trifluoromethylphenylthio, 4-methoxy-phenylthio, 3-ethoxyphenylthio, 4-chlorophenylthio, 3-bromophenylthio, 3,4-methylenedioxyphenylthio, 1-naphthylthio and 2-naphthylthio groups, of which we prefer the phenylthio group.

Where the substituent α is an arylsulfonyl group, this has from 6 to 10 carbon atoms in a carbocyclic ring, which is unsubstituted or has at least one substituent selected from the group consisting of substituents β, which are defined and exemplified above. Examples of such arylsulfonyl groups include the phenylsulfonyl, 4-methylphenylsulfonyl, 4-trifluoro-methylphenylsulfonyl, 4-methoxyphenylsulfonyl, 3-ethoxy-phenylsulfonyl, 4-chlorophenylsulfonyl, 3-bromophenyl-sulfonyl, 3,4-methylenedioxyphenylsulfonyl, 1-naphthyl-sulfonyl and 2-naphthylsulfonyl groups, of which we prefer the phenylsulfonyl group.

Where the substituent α is an arylsulfonylamino group, this has from 6 to 10 carbon atoms in a carbocyclic ring, which is unsubstituted or has at least one substituent selected from the group consisting of substituents β, which are defined and exemplified above. In addition, the nitrogen atom may bear as a substituent an alkyl group having from 1 to 6 carbon atoms (which may be as defined and exemplified above in relation to the corresponding groups which may be represented by $R^3$). Examples of such arylsulfonylamino groups include the phenylsulfonylamino, 4-methylphenylsulfonylamino, 4-trifluoromethylphenylsulfonylamino, 4-methoxyphenylsulfonylamino, 3-ethoxyphenylsulfonylamino, 4-chlorophenylsulfonylamino, 3-bromophenylsulfonylamino, 3,4-methylenedioxyphenylsulfonylamino, N-methylphenylsulfonylamino, 1-naphthylsulfonylamino, 2-naphthylsulfonylamino and N-methylnaphthylsulfonylamino groups, of which we prefer the phenylsulfonylamino and N-methylphenylsulfonylamino groups.

Where the substituent α is a group of formula —$R^x$, where $R^x$ represents an aromatic heterocyclic ring having 5 or 6 ring atoms of which from 1 to 3 are selected from the group consisting of nitrogen, oxygen and sulfur atoms or a fused ring system in which such an aromatic heterocyclic ring is fused to an aryl group having from 6 to 10 atoms in a carbocyclic ring or to such an aromatic heterocyclic ring, the aryl group may be any of those aryl groups defined and exemplified above in relation to substituents α, or, where there are two heterocyclic groups fused together, these may be the same as each other or they may be different from each other. Examples of such heterocyclic groups include the furyl, thienyl, oxazolyl, isoxazolyl, thiazolyl, imidazolyl, quinolyl, isoquinolyl, indolyl and pyridyl groups, of which we prefer the imidazolyl, quinolyl and pyridyl groups.

Where the substituent a is a group of formula —$OR^x$, where $R^x$ is as defined above, examples of such groups include the furyloxy, thienyloxy, oxazolyloxy, isoxazolyloxy, thiazolyloxy, imidazolyloxy, quinolyloxy, isoquinolyloxy, indolyloxy and pyridyloxy groups, of which we prefer the isoxazolyloxy and pyridyloxy groups.

Where the substituent a is a group of formula —$SR^x$, where $R^x$ is as defined above, examples of such groups include the furylthio, thienylthio, oxazolylthio, isoxazolylthio, thiazolylthio, imidazolylthio, quinolylthio, isoquinolylthio, indolylthio and pyridylthio groups, of which we prefer the isoxazolylthio and pyridylthio groups.

Where the substituent α is a group of formula —$SO_2R^x$, where $R^x$ is as defined above, examples of such groups include the furylsulfonyl, thienylsulfonyl, oxazolylsulfonyl, isoxazolylsulfonyl, thiazolylsulfonyl, imidazolylsulfonyl, quinolylsulfonyl, isoquinolylsulfonyl, indolylsulfonyl and pyridylsulfonyl groups, of which we prefer the imidazolylsulfonyl, isoxazolyl-sulfonyl and pyridylsulfonyl groups.

Where the substituent a represents a group of formula —$N(R^z)SO_2R^x$, where $R^x$ and $R^z$ are as defined above, examples of such groups include the furylsulfonylamino, thienylsulfonylamino, oxazolylsulfonylamino, isoxazolylsulfonylamino, thiazolylsulfonylamino, imidazolylsulfonylamino, N-methylimidazolylsulfonylamino, quinolylsulfonylamino, isoquinolylsulfonylamino, indolylsulfonylamino, pyridylsulfonylamino and N-methylpyridylsulfonylamino groups, of which we prefer the imidazolylsulfonylamino, N-methylimidazolylsulfonylamino, pyridylsulfonylamino and N-methylpyridylsulfonylamino groups.

Therefore, where X represents a substituted or unsubstituted aryl group having from 6 to 10 carbon atoms in a carocyclic ring or a substituted or unsubstituted aromatic heterocyclic group, specific examples of such preferred groups include: substituted or unsubstituted aryl groups having from 6 to 10 carbon atoms, such as the phenyl, 1-naphthyl, 2-naphthyl, m-tolyl, p-tolyl, 3-ethylphenyl, 4-ethylphenyl, 3-isopropylphenyl, 4-isopropylphenyl, 3-t-butylphenyl, 4-t-butylphenyl, 4-chloromethylphenyl, 4-bromomethyl-phenyl, 4-fluoromethylphenyl, 4-iodomethylphenyl, 3-difluoromethylphenyl, 4-trifluoromethylphenyl, 4-pentafluoroethylphenyl, 4-trichloromethylphenyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-methoxy-phenyl, 4-methoxyphenyl, 3-ethoxyphenyl, 4-ethoxyphenyl, 3-isopropoxyphenyl, 4-isopropoxyphenyl, 3,4-methylene-dioxyphenyl, benzyloxyphenyl, phenethyloxyphenyl, 1-naphthylmethoxyphenyl, 3-methylthiophenyl, 4-methylthiophenyl, 3-ethylthiophenyl, 4-ethylthiophenyl, 3-isopropylthiophenyl, 4-isopropylthiophenyl, 3-methylsulfonylphenyl, 4-methylsulfonylphenyl, 3-ethylsulfonylphenyl, 4-ethylsulfonylphenyl, 3-isopropylsulfonyl-phenyl, 4-isopropylsulfonylphenyl, 3-chlorophenyl, 4-chlorophenyl, 3-bromophenyl, 4-bromophenyl, 4-nitro-phenyl, 4-aminophenyl, 3-methylaminophenyl, 4-ethylaminophenyl, 3-propylaminophenyl, 4-butylaminophenyl, 3-dimethylaminophenyl, 4-diethylaminophenyl, 3-dipropylaminophenyl, 4-dibutylaminophenyl, 3-benzylphenyl, 4-benzylphenyl, 3-phenethylphenyl, 4-(1-naphthylmethyl)-phenyl, 3-biphenylyl, 4-biphenylyl, 3-(4-methylphenyl)-phenyl, 4-(4-methylphenyl)phenyl, 3-(4-ethylphenyl)-phenyl, 3-(4-trifluoromethylphenyl)phenyl, 4-(4-trifluoromethylphenyl)phenyl, 3-(4-methoxyphenyl)phenyl, 4-(4-methoxyphenyl)phenyl, 3-(2,4-dimethoxyphenyl)-phenyl, 4-(2,4-dimethoxyphenyl)phenyl, 3-(2,5-dimethoxyphenyl)phenyl, 4-(2,5-dimethoxyphenyl)phenyl, 4-(3-chlorophenyl)phenyl, 4-(4-chlorophenyl)phenyl, 4-(3-bromophenyl)phenyl, 4-(4-bromophenyl)phenyl, 3-(3,4-methylenedioxyphenyl)phenyl, 4-(3,4-methylene-dioxyphenyl)phenyl, 3-benzylphenyl, 4-benzylphenyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino)phenyl, N-methyl-3-(phenylsulfonylamino)phenyl, N-methyl-4-(phenylsulfonylamino)-phenyl, 3-(imidazol-1-yl)phenyl, 4-(imidazol-1-yl)-phenyl, 3-(1-methylimidazol-4-yl)phenyl, 4-(1-methyl-imidazol-4-yl)phenyl, 3-(2-furyl)phenyl, 4-(2-furyl)-phenyl, 3-(2-thienyl)phenyl, 4-(2-thienyl)phenyl, 3-(3-thienyl)phenyl, 4-(3-thienyl)phenyl, 3-(2-pyridyl)-phenyl, 4-(2-pyridyl)phenyl, 3-(3-pyridyl)phenyl, 4-(3-pyridyl)phenyl, 3-(4-pyridyl)phenyl, 4-(4-pyridyl)-phenyl, 4-(imidazol-1-ylthio)phenyl, 4-(2-furylthio)-phenyl, 4-(2-thienylthio)phenyl, 4-(2-pyridylthio)-phenyl, 4-(4-pyridylthio)phenyl, 3-(2-pyridylsulfonyl)-phenyl, 4-(2-pyridylsulfonyl)phenyl, 3-(3-pyridyl-sulfonyl)phenyl, 4-(3-pyridylsulfonyl)phenyl, 3-(2-pyridylsulfonylamino)phenyl, 3-(N-methyl-2-pyridylsulfonylamino)phenyl, 4-(2-pyridylsulfonylamino)phenyl, 4-(N-methyl-2-pyridylsulfonylamino)phenyl, 3-(3-pyridyl-sulfonylamino)phenyl, 3-(N-methyl-3-pyridylsulfonyl-amino)phenyl, 4-(3-pyridylsulfonylamino)phenyl, 4-(N-methyl-3-pyridylsulfonylamino)phenyl, 3-(oxazol-2-yl) phenyl, 4-(oxazol-2-yl)phenyl, 3-(oxazol-4-yl)phenyl, 4-(oxazol-4-yl)phenyl, 3-(oxazol-5-yl)phenyl, 4-(oxazol-5-yl)phenyl, 3-(thiazol-2-yl)phenyl, 4-(thiazol-2-yl)-phenyl, 3-(thiazol-4-yl)phenyl, 4-(thiazol-4-yl)phenyl, 3-(thiazol-5-yl)phenyl and 4-(thiazol-5-yl)phenyl groups; and substituted or unsubstituted aromatic heterocyclic groups, such as the 1-methyl-2-pyrrolyl, 1-phenyl-2,-pyrrolyl, 1-benzyl-2-pyrrolyl, 5-methyl-2-furyl, 5-phenyl-2-furyl, 5-methyl-2-thienyl, 5-phenyl-2-thienyl, 5-methyl-3-thienyl, 5-phenyl-3-thienyl, 1-methyl-3-pyrazolyl, 1-phenyl-3-pyrazolyl, 1-methyl-2-imidazolyl, 1-phenyl-2-imidazolyl, 1-methyl-4-imidazolyl, 1-phenyl-4-imidazolyl, 1-methyl-2-phenyl-4-imidazolyl, 1,5-dimethyl-2-phenyl-4-imidazolyl, 1,4-dimethyl-2-phenyl-5-imidazolyl, 4-oxazolyl, 5-oxazolyl, 2-methyl-4-oxazolyl, 2-phenyl-4-oxazolyl, 2-methyl-5-oxazolyl, 2-phenyl-5-oxazolyl, 4-methyl-2-phenyl-5-oxazolyl, 5-methyl-2-phenyl-4-oxazolyl, 4-thiazolyl, 5-thiazolyl, 2-methyl-4-thiazolyl, 2-phenyl-4-thiazolyl, 2-methyl-5-thiazolyl, 2-phenyl-5-thiazolyl, 4-methyl-2-phenyl-5-thiazolyl, 5-methyl-2-phenyl-4-thiazolyl, 1-methyl-3-pyrazolyl, 1-phenyl-3-pyrazolyl, 3-methyl-5-isoxazolyl, 3-phenyl-5-isoxazolyl, 2-pyridyl, 3-pyridyl, 4-pyridyl, 3-methyl-5-pyridyl, 3-ethyl-5-pyridyl, 3-phenyl-5-pyridyl, 2-methyl-5-pyridyl, 2-ethyl-5-pyridyl, 2-phenyl-5-pyridyl, 2-hydroxy-5-pyridyl, 2-methoxy-5-pyridyl, 2-ethoxy-5-pyridyl, 2-isopropoxy-5-pyridyl, 2-benzyl-oxy-5-pyridyl, 2-methylthio-5-pyridyl, 2-ethylthio-5-pyridyl, 2-isopropylthio-5-pyridyl, 2-methylsulfonyl-5-pyridyl, 2-ethylsulfonyl-5-pyridyl, 2-isopropylsulfonyl-5-pyridyl, 2-benzyl-5-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenyl-sulfonylamino)-5-pyridyl, 3-methyl-6-pyridyl, 3-phenyl-6-pyridyl, 2-methyl-6-pyridyl, 2-phenyl-6-pyridyl, 2-methyl-4-pyrimidinyl, 2-phenyl-4-pyrimidinyl, 2-methoxy-4-pyrimidinyl, 2-ethoxy-4-pyrimidinyl, 2-isopropoxy-4-pyrimidinyl, 2-methylthio-4-pyrimidinyl, 2-ethylthio-4-pyrimidinyl, 2-isopropylthio-4-pyrimidinyl, 2-phenylthio-4-pyrimidinyl, 2-methyl-sulfonyl-4-pyrimidinyl, 2-ethylsulfonyl-4-pyrimidinyl, 2-isopropylsulfonyl-4-pyrimidinyl, 2-phenylsulfonyl-4-pyrimidinyl, 2-methyl-5-pyrimidinyl, 2-phenyl-5-pyrimidinyl, 2-methoxy-5-pyrimidinyl, 2-ethoxy-5-pyrimidinyl, 2-isopropoxy-5-pyrimidinyl, 2-methylthio-5-pyrimidinyl, 2-ethylthio-5-pyrimidinyl, 2-isopropylthio-5-pyrimidinyl, 2-phenylthio-5-pyrimidinyl, 2-methyl-sulfonyl-5-pyrimidinyl, 2-ethylsulfonyl-5-pyrimidinyl, 2-isopropylsulfonyl-5-pyrimidinyl, 2-phenylsulfonyl-5-pyrimidinyl, 2-indolyl, 3-indolyl, 1-methyl-2-indolyl, 1-methyl-3-indolyl, 2-benzimidazolyl, 1-methyl-2-benzimidazolyl, 2-benzoxazolyl, 2-benzothiazolyl, 2-quinolyl, 3-quinolyl, 4-quinolyl, 1-isoquinolyl, 3-isoquinolyl, 4-isoquinolyl and 8-isoquinolyl groups.

Where Y represents a group of formula >N—$R^4$, $R^4$ represents a hydrogen atom, an alkyl group having from 1 to 6 carbon atoms or an acyl group having from 1 to 8 carbon atoms. Examples of alkyl groups which may be represented by $R^4$ include those defined and exemplified above in relation to $R^3$. Examples of alkyl groups which may be represented by $R^4$ include aliphatic acyl groups having from 1 to 8 carbon atoms (including alkanoyl groups having from 1 to 8 carbon atoms and alkenoyl groups having from 3 to 8 carbon atoms) and aromatic acyl groups, i.e. arylcarbonyl groups in which the aryl part is a phenyl group which may be unsubstituted or may be substituted by at least one (and preferably from 1 to 3) substituents selected from the group consisting of substituents α, defined and exemplified above). Specific examples of such groups of formula >N—$R^4$ include the imino, methylimino, ethylimino, propylimino, isopropylimino, butylimino, isobutylimino, sec-butylimino, t-butylimino, pentylimino, 1-methylbutylimino, 2-methylbutylimino, 3-methylbutylimino, 1,1-dimethylpropylimino, 1,2-dimethylpropylimino, 2,2-dimethylpropylimino, 1-ethylpropylimino, hexylimino, 1-methylpentylimino, 2-methylpentylimino, 3-methylpentylimino, 4-methyl-pentylimino, 1,1-dimethylbutylimino, 1,2-dimethylbutyl-imino, 1,3-dimethylbutylimino, 2,2-dimethylbutylimino, 2,3-dimethylbutylimino, 3,3-dimethylbutylimino, 1-ethylbutylimino, 1,1,2-trimethylpropylimino, 1,2,2-trimethylpropylimino, acetylimino, propionylimino, butyrylimino, pentanoylimino, hexanoylimino, heptanoylimino, octanoylimino, benzoylimino and 2-toluoylimino groups, of which we prefer the straight or branched chain alkylimino groups having from 1 to 4 carbon atoms and the acetylimino group. The most preferred groups are the imino, methylimino, ethylimino and acetylimino groups.

Each of the compounds of the present invention contains a basic group in its molecule, and can thus be converted to salts with acids by conventional methods. There is no particular restriction on the nature of such salts, provided that, where the compounds are to be used medically, the compounds are pharmaceutically acceptable, that is it is not less active, or unacceptably less active, nor more toxic, or unacceptably more toxic, than the parent compound. However, where the compound is to be used for non-medical uses, e.g. as an intermediate in the preparation of other compounds, even this restriction does not apply, and there is then no restriction on the nature of the salts which may be formed. Examples of such salts include: salts with mineral acids, especially hydrohalic acids (such as hydrofluoric acid, hydrochloric acid, hydrobromic acid or hydroiodic acid), nitric acid, perchloric acid, sulfuric acid or phosphoric acid; salts with lower alkylsulfonic acids, such as methane-sulfonic acid, trifluoromethanesulfonic acid or ethane-sulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid. We prefer the pharmaceutically acceptable salts.

Also, the compound of the present invention can be converted into a salt with a base by conventional methods. Examples of such salts include: salts with an alkali metal, such as sodium, potassium or lithium; salts with an alkaline earth metal, such as barium or calcium or magnesium; and salts with another metal, such as aluminum. Again, we prefer the pharmaceutically acceptable salts.

The compounds of formula (I) of the present invention can exist in the form of various isomers due to the presence of asymmetric carbon atoms. Thus, where Z represents a 2,4-dioxothiazolidin-5-ylmethyl group (Zb) or a 2,4-dioxooxazolidin-5-ylmethyl group (Zc), the carbon atom at the 5-position is asymmetric. Although these isomers are all represented herein by a single molecular formula (I), the present invention includes both the individual, isolated isomers and mixtures, including racemates, thereof and the isomers may be present in such mixtures in any proportions. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

The compounds of formula (I) wherein Z represents a 2,4-dioxothiazolidin-5-ylmethyl group (Zb), a 2,4-dioxothiazolidin-5-ylidenylmethyl group (Za), 2,4-dioxooxazolidin-5-ylmethyl group (Zc) or a 3,5-dioxo-oxadiazolidin-2-ylmethyl group (Zd) can exist in the form of various tautomeric isomers as shown in the following schemes α, β, γ and δ, respectively:

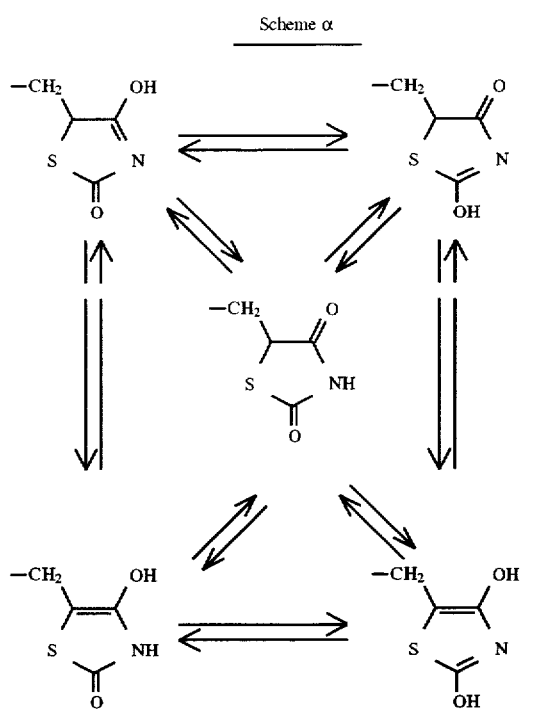

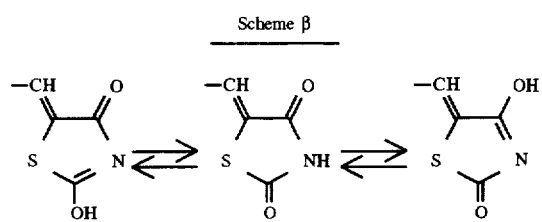

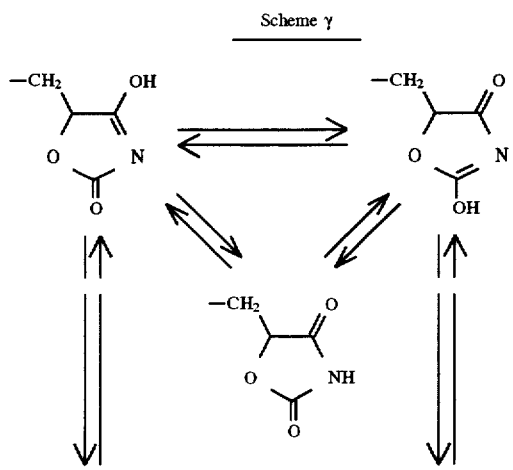

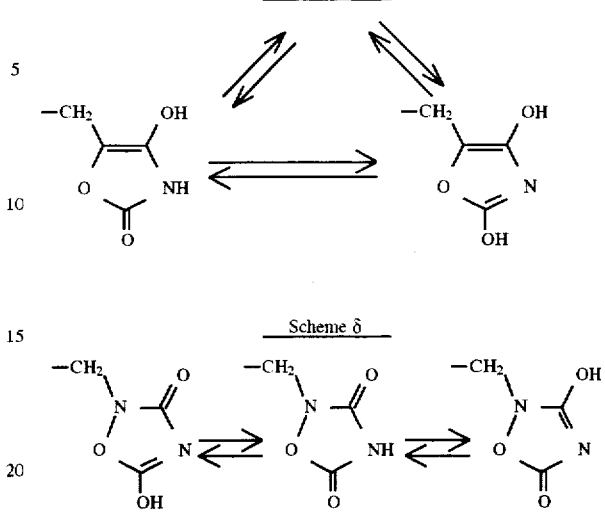

In the above formula (I), all tautomers based thereon and mixtures of equivalent weights or non-equivalent weights of these tautomers are represented by one formula. Thus, all of these isomers and mixtures of these isomers are included in the present invention.

In addition, the compounds of formula (I) can exist in the form of cis- and trans-isomers depending upon the geometrical isomerism of the oxime double bond. In the aforesaid formula (I), all of the isomers due to the geometrical isomerism and equimolar and non-equimolar mixtures of these isomers are represented by a single formula. Thus, all of these isomers and mixtures of these isomers are included in the present invention.

Moreover, the present invention also includes all solvates, for example hydrates, of the compounds of formula (I) and salts thereof, where the relevant compound is capable of forming a solvate.

The invention also embraces all compounds which could be converted in the living mammalian, for example human, body to a compound of formula (I) or a salt thereof by the action of the metabolism, that is so-called "pro-drugs" of the compounds of formula (I) and salts thereof.

Of the compounds of the present invention, we prefer those compounds of formula (I) and salts thereof, in which:

(A1) $R^1$ represents a hydrogen atom or an alkyl group having from 1 to 4 carbon atoms;

(A2) $R^2$ represents an alkylene group having from 2 to 5 carbon atoms;

(A3) $R^3$ represents a hydrogen atom, an alkyl group having from 1 to 4 carbon atoms, an alkoxy group having 1 or 2 carbon atoms, an alkylthio group having 1 or 2 carbon atoms or a halogen atom;

(A4) X represents: an aryl group, which has from 6 to 10 ring carbon atoms and is unsubstituted or is substituted by from 1 to 3 substituents selected from the group consisting of substituents $\alpha^1$, defined below; or an aromatic heterocyclic group which has from 5 to 10 ring atoms in one or two rings, of which atoms from 1 to 3 are hetero-atoms selected from the group consisting of nitrogen, oxygen and sulfur atoms, said group being unsubstituted or being substituted by from 1 to 3 substituents selected from the group consisting of substituents $\alpha^1$, defined below;

said substituents α¹ being selected from the group consisting of:

1) alkyl groups having from 1 to 6 carbon atoms,
2) halogenated alkyl groups having from 1 to 4 carbon atoms,
3) hydroxy groups,
4) acyloxy groups having from 1 to 4 carbon atoms,
5) alkoxy groups having from 1 to 4 carbon atoms,
6) alkylenedioxy groups having from 1 to 4 carbon atoms,
7) aralkyloxy groups having a total of from 7 to 12 carbon atoms,
8) alkylthio groups having from 1 to 4 carbon atoms,
9) alkylsulfonyl groups having from 1 to 4 carbon atoms,
10) halogen atoms,
11) aralkyl groups having a total of from 7 to 12 carbon atoms,
12) phenyl groups which are unsubstituted or are substituted by from 1 to 3 of substituents β¹, defined below,
13) phenoxy groups which are unsubstituted or are substituted by from 1 to 3 of substituents β¹, defined below,
14) phenylthio groups which are unsubstituted or are substituted by from 1 to 3 of substituents β¹, defined below,
15) phenylsulfonyl groups which are unsubstituted or are substituted by from 1 to 3 of substituents β¹, defined below,
16) phenylsulfonylamino groups in which the phenyl group is unsubstituted or is substituted by from 1 to 3 of substituents β¹, defined below, and the nitrogen atom is unsubstituted or is substituted by an alkyl group having from 1 to 6 carbon atoms,
17) furyl, thienyl, oxazolyl, isoxazolyl, thiazolyl, pyridyl, pyridyloxy, pyridylthio and pyridylsulfonyl groups,
18) imidazolyl groups in which a nitrogen atom is unsubstituted or is substituted by an alkyl group having from 1 to 6 carbon atoms,
19) pyridylsulfonylamino groups in which the amino group is unsubstituted or is substituted by an alkyl group having from 1 to 6 carbon atoms, said substituents β¹ being selected from the group consisting of alkyl groups having from 1 to 6 carbon atoms, halogenated alkyl groups having from 1 to 4 carbon atoms, alkoxy groups having from 1 to 4 carbon atoms, halogen atoms and alkylenedioxy groups having from 1 to 4 carbon atoms;

(A5) Y represents an oxygen atom, a sulfur atom or a group of formula >N—R⁴, in which R⁴ represents a hydrogen atom, an alkyl group having from 1 to 3 carbon atoms or an alkanoyl group having from 2 to 5 carbon atoms; and
(A6) Z represents a 2,4-dioxothiazolidin-5-ylmethyl, 2,4-dioxooxazolidin-5-ylmethyl or 3,5-dioxooxadiazolidin-2-ylmethyl group;

and especially compounds in which R¹ is as defined in (A1), R² is as defined in (A2), R³ is as defined in (A3), X is as defined in (A4), Y is as defined in (A5) and Z is as defined in (A6).

More preferred compounds of the present invention are those compounds of formula (I) and salts thereof, in which:
(B3) R³ represents a hydrogen atom;
(B4) X represents : an aryl group, which has from 6 to 10 ring carbon atoms and is unsubstituted or is substituted by from 1 to 3 substituents selected from the group consisting of substituents α², defined below; or an aromatic heterocyclic group which has from 5 to 10 ring atoms in one or two rings, of which atoms from 1 to 3 are hetero-atoms selected from the group consisting of nitrogen, oxygen and sulfur atoms, said group being unsubstituted or being substituted by from 1 to 3 substituents selected from the group consisting of substituents α², defined below;

said substituents α² being selected from the group consisting of:

1) alkyl groups having from 1 to 6 carbon atoms,
2) halogenated alkyl groups having from 1 to 4 carbon atoms,
3) hydroxy groups,
4) alkanoyloxy groups having from 1 to 4 carbon atoms,
5) alkoxy groups having from 1 to 4 carbon atoms,
6) alkylenedioxy groups having from 1 to 4 carbon atoms,
7) aralkyloxy groups having a total of from 7 to 12 carbon atoms,
8) alkylthio groups having from 1 to 4 carbon atoms,
9) alkylsulfonyl groups having from 1 to 4 carbon atoms,
10) fluorine atoms, chlorine atoms and bromine atoms,
11) aralkyl groups having a total of from 7 to 12 carbon atoms,
12) phenyl groups which are unsubstituted or are substituted by from 1 to 3 of substituents β¹, defined above,
13) phenoxy groups which are unsubstituted or are substituted by from 1 to 3 of substituents β¹, defined above,
14) phenylthio groups which are unsubstituted or are substituted by from 1 to 3 of substituents β¹, defined above,
15) phenylsulfonyl groups which are unsubstituted or are substituted by from 1 to 3 of substituents β¹, defined above,
16) phenylsulfonylamino group in which the phenyl group is unsubstituted or is substituted by from 1 to 3 of substituents β¹, defined above, and the nitrogen atom is unsubstituted or is substituted by an alkyl group having from 1 to 6 carbon atoms,
17) furyl thienyl, oxazolyl, isoxazolyl, thiazolyl, pyridyl, pyridyloxy, pyridylthio and pyridylsulfonyl groups;
18) imidazolyl groups in which a nitrogen atom is unsubstituted or is substituted by an alkyl group having from 1 to 6 carbon atoms,
19) pyridylsulfonylamino groups in which the amino group is unsubstituted or is substituted by an alkyl group having from 1 to 6 carbon atoms, (B5) Y represents an oxygen atom; and
(B6) Z represents a 2,4-dioxothiazolidin-5-ylmethyl or 2,4-dioxooxazolidin-5-ylmethyl group;
and especially compounds in which R¹ is as defined in (A1), R² is as defined in (A2), R³ is as defined in (B3), X is as defined in (B4), Y is as defined in (B5) and Z is as defined in (B6).

Still more preferred compounds of the present invention are those compounds of formula (I) and salts thereof, in which:
(C1) R¹ represents a hydrogen atom or an alkyl group having from 1 to 3 carbon atoms;
(C2) R² represents an alkylene group having from 2 or 3 carbon atoms;
(C4) X represents a phenyl, naphthyl, imidazolyl, oxazolyl, pyridyl, indolyl, quinolyl or isoquinolyl group, each of which is unsubstituted or is substituted by from 1 to 3 substituents selected from the group consisting of substituents α³, defined below;

said substituents α³ are selected from the group consisting of:
1) alkyl groups having from 1 to 6 carbon atoms,
2) halogenated alkyl groups having from 1 to 4 carbon atoms,
3) hydroxy groups,
4) alkanoyloxy groups having from 1 to 4 carbon atoms,
5) alkoxy groups having from 1 to 4 carbon atoms,
6) the methylenedioxy group,
7) aralkyloxy groups having a total of from 7 to 12 carbon atoms,
8) alkylthio groups having from 1 to 4 carbon atoms,
9) alkylsulfonyl groups having from 1 to 4 carbon atoms,
10) fluorine, chlorine and bromine atoms,
11) aralkyl groups having a total of from 7 to 12 carbon atoms,
12) phenyl groups which are unsubstituted or are substituted by from 1 to 3 of substituents $β^2$, defined below,
13) phenoxy groups which are unsubstituted or are substituted by from 1 to 3 of substituents $β^2$, defined below,
14) phenylthio groups which are unsubstituted or are substituted by from 1 to 3 of substituents $β^2$, defined below,
15) phenylsulfonyl groups which are unsubstituted or are substituted by from 1 to 3 of substituents $β^2$, defined below,
16) phenylsulfonylamino group in which the phenyl group is unsubstituted or is substituted by from 1 to 3 of substituents $β^2$, defined below, and the nitrogen atom is unsubstituted or is substituted by an alkyl group having from 1 to 6 carbon atoms,
17) furyl, thienyl, oxazolyl, isoxazolyl, thiazolyl, pyridyl, pyridyloxy, pyridylthio and pyridylsulfonyl groups;
18) imidazolyl groups in which a nitrogen atom is unsubstituted or is substituted by an alkyl group having from 1 to 6 carbon atoms,
19) pyridylsulfonylamino groups in which the amino group is unsubstituted or is substituted by an alkyl group having from 1 to 6 carbon atoms,
said substituents $β^2$ are selected from the group consisting of methyl groups, trifluoro-methyl groups, methoxy groups, fluorine atoms and methylenedioxy groups);
(C6) Z represents a 2,4-dioxothiazolidin-5-ylmethyl group;
and especially compounds in which $R^1$ is as defined in (C1), $R^2$ is as defined in (C2), $R^3$ is as defined in (B3), X is as defined in (C4), Y is as defined in (B5) and Z is as defined in (C6).

Still more preferred compounds of the present invention are those compounds of formula (I) and salts thereof, in which:
(D1) $R^1$ represents a hydrogen atom, a methyl or ethyl group;
(D2) R represents an ethylene, trimethylene or methylethylene group;
(D4) X represents a phenyl, naphthyl, imidazolyl, oxazolyl, pyridyl, indolyl, quinolyl or isoquinolyl group, each of which is unsubstituted or is substituted by from 1 to 3 substituents selected from the group consisting of substituents $α^4$, defined below;
said substituents $α^4$ are selected from the group consisting of:
1) alkyl groups having from 1 to 6 carbon atoms,
2) halogenated alkyl groups having from 1 to 4 carbon atoms,
3) hydroxy groups,
4) alkanoyloxy groups having from 1 to 4 carbon atoms,
5) alkoxy groups having from 1 to 4 carbon atoms,
6) methylenedioxy, benzyloxy, phenethyloxy and naphthylmethyloxy groups,
7) alkylthio groups having from 1 to 4 carbon atoms,
8) alkylsulfonyl groups having from 1 to 4 carbon atoms,
9) fluorine, chlorine and bromine atoms,
10) the benzyl group,
11) phenyl groups which are unsubstituted or are substituted by from 1 to 3 of substituents $β^2$, defined above,
12) phenoxy groups which are unsubstituted or are substituted by from 1 to 3 of substituents $β^2$, defined above,
13) the phenylthio, phenylsulfonyl, phenylsulfonylamino, N-methylphenylsulfonylamino, furyl, thienyl, oxazolyl, isoxazolyl, thiazolyl, pyridyl, pyridyloxy, pyridylthio, pyridyl-sulfonyl, pyridylsulfonylamino and N-methylpyridylsulfonylamino groups,
14) imidazolyl groups in which a nitrogen atom is unsubstituted or is substituted by an alkyl group having from 1 to 6 carbon atoms,
and especially compounds in which $R^1$ is as defined in (D1), $R^2$ is as defined in (D2), $R^3$ is as defined in (B3), X is as defined in (D4), Y is as defined in (B5) and Z is as defined in (C6).

Further preferred compounds of the present invention are those compounds of formula (I) and salts thereof, in which:
(E4) X represents a phenyl, naphthyl, pyridyl, indolyl, quinolyl or isoquinolyl group, each of which is unsubstituted or is substituted by from 1 to 3 substituents selected from the group consisting of substituents $α^5$, defined below;
said substituents $α^5$ are selected from the group consisting of:
1) alkyl groups having from 1 to 3 carbon atoms,
2) the trifluoromethyl, difluoromethyl, fluoromethyl, hydroxy, formyloxy and acetoxy groups,
3) alkoxy groups having from 1 to 3 carbon atoms,
4) the methylenedioxy, benzyloxy, methylthio, ethylthio, methylsulfonyl and ethylsulfonyl groups,
5) the fluorine, chlorine and bromine atoms, and
6) the benzyl, phenyl, 4-methylphenyl, 4-trifluoromethylphenyl, 4-methoxyphenyl, 4-fluorophenyl, 3,4-methylenedioxyphenyl, phenoxy, phenylthio, phenylsulfonyl, phenylsulfonylamino, N-methylphenylsulfonylamino, furyl, thienyl, oxazolyl, thiazolyl, imidazolyl, N-methylimidazolyl, pyridyl, pyridyloxy, pyridylthio, pyridylsulfonyl, pyridylsulfonylamino and/or N-methylpyridylsulfonylamino groups;
and especially compounds in which $R^1$ is as defined in (D1), $R^2$ is as defined in (D2), $R^3$ is as defined in (B3), X is as defined in (E4), Y is as defined in (B5) and Z is as defined in (C6).

Still further preferred compounds of the present invention are those compounds of formula (I) and salts thereof, in which:
(F2) $R^2$ represents an ethylene group;
(F4) X represents a phenyl, naphthyl, pyridyl, quinolyl or isoquinolyl group, each of which is unsubstituted or is substituted by from 1 to 3 substituents selected from the group consisting of substituents $\alpha^6$, defined below;

said substituents $\alpha^6$ are selected from the group consisting of: methyl, ethyl, isopropyl, trifluoromethyl, hydroxy, acetoxy, methoxy, ethoxy, isopropoxy, methylenedioxy, benzyloxy, methylthio, ethylthio, methylsulfonyl, ethylsulfonyl, benzyl, phenyl, phenoxy, phenylthio, phenylsulfonyl, phenylsulfonylamino, N-methylphenylsulfonylamino, pyridyl, pyridyloxy, pyridylthio, pyridylsulfonyl, pyridylsulfonylamino and N-methylpyridylsulfonyl-amino groups and chlorine atoms.

and especially compounds in which $R^1$ is as defined in (D1), $R^2$ is as defined in (F2), $R^3$ is as defined in (B3), X is as defined in (F4), Y is as defined in (B5) and Z is as defined in (C6).

The most preferred compounds of the present invention are those compounds of formula (I) and salts thereof, in which:

(G1) $R^1$ represents a methyl or ethyl group;

(G4a) X represents a phenyl group which is unsubstituted or is substituted by from 1 to 3 substituents selected from the group consisting of substituents $\alpha^7$, defined below;

said substituents $\alpha^7$ are selected from the group consisting of: methyl, hydroxy, acetoxy, benzyl, phenyl, phenoxy, phenylthio, phenylsulfonyl, phenylsulfonylamino, N-methylphenylsulfonylamino, pyridyl, pyridyloxy, pyridylthio and pyridylsulfonyl groups and chlorine atoms; or (G4b) X represents a pyridyl group which is unsubstituted or is substituted by from 1 to 3 substituents selected from the group consisting of substituents $\alpha^8$, defined below;

said substituents $\alpha^8$ are selected from the group consisting of: methoxy, ethoxy, isopropoxy, benzyloxy, methylthio, ethylthio, methylsulfonyl, ethylsulfonyl, benzyl, phenyl, phenoxy, phenylthio, phenylsulfonyl, phenylsulfonylamino and N-methylphenylsulfonylamino groups;

and especially compounds in which $R^1$ is as defined in (G1), $R^2$ is as defined in (F2), $R^3$ is as defined in (B3), X is as defined in (G4a) or (G4b), Y is as defined in (B5) and Z is as defined in (C6).

Examples of specific compounds of the present invention are those compounds of formula (I):

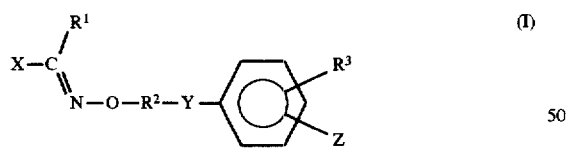

in which $R^1$, $R^2$, $R^3$, X, Y and Z are as defined in the following Tables 1 to 26. In these Tables, certain abbreviations are used, for the sake of convenience, and these abbreviations are as follows:

Ac: acetyl,
tBu: t-butyl,
Bimid: benzimidazolyl, e.g. Bimid-2 is 2-benzimidazolyl
Boxa: benzoxazolyl, e.g. Boxa-2 is 2-benzoxazolyl
Bthiz: benzothiazolyl, e.g. Bthiz-2 is 2-benzothiazolyl
Bz: benzyl,
Et: ethyl,
Fur: furyl,
Imid: imidazolyl, e.g. Imid-2 is 2-imidazolyl
Ind: indolyl, e.g. Ind-2 is 2-indolyl
Isox: isoxazolyl, e.g. Isox-4 is 4-isoxazolyl
MdO: methylenedioxy,
Me: methyl,
Np: naphthyl, e.g. Np-2 is 2-naphthyl
Oxa: oxazolyl, e.g. Oxa-2 is 2-oxazolyl
Ph: phenyl,
iPr: isopropyl,
Pym: pyrimidinyl, e.g. Pym-4 is 4-pyrimidinyl
Pyr: pyridyl, e.g. Pyr-2 is 2-pyridyl
Pyrr: pyrrolyl, e.g. Pyrr-2 is 2-pyrrolyl
Pyza: pyrazolyl, e.g. Pyza-4 is 4-pyrazolyl
Quin: quinolyl, e.g. Quin-2 is 2-quinolyl
iQuin: isoquinolyl, e.g. iQuin-4 is 4-isoquinolyl
Thi: thienyl, e.g. Thi-2 is 2-thienyl
Thiz: thiazolyl, e.g. Thiz-4 is 4-thiazolyl
Za: 2,4-dioxothiazolidin-5-ylidenylmethyl, i.e. formula (Za):

Zb: 2,4-dioxothiazolidin-5-ylmethyl, i.e. formula (Zb):

Zc: 2,4-dioxooxazolidin-5-ylmethyl, i.e. formula (Zc):

Zd: 3,5-dioxooxadiazolidin-2-ylmethyl, i.e. formula (Zd):

TABLE 1

| Cpd. No. | $R^1$ | $R^2$ | $R^3$ | X | Y | Z |
|---|---|---|---|---|---|---|
| 1-1 | H | (CH$_2$)$_2$ | H | Ph | O | 4-Zb |
| 1-2 | H | (CH$_2$)$_2$ | H | Np-1 | O | 4-Zb |
| 1-3 | H | (CH$_2$)$_2$ | H | Np-2 | O | 4-Zb |
| 1-4 | H | (CH$_2$)$_2$ | H | 4-Me-Ph | O | 4-Zb |
| 1-5 | H | (CH$_2$)$_2$ | H | 4-Et-Ph | O | 4-Zb |
| 1-6 | H | (CH$_2$)$_2$ | H | 3-iPr-Ph | O | 4-Zb |
| 1-7 | H | (CH$_2$)$_2$ | H | 4-iPr-Ph | O | 4-Zb |
| 1-8 | H | (CH$_2$)$_2$ | H | 3-tBu-Ph | O | 4-Zb |
| 1-9 | H | (CH$_2$)$_2$ | H | 4-tBu-Ph | O | 4-Zb |
| 1-10 | H | (CH$_2$)$_2$ | H | 3-Cl-Ph | O | 4-Zb |

TABLE 1-continued

| Cpd. No. | R¹ | R² | R³ | X | Y | Z |
|---|---|---|---|---|---|---|
| 1-11 | H | (CH$_2$)$_2$ | H | 4-Cl-Ph | O | 4-Zb |
| 1-12 | H | (CH$_2$)$_2$ | H | 3-Br-Ph | O | 4-Zb |
| 1-13 | H | (CH$_2$)$_2$ | H | 4-Br-Ph | O | 4-Zb |
| 1-14 | H | (CH$_2$)$_2$ | H | 3-Ph-Ph | O | 4-Zb |
| 1-15 | H | (CH$_2$)$_2$ | H | 4-Ph-Ph | O | 4-Zb |
| 1-16 | H | (CH$_2$)$_2$ | H | 3-Bz-Ph | O | 4-Zb |
| 1-17 | H | (CH$_2$)$_2$ | H | 4-Bz-Ph | O | 4-Zb |
| 1-18 | H | (CH$_2$)$_2$ | H | 3-PhO-Ph | O | 4-Zb |
| 1-19 | H | (CH$_2$)$_2$ | H | 4-PhO-Ph | O | 4-Zb |
| 1-20 | H | (CH$_2$)$_2$ | H | 3-PhS-Ph | O | 4-Zb |
| 1-21 | H | (CH$_2$)$_2$ | H | 4-PhS-Ph | O | 4-Zb |
| 1-22 | H | (CH$_2$)$_2$ | H | 3-PhSO$_2$-Ph | O | 4-Zb |
| 1-23 | H | (CH$_2$)$_2$ | H | 4-PhSO$_2$-Ph | O | 4-Zb |
| 1-24 | H | (CH$_2$)$_2$ | H | 3-(Imid-1)Ph | O | 4-Zb |
| 1-25 | H | (CH$_2$)$_2$ | H | 4-(Imid-1)Ph | O | 4-Zb |
| 1-26 | H | (CH$_2$)$_2$ | H | 3-(Imid-4)Ph | O | 4-Zb |
| 1-27 | H | (CH$_2$)$_2$ | H | 4-(Imid-4)Ph | O | 4-Zb |
| 1-28 | H | (CH$_2$)$_2$ | H | 3-(Fur-2)Ph | O | 4-Zb |
| 1-29 | H | (CH$_2$)$_2$ | H | 4-(Fur-2)Ph | O | 4-Zb |
| 1-30 | H | (CH$_2$)$_2$ | H | 3-(Thi-2)Ph | O | 4-Zb |
| 1-31 | H | (CH$_2$)$_2$ | H | 4-(Thi-2)Ph | O | 4-Zb |
| 1-32 | H | (CH$_2$)$_2$ | H | 3-(Thi-3)Ph | O | 4-Zb |
| 1-33 | H | (CH$_2$)$_2$ | H | 4-(Thi-3)Ph | O | 4-Zb |
| 1-34 | H | (CH$_2$)$_2$ | H | 3-(Pyr-2)Ph | O | 4-Zb |
| 1-35 | H | (CH$_2$)$_2$ | H | 4-(Pyr-2)Ph | O | 4-Zb |
| 1-36 | H | (CH$_2$)$_2$ | H | 3-(Pyr-3)Ph | O | 4-Zb |
| 1-37 | H | (CH$_2$)$_2$ | H | 4-(Pyr-3)Ph | O | 4-Zb |
| 1-38 | H | (CH$_2$)$_2$ | H | 3-Pyr-4)Ph | O | 4-Zb |
| 1-39 | H | (CH$_2$)$_2$ | H | 4-Pyr-4)Ph | O | 4-Zb |
| 1-40 | H | (CH$_2$)$_2$ | H | 3-(Oxa-2)Ph | O | 4-Zb |
| 1-41 | H | (CH$_2$)$_2$ | H | 4-(Oxa-2)Ph | O | 4-Zb |
| 1-42 | H | (CH$_2$)$_2$ | H | 3-(Oxa-4)Ph | O | 4-Zb |
| 1-43 | H | (CH$_2$)$_2$ | H | 4-(Oxa-4)Ph | O | 4-Zb |
| 1-44 | H | (CH$_2$)$_2$ | H | 3-(Oxa-5)Ph | O | 4-Zb |
| 1-45 | H | (CH$_2$)$_2$ | H | 4-(Oxa-5)Ph | O | 4-Zb |
| 1-46 | H | (CH$_2$)$_2$ | H | 3-(Thiz-2)Ph | O | 4-Zb |
| 1-47 | H | (CH$_2$)$_2$ | H | 4-(Thiz-2)Ph | O | 4-Zb |
| 1-48 | H | (CH$_2$)$_2$ | H | 3-(Thiz-4)Ph | 6 | 4-Zb |
| 1-49 | H | (CH$_2$)$_2$ | H | 4-(Thiz-4)Ph | O | 4-Zb |
| 1-50 | H | (CH$_2$)$_2$ | H | 3-(Thiz-5)Ph | O | 4-Zb |
| 1-51 | H | (CH$_2$)$_2$ | H | 4-(Thiz-5)Ph | O | 4-Zb |
| 1-52 | H | (CH$_2$)$_2$ | H | 1-Me-Pyrr-2 | O | 4-Zb |
| 1-53 | H | (CH$_2$)$_2$ | H | 1-Ph-Pyrr-2 | O | 4-Zb |
| 1-54 | H | (CH$_2$)$_2$ | H | 1-Bz-Pyrr-2 | O | 4-Zb |
| 1-55 | H | (CH$_2$)$_2$ | H | 5-Me-Fur-2 | O | 4-Zb |
| 1-56 | H | (CH$_2$)$_2$ | H | 5-Ph-Fur-2 | O | 4-Zb |
| 1-57 | H | (CH$_2$)$_2$ | H | 5-Me-Thi-2 | O | 4-Zb |
| 1-58 | H | (CH$_2$)$_2$ | H | 5-Ph-Thi-2 | O | 4-Zb |
| 1-59 | H | (CH$_2$)$_2$ | H | 5-Me-Thi-3 | O | 4-Zb |
| 1-60 | H | (CH$_2$)$_2$ | H | 5-Ph-Thi-3 | O | 4-Zb |
| 1-61 | H | (CH$_2$)$_2$ | H | 1-Me-Pyza-3 | O | 4-Zb |
| 1-62 | H | (CH$_2$)$_2$ | H | 1-Ph-Pyza-3 | O | 4-Zb |
| 1-63 | H | (CH$_2$)$_2$ | H | 1-Me-Imid-2 | O | 4-Zb |
| 1-64 | H | (CH$_2$)$_2$ | H | 1-Ph-Imid-2 | O | 4-Zb |
| 1-65 | H | (CH$_2$)$_2$ | H | 1-Me-Imid-4 | O | 4-Zb |
| 1-66 | H | (CH$_2$)$_2$ | H | 1-Ph-Imid-4 | O | 4-Zb |
| 1-67 | H | (CH$_2$)$_2$ | H | Oxa-4 | O | 4-Zb |
| 1-68 | H | (CH$_2$)$_2$ | H | Oxa-5 | O | 4-Zb |
| 1-69 | H | (CH$_2$)$_2$ | H | 2-Me-Oxa-4 | O | 4-Zb |
| 1-70 | H | (CH$_2$)$_2$ | H | 2-Ph-Oxa-4 | O | 4-Zb |
| 1-71 | H | (CH$_2$)$_2$ | H | 2-Me-Oxa-5 | O | 4-Zb |
| 1-72 | H | (CH$_2$)$_2$ | H | 2-Ph-Oxa-5 | O | 4-Zb |
| 1-73 | H | (CH$_2$)$_2$ | H | 4-Me-2-Ph-Oxa-5 | O | 4-Zb |
| 1-74 | H | (CH$_2$)$_2$ | H | 5-Me-2-Ph-Oxa-4 | O | 4-Zb |
| 1-75 | H | (CH$_2$)$_2$ | H | Thiz-4 | O | 4-Zb |
| 1-76 | H | (CH$_2$)$_2$ | H | Thiz-5 | O | 4-Zb |
| 1-77 | H | (CH$_2$)$_2$ | H | 2-Me-Thiz-4 | O | 4-Zb |
| 1-78 | H | (CH$_2$)$_2$ | H | 2-Ph-Thiz-4 | O | 4-Zb |
| 1-79 | H | (CH$_2$)$_2$ | H | 2-Me-Thiz-5 | O | 4-Zb |
| 1-80 | H | (CH$_2$)$_2$ | H | 2-Ph-Thiz-5 | O | 4-Zb |
| 1-81 | H | (CH$_2$)$_2$ | H | 4-Me-2-Ph-Thiz-5 | O | 4-Zb |
| 1-82 | H | (CH$_2$)$_2$ | H | 5-Me-2-Ph-Thiz-4 | O | 4-Zb |
| 1-83 | H | (CH$_2$)$_2$ | H | 1-Me-Pyza-4 | O | 4-Zb |
| 1-84 | H | (CH$_2$)$_2$ | H | 1-Ph-Pyza-4 | O | 4-Zb |
| 1-85 | H | (CH$_2$)$_2$ | H | 2-Me-Isox-4 | O | 4-Zb |
| 1-86 | H | (CH$_2$)$_2$ | H | 2-Ph-Isox-4 | O | 4-Zb |
| 1-87 | H | (CH$_2$)$_2$ | H | Pyr-2 | O | 4-Zb |
| 1-88 | H | (CH$_2$)$_2$ | H | Pyr-3 | O | 4-Zb |
| 1-89 | H | (CH$_2$)$_2$ | H | Pyr-4 | O | 4-Zb |
| 1-90 | H | (CH$_2$)$_2$ | H | 3-Me-Pyr-5 | O | 4-Zb |
| 1-91 | H | (CH$_2$)$_2$ | H | 3-Et-Pyr-5 | O | 4-Zb |
| 1-92 | H | (CH$_2$)$_2$ | H | 3-Ph-Pyr-5 | O | 4-Zb |
| 1-93 | H | (CH$_2$)$_2$ | H | 2-Me-Pyr-5 | O | 4-Zb |
| 1-94 | H | (CH$_2$)$_2$ | H | 2-Et-Pyr-5 | O | 4-Zb |
| 1-95 | H | (CH$_2$)$_2$ | H | 2-Ph-Pyr-5 | O | 4-Zb |
| 1-96 | H | (CH$_2$)$_2$ | H | 2-MeO-Pyr-5 | O | 4-Zb |
| 1-97 | H | (CH$_2$)$_2$ | H | 2-EtO-Pyr-5 | O | 4-Zb |
| 1-98 | H | (CH$_2$)$_2$ | H | 2-iPrO-Pyr-5 | O | 4-Zb |
| 1-99 | H | (CH$_2$)$_2$ | H | 2-MeS-Pyr-5 | O | 4-Zb |
| 1-100 | H | (CH$_2$)$_2$ | H | 2-EtS-Pyr-5 | O | 4-Zb |
| 1-101 | H | (CH$_2$)$_2$ | H | 2-iPrS-Pyr-5 | O | 4-Zb |
| 1-102 | H | (CH$_2$)$_2$ | H | 2-MeSO$_2$-Pyr-5 | O | 4-Zb |
| 1-103 | H | (CH$_2$)$_2$ | H | 2-EtSO$_2$-Pyr-5 | O | 4-Zb |
| 1-104 | H | (CH$_2$)$_2$ | H | 2-iPrSO$_2$-Pyr-5 | O | 4-Zb |
| 1-105 | H | (CH$_2$)$_2$ | H | 2-Bz-Pyr-5 | O | 4-Zb |
| 1-106 | H | (CH$_2$)$_2$ | H | 2-PhO-Pyr-5 | O | 4-Zb |
| 1-107 | H | (CH$_2$)$_2$ | H | 2-PhS-Pyr-5 | O | 4-Zb |
| 1-108 | H | (CH$_2$)$_2$ | H | 2-PhSO$_2$-Pyr-5 | O | 4-Zb |
| 1-109 | H | (CH$_2$)$_2$ | H | 3-Me-Pyr-6 | O | 4-Zb |
| 1-110 | H | (CH$_2$)$_2$ | H | 3-Ph-Pyr-6 | O | 4-Zb |
| 1-111 | H | (CH$_2$)$_2$ | H | 2-Me-Pyr-6 | O | 4-Zb |
| 1-112 | H | (CH$_2$)$_2$ | H | 2-Ph-Pyr-6 | O | 4-Zb |
| 1-113 | H | (CH$_2$)$_2$ | H | 2-Me-Pym-4 | O | 4-Zb |
| 1-114 | H | (CH$_2$)$_2$ | H | 2-Ph-Pym-4 | O | 4-Zb |
| 1-115 | H | (CH$_2$)$_2$ | H | 2-MeO-Pym-4 | O | 4-Zb |
| 1-116 | H | (CH$_2$)$_2$ | H | 2-EtO-Pym-4 | O | 4-Zb |
| 1-117 | H | (CH$_2$)$_2$ | H | 2-iPrO-Pym-4 | O | 4-Zb |
| 1-118 | H | (CH$_2$)$_2$ | H | 2-MeS-Pym-4 | O | 4-Zb |
| 1-119 | H | (CH$_2$)$_2$ | H | 2-EtS-Pym-4 | O | 4-Zb |
| 1-120 | H | (CH$_2$)$_2$ | H | 2-iPrS-Pym-4 | O | 4-Zb |
| 1-121 | H | (CH$_2$)$_2$ | H | 6-MeS-Pym-4 | O | 4-Zb |
| 1-122 | H | (CH$_2$)$_2$ | H | 6-EtS-Pym-4 | O | 4-Zb |
| 1-123 | H | (CH$_2$)$_2$ | H | 6-iPrS-Pym-4 | O | 4-Zb |
| 1-124 | H | (CH$_2$)$_2$ | H | 2-PhS-Pym-4 | O | 4-Zb |
| 1-125 | H | (CH$_2$)$_2$ | H | 2-MeSO$_2$-Pym-4 | O | 4-Zb |
| 1-126 | H | (CH$_2$)$_2$ | H | 2-EtSO$_2$-Pym-4 | O | 4-Zb |
| 1-127 | H | (CH$_2$)$_2$ | H | 2-iPrSO$_2$-Pym-4 | O | 4-Zb |
| 1-128 | H | (CH$_2$)$_2$ | H | 2-PhSO$_2$-Pym-4 | O | 4-Zb |
| 1-129 | H | (CH$_2$)$_2$ | H | 2-Me-Pym-5 | O | 4-Zb |
| 1-130 | H | (CH$_2$)$_2$ | H | 2-Ph-Pym-5 | O | 4-Zb |
| 1-131 | H | (CH$_2$)$_2$ | H | 2-MeO-Pym-5 | O | 4-Zb |
| 1-132 | H | (CH$_2$)$_2$ | H | 2-EtO-Pym-5 | O | 4-Zb |
| 1-133 | H | (CH$_2$)$_2$ | H | 2-iPrO-Pym-5 | O | 4-Zb |
| 1-134 | H | (CH$_2$)$_2$ | H | 2-MeS-Pym-5 | O | 4-Zb |
| 1-135 | H | (CH$_2$)$_2$ | H | 2-EtS-Pym-5 | O | 4-Zb |
| 1-136 | H | (CH$_2$)$_2$ | H | 2-iPrS-Pym-5 | O | 4-Zb |
| 1-137 | H | (CH$_2$)$_2$ | H | 2-PhS-Pym-5 | O | 4-Zb |
| 1-138 | H | (CH$_2$)$_2$ | H | 2-MeSO$_2$-Pym-5 | O | 4-Zb |
| 1-139 | H | (CH$_2$)$_2$ | H | 2-EtSO$_2$-Pym-5 | O | 4-Zb |
| 1-140 | H | (CH$_2$)$_2$ | H | 2-iPrSO$_2$-Pym-5 | O | 4-Zb |
| 1-141 | H | (CH$_2$)$_2$ | H | 2-PhSO$_2$-Pym-5 | O | 4-Zb |
| 1-142 | H | (CH$_2$)$_2$ | H | Ind-2 | O | 4-Zb |
| 1-143 | H | (CH$_2$)$_2$ | H | Ind-3 | O | 4-Zb |
| 1-144 | H | (CH$_2$)$_2$ | H | 1-Me-Ind-2 | O | 4-Zb |
| 1-145 | H | (CH$_2$)$_2$ | H | 1-Me-Ind-3 | O | 4-Zb |
| 1-146 | H | (CH$_2$)$_2$ | H | Bimid-2 | O | 4-Zb |
| 1-147 | H | (CH$_2$)$_2$ | H | Boxa-2 | O | 4-Zb |
| 1-148 | H | (CH$_2$)$_2$ | H | Bthiz-2 | O | 4-Zb |
| 1-149 | H | (CH$_2$)$_2$ | H | Quin-2 | O | 4-Zb |
| 1-150 | H | (CH$_2$)$_2$ | H | Quin-3 | O | 4-Zb |
| 1-151 | H | (CH$_2$)$_2$ | H | Quin-4 | O | 4-Zb |
| 1-152 | H | (CH$_2$)$_2$ | H | iQuin-1 | O | 4-Zb |
| 1-153 | H | (CH$_2$)$_2$ | H | iQuin-3 | O | 4-Zb |
| 1-154 | H | (CH$_2$)$_2$ | H | iQuin-4 | O | 4-Zb |
| 1-155 | H | (CH$_2$)$_2$ | H | 3-MeO-Ph | O | 4-Zb |
| 1-156 | H | (CH$_2$)$_2$ | H | 4-MeO-Ph | O | 4-Zb |
| 1-157 | H | (CH$_2$)$_2$ | H | 3-EtO-Ph | O | 4-Zb |
| 1-158 | H | (CH$_2$)$_2$ | H | 4-EtO-Ph | O | 4-Zb |
| 1-159 | H | (CH$_2$)$_2$ | H | 3-iPrO-Ph | O | 4-Zb |
| 1-160 | H | (CH$_2$)$_2$ | H | 4-iPrO-Ph | O | 4-Zb |
| 1-161 | H | (CH$_2$)$_2$ | H | 3-MeS-Ph | O | 4-Zb |
| 1-162 | H | (CH$_2$)$_2$ | H | 4-MeS-Ph | O | 4-Zb |

TABLE 1-continued

| Cpd. No. | R¹ | R² | R³ | X | Y | Z |
|---|---|---|---|---|---|---|
| 1-163 | H | (CH$_2$)$_2$ | H | 3-EtS-Ph | O | 4-Zb |
| 1-164 | H | (CH$_2$)$_2$ | H | 4-EtS-Ph | O | 4-Zb |
| 1-165 | H | (CH$_2$)$_2$ | H | 3-iPrS-Ph | O | 4-Zb |
| 1-166 | H | (CH$_2$)$_2$ | H | 4-iPrS-Ph | O | 4-Zb |
| 1-167 | H | (CH$_2$)$_2$ | H | 3-MeSO$_2$-Ph | O | 4-Zb |
| 1-168 | H | (CH$_2$)$_2$ | H | 4-MeSO$_2$-Ph | O | 4-Zb |
| 1-169 | H | (CH$_2$)$_2$ | H | 3-EtSO$_2$-Ph | O | 4-Zb |
| 1-170 | H | (CH$_2$)$_2$ | H | 4-EtSO$_2$-Ph | O | 4-Zb |
| 1-171 | H | (CH$_2$)$_2$ | H | 3-iPrSO$_2$-Ph | O | 4-Zb |
| 1-172 | H | (CH$_2$)$_2$ | H | 4-iPrSO$_2$-Ph | O | 4-Zb |
| 1-173 | H | (CH$_2$)$_2$ | H | 3-(1-Me-Imid-4)Ph | O | 4-Zb |
| 1-174 | H | (CH$_2$)$_2$ | H | 4-(1-Me-Imid-4)Ph | O | 4-Zb |
| 1-175 | H | (CH$_2$)$_2$ | H | 1-Me-2-Ph-Imid-4 | O | 4-Zb |
| 1-176 | H | (CH$_2$)$_2$ | H | 1,4-diMe-2-Ph-Imid-5 | O | 4-Zb |
| 1-177 | H | (CH$_2$)$_2$ | H | 1,5-diMe-2-Ph-Imid-4 | O | 4-Zb |
| 1-178 | H | (CH$_2$)$_2$ | H | 3,4-MdO-Ph | O | 4-Zb |
| 1-179 | H | (CH$_2$)$_2$ | H | 4-(4-MeO-Ph)Ph | O | 4-Zb |
| 1-180 | H | (CH$_2$)$_2$ | H | 4-(3,4-MdO-Ph)Ph | O | 4-Zb |
| 1-181 | H | (CH$_2$)$_2$ | H | 4-|PhSO$_2$N(Me)|Ph | O | 4-Zb |
| 1-182 | H | (CH$_2$)$_2$ | H | 4-|(Pyr-3)SO$_2$N(Me)|Ph | O | 4-Zb |
| 1-183 | H | (CH$_2$)$_2$ | H | 4-(PhSO$_2$NH)Ph | O | 4-Zb |
| 1-184 | H | (CH$_2$)$_2$ | H | 4-|(Pyr-3)SO$_2$NH|Ph | O | 4-Zb |
| 1-185 | H | (CH$_2$)$_2$ | H | 4-|(Pyr-2)SO$_2$|Ph | O | 4-Zb |
| 1-186 | H | (CH$_2$)$_2$ | H | 4-|(Pyr-3)SO$_2$|Ph | O | 4-Zb |
| 1-187 | H | (CH$_2$)$_2$ | H | 4-|(Pyr-2)SO$_2$N(Me)|Ph | O | 4-Zb |
| 1-188 | H | (CH$_2$)$_2$ | H | 4-|(Pyr-2)SO$_2$NH|Ph | O | 4-Zb |
| 1-189 | H | (CH$_2$)$_2$ | H | 4-(4-Me-Ph)Ph | O | 4-Zb |
| 1-190 | H | (CH$_2$)$_2$ | H | 4-(4-F-Ph)Ph | O | 4-Zb |
| 1-191 | H | (CH$_2$)$_2$ | H | 4-(4-CF$_3$-Ph)Ph | O | 4-Zb |
| 1-192 | H | (CH$_2$)$_2$ | H | 2-|4-Me-PhSO$_2$N(Me)|-Pry-5 | O | 4-Zb |
| 1-193 | H | (CH$_2$)$_2$ | H | 2-HO-Pyr-5 | O | 4-Zb |
| 1-194 | H | (CH$_2$)$_2$ | H | 2-BzO-Pyr-5 | O | 4-Zb |
| 1-195 | H | (CH$_2$)$_2$ | H | 4-|(Pyr-4)SO$_2$|Ph | O | 4-Zb |
| 1-196 | H | (CH$_2$)$_2$ | H | 4-(2,4-diMeO-Ph)Ph | O | 4-Zb |
| 1-197 | H | (CH$_2$)$_2$ | H | 4-(2,5-diMeO-Ph)Ph | O | 4-Zb |
| 1-198 | H | (CH$_2$)$_2$ | H | 3-HO-Ph | O | 4-Zb |
| 1-199 | H | (CH$_2$)$_2$ | H | 4-HO-Ph | O | 4-Zb |
| 1-200 | H | (CH$_2$)$_2$ | H | 5-AcO-2-HO-3,4,6-triMePh | O | 4-Zb |
| 1-201 | H | (CH$_2$)$_2$ | H | 4-HO-3,5-diMePh | O | 4-Zb |
| 1-202 | H | (CH$_2$)$_2$ | H | 3-AcO-Ph | O | 4-Zb |
| 1-203 | H | (CH$_2$)$_2$ | H | 4-AcO-Ph | O | 4-Zb |

TABLE 2

| Cpd. No. | R¹ | R² | R³ | X | Y | Z |
|---|---|---|---|---|---|---|
| 2-1 | Me | (CH$_2$)$_2$ | H | Ph | O | 4-Zb |
| 2-2 | Me | (CH$_2$)$_2$ | H | Np-1 | O | 4-Zb |
| 2-3 | Me | (CH$_2$)$_2$ | H | Np-2 | O | 4-Zb |
| 2-4 | Me | (CH$_2$)$_2$ | H | 4-Me-Ph | O | 4-Zb |
| 2-5 | Me | (CH$_2$)$_2$ | H | 4-Et-Ph | O | 4-Zb |
| 2-6 | Me | (CH$_2$)$_2$ | H | 3-iPr-Ph | O | 4-Zb |
| 2-7 | Me | (CH$_2$)$_2$ | H | 4-iPr-Ph | O | 4-Zb |
| 2-8 | Me | (CH$_2$)$_2$ | H | 3-tBu-Ph | O | 4-Zb |
| 2-9 | Me | (CH$_2$)$_2$ | H | 4-tBu-Ph | O | 4-Zb |
| 2-10 | Me | (CH$_2$)$_2$ | H | 3-Cl-Ph | O | 4-Zb |
| 2-11 | Me | (CH$_2$)$_2$ | H | 4-Cl-Ph | O | 4-Zb |
| 2-12 | Me | (CH$_2$)$_2$ | H | 3-Br-Ph | O | 4-Zb |
| 2-13 | Me | (CH$_2$)$_2$ | H | 4-Br-Ph | O | 4-Zb |
| 2-14 | Me | (CH$_2$)$_2$ | H | 3-Ph-Ph | O | 4-Zb |
| 2-15 | Me | (CH$_2$)$_2$ | H | 4-Ph-Ph | O | 4-Zb |
| 2-16 | Me | (CH$_2$)$_2$ | H | 3-Bz-Ph | O | 4-Zb |
| 2-17 | Me | (CH$_2$)$_2$ | H | 4-Bz-Ph | O | 4-Zb |
| 2-18 | Me | (CH$_2$)$_2$ | H | 3-PhO-Ph | O | 4-Zb |
| 2-19 | Me | (CH$_2$)$_2$ | H | 4-PhO-Ph | O | 4-Zb |
| 2-20 | Me | (CH$_2$)$_2$ | H | 3-PhS-Ph | O | 4-Zb |
| 2-21 | Me | (CH$_2$)$_2$ | H | 4-PhS-Ph | O | 4-Zb |
| 2-22 | Me | (CH$_2$)$_2$ | H | 3-PhSO$_2$-Ph | O | 4-Zb |
| 2-23 | Me | (CH$_2$)$_2$ | H | 4-PhSO$_2$-Ph | O | 4-Zb |
| 2-24 | Me | (CH$_2$)$_2$ | H | 3-(Imid-1)Ph | O | 4-Zb |
| 2-25 | Me | (CH$_2$)$_2$ | H | 4-(Imid-1)Ph | O | 4-Zb |
| 2-26 | Me | (CH$_2$)$_2$ | H | 3-(Imid-4)Ph | O | 4-Zb |

TABLE 2-continued

| Cpd. No. | R¹ | R² | R³ | X | Y | Z |
|---|---|---|---|---|---|---|
| 2-27 | Me | (CH$_2$)$_2$ | H | 4-(Imid-4)Ph | O | 4-Zb |
| 2-28 | Me | (CH$_2$)$_2$ | H | 3-(Fur-2)Ph | O | 4-Zb |
| 2-29 | Me | (CH$_2$)$_2$ | H | 4-(Fur-2)Ph | O | 4-Zb |
| 2-30 | Me | (CH$_2$)$_2$ | H | 3-(Thi-2)Ph | O | 4-Zb |
| 2-31 | Me | (CH$_2$)$_2$ | H | 4-(Thi-2)Ph | O | 4-Zb |
| 2-32 | Me | (CH$_2$)$_2$ | H | 3-(Thi-3)Ph | O | 4-Zb |
| 2-33 | Me | (CH$_2$)$_2$ | H | 4-(Thi-3)Ph | O | 4-Zb |
| 2-34 | Me | (CH$_2$)$_2$ | H | 3-(Pyr-2)Ph | O | 4-Zb |
| 2-35 | Me | (CH$_2$)$_2$ | H | 4-(Pyr-2)Ph | O | 4-Zb |
| 2-36 | Me | (CH$_2$)$_2$ | H | 3-(Pyr-3)Ph | O | 4-Zb |
| 2-37 | Me | (CH$_2$)$_2$ | H | 4-(Pyr-3)Ph | O | 4-Zb |
| 2-38 | Me | (CH$_2$)$_2$ | H | 3-(Pyr-4)Ph | O | 4-Zb |
| 2-39 | Me | (CH$_2$)$_2$ | H | 4-(Pyr-4)Ph | O | 4-Zb |
| 2-40 | Me | (CH$_2$)$_2$ | H | 3-(Oxa-2)Ph | O | 4-Zb |
| 2-41 | Me | (CH$_2$)$_2$ | H | 4-(Oxa-2)Ph | O | 4-Zb |
| 2-42 | Me | (CH$_2$)$_2$ | H | 3-(Oxa-4)Ph | O | 4-Zb |
| 2-43 | Me | (CH$_2$)$_2$ | H | 4-(Oxa-4)Ph | O | 4-Zb |
| 2-44 | Me | (CH$_2$)$_2$ | H | 3-(Oxa-5)Ph | O | 4-Zb |
| 2-45 | Me | (CH$_2$)$_2$ | H | 4-(Oxa-5)Ph | O | 4-Zb |
| 2-46 | Me | (CH$_2$)$_2$ | H | 3-(Thiz-2)Ph | O | 4-Zb |
| 2-47 | Me | (CH$_2$)$_2$ | H | 4-(Thiz-2)Ph | O | 4-Zb |
| 2-48 | Me | (CH$_2$)$_2$ | H | 3-(Thiz-4)Ph | O | 4-Zb |
| 2-49 | Me | (CH$_2$)$_2$ | H | 4-(Thiz-4)Ph | O | 4-Zb |
| 2-50 | Me | (CH$_2$)$_2$ | H | 3-(Thiz-5)Ph | O | 4-Zb |
| 2-51 | Me | (CH$_2$)$_2$ | H | 4-(Thiz-5)Ph | O | 4-Zb |
| 2-52 | Me | (CH$_2$)$_2$ | H | 1-Me-Pyrr-2 | O | 4-Zb |
| 2-53 | Me | (CH$_2$)$_2$ | H | 1-Ph-Pyrr-2 | O | 4-Zb |
| 2-54 | Me | (CH$_2$)$_2$ | H | 1-Bz-Pyrr-2 | O | 4-Zb |
| 2-55 | Me | (CH$_2$)$_2$ | H | 5-Me-Fur-2 | O | 4-Zb |
| 2-56 | Me | (CH$_2$)$_2$ | H | 5-Ph-Fur-2 | O | 4-Zb |
| 2-57 | Me | (CH$_2$)$_2$ | H | 5-Me-Thi-2 | O | 4-Zb |
| 2-58 | Me | (CH$_2$)$_2$ | H | 5-Ph-Thi-2 | O | 4-Zb |
| 2-59 | Me | (CH$_2$)$_2$ | H | 5-Me-Thi-3 | O | 4-Zb |
| 2-60 | Me | (CH$_2$)$_2$ | H | 5-Ph-Thi-3 | O | 4-Zb |
| 2-61 | Me | (CH$_2$)$_2$ | H | 1-Me-Pyza-3 | O | 4-Zb |
| 2-62 | Me | (CH$_2$)$_2$ | H | 1-Ph-Pyza-3 | O | 4-Zb |
| 2-63 | Me | (CH$_2$)$_2$ | H | 1-Me-Imid-2 | O | 4-Zb |
| 2-64 | Me | (CH$_2$)$_2$ | H | 1-Ph-Imid-2 | O | 4-Zb |
| 2-65 | Me | (CH$_2$)$_2$ | H | 1-Me-Imid-4 | O | 4-Zb |
| 2-66 | Me | (CH$_2$)$_2$ | H | 1-Ph-Imid-4 | O | 4-Zb |
| 2-67 | Me | (CH$_2$)$_2$ | H | Oxa-4 | O | 4-Zb |
| 2-68 | Me | (CH$_2$)$_2$ | H | Oxa-5 | O | 4-Zb |
| 2-69 | Me | (CH$_2$)$_2$ | H | 2-Me-Oxa-4 | O | 4-Zb |
| 2-70 | Me | (CH$_2$)$_2$ | H | 2-Ph-Oxa-4 | O | 4-Zb |
| 2-71 | Me | (CH$_2$)$_2$ | H | 2-Me-Oxa-5 | O | 4-Zb |
| 2-72 | Me | (CH$_2$)$_2$ | H | 2-Ph-Oxa-5 | O | 4-Zb |
| 2-73 | Me | (CH$_2$)$_2$ | H | 4-Me-2-Ph-Oxa-5 | O | 4-Zb |
| 2-74 | Me | (CH$_2$)$_2$ | H | 5-Me-2-Ph-Oxa-4 | O | 4-Zb |
| 2-75 | Me | (CH$_2$)$_2$ | H | Thiz-4 | O | 4-Zb |
| 2-76 | Me | (CH$_2$)$_2$ | H | Thiz-5 | O | 4-Zb |
| 2-77 | Me | (CH$_2$)$_2$ | H | 2-Me-Thiz-4 | O | 4-Zb |
| 2-78 | Me | (CH$_2$)$_2$ | H | 2-Ph-Thiz-4 | O | 4-Zb |
| 2-79 | Me | (CH$_2$)$_2$ | H | 2-Me-Thiz-5 | O | 4-Zb |
| 2-80 | Me | (CH$_2$)$_2$ | H | 2-Ph-Thiz-5 | O | 4-Zb |
| 2-81 | Me | (CH$_2$)$_2$ | H | 4-Me-2-Ph-Thiz-5 | O | 4-Zb |
| 2-82 | Me | (CH$_2$)$_2$ | H | 5-Me-2-Ph-Thiz-4 | O | 4-Zb |
| 2-83 | Me | (CH$_2$)$_2$ | H | 1-Me-Pyza-4 | O | 4-Zb |
| 2-84 | Me | (CH$_2$)$_2$ | H | 1-Ph-Pyza-4 | O | 4-Zb |
| 2-85 | Me | (CH$_2$)$_2$ | H | 2-Me-Isox-4 | O | 4-Zb |
| 2-86 | Me | (CH$_2$)$_2$ | H | 2-Ph-Isox-4 | O | 4-Zb |
| 2-87 | Me | (CH$_2$)$_2$ | H | Pyr-2 | O | 4-Zb |
| 2-88 | Me | (CH$_2$)$_2$ | H | Pyr-3 | O | 4-Zb |
| 2-89 | Me | (CH$_2$)$_2$ | H | Pyr-4 | O | 4-Zb |
| 2-90 | Me | (CH$_2$)$_2$ | H | 3-Me-Pyr-5 | O | 4-Zb |
| 2-91 | Me | (CH$_2$)$_2$ | H | 3-Et-Pyr-5 | O | 4-Zb |
| 2-92 | Me | (CH$_2$)$_2$ | H | 3-Ph-Pyr-5 | O | 4-Zb |
| 2-93 | Me | (CH$_2$)$_2$ | H | 2-Me-Pyr-5 | O | 4-Zb |
| 2-94 | Me | (CH$_2$)$_2$ | H | 2-Et-Pyr-5 | O | 4-Zb |
| 2-95 | Me | (CH$_2$)$_2$ | H | 2-Ph-Pyr-5 | O | 4-Zb |
| 2-96 | Me | (CH$_2$)$_2$ | H | 2-MeO-Pyr-5 | O | 4-Zb |
| 2-97 | Me | (CH$_2$)$_2$ | H | 2-EtO-Pyr-5 | O | 4-Zb |
| 2-98 | Me | (CH$_2$)$_2$ | H | 2-iPrO-Pyr-5 | O | 4-Zb |
| 2-99 | Me | (CH$_2$)$_2$ | H | 2-MeS-Pyr-5 | O | 4-Zb |
| 2-100 | Me | (CH$_2$)$_2$ | H | 2-EtS-Pyr-5 | O | 4-Zb |
| 2-101 | Me | (CH$_2$)$_2$ | H | 2-iPrS-Pyr-5 | O | 4-Zb |
| 2-102 | Me | (CH$_2$)$_2$ | H | 2-MeSO$_2$-Pyr-5 | O | 4-Zb |

TABLE 2-continued

| Cpd. No. | R¹ | R² | R³ | X | Y | Z |
|---|---|---|---|---|---|---|
| 2-103 | Me | (CH₂)₂ | H | 2-EtSO₂-Pyr-5 | O | 4-Zb |
| 2-104 | Me | (CH₂)₂ | H | 2-iPrSO₂-Pyr-5 | O | 4-Zb |
| 2-105 | Me | (CH₂)₂ | H | 2-Bz-Pyr-5 | O | 4-Zb |
| 2-106 | Me | (CH₂)₂ | H | 2-PhO-Pyr-5 | O | 4-Zb |
| 2-107 | Me | (CH₂)₂ | H | 2-PhS-Pyr-5 | O | 4-Zb |
| 2-108 | Me | (CH₂)₂ | H | 2-PhSO₂-Pyr-5 | O | 4-Zb |
| 2-109 | Me | (CH₂)₂ | H | 3-Me-Pyr-6 | O | 4-Zb |
| 2-110 | Me | (CH₂)₂ | H | 3-Ph-Pyr-6 | O | 4-Zb |
| 2-111 | Me | (CH₂)₂ | H | 2-Me-Pyr-6 | O | 4-Zb |
| 2-112 | Me | (CH₂)₂ | H | 2-Ph-Pyr-6 | O | 4-Zb |
| 2-113 | Me | (CH₂)₂ | H | 2-Me-Pym-4 | O | 4-Zb |
| 2-114 | Me | (CH₂)₂ | H | 2-Ph-Pym-4 | O | 4-Zb |
| 2-115 | Me | (CH₂)₂ | H | 2-MeO-Pym-4 | O | 4-Zb |
| 2-116 | Me | (CH₂)₂ | H | 2-EtO-Pym-4 | O | 4-Zb |
| 2-117 | Me | (CH₂)₂ | H | 2-iPrO-Pym-4 | O | 4-Zb |
| 2-118 | Me | (CH₂)₂ | H | 2-MeS-Pym-4 | O | 4-Zb |
| 2-119 | Me | (CH₂)₂ | H | 2-EtS-Pym-4 | O | 4-Zb |
| 2-120 | Me | (CH₂)₂ | H | 2-iPrS-Pym-4 | O | 4-Zb |
| 2-121 | Me | (CH₂)₂ | H | 6-MeS-Pym-4 | O | 4-Zb |
| 2-122 | Me | (CH₂)₂ | H | 6-EtS-Pym-4 | O | 4-Zb |
| 2-123 | Me | (CH₂)₂ | H | 6-iPrS-Pym-4 | O | 4-Zb |
| 2-124 | Me | (CH₂)₂ | H | 2-PhS-Pym-4 | O | 4-Zb |
| 2-125 | Me | (CH₂)₂ | H | 2-MeSO₂-Pym-4 | O | 4-Zb |
| 2-126 | Me | (CH₂)₂ | H | 2-EtSO₂-Pym-4 | O | 4-Zb |
| 2-127 | Me | (CH₂)₂ | H | 2-iPrSO₂-Pym-4 | O | 4-Zb |
| 2-128 | Me | (CH₂)₂ | H | 2-PhSO₂-Pym-4 | O | 4-Zb |
| 2-129 | Me | (CH₂)₂ | H | 2-Me-Pym-5 | O | 4-Zb |
| 2-130 | Me | (CH₂)₂ | H | 2-Ph-Pym-5 | O | 4-Zb |
| 2-131 | Me | (CH₂)₂ | H | 2-MeO-Pym-5 | O | 4-Zb |
| 2-132 | Me | (CH₂)₂ | H | 2-EtO-Pym-5 | O | 4-Zb |
| 2-133 | Me | (CH₂)₂ | H | 2-iPrO-Pym-5 | O | 4-Zb |
| 2-134 | Me | (CH₂)₂ | H | 2-MeS-Pym-5 | O | 4-Zb |
| 2-135 | Me | (CH₂)₂ | H | 2-EtS-Pym-5 | O | 4-Zb |
| 2-136 | Me | (CH₂)₂ | H | 2-iPrS-Pym-5 | O | 4-Zb |
| 2-137 | Me | (CH₂)₂ | H | 2-PhS-Pym-5 | O | 4-Zb |
| 2-138 | Me | (CH₂)₂ | H | 2-MeSO₂-Pym-5 | O | 4-Zb |
| 2-139 | Me | (CH₂)₂ | H | 2-EtSO₂-Pym-5 | O | 4-Zb |
| 2-140 | Me | (CH₂)₂ | H | 2-iPrSO₂-Pym-5 | O | 4-Zb |
| 2-141 | Me | (CH₂)₂ | H | 2-PhSO₂-Pym-5 | O | 4-Zb |
| 2-142 | Me | (CH₂)₂ | H | Ind-2 | O | 4-Zb |
| 2-143 | Me | (CH₂)₂ | H | Ind-3 | O | 4-Zb |
| 2-144 | Me | (CH₂)₂ | H | 1-Me-Ind-2 | O | 4-Zb |
| 2-145 | Me | (CH₂)₂ | H | 1-Me-Ind-3 | O | 4-Zb |
| 2-146 | Me | (CH₂)₂ | H | Bimid-2 | O | 4-Zb |
| 2-147 | Me | (CH₂)₂ | H | Boxa-2 | O | 4-Zb |
| 2-148 | Me | (CH₂)₂ | H | Bthiz-2 | O | 4-Zb |
| 2-149 | Me | (CH₂)₂ | H | Quin-2 | O | 4-Zb |
| 2-150 | Me | (CH₂)₂ | H | Quin-3 | O | 4-Zb |
| 2-151 | Me | (CH₂)₂ | H | Quin-4 | O | 4-Zb |
| 2-152 | Me | (CH₂)₂ | H | iQuin-1 | O | 4-Zb |
| 2-153 | Me | (CH₂)₂ | H | iQuin-3 | O | 4-Zb |
| 2-154 | Me | (CH₂)₂ | H | iQuin-4 | O | 4-Zb |
| 2-155 | Me | (CH₂)₂ | H | 3-MeO-Ph | O | 4-Zb |
| 2-156 | Me | (CH₂)₂ | H | 4-MeO-Ph | O | 4-Zb |
| 2-157 | Me | (CH₂)₂ | H | 3-EtO-Ph | O | 4-Zb |
| 2-158 | Me | (CH₂)₂ | H | 4-EtO-Ph | O | 4-Zb |
| 2-159 | Me | (CH₂)₂ | H | 3-iPrO-Ph | O | 4-Zb |
| 2-160 | Me | (CH₂)₂ | H | 4-iPrO-Ph | O | 4-Zb |
| 2-161 | Me | (CH₂)₂ | H | 3-MeS-Ph | O | 4-Zb |
| 2-162 | Me | (CH₂)₂ | H | 4-MeS-Ph | O | 4-Zb |
| 2-163 | Me | (CH₂)₂ | H | 3-EtS-Ph | O | 4-Zb |
| 2-164 | Me | (CH₂)₂ | H | 4-EtS-Ph | O | 4-Zb |
| 2-165 | Me | (CH₂)₂ | H | 3-iPrS-Ph | O | 4-Zb |
| 2-166 | Me | (CH₂)₂ | H | 4-iPrS-Ph | O | 4-Zb |
| 2-167 | Me | (CH₂)₂ | H | 3-MeSO₂-Ph | O | 4-Zb |
| 2-168 | Me | (CH₂)₂ | H | 4-MeSO₂-Ph | O | 4-Zb |
| 2-169 | Me | (CH₂)₂ | H | 3-EtSO₂-Ph | O | 4-Zb |
| 2-170 | Me | (CH₂)₂ | H | 4-EtSO₂-Ph | O | 4-Zb |
| 2-171 | Me | (CH₂)₂ | H | 3-iPrSO₂-Ph | O | 4-Zb |
| 2-172 | Me | (CH₂)₂ | H | 4-iPrSO₂-Ph | O | 4-Zb |
| 2-173 | Me | (CH₂)₂ | H | 3-(1-Me-Imid-4)Ph | O | 4-Zb |
| 2-174 | Me | (CH₂)₂ | H | 4-(1-Me-Imid-4)Ph | O | 4-Zb |
| 2-175 | Me | (CH₂)₂ | H | 1-Me-2-Ph-Imid-4 | O | 4-Zb |
| 2-176 | Me | (CH₂)₂ | H | 1,4-diMe-2-Ph-Imid-5 | O | 4-Zb |
| 2-177 | Me | (CH₂)₂ | H | 1,5-diMe-2-Ph-Imid-4 | O | 4-Zb |
| 2-178 | Me | (CH₂)₂ | H | 3,4-MdO-Ph | O | 4-Zb |
| 2-179 | Me | (CH₂)₂ | H | 4-(4-MeO-Ph)Ph | O | 4-Zb |
| 2-180 | Me | (CH₂)₂ | H | 4-(3,4-MdO-Ph)Ph | O | 4-Zb |
| 2-181 | Me | (CH₂)₂ | H | 4-[PhSO₂N(Me)]Ph | O | 4-Zb |
| 2-182 | Me | (CH₂)₂ | H | 4-[(Pyr-3)SO₂—N(Me)]Ph | O | 4-Zb |
| 2-183 | Me | (CH₂)₂ | H | 4-(PhSO₂NH)Ph | O | 4-Zb |
| 2-184 | Me | (CH₂)₂ | H | 4-[(Pyr-3)SO₂NH]-Ph | O | 4-Zb |
| 2-185 | Me | (CH₂)₂ | H | 4-[(Pyr-2)SO₂]Ph | O | 4-Zb |
| 2-186 | Me | (CH₂)₂ | H | 4-[(Pyr-3)SO₂]Ph | O | 4-Zb |
| 2-187 | Me | (CH₂)₂ | H | 4-[(Pyr-2)SO₂—N(Me)]Ph | O | 4-Zb |
| 2-188 | Me | (CH₂)₂ | H | 4-[(Pyr-2)SO₂—NH]Ph | O | 4-Zb |
| 2-189 | Me | (CH₂)₂ | H | 4-(4-Me-Ph)Ph | O | 4-Zb |
| 2-190 | Me | (CH₂)₂ | H | 4-(4-F-Ph)Ph | O | 4-Zb |
| 2-191 | Me | (CH₂)₂ | H | 4-(4-CF₃-Ph)Ph | O | 4-Zb |
| 2-192 | Me | (CH₂)₂ | H | 2-[4-Me-PhSO₂—N(Me)]-Pyr-5 | O | 4-Zb |
| 2-193 | Me | (CH₂)₂ | H | 2-HO-Pyr-5 | O | 4-Zb |
| 2-194 | Me | (CH₂)₂ | H | 2-BzO-Pyr-5 | O | 4-Zb |
| 2-195 | Me | (CH₂)₂ | H | 4-[(Pyr4)SO₂]Ph | O | 4-Zb |
| 2-196 | Me | (CH₂)₂ | H | 4-(2,4-diMeO-Ph)Ph | O | 4-Zb |
| 2-197 | Me | (CH₂)₂ | H | 4-(2,5-diMeO-Ph)Ph | O | 4-Zb |
| 2-198 | Me | (CH₂)₂ | H | 3-HO-Ph | O | 4-Zb |
| 2-199 | Me | (CH₂)₂ | H | 4-HO-Ph | O | 4-Zb |
| 2-200 | Me | (CH₂)₂ | H | 5-AcO-2-HO-3,4,6-triMe-Ph | O | 4-Zb |
| 2-201 | Me | (CH₂)₂ | H | 4-HO-3,5-diMe-Ph | O | 4-Zb |
| 2-202 | Me | (CH₂)₂ | H | 3-AcO-Ph | O | 4-Zb |
| 2-203 | Me | (CH₂)₂ | H | 4-AcO-Ph | O | 4-Zb |

TABLE 3

| Cpd. No. | R¹ | R² | R³ | X | Y | Z |
|---|---|---|---|---|---|---|
| 3-1 | Et | (CH₂)₂ | H | Ph | O | 4-Zb |
| 3-2 | Et | (CH₂)₂ | H | Np-1 | O | 4-Zb |
| 3-3 | Et | (CH₂)₂ | H | Np-2 | O | 4-Zb |
| 3-4 | Et | (CH₂)₂ | H | 4-Me-Ph | O | 4-Zb |
| 3-5 | Et | (CH₂)₂ | H | 4-Et-Ph | O | 4-Zb |
| 3-6 | Et | (CH₂)₂ | H | 3-iPr-Ph | O | 4-Zb |
| 3-7 | Et | (CH₂)₂ | H | 4-iPr-Ph | O | 4-Zb |
| 3-8 | Et | (CH₂)₂ | H | 3-tBu-Ph | O | 4-Zb |
| 3-9 | Et | (CH₂)₂ | H | 4-tBu-Ph | O | 4-Zb |
| 3-10 | Et | (CH₂)₂ | H | 3-Cl-Ph | O | 4-Zb |
| 3-11 | Et | (CH₂)₂ | H | 4-Cl-Ph | O | 4-Zb |
| 3-12 | Et | (CH₂)₂ | H | 3-Br-Ph | 6 | 4-Zb |
| 3-13 | Et | (CH₂)₂ | H | 4-Br-Ph | O | 4-Zb |
| 3-14 | Et | (CH₂)₂ | H | 3-Ph-Ph | O | 4-Zb |
| 3-15 | Et | (CH₂)₂ | H | 4-Ph-Ph | O | 4-Zb |
| 3-16 | Et | (CH₂)₂ | H | 3-Bz-Ph | O | 4-Zb |
| 3-17 | Et | (CH₂)₂ | H | 4-Bz-Ph | O | 4-Zb |
| 3-18 | Et | (CH₂)₂ | H | 3-PhO-Ph | O | 4-Zb |
| 3-19 | Et | (CH₂)₂ | H | 4-PhO-Ph | O | 4-Zb |
| 3-20 | Et | (CH₂)₂ | H | 3-PhS-Ph | O | 4-Zb |
| 3-21 | Et | (CH₂)₂ | H | 4-PhS-Ph | O | 4-Zb |
| 3-22 | Et | (CH₂)₂ | H | 3-PhSO₂-Ph | O | 4-Zb |
| 3-23 | Et | (CH₂)₂ | H | 4-PhSO₂-Ph | O | 4-Zb |
| 3-24 | Et | (CH₂)₂ | H | 3-(Imid-1)Ph | O | 4-Zb |
| 3-25 | Et | (CH₂)₂ | H | 4-(Imid-1)Ph | O | 4-Zb |
| 3-26 | Et | (CH₂)₂ | H | 3-(Imid-4)Ph | O | 4-Zb |
| 3-27 | Et | (CH₂)₂ | H | 4-(Imid-4)Ph | O | 4-Zb |
| 3-28 | Et | (CH₂)₂ | H | 3-(Fur-2)Ph | O | 4-Zb |
| 3-29 | Et | (CH₂)₂ | H | 4-(Fur-2)Ph | O | 4-Zb |
| 3-30 | Et | (CH₂)₂ | H | 3-(Thi-2)Ph | O | 4-Zb |
| 3-31 | Et | (CH₂)₂ | H | 4-(Thi-2)Ph | O | 4-Zb |
| 3-32 | Et | (CH₂)₂ | H | 3-(Thi-3)Ph | O | 4-Zb |
| 3-33 | Et | (CH₂)₂ | H | 4-(Thi-3)Ph | O | 4-Zb |
| 3-34 | Et | (CH₂)₂ | H | 3-(Pyr-2)Ph | O | 4-Zb |
| 3-35 | Et | (CH₂)₂ | H | 4-(Pyr-2)Ph | O | 4-Zb |
| 3-36 | Et | (CH₂)₂ | H | 3-(Pyr-3)Ph | O | 4-Zb |
| 3-37 | Et | (CH₂)₂ | H | 4-(Pyr-3)Ph | O | 4-Zb |
| 3-38 | Et | (CH₂)₂ | H | 3-(Pyr-4)Ph | O | 4-Zb |
| 3-39 | Et | (CH₂)₂ | H | 4-(Pyr-4)Ph | O | 4-Zb |
| 3-40 | Et | (CH₂)₂ | H | 3-(Oxa-2)Ph | O | 4-Zb |
| 3-41 | Et | (CH₂)₂ | H | 4-(Oxa-2)Ph | O | 4-Zb |
| 3-42 | Et | (CH₂)₂ | H | 3-(Oxa-4)Ph | O | 4-Zb |

TABLE 3-continued

| Cpd. No. | R¹ | R² | R³ | X | Y | Z |
|---|---|---|---|---|---|---|
| 3-43 | Et | (CH₂)₂ | H | 4-(Oxa-4)Ph | O | 4-Zb |
| 3-44 | Et | (CH₂)₂ | H | 3-(Oxa-5)Ph | O | 4-Zb |
| 3-45 | Et | (CH₂)₂ | H | 4-(Oxa-5)Ph | O | 4-Zb |
| 3-46 | Et | (CH₂)₂ | H | 3-(Thiz-2)Ph | O | 4-Zb |
| 3-47 | Et | (CH₂)₂ | H | 4-(Thiz-2)Ph | O | 4-Zb |
| 3-48 | Et | (CH₂)₂ | H | 3-(Thiz-4)Ph | O | 4-Zb |
| 3-49 | Et | (CH₂)₂ | H | 4-(Thiz-4)Ph | O | 4-Zb |
| 3-50 | Et | (CH₂)₂ | H | 3-(Thiz-5)Ph | O | 4-Zb |
| 3-51 | Et | (CH₂)₂ | H | 4-(Thiz-5)Ph | O | 4-Zb |
| 3-52 | Et | (CH₂)₂ | H | 1-Me-Pyrr-2 | O | 4-Zb |
| 3-53 | Et | (CH₂)₂ | H | 1-Ph-Pyrr-2 | O | 4-Zb |
| 3-54 | Et | (CH₂)₂ | H | 1-Bz-Pyrr-2 | O | 4-Zb |
| 3-55 | Et | (CH₂)₂ | H | 5-Me-Fur-2 | O | 4-Zb |
| 3-56 | Et | (CH₂)₂ | H | 5-Ph-Fur-2 | O | 4-Zb |
| 3-57 | Et | (CH₂)₂ | H | 5-Me-Thi-2 | O | 4-Zb |
| 3-58 | Et | (CH₂)₂ | H | 5-Ph-Thi-2 | O | 4-Zb |
| 3-59 | Et | (CH₂)₂ | H | 5-Me-Thi-3 | O | 4-Zb |
| 3-60 | Et | (CH₂)₂ | H | 5-Ph-Thi-3 | O | 4-Zb |
| 3-61 | Et | (CH₂)₂ | H | 1-Me-Pyza-3 | O | 4-Zb |
| 3-62 | Et | (CH₂)₂ | H | 1-Ph-Pyza-3 | O | 4-Zb |
| 3-63 | Et | (CH₂)₂ | H | 1-Me-Imid-2 | O | 4-Zb |
| 3-64 | Et | (CH₂)₂ | H | 1-Ph-Imid-2 | O | 4-Zb |
| 3-65 | Et | (CH₂)₂ | H | 1-Me-Imid-4 | O | 4-Zb |
| 3-66 | Et | (CH₂)₂ | H | 1-Ph-Imid-4 | O | 4-Zb |
| 3-67 | Et | (CH₂)₂ | H | Oxa-4 | O | 4-Zb |
| 3-68 | Et | (CH₂)₂ | H | Oxa-5 | O | 4-Zb |
| 3-69 | Et | (CH₂)₂ | H | 2-Me-OxaA | O | 4-Zb |
| 3-70 | Et | (CH₂)₂ | H | 2-Ph-Oxa-4 | O | 4-Zb |
| 3-71 | Et | (CH₂)₂ | H | 2-Me-Oxa-5 | O | 4-Zb |
| 3-72 | Et | (CH₂)₂ | H | 2-Ph-Oxa-5 | O | 4-Zb |
| 3-73 | Et | (CH₂)₂ | H | 4-Me-2-Ph-Oxa-5 | O | 4-Zb |
| 3-74 | Et | (CH₂)₂ | H | 5-Me-2-Ph-Oxa-4 | O | 4-Zb |
| 3-75 | Et | (CH₂)₂ | H | Thiz-4 | O | 4-Zb |
| 3-76 | Et | (CH₂)₂ | H | Thiz-5 | O | 4-Zb |
| 3-77 | Et | (CH₂)₂ | H | 2-Me-Thiz-4 | O | 4-Zb |
| 3-78 | Et | (CH₂)₂ | H | 2-Ph-Thiz-4 | O | 4-Zb |
| 3-79 | Et | (CH₂)₂ | H | 2-Me-Thiz-5 | O | 4-Zb |
| 3-80 | Et | (CH₂)₂ | H | 2-Ph-Thiz-5 | O | 4-Zb |
| 3-81 | Et | (CH₂)₂ | H | 4-Me-2-Ph-Thiz-5 | O | 4-Zb |
| 3-82 | Et | (CH₂)₂ | H | 5-Me-2-Ph-Thiz-4 | O | 4-Zb |
| 3-83 | Et | (CH₂)₂ | H | 1-Me-Pyza-4 | O | 4-Zb |
| 3-84 | Et | (CH₂)₂ | H | 1-Ph-Pyza-4 | O | 4-Zb |
| 3-85 | Et | (CH₂)₂ | H | 2-Me-Isox-4 | O | 4-Zb |
| 3-86 | Et | (CH₂)₂ | H | 2-Ph-Isox-4 | O | 4-Zb |
| 3-87 | Et | (CH₂)₂ | H | Pyr-2 | O | 4-Zb |
| 3-88 | Et | (CH₂)₂ | H | Pyr-3 | O | 4-Zb |
| 3-89 | Et | (CH₂)₂ | H | Pyr-4 | O | 4-Zb |
| 3-90 | Et | (CH₂)₂ | H | 3-Me-Pyr-5 | O | 4-Zb |
| 3-91 | Et | (CH₂)₂ | H | 3-Et-Pyr-5 | O | 4-Zb |
| 3-92 | Et | (CH₂)₂ | H | 3-Ph-Pyr-5 | O | 4-Zb |
| 3-93 | Et | (CH₂)₂ | H | 2-Me-Pyr-5 | O | 4-Zb |
| 3-94 | Et | (CH₂)₂ | H | 2-Et-Pyr-5 | O | 4-Zb |
| 3-95 | Et | (CH₂)₂ | H | 2-Ph-Pyr-5 | O | 4-Zb |
| 3-96 | Et | (CH₂)₂ | H | 2-MeO-Pyr-5 | O | 4-Zb |
| 3-97 | Et | (CH₂)₂ | H | 2-EtO-Pyr-5 | O | 4-Zb |
| 3-98 | Et | (CH₂)₂ | H | 2-iPrO-Pyr-5 | O | 4-Zb |
| 3-99 | Et | (CH₂)₂ | H | 2-MeS-Pyr-5 | O | 4-Zb |
| 3-100 | Et | (CH₂)₂ | H | 2-EtS-Pyr-5 | O | 4-Zb |
| 3-101 | Et | (CH₂)₂ | H | 2-iPrS-Pyr-5 | O | 4-Zb |
| 3-102 | Et | (CH₂)₂ | H | 2-MeSO₂-Pyr-5 | O | 4-Zb |
| 3-103 | Et | (CH₂)₂ | H | 2-EtSO₂-Pyr-5 | O | 4-Zb |
| 3-104 | Et | (CH₂)₂ | H | 2-iPrSO₂-Pyr-5 | O | 4-Zb |
| 3-105 | Et | (CH₂)₂ | H | 2-Bz-Pyr-5 | O | 4-Zb |
| 3-106 | Et | (CH₂)₂ | H | 2-PhO-Pyr-5 | O | 4-Zb |
| 3-107 | Et | (CH₂)₂ | H | 2-PhS-Pyr-5 | O | 4-Zb |
| 3-108 | Et | (CH₂)₂ | H | 2-PhSO₂-Pyr-5 | O | 4-Zb |
| 3-109 | Et | (CH₂)₂ | H | 3-Me-Pyr-6 | O | 4-Zb |
| 3-110 | Et | (CH₂)₂ | H | 3-Ph-Pyr-6 | O | 4-Zb |
| 3-111 | Et | (CH₂)₂ | H | 2-Me-Pyr-6 | O | 4-Zb |
| 3-112 | Et | (CH₂)₂ | H | 2-Ph-Pyr-6 | O | 4-Zb |
| 3-113 | Et | (CH₂)₂ | H | 2-Me-Pym-4 | O | 4-Zb |
| 3-114 | Et | (CH₂)₂ | H | 2-Ph-Pym-4 | O | 4-Zb |
| 3-115 | Et | (CH₂)₂ | H | 2-MeO-Pym-4 | O | 4-Zb |
| 3-116 | Et | (CH₂)₂ | H | 2-EtO-Pym-4 | O | 4-Zb |
| 3-117 | Et | (CH₂)₂ | H | 2-iPO-Pym-4 | O | 4-Zb |
| 3-118 | Et | (CH₂)₂ | H | 2-MeS-Pym-4 | O | 4-Zb |
| 3-119 | Et | (CH₂)₂ | H | 2EtS-Pym-4 | O | 4-Zb |
| 3-120 | Et | (CH₂)₂ | H | 2-iPrS-Pym-4 | O | 4-Zb |
| 3-121 | Et | (CH₂)₂ | H | 6-MeS-Pym-4 | O | 4-Zb |
| 3-122 | Et | (CH₂)₂ | H | 6-EtS-Pym-4 | O | 4-Zb |
| 3-123 | Et | (CH₂)₂ | H | 6-iPrS-Pym-4 | O | 4-Zb |
| 3-124 | Et | (CH₂)₂ | H | 2-PhS-Pym-4 | O | 4-Zb |
| 3-125 | Et | (CH₂)₂ | H | 2-MeSO₂-Pym-4 | O | 4-Zb |
| 3-126 | Et | (CH₂)₂ | H | 2-EtSO₂-Pym-4 | O | 4-Zb |
| 3-127 | Et | (CH₂)₂ | H | 2-iPrSO₂-Pym-4 | O | 4-Zb |
| 3-128 | Et | (CH₂)₂ | H | 2-PhSO₂-Pym-4 | O | 4-Zb |
| 3-129 | Et | (CH₂)₂ | H | 2-Me-Pym-5 | O | 4-Zb |
| 3-130 | Et | (CH₂)₂ | H | 2-Ph-Pym-5 | O | 4-Zb |
| 3-131 | Et | (CH₂)₂ | H | 2-MeO-Pym-5 | O | 4-Zb |
| 3-132 | Et | (CH₂)₂ | H | 2-EtO-Pym-5 | O | 4-Zb |
| 3-133 | Et | (CH₂)₂ | H | 2-iPrO-Pym-5 | O | 4-Zb |
| 3-134 | Et | (CH₂)₂ | H | 2-MeS-Pym-5 | O | 4-Zb |
| 3-135 | Et | (CH₂)₂ | H | 2-EtS-Pym-5 | O | 4-Zb |
| 3-136 | Et | (CH₂)₂ | H | 2-iPrS-Pym-5 | O | 4-Zb |
| 3-137 | Et | (CH₂)₂ | H | 2-PhS-Pym-5 | O | 4-Zb |
| 3-138 | Et | (CH₂)₂ | H | 2-MeSO₂-Pym-5 | O | 4-Zb |
| 3-139 | Et | (CH₂)₂ | H | 2-EtSO₂-Pym-5 | O | 4-Zb |
| 3-140 | Et | (CH₂)₂ | H | 2-iPrSO₂-Pym-5 | O | 4-Zb |
| 3-141 | Et | (CH₂)₂ | H | 2-PhSO₂-Pym-5 | O | 4-Zb |
| 3-142 | Et | (CH₂)₂ | H | Ind-2 | O | 4-Zb |
| 3-143 | Et | (CH₂)₂ | H | Ind-3 | O | 4-Zb |
| 3-144 | Et | (CH₂)₂ | H | 1-Me-Ind-2 | O | 4-Zb |
| 3-145 | Et | (CH₂)₂ | H | 1-Me-Ind-3 | O | 4-Zb |
| 3-146 | Et | (CH₂)₂ | H | Bimid-2 | O | 4-Zb |
| 3-147 | Et | (CH₂)₂ | H | Boxa-2 | O | 4-Zb |
| 3-148 | Et | (CH₂)₂ | H | Bthiz-2 | O | 4-Zb |
| 3-149 | Et | (CH₂)₂ | H | Quin-2 | O | 4-Zb |
| 3-150 | Et | (CH₂)₂ | H | Quin-3 | O | 4-Zb |
| 3-151 | Et | (CH₂)₂ | H | Quin-4 | O | 4-Zb |
| 3-152 | Et | (CH₂)₂ | H | iQuin-1 | O | 4-Zb |
| 3-153 | Et | (CH₂)₂ | H | iQuin-3 | O | 4-Zb |
| 3-154 | Et | (CH₂)₂ | H | iQuin-4 | O | 4-Zb |
| 3-155 | Et | (CH₂)₂ | H | 3-MeO-Ph | O | 4-Zb |
| 3-156 | Et | (CH₂)₂ | H | 4-MeO-Ph | O | 4-Zb |
| 3-157 | Et | (CH₂)₂ | H | 3-EtO-Ph | O | 4-Zb |
| 3-158 | Et | (CH₂)₂ | H | 4-EtO-Ph | O | 4-Zb |
| 3-159 | Et | (CH₂)₂ | H | 3-iPrO-Ph | O | 4-Zb |
| 3-160 | Et | (CH₂)₂ | H | 4-iPrO-Ph | O | 4-Zb |
| 3-161 | Et | (CH₂)₂ | H | 3-MeS-Ph | O | 4-Zb |
| 3-162 | Et | (CH₂)₂ | H | 4-MeS-Ph | O | 4-Zb |
| 3-163 | Et | (CH₂)₂ | H | 3-EtS-Ph | O | 4-Zb |
| 3-164 | Et | (CH₂)₂ | H | 4-EtS-Ph | O | 4-Zb |
| 3-165 | Et | (CH₂)₂ | H | 3-iPrS-Ph | O | 4-Zb |
| 3-166 | Et | (CH₂)₂ | H | 4-iPrS-Ph | O | 4-Zb |
| 3-167 | Et | (CH₂)₂ | H | 3-MeSO₂-Ph | O | 4-Zb |
| 3-168 | Et | (CH₂)₂ | H | 4-MeSO₂-Ph | O | 4-Zb |
| 3-169 | Et | (CH₂)₂ | H | 3-EtSO₂-Ph | O | 4-Zb |
| 3-170 | Et | (CH₂)₂ | H | 4-EtSO₂-Ph | O | 4-Zb |
| 3-171 | Et | (CH₂)₂ | H | 3-iPrSO₂-Ph | O | 4-Zb |
| 3-172 | Et | (CH₂)₂ | H | 4-iPrSO₂-Ph | O | 4-Zb |
| 3-173 | Et | (CH₂)₂ | H | 3-(1-Me-Imid-4)Ph | O | 4-Zb |
| 3-174 | Et | (CH₂)₂ | H | 4-(1-Me-Imid-4)Ph | O | 4-Zb |
| 3-175 | Et | (CH₂)₂ | H | 1-Me-2-Ph-Imid-4 | O | 4-Zb |
| 3-176 | Et | (CH₂)₂ | H | 1,4-diMe-2-Ph-Imid-5 | O | 4-Zb |
| 3-177 | Et | (CH₂)₂ | H | 1,5-diMe-2-Ph-Imid-4 | O | 4-Zb |
| 3-178 | Et | (CH₂)₂ | H | 3,4-MdO-Ph | O | 4-Zb |
| 3-179 | Et | (CH₂)₂ | H | 4-(4-MeO-Ph)Ph | O | 4-Zb |
| 3-180 | Et | (CH₂)₂ | H | 4-(3,4-MdO-Ph)Ph | O | 4-Zb |
| 3-181 | Et | (CH₂)₂ | H | 4-[PhSO₂N(Me)]Ph | O | 4-Zb |
| 3-182 | Et | (CH₂)₂ | H | 4-[(Pyr-3)SO₂-N(Me)]Ph | O | 4-Zb |
| 3-183 | Et | (CH₂)₂ | H | 4-(PhSO₂NH)Ph | O | 4-Zb |
| 3-184 | Et | (CH₂)₂ | H | 4-[(Pyr-3)SO₂-NH]Ph | O | 4-Zb |
| 3-185 | Et | (CH₂)₂ | H | 4-[(Pyr-2)SO₂]Ph | O | 4-Zb |
| 3-186 | Et | (CH₂)₂ | H | 4-[(Pyr-3)SO₂]Ph | O | 4-Zb |
| 3-187 | Et | (CH₂)₂ | H | 4-[(Pyr-2)SO₂-N(Me)]Ph | O | 4-Zb |
| 3-188 | Et | (CH₂)₂ | H | 4-[(Pyr-2)SO₂-NH]Ph | O | 4-Zb |
| 3-189 | Et | (CH₂)₂ | H | 4-(4-Me-Ph)Ph | O | 4-Zb |
| 3-190 | Et | (CH₂)₂ | H | 4-(4-F-Ph)Ph | O | 4-Zb |
| 3-191 | Et | (CH₂)₂ | H | 4-(4-CF₃-Ph)Ph | O | 4-Zb |
| 3-192 | Et | (CH₂)₂ | H | 2-[4-Me-PhSO₂-N(Me)]-Pyr-5 | O | 4-Zb |
| 3-193 | Et | (CH₂)₂ | H | 2-HO-Pyr-5 | O | 4-Zb |
| 3-194 | Et | (CH₂)₂ | H | 2-BzO-Pyr-5 | O | 4-Zb |

TABLE 3-continued

| Cpd. No. | R¹ | R² | R³ | X | Y | Z |
|---|---|---|---|---|---|---|
| 3-195 | Et | (CH$_2$)$_2$ | H | 4-[(Pyr-4)SO$_2$]Ph | O | 4-Zb |
| 3-196 | Et | (CH$_2$)$_2$ | H | 4-(2,4-diMeO-Ph)Ph | O | 4-Zb |
| 3-197 | Et | (CH$_2$)$_2$ | H | 4-(2,5-diMeO-Ph)Ph | O | 4-Zb |
| 3-198 | Et | (CH$_2$)$_2$ | H | 3-HO-Ph | O | 4-Zb |
| 3-199 | Et | (CH$_2$)$_2$ | H | 4-HO-Ph | O | 4-Zb |
| 3-200 | Et | (CH$_2$)$_2$ | H | 5-AcO-2-HO-3,4,6-triMe-Ph | O | 4-Zb |
| 3-201 | Et | (CH$_2$)$_2$ | H | 4-HO-3,5-diMe-Ph | O | 4-Zb |
| 3-202 | Et | (CH$_2$)$_2$ | H | 3-AcO-Ph | O | 4-Zb |
| 3-203 | Et | (CH$_2$)$_2$ | H | 4-AcO-Ph | O | 4-Zb |

TABLE 4

| Cpd. No. | R¹ | R² | R³ | X | Y | Z |
|---|---|---|---|---|---|---|
| 4-1 | iPr | (CH$_2$)$_2$ | H | Ph | O | 4-Zb |
| 4-2 | iPr | (CH$_2$)$_2$ | H | Np-1 | O | 4-Zb |
| 4-3 | iPr | (CH$_2$)$_2$ | H | Np-2 | O | 4-Zb |
| 4-4 | iPr | (CH$_2$)$_2$ | H | 4-Me-Ph | O | 4-Zb |
| 4-5 | iPr | (CH$_2$)$_2$ | H | 4-Et-Ph | O | 4-Zb |
| 4-6 | iPr | (CH$_2$)$_2$ | H | 3-iPr-Ph | O | 4-Zb |
| 4-7 | iPr | (CH$_2$)$_2$ | H | 4-iPr-Ph | O | 4-Zb |
| 4-8 | iPr | (CH$_2$)$_2$ | H | 3-tBu-Ph | O | 4-Zb |
| 4-9 | iPr | (CH$_2$)$_2$ | H | 4-tBu-Ph | O | 4-Zb |
| 4-10 | iPr | (CH$_2$)$_2$ | H | 3-Cl-Ph | O | 4-Zb |
| 4-11 | iPr | (CH$_2$)$_2$ | H | 4-Cl-Ph | O | 4-Zb |
| 4-12 | iPr | (CH$_2$)$_2$ | H | 3-Br-Ph | O | 4-Zb |
| 4-13 | iPr | (CH$_2$)$_2$ | H | 4-Br-Ph | O | 4-Zb |
| 4-14 | iPr | (CH$_2$)$_2$ | H | 3-Ph-Ph | O | 4-Zb |
| 4-15 | iPr | (CH$_2$)$_2$ | H | 4-Ph-Ph | O | 4-Zb |
| 4-16 | iPr | (CH$_2$)$_2$ | H | 3-Bz-Ph | O | 4-Zb |
| 4-17 | iPr | (CH$_2$)$_2$ | H | 4-Bz-Ph | O | 4-Zb |
| 4-18 | iPr | (CH$_2$)$_2$ | H | 3-PhO-Ph | O | 4-Zb |
| 4-19 | iPr | (CH$_2$)$_2$ | H | 4-PhO-Ph | O | 4-Zb |
| 4-20 | iPr | (CH$_2$)$_2$ | H | 3-PhS-Ph | O | 4-Zb |
| 4-21 | iPr | (CH$_2$)$_2$ | H | 4-PhS-Ph | O | 4-Zb |
| 4-22 | iPr | (CH$_2$)$_2$ | H | 3-PhSO$_2$-Ph | O | 4-Zb |
| 4-23 | iPr | (CH$_2$)$_2$ | H | 4-PhSO$_2$-Ph | O | 4-Zb |
| 4-24 | iPr | (CH$_2$)$_2$ | H | 3-(Imid-1)Ph | O | 4-Zb |
| 4-25 | iPr | (CH$_2$)$_2$ | H | 4-(Imid-1)Ph | O | 4-Zb |
| 4-26 | iPr | (CH$_2$)$_2$ | H | 3-(Imid-4)Ph | O | 4-Zb |
| 4-27 | iPr | (CH$_2$)$_2$ | H | 4-(Imid-4)Ph | O | 4-Zb |
| 4-28 | iPr | (CH$_2$)$_2$ | H | 3-(Fur-2)Ph | O | 4-Zb |
| 4-29 | iPr | (CH$_2$)$_2$ | H | 4-(Fur-2)Ph | O | 4-Zb |
| 4-30 | iPr | (CH$_2$)$_2$ | H | 3-(Thi-2)Ph | O | 4-Zb |
| 4-31 | iPr | (CH$_2$)$_2$ | H | 4-(Thi-2)Ph | O | 4-Zb |
| 4-32 | iPr | (CH$_2$)$_2$ | H | 3-(Thi-3)Ph | O | 4-Zb |
| 4-33 | iPr | (CH$_2$)$_2$ | H | 4-(Thi-3)Ph | O | 4-Zb |
| 4-34 | iPr | (CH$_2$)$_2$ | H | 3-(Pyr-2)Ph | O | 4-Zb |
| 4-35 | iPr | (CH$_2$)$_2$ | H | 4-(Pyr-2)Ph | O | 4-Zb |
| 4-36 | iPr | (CH$_2$)$_2$ | H | 3-(Pyr-3)Ph | O | 4-Zb |
| 4-37 | iPr | (CH$_2$)$_2$ | H | 4-(Pyr-3)Ph | O | 4-Zb |
| 4-38 | iPr | (CH$_2$)$_2$ | H | 3-(Pyr-4)Ph | O | 4-Zb |
| 4-39 | iPr | (CH$_2$)$_2$ | H | 4-(Pyr-4)Ph | O | 4-Zb |
| 4-40 | iPr | (CH$_2$)$_2$ | H | 3-(Oxa-2)Ph | O | 4-Zb |
| 4-41 | iPr | (CH$_2$)$_2$ | H | 4-(Oxa-2)Ph | O | 4-Zb |
| 4-42 | iPr | (CH$_2$)$_2$ | H | 3-(Oxa-4)Ph | O | 4-Zb |
| 4-43 | iPr | (CH$_2$)$_2$ | H | 4-(Oxa-4)Ph | O | 4-Zb |
| 4-44 | iPr | (CH$_2$)$_2$ | H | 3-(Oxa-5)Ph | O | 4-Zb |
| 4-45 | iPr | (CH$_2$)$_2$ | H | 4-(Oxa-5)Ph | O | 4-Zb |
| 4-46 | iPr | (CH$_2$)$_2$ | H | 3-(Thiz-2)Ph | O | 4-Zb |
| 4-47 | iPr | (CH$_2$)$_2$ | H | 4-(Thiz-2)Ph | O | 4-Zb |
| 4-48 | iPr | (CH$_2$)$_2$ | H | 3-(Thiz-4)Ph | O | 4-Zb |
| 4-49 | iPr | (CH$_2$)$_2$ | H | 4-(Thiz-4)Ph | O | 4-Zb |
| 4-50 | iPr | (CH$_2$)$_2$ | H | 3-(Thiz-5)Ph | O | 4-Zb |
| 4-51 | iPr | (CH$_2$)$_2$ | H | 4-(Thiz-5)Ph | O | 4-Zb |
| 4-52 | iPr | (CH$_2$)$_2$ | H | 1-Me-Pyrr-2 | O | 4-Zb |
| 4-53 | iPr | (CH$_2$)$_2$ | H | 1-Ph-Pyrr-2 | O | 4-Zb |
| 4-54 | iPr | (CH$_2$)$_2$ | H | 1-Bz-Pyrr-2 | O | 4-Zb |
| 4-55 | iPr | (CH$_2$)$_2$ | H | 5-Me-Fur-2 | O | 4-Zb |
| 4-56 | iPr | (CH$_2$)$_2$ | H | 5-Ph-Fur-2 | O | 4-Zb |
| 4-57 | iPr | (CH$_2$)$_2$ | H | 5-Me-Thi-2 | O | 4-Zb |
| 4-58 | iPr | (CH$_2$)$_2$ | H | 5-Ph-Thi-2 | O | 4-Zb |

TABLE 4-continued

| Cpd. No. | R¹ | R² | R³ | X | Y | Z |
|---|---|---|---|---|---|---|
| 4-59 | iPr | (CH$_2$)$_2$ | H | 5-Me-Thi-3 | O | 4-Zb |
| 4-60 | iPr | (CH$_2$)$_2$ | H | 5-Ph-Thi-3 | O | 4-Zb |
| 4-61 | iPr | (CH$_2$)$_2$ | H | 1-Me-Pyza-3 | O | 4-Zb |
| 4-62 | iPr | (CH$_2$)$_2$ | H | 1-Ph-Pyza-3 | O | 4-Zb |
| 4-63 | iPr | (CH$_2$)$_2$ | H | 1-Me-Imid-2 | O | 4-Zb |
| 4-64 | iPr | (CH$_2$)$_2$ | H | 1-Ph-Imid-2 | O | 4-Zb |
| 4-65 | iPr | (CH$_2$)$_2$ | H | 1-Me-Imid-4 | O | 4-Zb |
| 4-66 | iPr | (CH$_2$)$_2$ | H | 1-Ph-Imid-4 | O | 4-Zb |
| 4-67 | iPr | (CH$_2$)$_2$ | H | Oxa-4 | O | 4-Zb |
| 4-68 | iPr | (CH$_2$)$_2$ | H | Oxa-5 | O | 4-Zb |
| 4-69 | iPr | (CH$_2$)$_2$ | H | 2-Me-Oxa-4 | O | 4-Zb |
| 4-70 | iPr | (CH$_2$)$_2$ | H | 2-Ph-Oxa-4 | O | 4-Zb |
| 4-71 | iPr | (CH$_2$)$_2$ | H | 2-Me-Oxa-5 | O | 4-Zb |
| 4-72 | iPr | (CH$_2$)$_2$ | H | 2-Ph-Oxa-5 | O | 4-Zb |
| 4-73 | iPr | (CH$_2$)$_2$ | H | 4-Me-2-Ph-Oxa-5 | O | 4-Zb |
| 4-74 | iPr | (CH$_2$)$_2$ | H | 5-Me-2-Ph-Oxa-4 | O | 4-Zb |
| 4-75 | iPr | (CH$_2$)$_2$ | H | Thiz-4 | O | 4-Zb |
| 4-76 | iPr | (CH$_2$)$_2$ | H | Thiz-5 | O | 4-Zb |
| 4-77 | iPr | (CH$_2$)$_2$ | H | 2-Me-Thiz-4 | O | 4-Zb |
| 4-78 | iPr | (CH$_2$)$_2$ | H | 2-Ph-Thiz-4 | O | 4-Zb |
| 4-79 | iPr | (CH$_2$)$_2$ | H | 2-Me-Thiz-5 | O | 4-Zb |
| 4-80 | iPr | (CH$_2$)$_2$ | H | 2-Ph-Thiz-5 | O | 4-Zb |
| 4-81 | iPr | (CH$_2$)$_2$ | H | 4-Me-2-Ph-Thiz-5 | O | 4-Zb |
| 4-82 | iPr | (CH$_2$)$_2$ | H | 5-Me-2-Ph-Thiz-4 | O | 4-Zb |
| 4-83 | iPr | (CH$_2$)$_2$ | H | 1-Me-Pyza-4 | O | 4-Zb |
| 4-84 | iPr | (CH$_2$)$_2$ | H | 1-Ph-Pyza-4 | O | 4-Zb |
| 4-85 | iPr | (CH$_2$)$_2$ | H | 2-Me-Isox-4 | O | 4-Zb |
| 4-86 | iPr | (CH$_2$)$_2$ | H | 2-Ph-Isox-4 | O | 4-Zb |
| 4-87 | iPr | (CH$_2$)$_2$ | H | Pyr-2 | O | 4-Zb |
| 4-88 | iPr | (CH$_2$)$_2$ | H | Pyr-3 | O | 4-Zb |
| 4-89 | iPr | (CH$_2$)$_2$ | H | Pyr-4 | O | 4-Zb |
| 4-90 | iPr | (CH$_2$)$_2$ | H | 3-Me-Pyr-5 | O | 4-Zb |
| 4-91 | iPr | (CH$_2$)$_2$ | H | 3-Et-Pyr-5 | O | 4-Zb |
| 4-92 | iPr | (CH$_2$)$_2$ | H | 3-Ph-Pyr-5 | O | 4-Zb |
| 4-93 | iPr | (CH$_2$)$_2$ | H | 2-Me-Pyr-5 | O | 4-Zb |
| 4-94 | iPr | (CH$_2$)$_2$ | H | 2-Et-Pyr-5 | O | 4-Zb |
| 4-95 | iPr | (CH$_2$)$_2$ | H | 2-Ph-Pyr-5 | O | 4-Zb |
| 4-96 | iPr | (CH$_2$)$_2$ | H | 2-MeO-Pyr-5 | O | 4-Zb |
| 4-97 | iPr | (CH$_2$)$_2$ | H | 2-EtO-Pyr-5 | O | 4-Zb |
| 4-98 | iPr | (CH$_2$)$_2$ | H | 2-iPrO-Pyr-5 | O | 4-Zb |
| 4-99 | iPr | (CH$_2$)$_2$ | H | 2-MeS-Pyr-5 | O | 4-Zb |
| 4-100 | iPr | (CH$_2$)$_2$ | H | 2-EtS-Pyr-5 | O | 4-Zb |
| 4-101 | iPr | (CH$_2$)$_2$ | H | 2-iPrS-Pyr-5 | O | 4-Zb |
| 4-102 | iPr | (CH$_2$)$_2$ | H | 2-MeSO$_2$-Pyr-5 | O | 4-Zb |
| 4-103 | iPr | (CH$_2$)$_2$ | H | 2-EtSO$_2$-Pyr-5 | O | 4-Zb |
| 4-104 | iPr | (CH$_2$)$_2$ | H | 2-iPrSO$_2$-Pyr-5 | O | 4-Zb |
| 4-105 | iPr | (CH$_2$)$_2$ | H | 2-Bz-Pyr-5 | O | 4-Zb |
| 4-106 | iPr | (CH$_2$)$_2$ | H | 2-PhO-Pyr-5 | O | 4-Zb |
| 4-107 | iPr | (CH$_2$)$_2$ | H | 2-PhS-Pyr-5 | O | 4-Zb |
| 4-108 | iPr | (CH$_2$)$_2$ | H | 2-PhSO$_2$-Pyr-5 | O | 4-Zb |
| 4-109 | iPr | (CH$_2$)$_2$ | H | 3-Me-Pyr-6 | O | 4-Zb |
| 4-110 | iPr | (CH$_2$)$_2$ | H | 3-Ph-Pyr-6 | O | 4-Zb |
| 4-111 | iPr | (CH$_2$)$_2$ | H | 2-Me-Pyr-6 | O | 4-Zb |
| 4-112 | iPr | (CH$_2$)$_2$ | H | 2-Ph-Pyr-6 | O | 4-Zb |
| 4-113 | iPr | (CH$_2$)$_2$ | H | 2-Me-Pym-4 | O | 4-Zb |
| 4-114 | iPr | (CH$_2$)$_2$ | H | 2-Ph-Pym-4 | O | 4-Zb |
| 4-115 | iPr | (CH$_2$)$_2$ | H | 2-MeO-Pym-4 | O | 4-Zb |
| 4-116 | iPr | (CH$_2$)$_2$ | H | 2-EtO-Pym-4 | O | 4-Zb |
| 4-117 | iPr | (CH$_2$)$_2$ | H | 2-iPrO-Pym-4 | O | 4-Zb |
| 4-118 | iPr | (CH$_2$)$_2$ | H | 2-MeS-Pym-4 | O | 4-Zb |
| 4-119 | iPr | (CH$_2$)$_2$ | H | 2-EtS-Pym-4 | O | 4-Zb |
| 4-120 | iPr | (CH$_2$)$_2$ | H | 2-iPrS-Pym-4 | O | 4-Zb |
| 4-121 | iPr | (CH$_2$)$_2$ | H | 6-MeS-Pym-4 | O | 4-Zb |
| 4-122 | iPr | (CH$_2$)$_2$ | H | 6-EtS-Pym-4 | O | 4-Zb |
| 4-123 | iPr | (CH$_2$)$_2$ | H | 6-iPrS-Pym-4 | O | 4-Zb |
| 4-124 | iPr | (CH$_2$)$_2$ | H | 2-PhS-Pym-4 | O | 4-Zb |
| 4-125 | iPr | (CH$_2$)$_2$ | H | 2-MeSO$_2$-Pym-4 | O | 4-Zb |
| 4-126 | iPr | (CH$_2$)$_2$ | H | 2-EtSO$_2$-Pym-4 | O | 4-Zb |
| 4-127 | iPr | (CH$_2$)$_2$ | H | 2-iPrSO$_2$-Pym-4 | O | 4-Zb |
| 4-128 | iPr | (CH$_2$)$_2$ | H | 2-PhSO$_2$-Pym-4 | O | 4-Zb |
| 4-129 | iPr | (CH$_2$)$_2$ | H | 2-Me-Pym-5 | O | 4-Zb |
| 4-130 | iPr | (CH$_2$)$_2$ | H | 2-Ph-Pym-5 | O | 4-Zb |
| 4-131 | iPr | (CH$_2$)$_2$ | H | 2-MeO-Pym-5 | O | 4-Zb |
| 4-132 | iPr | (CH$_2$)$_2$ | H | 2-EtO-Pym-5 | O | 4-Zb |
| 4-133 | iPr | (CH$_2$)$_2$ | H | 2-iPrO-Pym-5 | O | 4-Zb |
| 4-134 | iPr | (CH$_2$)$_2$ | H | 2-MeS-Pym-5 | O | 4-Zb |

TABLE 4-continued

| Cpd. No. | R¹ | R² | R³ | X | Y | Z |
|---|---|---|---|---|---|---|
| 4-135 | iPr | (CH$_2$)$_2$ | H | 2-EtS-Pym-5 | O | 4-Zb |
| 4-136 | iPr | (CH$_2$)$_2$ | H | 2-iPrS-Pym-5 | O | 4-Zb |
| 4-137 | iPr | (CH$_2$)$_2$ | H | 2-PhS-Pym-5 | O | 4-Zb |
| 4-138 | iPr | (CH$_2$)$_2$ | H | 2-MeSO$_2$-Pym-5 | O | 4-Zb |
| 4-139 | iPr | (CH$_2$)$_2$ | H | 2-EtSO$_2$-Pym-5 | O | 4-Zb |
| 4-140 | iPr | (CH$_2$)$_2$ | H | 2-iPrSO$_2$-Pym-5 | O | 4-Zb |
| 4-141 | iPr | (CH$_2$)$_2$ | H | 2-PhSO$_2$-Pym-5 | O | 4-Zb |
| 4-142 | iPr | (CH$_2$)$_2$ | H | Ind-2 | O | 4-Zb |
| 4-143 | iPr | (CH$_2$)$_2$ | H | Ind-3 | O | 4-Zb |
| 4-144 | iPr | (CH$_2$)$_2$ | H | 1-Me-Ind-2 | O | 4-Zb |
| 4-145 | iPr | (CH$_2$)$_2$ | H | 1-Me-Ind-3 | O | 4-Zb |
| 4-146 | iPr | (CH$_2$)$_2$ | H | Bimid-2 | O | 4-Zb |
| 4-147 | iPr | (CH$_2$)$_2$ | H | Boxa-2 | O | 4-Zb |
| 4-148 | iPr | (CH$_2$)$_2$ | H | Bthiz-2 | O | 4-Zb |
| 4-149 | iPr | (CH$_2$)$_2$ | H | Quin-2 | O | 4-Zb |
| 4-150 | iPr | (CH$_2$)$_2$ | H | Quin-3 | O | 4-Zb |
| 4-151 | iPr | (CH$_2$)$_2$ | H | Quin-4 | O | 4-Zb |
| 4-152 | iPr | (CH$_2$)$_2$ | H | iQuin-1 | O | 4-Zb |
| 4-153 | iPr | (CH$_2$)$_2$ | H | iQuin-3 | O | 4-Zb |
| 4-154 | iPr | (CH$_2$)$_2$ | H | iQuin-4 | O | 4-Zb |
| 4-155 | iPr | (CH$_2$)$_2$ | H | 3-MeO-Ph | O | 4-Zb |
| 4-156 | iPr | (CH$_2$)$_2$ | H | 4-MeO-Ph | O | 4-Zb |
| 4-157 | iPr | (CH$_2$)$_2$ | H | 3-EtO-Ph | O | 4-Zb |
| 4-158 | iPr | (CH$_2$)$_2$ | H | 4-EtO-Ph | O | 4-Zb |
| 4-159 | iPr | (CH$_2$)$_2$ | H | 3-iPrO-Ph | O | 4-Zb |
| 4-160 | iPr | (CH$_2$)$_2$ | H | 4-iPrO-Ph | O | 4-Zb |
| 4-161 | iPr | (CH$_2$)$_2$ | H | 3-MeS-Ph | O | 4-Zb |
| 4-162 | iPr | (CH$_2$)$_2$ | H | 4-MeS-Ph | O | 4-Zb |
| 4-163 | iPr | (CH$_2$)$_2$ | H | 3-EtS-Ph | O | 4-Zb |
| 4-164 | iPr | (CH$_2$)$_2$ | H | 4-EtS-Ph | O | 4-Zb |
| 4-165 | iPr | (CH$_2$)$_2$ | H | 3-iPrS-Ph | O | 4-Zb |
| 4-166 | iPr | (CH$_2$)$_2$ | H | 4-iPrS-Ph | O | 4-Zb |
| 4-167 | iPr | (CH$_2$)$_2$ | H | 3-MeSO$_2$-Ph | O | 4-Zb |
| 4-168 | iPr | (CH$_2$)$_2$ | H | 4-MeSO$_2$-Ph | O | 4-Zb |
| 4-169 | iPr | (CH$_2$)$_2$ | H | 3-EtSO$_2$-Ph | O | 4-Zb |
| 4-170 | iPr | (CH$_2$)$_2$ | H | 4-EtSO$_2$-Ph | O | 4-Zb |
| 4-171 | iPr | (CH$_2$)$_2$ | H | 3-iPrSO$_2$-Ph | O | 4-Zb |
| 4-172 | iPr | (CH$_2$)$_2$ | H | 4-iPrSO$_2$-Ph | O | 4-Zb |
| 4-173 | iPr | (CH$_2$)$_2$ | H | 3-(1-Me-Imid-4)Ph | O | 4-Zb |
| 4-174 | iPr | (CH$_2$)$_2$ | H | 4-(1-Me-Imid-4)Ph | O | 4-Zb |
| 4-175 | iPr | (CH$_2$)$_2$ | H | 1-Me-2-Ph-Imid-4 | O | 4-Zb |
| 4-176 | iPr | (CH$_2$)$_2$ | H | 1,4-diMe-2-Ph-Imid-5 | O | 4-Zb |
| 4-177 | iPr | (CH$_2$)$_2$ | H | 1,5-diMe-2-Ph-Imid-4 | O | 4-Zb |
| 4-178 | iPr | (CH$_2$)$_2$ | H | 3,4-MdO-Ph | O | 4-Zb |
| 4-179 | iPr | (CH$_2$)$_2$ | H | 4-(4-MeO-Ph)Ph | O | 4-Zb |
| 4-180 | iPr | (CH$_2$)$_2$ | H | 4-(3,4-MdO-Ph)Ph | O | 4-Zb |
| 4-181 | iPr | (CH$_2$)$_2$ | H | 4-[PhSO$_2$-N(Me)]Ph | O | 4-Zb |
| 4-182 | iPr | (CH$_2$)$_2$ | H | 4-[(Pyr-3)SO$_2$-N(Me)]Ph | O | 4-Zb |
| 4-183 | iPr | (CH$_2$)$_2$ | H | 4-(PhSO$_2$NH)Ph | O | 4-Zb |
| 4-184 | iPr | (CH$_2$)$_2$ | H | 4-[(Pyr-3)SO$_2$-NH]Ph | O | 4-Zb |
| 4-185 | iPr | (CH$_2$)$_2$ | H | 4-[(Pyr-2)SO$_2$]Ph | O | 4-Zb |
| 4-186 | iPr | (CH$_2$)$_2$ | H | 4-[(Pyr-3)SO$_2$]Ph | O | 4-Zb |
| 4-187 | iPr | (CH$_2$)$_2$ | H | 4-[(Pyr-2)SO$_2$-N(Me)]Ph | O | 4-Zb |
| 4-188 | iPr | (CH$_2$)$_2$ | H | 4-[(Pyr-2)SO$_2$-NH]Ph | O | 4-Zb |
| 4-189 | iPr | (CH$_2$)$_2$ | H | 4-(4-Me-Ph)Ph | O | 4-Zb |
| 4-190 | iPr | (CH$_2$)$_2$ | H | 4-(4-F-Ph)Ph | O | 4-Zb |
| 4-191 | iPr | (CH$_2$)$_2$ | H | 4-(4-CF$_3$-Ph)Ph | O | 4-Zb |
| 4-192 | iPr | (CH$_2$)$_2$ | H | 2-[4-Me-PhSO$_2$-N(Me)]-Pyr-5 | O | 4-Zb |
| 4-193 | iPr | (CH$_2$)$_2$ | H | 2-HO-Pyr-5 | O | 4-Zb |
| 4-194 | iPr | (CH$_2$)$_2$ | H | 2-BzO-Pyr-5 | O | 4-Zb |
| 4-195 | iPr | (CH$_2$)$_2$ | H | 4-[(Pyr-4)SO$_2$]Ph | O | 4-Zb |
| 4-196 | iPr | (CH$_2$)$_2$ | H | 4-(2,4-diMeO-Ph)Ph | O | 4-Zb |
| 4-197 | iPr | (CH$_2$)$_2$ | H | 4-(2,5-diMeO-Ph)Ph | O | 4-Zb |
| 4-198 | iPr | (CH$_2$)$_2$ | H | 3-HO-Ph | O | 4-Zb |
| 4-199 | iPr | (CH$_2$)$_2$ | H | 4-HO-Ph | O | 4-Zb |
| 4-200 | iPr | (CH$_2$)$_2$ | H | 5-AcO-2-HO-3,4,6-triMe-Ph | O | 4-Zb |
| 4-201 | iPr | (CH$_2$)$_2$ | H | 4-HO-3,5-diMe-Ph | O | 4-Zb |
| 4-202 | iPr | (CH$_2$)$_2$ | H | 3-AcO-Ph | O | 4-Zb |
| 4-203 | iPr | (CH$_2$)$_2$ | H | 4-AcO-Ph | O | 4-Zb |

TABLE 5

| Cpd. No. | R¹ | R² | R³ | X | Y | Z |
|---|---|---|---|---|---|---|
| 5-1 | H | (CH$_2$)$_2$ | H | Ph | O | 4-Zc |
| 5-2 | H | (CH$_2$)$_2$ | H | Np-1 | O | 4-Zc |
| 5-3 | H | (CH$_2$)$_2$ | H | Np-2 | O | 4-Zc |
| 5-4 | H | (CH$_2$)$_2$ | H | 4-Me-Ph | O | 4-Zc |
| 5-5 | H | (CH$_2$)$_2$ | H | 4-Et-Ph | O | 4-Zc |
| 5-6 | H | (CH$_2$)$_2$ | H | 3-iPr-Ph | O | 4-Zc |
| 5-7 | H | (CH$_2$)$_2$ | H | 4-iPr-Ph | O | 4-Zc |
| 5-8 | H | (CH$_2$)$_2$ | H | 3-tBu-Ph | O | 4-Zc |
| 5-9 | H | (CH$_2$)$_2$ | H | 4-tBu-Ph | O | 4-Zc |
| 5-10 | H | (CH$_2$)$_2$ | H | 3-Cl-Ph | O | 4-Zc |
| 5-11 | H | (CH$_2$)$_2$ | H | 4-Cl-Ph | O | 4-Zc |
| 5-12 | H | (CH$_2$)$_2$ | H | 3-Br-Ph | O | 4-Zc |
| 5-13 | H | (CH$_2$)$_2$ | H | 4-Br-Ph | O | 4-Zc |
| 5-14 | H | (CH$_2$)$_2$ | H | 3-Ph-Ph | O | 4-Zc |
| 5-15 | H | (CH$_2$)$_2$ | H | 4-Ph-Ph | O | 4-Zc |
| 5-16 | H | (CH$_2$)$_2$ | H | 3-Bz-Ph | O | 4-Zc |
| 5-17 | H | (CH$_2$)$_2$ | H | 4-Bz-Ph | O | 4-Zc |
| 5-18 | H | (CH$_2$)$_2$ | H | 3-PhO-Ph | O | 4-Zc |
| 5-19 | H | (CH$_2$)$_2$ | H | 4-PhO-Ph | O | 4-Zc |
| 5-20 | H | (CH$_2$)$_2$ | H | 3-PhS-Ph | O | 4-Zc |
| 5-21 | H | (CH$_2$)$_2$ | H | 4-PhS-Ph | O | 4-Zc |
| 5-22 | H | (CH$_2$)$_2$ | H | 3-PhSO$_2$-Ph | O | 4-Zc |
| 5-23 | H | (CH$_2$)$_2$ | H | 4-PhSO$_2$-Ph | O | 4-Zc |
| 5-24 | H | (CH$_2$)$_2$ | H | 3-(Imid-1)Ph | O | 4-Zc |
| 5-25 | H | (CH$_2$)$_2$ | H | 4-(Imid-1)Ph | O | 4-Zc |
| 5-26 | H | (CH$_2$)$_2$ | H | 3-(Imid-4)Ph | O | 4-Zc |
| 5-27 | H | (CH$_2$)$_2$ | H | 4-(Imid-4)Ph | O | 4-Zc |
| 5-28 | H | (CH$_2$)$_2$ | H | 3-(Fur-2)Ph | O | 4-Zc |
| 5-29 | H | (CH$_2$)$_2$ | H | 4-(Fur-2)Ph | O | 4-Zc |
| 5-30 | H | (CH$_2$)$_2$ | H | 3-(Thi-2)Ph | O | 4-Zc |
| 5-31 | H | (CH$_2$)$_2$ | H | 4-(Thi-2)Ph | O | 4-Zc |
| 5-32 | H | (CH$_2$)$_2$ | H | 3-(Thi-3)Ph | O | 4-Zc |
| 5-33 | H | (CH$_2$)$_2$ | H | 4-(Thi-3)Ph | O | 4-Zc |
| 5-34 | H | (CH$_2$)$_2$ | H | 3-(Pyr-2)Ph | O | 4-Zc |
| 5-35 | H | (CH$_2$)$_2$ | H | 4-(Pyr-2)Ph | O | 4-Zc |
| 5-36 | H | (CH$_2$)$_2$ | H | 3-(Pyr-3)Ph | O | 4-Zc |
| 5-37 | H | (CH$_2$)$_2$ | H | 4-(Pyr-3)Ph | O | 4-Zc |
| 5-38 | H | (CH$_2$)$_2$ | H | 3-(Pyr-4)Ph | O | 4-Zc |
| 5-39 | H | (CH$_2$)$_2$ | H | 4-(Pyr-4)Ph | O | 4-Zc |
| 5-40 | H | (CH$_2$)$_2$ | H | 3-(Oxa-2)Ph | O | 4-Zc |
| 5-41 | H | (CH$_2$)$_2$ | H | 4-(Oxa-2)Ph | O | 4-Zc |
| 5-42 | H | (CH$_2$)$_2$ | H | 3-(Oxa-4)Ph | O | 4-Zc |
| 5-43 | H | (CH$_2$)$_2$ | H | 4-(Oxa-4)Ph | O | 4-Zc |
| 5-44 | H | (CH$_2$)$_2$ | H | 3-(Oxa-5)Ph | O | 4-Zc |
| 5-45 | H | (CH$_2$)$_2$ | H | 4-(Oxa-5)Ph | O | 4-Zc |
| 5-46 | H | (CH$_2$)$_2$ | H | 3-(Thiz-2)Ph | O | 4-Zc |
| 5-47 | H | (CH$_2$)$_2$ | H | 4-(Thiz-2)Ph | O | 4-Zc |
| 5-48 | H | (CH$_2$)$_2$ | H | 3-(Thiz-4)Ph | O | 4-Zc |
| 5-49 | H | (CH$_2$)$_2$ | H | 4-(Thiz-4)Ph | O | 4-Zc |
| 5-50 | H | (CH$_2$)$_2$ | H | 3-(Thiz-5)Ph | O | 4-Zc |
| 5-51 | H | (CH$_2$)$_2$ | H | 4-(Thiz-5)Ph | O | 4-Zc |
| 5-52 | H | (CH$_2$)$_2$ | H | 1-Me-Pyrr-2 | O | 4-Zc |
| 5-53 | H | (CH$_2$)$_2$ | H | 1-Ph-Pyrr-2 | O | 4-Zc |
| 5-54 | H | (CH$_2$)$_2$ | H | 1-Bz-Pyrr-2 | O | 4-Zc |
| 5-55 | H | (CH$_2$)$_2$ | H | 5-Me-Fur-2 | O | 4-Zc |
| 5-56 | H | (CH$_2$)$_2$ | H | 5-Ph-Fur-2 | O | 4-Zc |
| 5-57 | H | (CH$_2$)$_2$ | H | 5-Me-Thi-2 | O | 4-Zc |
| 5-58 | H | (CH$_2$)$_2$ | H | 5-Ph-Thi-2 | O | 4-Zc |
| 5-59 | H | (CH$_2$)$_2$ | H | 5-Me-Thi-3 | O | 4-Zc |
| 5-60 | H | (CH$_2$)$_2$ | H | 5-Ph-Thi-3 | O | 4-Zc |
| 5-61 | H | (CH$_2$)$_2$ | H | 1-Me-Pyza-3 | O | 4-Zc |
| 5-62 | H | (CH$_2$)$_2$ | H | 1-Ph-Pyza-3 | O | 4-Zc |
| 5-63 | H | (CH$_2$)$_2$ | H | 1-Me-Imid-2 | O | 4-Zc |
| 5-64 | H | (CH$_2$)$_2$ | H | 1-Ph-Imid-2 | O | 4-Zc |
| 5-65 | H | (CH$_2$)$_2$ | H | 1-Me-Imid-4 | O | 4-Zc |
| 5-66 | H | (CH$_2$)$_2$ | H | 1-Ph-Imid-4 | O | 4-Zc |
| 5-67 | H | (CH$_2$)$_2$ | H | Oxa-4 | O | 4-Zc |
| 5-68 | H | (CH$_2$)$_2$ | H | Oxa-5 | O | 4-Zc |
| 5-69 | H | (CH$_2$)$_2$ | H | 2-Me-Oxa-4 | O | 4-Zc |
| 5-70 | H | (CH$_2$)$_2$ | H | 2-Ph-Oxa-4 | O | 4-Zc |
| 5-71 | H | (CH$_2$)$_2$ | H | 2-Me-Oxa-5 | O | 4-Zc |
| 5-72 | H | (CH$_2$)$_2$ | H | 2-Ph-Oxa-5 | O | 4-Zc |
| 5-73 | H | (CH$_2$)$_2$ | H | 4-Me-2-Ph-Oxa-5 | O | 4-Zc |
| 5-74 | H | (CH$_2$)$_2$ | H | 5-Me-2-Ph-Oxa-4 | O | 4-Zc |
| 5-75 | H | (CH$_2$)$_2$ | H | Thiz-4 | O | 4-Zc |
| 5-76 | H | (CH$_2$)$_2$ | H | Thiz-5 | O | 4-Zc |

TABLE 5-continued

| Cpd. No. | R¹ | R² | R³ | X | Y | Z |
|---|---|---|---|---|---|---|
| 5-77 | H | (CH₂)₂ | H | 2-Me-Thiz-4 | O | 4-Zc |
| 5-78 | H | (CH₂)₂ | H | 2-Ph-Thiz-4 | O | 4-Zc |
| 5-79 | H | (CH₂)₂ | H | 2-Me-Thiz-5 | O | 4-Zc |
| 5-80 | H | (CH₂)₂ | H | 2-Ph-Thiz-5 | O | 4-Zc |
| 5-81 | H | (CH₂)₂ | H | 4-Me-2-Ph-Thiz-5 | O | 4-Zc |
| 5-82 | H | (CH₂)₂ | H | 5-Me-2-Ph-Thiz-4 | O | 4-Zc |
| 5-83 | H | (CH₂)₂ | H | 1-Me-Pyza-4 | O | 4-Zc |
| 5-84 | H | (CH₂)₂ | H | 1-Ph-Pyza-4 | O | 4-Zc |
| 5-85 | H | (CH₂)₂ | H | 2-Me-Isox-4 | O | 4-Zc |
| 5-86 | H | (CH₂)₂ | H | 2-Ph-Isox-4 | O | 4-Zc |
| 5-87 | H | (CH₂)₂ | H | Pyr-2 | O | 4-Zc |
| 5-88 | H | (CH₂)₂ | H | Pyr-3 | O | 4-Zc |
| 5-89 | H | (CH₂)₂ | H | Pyr-4 | O | 4-Zc |
| 5-90 | H | (CH₂)₂ | H | 3-Me-Pyr-5 | O | 4-Zc |
| 5-91 | H | (CH₂)₂ | H | 3-Et-Pyr-5 | O | 4-Zc |
| 5-92 | H | (CH₂)₂ | H | 3-Ph-Pyr-5 | O | 4-Zc |
| 5-93 | H | (CH₂)₂ | H | 2-Me-Pyr-5 | O | 4-Zc |
| 5-94 | H | (CH₂)₂ | H | 2-Et-Pyr-5 | O | 4-Zc |
| 5-95 | H | (CH₂)₂ | H | 2-Ph-Pyr-5 | O | 4-Zc |
| 5-96 | H | (CH₂)₂ | H | 2-MeO-Pyr-5 | O | 4-Zc |
| 5-97 | H | (CH₂)₂ | H | 2-EtO-Pyr-5 | O | 4-Zc |
| 5-98 | H | (CH₂)₂ | H | 2-iPrO-Pyr-5 | O | 4-Zc |
| 5-99 | H | (CH₂)₂ | H | 2-MeS-Pyr-5 | O | 4-Zc |
| 5-100 | H | (CH₂)₂ | H | 2-EtS-Pyr-5 | O | 4-Zc |
| 5-101 | H | (CH₂)₂ | H | 2-iPrS-Pyr-5 | O | 4-Zc |
| 5-102 | H | (CH₂)₂ | H | 2-MeSO₂-Pyr-5 | O | 4-Zc |
| 5-103 | H | (CH₂)₂ | H | 2-EtSO₂-Pyr-5 | O | 4-Zc |
| 5-104 | H | (CH₂)₂ | H | 2-iPrSO₂-Pyr-5 | O | 4-Zc |
| 5-105 | H | (CH₂)₂ | H | 2-Bz-Pyr-5 | O | 4-Zc |
| 5-106 | H | (CH₂)₂ | H | 2-PhO-Pyr-5 | O | 4-Zc |
| 5-107 | H | (CH₂)₂ | H | 2-PhS-Pyr-5 | O | 4-Zc |
| 5-108 | H | (CH₂)₂ | H | 2-PhSO₂-Pyr-5 | O | 4-Zc |
| 5-109 | H | (CH₂)₂ | H | 3-Me-Pyr-6 | O | 4-Zc |
| 5-110 | H | (CH₂)₂ | H | 3-Ph-Pyr-6 | O | 4-Zc |
| 5-111 | H | (CH₂)₂ | H | 2-Me-Pyr-6 | O | 4-Zc |
| 5-112 | H | (CH₂)₂ | H | 2-Ph-Pyr-6 | O | 4-Zc |
| 5-113 | H | (CH₂)₂ | H | 2-Me-Pym-4 | O | 4-Zc |
| 5-114 | H | (CH₂)₂ | H | 2-Ph-Pym-4 | O | 4-Zc |
| 5-115 | H | (CH₂)₂ | H | 2-MeO-Pym-4 | O | 4-Zc |
| 5-116 | H | (CH₂)₂ | H | 2-EtO-Pym-4 | O | 4-Zc |
| 5-117 | H | (CH₂)₂ | H | 2-iPro-Pym-4 | O | 4-Zc |
| 5-118 | H | (CH₂)₂ | H | 2-MeS-Pym-4 | O | 4-Zc |
| 5-119 | H | (CH₂)₂ | H | 2-EtS-Pym4 | O | 4-Zc |
| 5-120 | H | (CH₂)₂ | H | 2-iPrS-Pym-4 | O | 4-Zc |
| 5-121 | H | (CH₂)₂ | H | 6-MeS-Pym-4 | O | 4-Zc |
| 5-122 | H | (CH₂)₂ | H | 6-EtS-Pym-4 | O | 4-Zc |
| 5-123 | H | (CH₂)₂ | H | 6-iPrS-PymA | O | 4-Zc |
| 5-124 | H | (CH₂)₂ | H | 2-PhS-Pym-4 | O | 4-Zc |
| 5-125 | H | (CH₂)₂ | H | 2-MeSO₂-Pym-4 | O | 4-Zc |
| 5-126 | H | (CH₂)₂ | H | 2-EtSO₂-Pym-4 | O | 4-Zc |
| 5-127 | H | (CH₂)₂ | H | 2-iPrSO₂-Pym-4 | O | 4-Zc |
| 5-128 | H | (CH₂)₂ | H | 2-PhSO₂-Pym-4 | O | 4-Zc |
| 5-129 | H | (CH₂)₂ | H | 2-Me-Pym-5 | O | 4-Zc |
| 5-130 | H | (CH₂)₂ | H | 2-Ph-Pym-5 | O | 4-Zc |
| 5-131 | H | (CH₂)₂ | H | 2-MeO-Pym-5 | O | 4-Zc |
| 5-132 | H | (CH₂)₂ | H | 2-EtO-Pym-5 | O | 4-Zc |
| 5-133 | H | (CH₂)₂ | H | 2-iPrO-Pym-5 | O | 4-Zc |
| 5-134 | H | (CH₂)₂ | H | 2-MeS-Pym-5 | O | 4-Zc |
| 5-135 | H | (CH₂)₂ | H | 2-EtS-Pym-5 | O | 4-Zc |
| 5-136 | H | (CH₂)₂ | H | 2-iPrS-Pym-5 | O | 4-Zc |
| 5-137 | H | (CH₂)₂ | H | 2-PhS-Pym-5 | O | 4-Zc |
| 5-138 | H | (CH₂)₂ | H | 2-MeSO₂-Pym-5 | O | 4-Zc |
| 5-139 | H | (CH₂)₂ | H | 2-EtSO₂-Pym-5 | O | 4-Zc |
| 5-140 | H | (CH₂)₂ | H | 2-iPrSO₂-Pym-5 | O | 4-Zc |
| 5-141 | H | (CH₂)₂ | H | 2-PhSO₂-Pym-5 | O | 4-Zc |
| 5-142 | H | (CH₂)₂ | H | Ind-2 | O | 4-Zc |
| 5-143 | H | (CH₂)₂ | H | Ind-3 | O | 4-Zc |
| 5-144 | H | (CH₂)₂ | H | 1-Me-Ind-2 | O | 4-Zc |
| 5-145 | H | (CH₂)₂ | H | 1-Me-Ind-3 | O | 4-Zc |
| 5-146 | H | (CH₂)₂ | H | Bimid-2 | O | 4-Zc |
| 5-147 | H | (CH₂)₂ | H | Boxa-2 | O | 4-Zc |
| 5-148 | H | (CH₂)₂ | H | Bthiz-2 | O | 4-Zc |
| 5-149 | H | (CH₂)₂ | H | Quin-2 | O | 4-Zc |
| 5-150 | H | (CH₂)₂ | H | Quin-3 | O | 4-Zc |
| 5-151 | H | (CH₂)₂ | H | Quin-4 | O | 4-Zc |
| 5-152 | H | (CH₂)₂ | H | iQuin-1 | O | 4-Zc |
| 5-153 | H | (CH₂)₂ | H | iQuin-3 | O | 4-Zc |
| 5-154 | H | (CH₂)₂ | H | iQuin4 | O | 4-Zc |
| 5-155 | H | (CH₂)₂ | H | 3-MeO-Ph | O | 4-Zc |
| 5-156 | H | (CH₂)₂ | H | 4-MeO-Ph | O | 4-Zc |
| 5-157 | H | (CH₂)₂ | H | 3-EtO-Ph | O | 4-Zc |
| 5-158 | H | (CH₂)₂ | H | 4-EtO-Ph | O | 4-Zc |
| 5-159 | H | (CH₂)₂ | H | 3-iPro-Ph | O | 4-Zc |
| 5-160 | H | (CH₂)₂ | H | 4-iPrO-Ph | O | 4-Zc |
| 5-161 | H | (CH₂)₂ | H | 3-MeS-Ph | O | 4-Zc |
| 5-162 | H | (CH₂)₂ | H | 4-MeS-Ph | O | 4-Zc |
| 5-163 | H | (CH₂)₂ | H | 3-EtS-Ph | O | 4-Zc |
| 5-164 | H | (CH₂)₂ | H | 4-EtS-Ph | O | 4-Zc |
| 5-165 | H | (CH₂)₂ | H | 3-iPrS-Ph | O | 4-Zc |
| 5-166 | H | (CH₂)₂ | H | 4-iPrS-Ph | O | 4-Zc |
| 5-167 | H | (CH₂)₂ | H | 3-MeSO₂-Ph | O | 4-Zc |
| 5-168 | H | (CH₂)₂ | H | 4-MeSO₂-Ph | O | 4-Zc |
| 5-169 | H | (CH₂)₂ | H | 3-EtSO₂-Ph | O | 4-Zc |
| 5-170 | H | (CH₂)₂ | H | 4-EtSO₂-Ph | O | 4-Zc |
| 5-171 | H | (CH₂)₂ | H | 3-iPrSO₂-Ph | O | 4-Zc |
| 5-172 | H | (CH₂)₂ | H | 4-iPrSO₂-Ph | O | 4-Zc |
| 5-173 | H | (CH₂)₂ | H | 3-(1-Me-Imid-4)Ph | O | 4-Zc |
| 5-174 | H | (CH₂)₂ | H | 4-(1-Me-Imid-4)Ph | O | 4-Zc |
| 5-175 | H | (CH₂)₂ | H | 1-Me-2-Ph-Imid-4 | O | 4-Zc |
| 5-176 | H | (CH₂)₂ | H | 1,4-diMe-2-Ph-Imid-5 | O | 4-Zc |
| 5-177 | H | (CH₂)₂ | H | 1,5-diMe-2-Ph-Imid-4 | O | 4-Zc |
| 5-178 | H | (CH₂)₂ | H | 3,4-MdO-Ph | O | 4-Zc |
| 5-179 | H | (CH₂)₂ | H | 4-(4-MeO-Ph)Ph | O | 4-Zc |
| 5-180 | H | (CH₂)₂ | H | 4-(3,4-MdO-Ph)Ph | O | 4-Zc |
| 5-181 | H | (CH₂)₂ | H | 4-[PhSO₂-N(Me)]Ph | O | 4-Zc |
| 5-182 | H | (CH₂)₂ | H | 4-[(Pyr-3)SO₂-N(Me)]Ph | O | 4-Zc |
| 5-183 | H | (CH₂)₂ | H | 4-(PhSO₂NH)Ph | O | 4-Zc |
| 5-184 | H | (CH₂)₂ | H | 4-[(Pyr-3)SO₂-NH]Ph | O | 4-Zc |
| 5-185 | H | (CH₂)₂ | H | 4-[(Pyr-2)SO₂]Ph | O | 4-Zc |
| 5-186 | H | (CH₂)₂ | H | 4-[(Pyr-3)SO₂]Ph | O | 4-Zc |
| 5-187 | H | (CH₂)₂ | H | 4-[(Pyr-2)SO₂-N(Me)]Ph | O | 4-Zc |
| 5-188 | H | (CH₂)₂ | H | 4-[(Pyr-2)SO₂-NH]Ph | O | 4-Zc |
| 5-189 | H | (CH₂)₂ | H | 4-(4-Me-Ph)Ph | O | 4-Zc |
| 5-190 | H | (CH₂)₂ | H | 4-(4-F-Ph)Ph | O | 4-Zc |
| 5-191 | H | (CH₂)₂ | H | 4-(4-CF₃-Ph)Ph | O | 4-Zc |
| 5-192 | H | (CH₂)₂ | H | 2-[4-Me-PhSO₂-N(Me)]-Pyr-5 | O | 4-Zc |
| 5-193 | H | (CH₂)₂ | H | 2-HO-Pyr-5 | O | 4-Zc |
| 5-194 | H | (CH₂)₂ | H | 2-BzO-Pyr-5 | O | 4-Zc |
| 5-195 | H | (CH₂)₂ | H | 4-[(Pyr4)SO₂]Ph | O | 4-Zc |
| 5-196 | H | (CH₂)₂ | H | 4-(2,4-diMeO-Ph)Ph | O | 4-Zc |
| 5-197 | H | (CH₂)₂ | H | 4-(2,5-diMeO-Ph)Ph | O | 4-Zc |
| 5-198 | H | (CH₂)₂ | H | 3-HO-Ph | O | 4-Zc |
| 5-199 | H | (CH₂)₂ | H | 4-HO-Ph | O | 4-Zc |
| 5-200 | H | (CH₂)₂ | H | 5-AcO-2-HO-3,4,6-triMe-Ph | O | 4-Zc |
| 5-201 | H | (CH₂)₂ | H | 4-HO-3,5-diMe-Ph | O | 4-Zc |
| 5-202 | H | (CH₂)₂ | H | 3-AcO-Ph | O | 4-Zc |
| 5-203 | H | (CH₂)₂ | H | 4-AcO-Ph | O | 4-Zc |

TABLE 6

| Cpd. No. | R¹ | R² | R³ | X | Y | Z |
|---|---|---|---|---|---|---|
| 6-1 | Me | (CH₂)₂ | H | Ph | O | 4-Zc |
| 6-2 | Me | (CH₂)₂ | H | Np-1 | O | 4-Zc |
| 6-3 | Me | (CH₂)₂ | H | Np-2 | O | 4-Zc |
| 6-4 | Me | (CH₂)₂ | H | 4-Me-Ph | O | 4-Zc |
| 6-5 | Me | (CH₂)₂ | H | 4-Et-Ph | O | 4-Zc |
| 6-6 | Me | (CH₂)₂ | H | 3-iPr-Ph | O | 4-Zc |
| 6-7 | Me | (CH₂)₂ | H | 4-iPr-Ph | O | 4-Zc |
| 6-8 | Me | (CH₂)₂ | H | 3-tBu-Ph | O | 4-Zc |
| 6-9 | Me | (CH₂)₂ | H | 4-tBu-Ph | O | 4-Zc |
| 6-10 | Me | (CH₂)₂ | H | 3-Cl-Ph | O | 4-Zc |
| 6-11 | Me | (CH₂)₂ | H | 4-Cl-Ph | O | 4-Zc |
| 6-12 | Me | (CH₂)₂ | H | 3-Br-Ph | O | 4-Zc |
| 6-13 | Me | (CH₂)₂ | H | 4-Br-Ph | O | 4-Zc |
| 6-14 | Me | (CH₂)₂ | H | 3-Ph-Ph | O | 4-Zc |
| 6-15 | Me | (CH₂)₂ | H | 4-Ph-Ph | O | 4-Zc |
| 6-16 | Me | (CH₂)₂ | H | 3-Bz-Ph | O | 4-Zc |

TABLE 6-continued

| Cpd. No. | R¹ | R² | R³ | X | Y | Z |
|---|---|---|---|---|---|---|
| 6-17 | Me | (CH$_2$)$_2$ | H | 4-Bz-Ph | O | 4-Zc |
| 6-18 | Me | (CH$_2$)$_2$ | H | 3-PhO-Ph | O | 4-Zc |
| 6-19 | Me | (CH$_2$)$_2$ | H | 4-PhO-Ph | O | 4-Zc |
| 6-20 | Me | (CH$_2$)$_2$ | H | 3-PhS-Ph | O | 4-Zc |
| 6-21 | Me | (CH$_2$)$_2$ | H | 4-PhS-Ph | O | 4-Zc |
| 6-22 | Me | (CH$_2$)$_2$ | H | 3-PhSO$_2$-Ph | O | 4-Zc |
| 6-23 | Me | (CH$_2$)$_2$ | H | 4-PhSO$_2$-Ph | O | 4-Zc |
| 6-24 | Me | (CH$_2$)$_2$ | H | 3-(Imid-1)Ph | O | 4-Zc |
| 6-25 | Me | (CH$_2$)$_2$ | H | 4-(Imid-1)Ph | O | 4-Zc |
| 6-26 | Me | (CH$_2$)$_2$ | H | 3-(Imid-4)Ph | O | 4-Zc |
| 6-27 | Me | (CH$_2$)$_2$ | H | 4-(Imid-4)Ph | O | 4-Zc |
| 6-28 | Me | (CH$_2$)$_2$ | H | 3-(Fur-2)Ph | O | 4-Zc |
| 6-29 | Me | (CH$_2$)$_2$ | H | 4-(Fur-2)Ph | O | 4-Zc |
| 6-30 | Me | (CH$_2$)$_2$ | H | 3-(Thi-2)Ph | O | 4-Zc |
| 6-31 | Me | (CH$_2$)$_2$ | H | 4-(Thi-2)Ph | O | 4-Zc |
| 6-32 | Me | (CH$_2$)$_2$ | H | 3-(Thi-3)Ph | O | 4-Zc |
| 6-33 | Me | (CH$_2$)$_2$ | H | 4-(Thi-3)Ph | O | 4-Zc |
| 6-34 | Me | (CH$_2$)$_2$ | H | 3-(Pyr-2)Ph | O | 4-Zc |
| 6-35 | Me | (CH$_2$)$_2$ | H | 4-(Pyr-2)Ph | O | 4-Zc |
| 6-36 | Me | (CH$_2$)$_2$ | H | 3-(Pyr-3)Ph | O | 4-Zc |
| 6-37 | Me | (CH$_2$)$_2$ | H | 4-(Pyr-3)Ph | O | 4-Zc |
| 6-38 | Me | (CH$_2$)$_2$ | H | 3-(Pyr-4)Ph | O | 4-Zc |
| 6-39 | Me | (CH$_2$)$_2$ | H | 4-(Pyr-4)Ph | O | 4-Zc |
| 6-40 | Me | (CH$_2$)$_2$ | H | 3-(Oxa-2)Ph | O | 4-Zc |
| 6-41 | Me | (CH$_2$)$_2$ | H | 4-(Oxa-2)Ph | O | 4-Zc |
| 6-42 | Me | (CH$_2$)$_2$ | H | 3-(Oxa-4)Ph | O | 4-Zc |
| 6-43 | Me | (CH$_2$)$_2$ | H | 4-(Oxa-4)Ph | O | 4-Zc |
| 6-44 | Me | (CH$_2$)$_2$ | H | 3-(Oxa-5)Ph | O | 4-Zc |
| 6-45 | Me | (CH$_2$)$_2$ | H | 4-(Oxa-5)Ph | O | 4-Zc |
| 6-46 | Me | (CH$_2$)$_2$ | H | 3-(Thiz-2)Ph | O | 4-Zc |
| 6-47 | Me | (CH$_2$)$_2$ | H | 4-(Thiz-2)Ph | O | 4-Zc |
| 6-48 | Me | (CH$_2$)$_2$ | H | 3-(Thiz-4)Ph | O | 4-Zc |
| 6-49 | Me | (CH$_2$)$_2$ | H | 4-(Thiz-4)Ph | O | 4-Zc |
| 6-50 | Me | (CH$_2$)$_2$ | H | 3-(Thiz-5)Ph | O | 4-Zc |
| 6-51 | Me | (CH$_2$)$_2$ | H | 4-(Thiz-5)Ph | O | 4-Zc |
| 6-52 | Me | (CH$_2$)$_2$ | H | 1-Me-Pyrr-2 | O | 4-Zc |
| 6-53 | Me | (CH$_2$)$_2$ | H | 1-Ph-Pyrr-2 | O | 4-Zc |
| 6-54 | Me | (CH$_2$)$_2$ | H | 1-Bz-Pyrr-2 | O | 4-Zc |
| 6-55 | Me | (CH$_2$)$_2$ | H | 5-Me-Fur-2 | O | 4-Zc |
| 6-56 | Me | (CH$_2$)$_2$ | H | 5-Ph-Fur-2 | O | 4-Zc |
| 6-57 | Me | (CH$_2$)$_2$ | H | 5-Me-Thi-2 | O | 4-Zc |
| 6-58 | Me | (CH$_2$)$_2$ | H | 5-Ph-Thi-2 | O | 4-Zc |
| 6-59 | Me | (CH$_2$)$_2$ | H | 5-Me-Thi-3 | O | 4-Zc |
| 6-60 | Me | (CH$_2$)$_2$ | H | 5-Ph-Thi-3 | O | 4-Zc |
| 6-61 | Me | (CH$_2$)$_2$ | H | 1-Me-Pyza-3 | O | 4-Zc |
| 6-62 | Me | (CH$_2$)$_2$ | H | 1-Ph-Pyza-3 | O | 4-Zc |
| 6-63 | Me | (CH$_2$)$_2$ | H | 1-Me-Imid-2 | O | 4-Zc |
| 6-64 | Me | (CH$_2$)$_2$ | H | 1-Ph-Imid-2 | O | 4-Zc |
| 6-65 | Me | (CH$_2$)$_2$ | H | 1-Me-Imid-4 | O | 4-Zc |
| 6-66 | Me | (CH$_2$)$_2$ | H | 1-Ph-Imid-4 | O | 4-Zc |
| 6-67 | Me | (CH$_2$)$_2$ | H | Oxa-4 | O | 4-Zc |
| 6-68 | Me | (CH$_2$)$_2$ | H | Oxa-5 | O | 4-Zc |
| 6-69 | Me | (CH$_2$)$_2$ | H | 2-Me-Oxa-4 | O | 4-Zc |
| 6-70 | Me | (CH$_2$)$_2$ | H | 2-Ph-Oxa-4 | O | 4-Zc |
| 6-71 | Me | (CH$_2$)$_2$ | H | 2-Me-Oxa-5 | O | 4-Zc |
| 6-72 | Me | (CH$_2$)$_2$ | H | 2-Ph-Oxa-5 | O | 4-Zc |
| 6-73 | Me | (CH$_2$)$_2$ | H | 4-Me-2-Ph-Oxa-5 | O | 4-Zc |
| 6-74 | Me | (CH$_2$)$_2$ | H | 5-Me-2-Ph-Oxa-4 | O | 4-Zc |
| 6-75 | Me | (CH$_2$)$_2$ | H | Thiz-4 | O | 4-Zc |
| 6-76 | Me | (CH$_2$)$_2$ | H | Thiz-5 | O | 4-Zc |
| 6-77 | Me | (CH$_2$)$_2$ | H | 2-Me-Thiz-4 | O | 4-Zc |
| 6-78 | Me | (CH$_2$)$_2$ | H | 2-Ph-Thiz-4 | O | 4-Zc |
| 6-79 | Me | (CH$_2$)$_2$ | H | 2-Me-Thiz-5 | O | 4-Zc |
| 6-80 | Me | (CH$_2$)$_2$ | H | 2-Ph-Thiz-5 | O | 4-Zc |
| 6-81 | Me | (CH$_2$)$_2$ | H | 4-Me-2-Ph-Thiz-5 | O | 4-Zc |
| 6-82 | Me | (CH$_2$)$_2$ | H | 5-Me-2-Ph-Thiz-4 | O | 4-Zc |
| 6-83 | Me | (CH$_2$)$_2$ | H | 1-Me-Pyza-4 | O | 4-Zc |
| 6-84 | Me | (CH$_2$)$_2$ | H | 1-Ph-Pyza-4 | O | 4-Zc |
| 6-85 | Me | (CH$_2$)$_2$ | H | 2-Me-Isox-4 | O | 4-Zc |
| 6-86 | Me | (CH$_2$)$_2$ | H | 2-Ph-Isox-4 | O | 4-Zc |
| 6-87 | Me | (CH$_2$)$_2$ | H | Pyr-2 | O | 4-Zc |
| 6-88 | Me | (CH$_2$)$_2$ | H | Pyr-3 | O | 4-Zc |
| 6-89 | Me | (CH$_2$)$_2$ | H | Pyr-4 | O | 4-Zc |
| 6-90 | Me | (CH$_2$)$_2$ | H | 3-Me-Pyr-5 | O | 4-Zc |
| 6-91 | Me | (CH$_2$)$_2$ | H | 3-Et-Pyr-5 | O | 4-Zc |
| 6-92 | Me | (CH$_2$)$_2$ | H | 3-Ph-Pyr-5 | O | 4-Zc |
| 6-93 | Me | (CH$_2$)$_2$ | H | 2-Me-Pyr-5 | O | 4-Zc |
| 6-94 | Me | (CH$_2$)$_2$ | H | 2-Et-Pyr-5 | O | 4-Zc |
| 6-95 | Me | (CH$_2$)$_2$ | H | 2-Ph-Pyr-5 | O | 4-Zc |
| 6-96 | Me | (CH$_2$)$_2$ | H | 2-MeO-Pyr-5 | O | 4-Zc |
| 6-97 | Me | (CH$_2$)$_2$ | H | 2-EtO-Pyr-5 | O | 4-Zc |
| 6-98 | Me | (CH$_2$)$_2$ | H | 2-iPrO-Pyr-5 | O | 4-Zc |
| 6-99 | Me | (CH$_2$)$_2$ | H | 2-MeS-Pyr-5 | O | 4-Zc |
| 6-100 | Me | (CH$_2$)$_2$ | H | 2-EtS-Pyr-5 | O | 4-Zc |
| 6-101 | Me | (CH$_2$)$_2$ | H | 2-iPrS-Pyr-5 | O | 4-Zc |
| 6-102 | Me | (CH$_2$)$_2$ | H | 2-MeSO$_2$-Pyr-5 | O | 4-Zc |
| 6-103 | Me | (CH$_2$)$_2$ | H | 2-EtSO$_2$-Pyr-5 | O | 4-Zc |
| 6-104 | Me | (CH$_2$)$_2$ | H | 2-iPrSO$_2$-Pyr-5 | O | 4-Zc |
| 6-105 | Me | (CH$_2$)$_2$ | H | 2-Bz-Pyr-5 | O | 4-Zc |
| 6-106 | Me | (CH$_2$)$_2$ | H | 2-PhO-Pyr-5 | O | 4-Zc |
| 6-107 | Me | (CH$_2$)$_2$ | H | 2-PhS-Pyr-5 | O | 4-Zc |
| 6-108 | Me | (CH$_2$)$_2$ | H | 2-PhSO$_2$-Pyr-5 | O | 4-Zc |
| 6-109 | Me | (CH$_2$)$_2$ | H | 3-Me-Pyr-6 | O | 4-Zc |
| 6-110 | Me | (CH$_2$)$_2$ | H | 3-Ph-Pyr-6 | O | 4-Zc |
| 6-111 | Me | (CH$_2$)$_2$ | H | 2-Me-Pyr-6 | O | 4-Zc |
| 6-112 | Me | (CH$_2$)$_2$ | H | 2-Ph-Pyr-6 | O | 4-Zc |
| 6-113 | Me | (CH$_2$)$_2$ | H | 2-Me-Pym-4 | O | 4-Zc |
| 6-114 | Me | (CH$_2$)$_2$ | H | 2-Ph-Pym-4 | O | 4-Zc |
| 6-115 | Me | (CH$_2$)$_2$ | H | 2-MeO-Pym-4 | O | 4-Zc |
| 6-116 | Me | (CH$_2$)$_2$ | H | 2-EtO-Pym-4 | O | 4-Zc |
| 6-117 | Me | (CH$_2$)$_2$ | H | 2-iPrO-Pym-4 | O | 4-Zc |
| 6-118 | Me | (CH$_2$)$_2$ | H | 2-MeS-Pym-4 | O | 4-Zc |
| 6-119 | Me | (CH$_2$)$_2$ | H | 2-EtS-Pym-4 | O | 4-Zc |
| 6-120 | Me | (CH$_2$)$_2$ | H | 2-iPrS-Pym-4 | O | 4-Zc |
| 6-121 | Me | (CH$_2$)$_2$ | H | 6-MeS-Pym-4 | O | 4-Zc |
| 6-122 | Me | (CH$_2$)$_2$ | H | 6-EtS-Pym-4 | O | 4-Zc |
| 6-123 | Me | (CH$_2$)$_2$ | H | 6-iPrS-Pym-4 | O | 4-Zc |
| 6-124 | Me | (CH$_2$)$_2$ | H | 2-PhS-Pym-4 | O | 4-Zc |
| 6-125 | Me | (CH$_2$)$_2$ | H | 2-MeSO$_2$-Pym-4 | O | 4-Zc |
| 6-126 | Me | (CH$_2$)$_2$ | H | 2-EtSO$_2$-Pym-4 | O | 4-Zc |
| 6-127 | Me | (CH$_2$)$_2$ | H | 2-iPrSO$_2$-Pym-4 | O | 4-Zc |
| 6-128 | Me | (CH$_2$)$_2$ | H | 2-PhSO$_2$-Pym-4 | O | 4-Zc |
| 6-129 | Me | (CH$_2$)$_2$ | H | 2-Me-Pym-5 | O | *4-Zc |
| 6-130 | Me | (CH$_2$)$_2$ | H | 2-Ph-Pym-5 | O | 4-Zc |
| 6-131 | Me | (CH$_2$)$_2$ | H | 2-MeO-Pym-5 | O | 4-Zc |
| 6-132 | Me | (CH$_2$)$_2$ | H | 2-EtO-Pym-5 | O | 4-Zc |
| 6-133 | Me | (CH$_2$)$_2$ | H | 2-iPrO-Pym-5 | O | 4-Zc |
| 6-134 | Me | (CH$_2$)$_2$ | H | 2-MeS-Pym-5 | O | 4-Zc |
| 6-135 | Me | (CH$_2$)$_2$ | H | 2-EtS-Pym-5 | O | 4-Zc |
| 6-136 | Me | (CH$_2$)$_2$ | H | 2-iPrS-Pym-5 | O | 4-Zc |
| 6-137 | Me | (CH$_2$)$_2$ | H | 2-PhS-Pym-5 | O | 4-Zc |
| 6-138 | Me | (CH$_2$)$_2$ | H | 2-MeSO$_2$-Pym-5 | O | 4-Zc |
| 6-139 | Me | (CH$_2$)$_2$ | H | 2-EtSO$_2$-Pym-5 | O | 4-Zc |
| 6-140 | Me | (CH$_2$)$_2$ | H | 2-iPrSO$_2$-Pym-5 | O | 4-Zc |
| 6-141 | Me | (CH$_2$)$_2$ | H | 2-PhSO$_2$-Pym-5 | O | 4-Zc |
| 6-142 | Me | (CH$_2$)$_2$ | H | Ind-2 | O | 4-Zc |
| 6-143 | Me | (CH$_2$)$_2$ | H | Ind-3 | O | 4-Zc |
| 6-144 | Me | (CH$_2$)$_2$ | H | 1-Me-Ind-2 | O | 4-Zc |
| 6-145 | Me | (CH$_2$)$_2$ | H | 1-Me-Ind-3 | O | 4-Zc |
| 6-146 | Me | (CH$_2$)$_2$ | H | Bimid-2 | O | 4-Zc |
| 6-147 | Me | (CH$_2$)$_2$ | H | Boxa-2 | O | 4-Zc |
| 6-148 | Me | (CH$_2$)$_2$ | H | Bthiz-2 | O | 4-Zc |
| 6-149 | Me | (CH$_2$)$_2$ | H | Quin-2 | O | 4-Zc |
| 6-150 | Me | (CH$_2$)$_2$ | H | Quin-3 | O | 4-Zc |
| 6-151 | Me | (CH$_2$)$_2$ | H | Quin-4 | O | 4-Zc |
| 6-152 | Me | (CH$_2$)$_2$ | H | iQuin-1 | O | 4-Zc |
| 6-153 | Me | (CH$_2$)$_2$ | H | iQuin-3 | O | 4-Zc |
| 6-154 | Me | (CH$_2$)$_2$ | H | iQuin-4 | O | 4-Zc |
| 6-155 | Me | (CH$_2$)$_2$ | H | 3-MeO-Ph | O | 4-Zc |
| 6-156 | Me | (CH$_2$)$_2$ | H | 4-MeO-Ph | O | 4-Zc |
| 6-157 | Me | (CH$_2$)$_2$ | H | 3-EtO-Ph | O | 4-Zc |
| 6-158 | Me | (CH$_2$)$_2$ | H | 4-EtO-Ph | O | 4-Zc |
| 6-159 | Me | (CH$_2$)$_2$ | H | 3-iPrO-Ph | O | 4-Zc |
| 6-160 | Me | (CH$_2$)$_2$ | H | 4-iPrO-Ph | O | 4-Zc |
| 6-161 | Me | (CH$_2$)$_2$ | H | 3-MeS-Ph | O | 4-Zc |
| 6-162 | Me | (CH$_2$)$_2$ | H | 4-MeS-Ph | O | 4-Zc |
| 6-163 | Me | (CH$_2$)$_2$ | H | 3-EtS-Ph | O | 4-Zc |
| 6-164 | Me | (CH$_2$)$_2$ | H | 4-EtS-Ph | O | 4-Zc |
| 6-165 | Me | (CH$_2$)$_2$ | H | 3-iPrS-Ph | O | 4-Zc |
| 6-166 | Me | (CH$_2$)$_2$ | H | 4-iPrS-Ph | O | 4-Zc |
| 6-167 | Me | (CH$_2$)$_2$ | H | 3-MeSO$_2$-Ph | O | 4-Zc |
| 6-168 | Me | (CH$_2$)$_2$ | H | 4-MeSO$_2$-Ph | O | 4-Zc |

TABLE 6-continued

| Cpd. No. | R¹ | R² | R³ | X | Y | Z |
|---|---|---|---|---|---|---|
| 6-169 | Me | (CH₂)₂ | H | 3-EtSO₂-Ph | O | 4-Zc |
| 6-170 | Me | (CH₂)₂ | H | 4-EtSO₂-Ph | O | 4-Zc |
| 6-171 | Me | (CH₂)₂ | H | 3-iPrSO₂-Ph | O | 4-Zc |
| 6-172 | Me | (CH₂)₂ | H | 4-iPrSO₂-Ph | O | 4-Zc |
| 6-173 | Me | (CH₂)₂ | H | 3-(1-Me-Imid-4)Ph | O | 4-Zc |
| 6-174 | Me | (CH₂)₂ | H | 4-(1-Me-Imid-4)Ph | O | 4-Zc |
| 6-175 | Me | (CH₂)₂ | H | 1-Me-2-Ph-Imid-4 | O | 4-Zc |
| 6-176 | Me | (CH₂)₂ | H | 1,4-diMe-2-Ph-Imid-5 | O | 4-Zc |
| 6-177 | Me | (CH₂)₂ | H | 1,5-diMe-2-Ph-Imid-4 | O | 4-Zc |
| 6-178 | Me | (CH₂)₂ | H | 3,4-MdO-Ph | O | 4-Zc |
| 6-179 | Me | (CH₂)₂ | H | 4-(4-MeO-Ph)Ph | O | 4-Zc |
| 6-180 | Me | (CH₂)₂ | H | 4-(3,4-MdO-Ph)Ph | O | 4-Zc |
| 6-181 | Me | (CH₂)₂ | H | 4-[PhSO₂-N(Me)]Ph | O | 4-Zc |
| 6-182 | Me | (CH₂)₂ | H | 4-[(Pyr-3)SO₂-N(Me)]Ph | O | 4-Zc |
| 6-183 | Me | (CH₂)₂ | H | 4-(PhSO₂NH)Ph | O | 4-Zc |
| 6-184 | Me | (CH₂)₂ | H | 4-[(Pyr-3)SO₂-NH]Ph | O | 4-Zc |
| 6-185 | Me | (CH₂)₂ | H | 4-[(Pyr-2)SO₂]Ph | O | 4-Zc |
| 6-186 | Me | (CH₂)₂ | H | 4-[(Pyr-3)SO₂]Ph | O | 4-Zc |
| 6-187 | Me | (CH₂)₂ | H | 4-[(Pyr-2)SO₂-N(Me)]Ph | O | 4-Zc |
| 6-188 | Me | (CH₂)₂ | H | 4-[(Pyr-2)SO₂-NH]Ph | O | 4-Zc |
| 6-189 | Me | (CH₂)₂ | H | 4-(4-Me-Ph)Ph | O | 4-Zc |
| 6-190 | Me | (CH₂)₂ | H | 4-(4-F-Ph)Ph | O | 4-Zc |
| 6-191 | Me | (CH₂)₂ | H | 4-(4-CF₃-Ph)Ph | O | 4-Zc |
| 6-192 | Me | (CH₂)₂ | H | 2-[4-Me-PhSO₂-N(Me)]-Pyr-5 | O | 4-Zc |
| 6-193 | Me | (CH₂)₂ | H | 2-HO-Pyr-5 | O | 4-Zc |
| 6-194 | Me | (CH₂)₂ | H | 2-BzG-Pyr-5 | O | 4-Zc |
| 6-195 | Me | (CH₂)₂ | H | 4-[(Pyr-4)SO₂]Ph | O | 4-Zc |
| 6-196 | Me | (CH₂)₂ | H | 4-(2,4-diMeO-Ph)Ph | O | 4-Zc |
| 6-197 | Me | (CH₂)₂ | H | 4-(2,5-diMeO-Ph)Ph | O | 4-Zc |
| 6-198 | Me | (CH₂)₂ | H | 3-HO-Ph | O | 4-Zc |
| 6-199 | Me | (CH₂)₂ | H | 4-HO-Ph | O | 4-Zc |
| 6-200 | Me | (CH₂)₂ | H | 5-AcO-2-HO-3,4,6-triMe-Ph | O | 4-Zc |
| 6-201 | Me | (CH₂)₂ | H | 4-HO-3,5-diMe-Ph | O | 4-Zc |
| 6-202 | Me | (CH₂)₂ | H | 3-AcO-Ph | O | 4-Zc |
| 6-203 | Me | (CH₂)₂ | H | 4-AcO-Ph | O | 4-Zc |

TABLE 7

| Cpd. No. | R¹ | R² | R³ | X | Y | Z |
|---|---|---|---|---|---|---|
| 7-1 | H | (CH₂)₃ | H | Ph | O | 4-Zb |
| 7-2 | H | (CH₂)₃ | H | Np-1 | O | 4-Zb |
| 7-3 | H | (CH₂)₃ | H | Np-2 | O | 4-Zb |
| 7-4 | H | (CH₂)₃ | H | 4-Me-Ph | O | 4-Zb |
| 7-5 | H | (CH₂)₃ | H | 4-Et-Ph | O | 4-Zb |
| 7-6 | H | (CH₂)₃ | H | 3-iPr-Ph | O | 4-Zb |
| 7-7 | H | (CH₂)₃ | H | 4-iPr-Ph | O | 4-Zb |
| 7-8 | H | (CH₂)₃ | H | 3-tBu-Ph | O | 4-Zb |
| 7-9 | H | (CH₂)₃ | H | 4-tBu-Ph | O | 4-Zb |
| 7-10 | H | (CH₂)₃ | H | 3-Cl-Ph | O | 4-Zb |
| 7-11 | H | (CH₂)₃ | H | 4-Cl-Ph | O | 4-Zb |
| 7-12 | H | (CH₂)₃ | H | 3-Br-Ph | O | 4-Zb |
| 7-13 | H | (CH₂)₃ | H | 4-Br-Ph | O | 4-Zb |
| 7-14 | H | (CH₂)₃ | H | 3-Ph-Ph | O | 4-Zb |
| 7-15 | H | (CH₂)₃ | H | 4-Ph-Ph | O | 4-Zb |
| 7-16 | H | (CH₂)₃ | H | 3-Bz-Ph | O | 4-Zb |
| 7-17 | H | (CH₂)₃ | H | 4-Bz-Ph | O | 4-Zb |
| 7-18 | H | (CH₂)₃ | H | 3-PhO-Ph | O | 4-Zb |
| 7-19 | H | (CH₂)₃ | H | 4-PhO-Ph | O | 4-Zb |
| 7-20 | H | (CH₂)₃ | H | 3-PhS-Ph | O | 4-Zb |
| 7-21 | H | (CH₂)₃ | H | 4-PhS-Ph | O | 4-Zb |
| 7-22 | H | (CH₂)₃ | H | 3-PhSO₂-Ph | O | 4-Zb |
| 7-23 | H | (CH₂)₃ | H | 4-PhSO₂-Ph | O | 4-Zb |
| 7-24 | H | (CH₂)₃ | H | 3-(Imid-1)Ph | O | 4-Zb |
| 7-25 | H | (CH₂)₃ | H | 4-(Imid-1)Ph | O | 4-Zb |
| 7-26 | H | (CH₂)₃ | H | 3-(Imid-4)Ph | O | 4-Zb |
| 7-27 | H | (CH₂)₃ | H | 4-(Imid-4)Ph | O | 4-Zb |
| 7-28 | H | (CH₂)₃ | H | 3-(Fur-2)Ph | O | 4-Zb |
| 7-29 | H | (CH₂)₃ | H | 4-(Fur-2)Ph | O | 4-Zb |
| 7-30 | H | (CH₂)₃ | H | 3-(Thi-2)Ph | O | 4-Zb |
| 7-31 | H | (CH₂)₃ | H | 4-(Thi-2)Ph | O | 4-Zb |
| 7-32 | H | (CH₂)₃ | H | 3-(Thi-3)Ph | O | 4-Zb |

TABLE 7-continued

| Cpd. No. | R¹ | R² | R³ | X | Y | Z |
|---|---|---|---|---|---|---|
| 7-33 | H | (CH₂)₃ | H | 4-(Thi-3)Ph | O | 4-Zb |
| 7-34 | H | (CH₂)₃ | H | 3-(Pyr-2)Ph | O | 4-Zb |
| 7-35 | H | (CH₂)₃ | H | 4-(Pyr-2)Ph | O | 4-Zb |
| 7-36 | H | (CH₂)₃ | H | 3-(Pyr-3)Ph | O | 4-Zb |
| 7-37 | H | (CH₂)₃ | H | 4-(Pyr-3)Ph | O | 4-Zb |
| 7-38 | H | (CH₂)₃ | H | 3-(Pyr-4)Ph | O | 4-Zb |
| 7-39 | H | (CH₂)₃ | H | 4-(Pyr-4)Ph | O | 4-Zb |
| 7-40 | H | (CH₂)₃ | H | 3-(Oxa-2)Ph | O | 4-Zb |
| 7-41 | H | (CH₂)₃ | H | 4-(Oxa-2)Ph | O | 4-Zb |
| 7-42 | H | (CH₂)₃ | H | 3-(Oxa-4)Ph | O | 4-Zb |
| 7-43 | H | (CH₂)₃ | H | 4-(Oxa-4)Ph | O | 4-Zb |
| 7-44 | H | (CH₂)₃ | H | 3-(Oxa-5)Ph | O | 4-Zb |
| 7-45 | H | (CH₂)₃ | H | 4-(Oxa-5)Ph | O | 4-Zb |
| 7-46 | H | (CH₂)₃ | H | 3-(Thiz-2)Ph | O | 4-Zb |
| 7-47 | H | (CH₂)₃ | H | 4-(Thiz-2)Ph | O | 4-Zb |
| 7-48 | H | (CH₂)₃ | H | 3-(Thiz-4)Ph | O | 4-Zb |
| 7-49 | H | (CH₂)₃ | H | 4-(Thiz-4)Ph | O | 4-Zb |
| 7-50 | H | (CH₂)₃ | H | 3-(Thiz-5)Ph | O | 4-Zb |
| 7-51 | H | (CH₂)₃ | H | 4-(Thiz-5)Ph | O | 4-Zb |
| 7-52 | H | (CH₂)₃ | H | 1-Me-Pyrr-2 | O | 4-Zb |
| 7-53 | H | (CH₂)₃ | H | 1-Ph-Pyrr-2 | O | 4-Zb |
| 7-54 | H | (CH₂)₃ | H | 1-Bz-Pyrr-2 | O | 4-Zb |
| 7-55 | H | (CH₂)₃ | H | 5-Me-Fur-2 | O | 4-Zb |
| 7-56 | H | (CH₂)₃ | H | 5-Ph-Fur-2 | O | 4-Zb |
| 7-57 | H | (CH₂)₃ | H | 5-Me-Thi-2 | O | 4-Zb |
| 7-58 | H | (CH₂)₃ | H | 5-Ph-Thi-2 | O | 4-Zb |
| 7-59 | H | (CH₂)₃ | H | 5-Me-Thi-3 | O | 4-Zb |
| 7-60 | H | (CH₂)₃ | H | 5-Ph-Thi-3 | O | 4-Zb |
| 7-61 | H | (CH₂)₃ | H | 1-Me-Pyza-3 | O | 4-Zb |
| 7-62 | H | (CH₂)₃ | H | 1-Ph-Pyza-3 | O | 4-Zb |
| 7-63 | H | (CH₂)₃ | H | 1-Me-Imid-2 | O | 4-Zb |
| 7-64 | H | (CH₂)₃ | H | 1-Ph-Imid-2 | O | 4-Zb |
| 7-65 | H | (CH₂)₃ | H | 1-Me-Imid-4 | O | 4-Zb |
| 7-66 | H | (CH₂)₃ | H | 1-Ph-Imid-4 | O | 4-Zb |
| 7-67 | H | (CH₂)₃ | H | Oxa-4 | O | 4-Zb |
| 7-68 | H | (CH₂)₃ | H | Oxa-5 | O | 4-Zb |
| 7-69 | H | (CH₂)₃ | H | 2-Me-Oxa-4 | O | 4-Zb |
| 7-70 | H | (CH₂)₃ | H | 2-Ph-Oxa-4 | O | 4-Zb |
| 7-71 | H | (CH₂)₃ | H | 2-Me-Oxa-5 | O | 4-Zb |
| 7-72 | H | (CH₂)₃ | H | 2-Ph-Oxa-5 | O | 4-Zb |
| 7-73 | H | (CH₂)₃ | H | 4-Me-2-Ph-Oxa-5 | O | 4-Zb |
| 7-74 | H | (CH₂)₃ | H | 5-Me-2-Ph-Oxa-4 | O | 4-Zb |
| 7-75 | H | (CH₂)₃ | H | Thiz-4 | O | 4-Zb |
| 7-76 | H | (CH₂)₃ | H | Thiz-5 | O | 4-Zb |
| 7-77 | H | (CH₂)₃ | H | 2-Me-Thiz-4 | O | 4-Zb |
| 7-78 | H | (CH₂)₃ | H | 2-Ph-Thiz-4 | O | 4-Zb |
| 7-79 | H | (CH₂)₃ | H | 2-Me-Thiz-5 | O | 4-Zb |
| 7-80 | H | (CH₂)₃ | H | 2-Ph-Thiz-5 | O | 4-Zb |
| 7-81 | H | (CH₂)₃ | H | 4-Me-2-Ph-Thiz-5 | O | 4-Zb |
| 7-82 | H | (CH₂)₃ | H | 5-Me-2-Ph-Thiz-4 | O | 4-Zb |
| 7-83 | H | (CH₂)₃ | H | 1-Me-Pyza-4 | O | 4-Zb |
| 7-84 | H | (CH₂)₃ | H | 1-Ph-Pyza-4 | O | 4-Zb |
| 7-85 | H | (CH₂)₃ | H | 2-Me-Isox-4 | O | 4-Zb |
| 7-86 | H | (CH₂)₃ | H | 2-Ph-Isox-4 | O | 4-Zb |
| 7-87 | H | (CH₂)₃ | H | Pyr-2 | O | 4-Zb |
| 7-88 | H | (CH₂)₃ | H | Pyr-3 | O | 4-Zb |
| 7-89 | H | (CH₂)₃ | H | Pyr-4 | O | 4-Zb |
| 7-90 | H | (CH₂)₃ | H | 3-Me-Pyr-5 | O | 4-Zb |
| 7-91 | H | (CH₂)₃ | H | 3-Et-Pyr-5 | O | 4-Zb |
| 7-92 | H | (CH₂)₃ | H | 3-Ph-Pyr-5 | O | 4-Zb |
| 7-93 | H | (CH₂)₃ | H | 2-Me-Pyr-5 | O | 4-Zb |
| 7-94 | H | (CH₂)₃ | H | 2-Et-Pyr-5 | O | 4-Zb |
| 7-95 | H | (CH₂)₃ | H | 2-Ph-Pyr-5 | O | 4-Zb |
| 7-96 | H | (CH₂)₃ | H | 2-MeO-Pyr-5 | O | 4-Zb |
| 7-97 | H | (CH₂)₃ | H | 2-EtO-Pyr-5 | O | 4-Zb |
| 7-98 | H | (CH₂)₃ | H | 2-iPrO-Pyr-5 | O | 4-Zb |
| 7-99 | H | (CH₂)₃ | H | 2-MeS-Pyr-5 | O | 4-Zb |
| 7-100 | H | (CH₂)₃ | H | 2-EtS-Pyr-5 | O | 4-Zb |
| 7-101 | H | (CH₂)₃ | H | 2-iPrS-Pyr-5 | O | 4-Zb |
| 7-102 | H | (CH₂)₃ | H | 2-MeSO₂-Pyr-5 | O | 4-Zb |
| 7-103 | H | (CH₂)₃ | H | 2-EtSO₂-Pyr-5 | O | 4-Zb |
| 7-104 | H | (CH₂)₃ | H | 2-iPrSO₂-Pyr-5 | O | 4-Zb |
| 7-105 | H | (CH₂)₃ | H | 2-Bz-Pyr-5 | O | 4-Zb |
| 7-106 | H | (CH₂)₃ | H | 2-PhO-Pyr-5 | O | 4-Zb |
| 7-107 | H | (CH₂)₃ | H | 2-PhS-Pyr-5 | O | 4-Zb |
| 7-108 | H | (CH₂)₃ | H | 2-PhSO₂-Pyr-5 | O | 4-Zb |

TABLE 7-continued

| Cpd. No. | R¹ | R² | R³ | X | Y | Z |
|---|---|---|---|---|---|---|
| 7-109 | H | (CH$_2$)$_3$ | H | 3-Me-Pyr-6 | O | 4-Zb |
| 7-110 | H | (CH$_2$)$_3$ | H | 3-Ph-Pyr-6 | O | 4-Zb |
| 7-111 | H | (CH$_2$)$_3$ | H | 2-Me-Pyr-6 | O | 4-Zb |
| 7-112 | H | (CH$_2$)$_3$ | H | 2-Ph-Pyr-6 | O | 4-Zb |
| 7-113 | H | (CH$_2$)$_3$ | H | 2-Me-Pym-4 | O | 4-Zb |
| 7-114 | H | (CH$_2$)$_3$ | H | 2-Ph-Pym-4 | O | 4-Zb |
| 7-115 | H | (CH$_2$)$_3$ | H | 2-MeO-Pym-4 | O | 4-Zb |
| 7-116 | H | (CH$_2$)$_3$ | H | 2-EtO-Pym-4 | O | 4-Zb |
| 7-117 | H | (CH$_2$)$_3$ | H | 2-iPrO-Pym-4 | O | 4-Zb |
| 7-118 | H | (CH$_2$)$_3$ | H | 2-MeS-Pym-4 | O | 4-Zb |
| 7-119 | H | (CH$_2$)$_3$ | H | 2-EtS-Pym-4 | O | 4-Zb |
| 7-120 | H | (CH$_2$)$_3$ | H | 2-iPrS-Pym-4 | O | 4-Zb |
| 7-121 | H | (CH$_2$)$_3$ | H | 6-MeS-Pym-4 | O | 4-Zb |
| 7-122 | H | (CH$_2$)$_3$ | H | 6-EtS-Pym-4 | O | 4-Zb |
| 7-123 | H | (CH$_2$)$_3$ | H | 6-iPrS-Pym-4 | O | 4-Zb |
| 7-124 | H | (CH$_2$)$_3$ | H | 2-PhS-Pym-4 | O | 4-Zb |
| 7-125 | H | (CH$_2$)$_3$ | H | 2-MeSO$_2$-Pym-4 | O | 4-Zb |
| 7-126 | H | (CH$_2$)$_3$ | H | 2-EtSO$_2$-Pym-4 | O | 4-Zb |
| 7-127 | H | (CH$_2$)$_3$ | H | 2-iPrSO$_2$-Pym-4 | O | 4-Zb |
| 7-128 | H | (CH$_2$)$_3$ | H | 2-PhSO$_2$-Pym-4 | O | 4-Zb |
| 7-129 | H | (CH$_2$)$_3$ | H | 2-Me-Pym-5 | O | 4-Zb |
| 7-130 | H | (CH$_2$)$_3$ | H | 2-Ph-Pym-5 | O | 4-Zb |
| 7-131 | H | (CH$_2$)$_3$ | H | 2-MeO-Pym-5 | O | 4-Zb |
| 7-132 | H | (CH$_2$)$_3$ | H | 2-EtO-Pym-5 | O | 4-Zb |
| 7-133 | H | (CH$_2$)$_3$ | H | 2-iPrO-Pym-5 | O | 4-Zb |
| 7-134 | H | (CH$_2$)$_3$ | H | 2-MeS-Pym-5 | O | 4-Zb |
| 7-135 | H | (CH$_2$)$_3$ | H | 2-EtS-Pym-5 | O | 4-Zb |
| 7-136 | H | (CH$_2$)$_3$ | H | 2-iPrS-Pym-5 | O | 4-Zb |
| 7-137 | H | (CH$_2$)$_3$ | H | 2-PhS-Pym-5 | O | 4-Zb |
| 7-138 | H | (CH$_2$)$_3$ | H | 2-MeSO$_2$-Pym-5 | O | 4-Zb |
| 7-139 | H | (CH$_2$)$_3$ | H | 2-EtSO$_2$-Pym-5 | O | 4-Zb |
| 7-140 | H | (CH$_2$)$_3$ | H | 2-iPrSO$_2$-Pym-5 | O | 4-Zb |
| 7-141 | H | (CH$_2$)$_3$ | H | 2-PhSO$_2$-Pym-5 | O | 4-Zb |
| 7-142 | H | (CH$_2$)$_3$ | H | Ind-2 | O | 4-Zb |
| 7-143 | H | (CH$_2$)$_3$ | H | Ind-3 | O | 4-Zb |
| 7-144 | H | (CH$_2$)$_3$ | H | 1-Me-Ind-2 | O | 4-Zb |
| 7-145 | H | (CH$_2$)$_3$ | H | 1-Me-Ind-3 | O | 4-Zb |
| 7-146 | H | (CH$_2$)$_3$ | H | Bimid-2 | O | 4-Zb |
| 7-147 | H | (CH$_2$)$_3$ | H | Boxa-2 | O | 4-Zb |
| 7-148 | H | (CH$_2$)$_3$ | H | Bthiz-2 | O | 4-Zb |
| 7-149 | H | (CH$_2$)$_3$ | H | Quin-2 | O | 4-Zb |
| 7-150 | H | (CH$_2$)$_3$ | H | Quin-3 | O | 4-Zb |
| 7-151 | H | (CH$_2$)$_3$ | H | Quin-4 | O | 4-Zb |
| 7-152 | H | (CH$_2$)$_3$ | H | iQuin-1 | O | 4-Zb |
| 7-153 | H | (CH$_2$)$_3$ | H | iQuin-3 | O | 4-Zb |
| 7-154 | H | (CH$_2$)$_3$ | H | iQuin-4 | O | 4-Zb |
| 7-155 | H | (CH$_2$)$_3$ | H | 3-MeO-Ph | O | 4-Zb |
| 7-156 | H | (CH$_2$)$_3$ | H | 4-MeO-Ph | O | 4-Zb |
| 7-157 | H | (CH$_2$)$_3$ | H | 3-EtO-Ph | O | 4-Zb |
| 7-158 | H | (CH$_2$)$_3$ | H | 4-EtO-Ph | O | 4-Zb |
| 7-159 | H | (CH$_2$)$_3$ | H | 3-iPrO-Ph | O | 4-Zb |
| 7-160 | H | (CH$_2$)$_3$ | H | 4-iPrO-Ph | O | 4-Zb |
| 7-161 | H | (CH$_2$)$_3$ | H | 3-MeS-Ph | O | 4-Zb |
| 7-162 | H | (CH$_2$)$_3$ | H | 4-MeS-Ph | O | 4-Zb |
| 7-163 | H | (CH$_2$)$_3$ | H | 3-EtS-Ph | O | 4-Zb |
| 7-164 | H | (CH$_2$)$_3$ | H | 4-EtS-Ph | O | 4-Zb |
| 7-165 | H | (CH$_2$)$_3$ | H | 3-iPrS-Ph | O | 4-Zb |
| 7-166 | H | (CH$_2$)$_3$ | H | 4-iPrS-Ph | O | 4-Zb |
| 7-167 | H | (CH$_2$)$_3$ | H | 3-MeSO$_2$-Ph | O | 4-Zb |
| 7-168 | H | (CH$_2$)$_3$ | H | 4-MeSO$_2$-Ph | O | 4-Zb |
| 7-169 | H | (CH$_2$)$_3$ | H | 3-EtSO$_2$-Ph | O | 4-Zb |
| 7-170 | H | (CH$_2$)$_3$ | H | 4-EtSO$_2$-Ph | O | 4-Zb |
| 7-171 | H | (CH$_2$)$_3$ | H | 3-iPrSO$_2$-Ph | O | 4-Zb |
| 7-172 | H | (CH$_2$)$_3$ | H | 4-iPrSO$_2$-Ph | O | 4-Zb |
| 7-173 | H | (CH$_2$)$_3$ | H | 3-(1-Me-Imid-4)Ph | O | 4-Zb |
| 7-174 | H | (CH$_2$)$_3$ | H | 4-(1-Me-Imid-4)Ph | O | 4-Zb |
| 7-175 | H | (CH$_2$)$_3$ | H | 1-Me-2-Ph-Imid-4 | O | 4-Zb |
| 7-176 | H | (CH$_2$)$_3$ | H | 1,4-diMe-2-Ph-Imid-5 | O | 4-Zb |
| 7-177 | H | (CH$_2$)$_3$ | H | 1,5-diMe-2-Ph-Imid-4 | O | 4-Zb |
| 7-178 | H | (CH$_2$)$_3$ | H | 3,4-MdO-Ph | O | 4-Zb |
| 7-179 | H | (CH$_2$)$_3$ | H | 4-(4-MeO-Ph)Ph | O | 4-Zb |
| 7-180 | H | (CH$_2$)$_3$ | H | 4-(3,4-MdO-Ph)Ph | O | 4-Zb |
| 7-181 | H | (CH$_2$)$_3$ | H | 4-[PhSO$_2$-N(Me)]Ph | O | 4-Zb |
| 7-182 | H | (CH$_2$)$_3$ | H | 4-[(Pyr-3)SO$_2$-N(Me)]Ph | O | 4-Zb |
| 7-183 | H | (CH$_2$)$_3$ | H | 4-(PhSO$_2$NH)Ph | O | 4-Zb |
| 7-184 | H | (CH$_2$)$_3$ | H | 4-[(Pyr-3)SO$_2$-NH]Ph | O | 4-Zb |
| 7-185 | H | (CH$_2$)$_3$ | H | 4-[(Pyr-2)SO$_2$]Ph | O | 4-Zb |
| 7-186 | H | (CH$_2$)$_3$ | H | 4-[(Pyr-3)SO$_2$]Ph | O | 4-Zb |
| 7-187 | H | (CH$_2$)$_3$ | H | 4-[(Pyr-2)SO$_2$-N(Me)]Ph | O | 4-Zb |
| 7-188 | H | (CH$_2$)$_3$ | H | 4-[(Pyr-2)SO$_2$-NH]Ph | O | 4-Zb |
| 7-189 | H | (CH$_2$)$_3$ | H | 4-(4-Me-Ph)Ph | O | 4-Zb |
| 7-190 | H | (CH$_2$)$_3$ | H | 4-(4-F-Ph)Ph | O | 4-Zb |
| 7-191 | H | (CH$_2$)$_3$ | H | 4-(4-CF$_3$-Ph)Ph | O | 4-Zb |
| 7-192 | H | (CH$_2$)$_3$ | H | 2-[4-Me-PhSO$_2$-N(Me)]-Pyr-5 | O | 4-Zb |
| 7-193 | H | (CH$_2$)$_3$ | H | 2-HO-Pyr-5 | O | 4-Zb |
| 7-194 | H | (CH$_2$)$_3$ | H | 2-BzO-Pyr-5 | O | 4-Zb |
| 7-195 | H | (CH$_2$)$_3$ | H | 4-[(Pyr-4)SO$_2$]Ph | O | 4-Zb |
| 7-196 | H | (CH$_2$)$_3$ | H | 4-(2,4-diMeO-Ph)Ph | O | 4-Zb |
| 7-197 | H | (CH$_2$)$_3$ | H | 4-(2,5-diMeO-Ph)Ph | O | 4-Zb |
| 7-198 | H | (CH$_2$)$_3$ | H | 3-HO-Ph | O | 4-Zb |
| 7-199 | H | (CH$_2$)$_3$ | H | 4-HO-Ph | O | 4-Zb |
| 7-200 | H | (CH$_2$)$_3$ | H | 5-AcO-2-HO-3,4,6-triMe-Ph | O | 4-Zb |
| 7-201 | H | (CH$_2$)$_3$ | H | 4-HO-3,5-diMe-Ph | O | 4-Zb |
| 7-202 | H | (CH$_2$)$_3$ | H | 3-AcO-Ph | O | 4-Zb |
| 7-203 | H | (CH$_2$)$_3$ | H | 4-AcO-Ph | O | 4-Zb |

TABLE 8

| Cpd. No. | R¹ | R² | R³ | X | Y | Z |
|---|---|---|---|---|---|---|
| 8-1 | Me | (CH$_2$)$_3$ | H | Ph | O | 4-Zb |
| 8-2 | Me | (CH$_2$)$_3$ | H | Np-1 | O | 4-Zb |
| 8-3 | Me | (CH$_2$)$_3$ | H | Np-2 | O | 4-Zb |
| 8-4 | Me | (CH$_2$)$_3$ | H | 4-Me—Ph | O | 4-Zb |
| 8-5 | Me | (CH$_2$)$_3$ | H | 4-Et—Ph | O | 4-Zb |
| 8-6 | Me | (CH$_2$)$_3$ | H | 3-iPr—Ph | O | 4-Zb |
| 8-7 | Me | (CH$_2$)$_3$ | H | 4-iPr—Ph | O | 4-Zb |
| 8-8 | Me | (CH$_2$)$_3$ | H | 3-tBu—Ph | O | 4-Zb |
| 8-9 | Me | (CH$_2$)$_3$ | H | 4-tBu—Ph | O | 4-Zb |
| 8-10 | Me | (CH$_2$)$_3$ | H | 3-Cl—Ph | O | 4-Zb |
| 8-11 | Me | (CH$_2$)$_3$ | H | 4-Cl—Ph | O | 4-Zb |
| 8-12 | Me | (CH$_2$)$_3$ | H | 3-Br—Ph | O | 4-Zb |
| 8-13 | Me | (CH$_2$)$_3$ | H | 4-Br—Ph | O | 4-Zb |
| 8-14 | Me | (CH$_2$)$_3$ | H | 3-Ph—Ph | O | 4-Zb |
| 8-15 | Me | (CH$_2$)$_3$ | H | 4-Ph—Ph | O | 4-Zb |
| 8-16 | Me | (CH$_2$)$_3$ | H | 3-Bz—Ph | O | 4-Zb |
| 8-17 | Me | (CH$_2$)$_3$ | H | 4-Bz—Ph | O | 4-Zb |
| 8-18 | Me | (CH$_2$)$_3$ | H | 3-PhO—Ph | O | 4-Zb |
| 8-19 | Me | (CH$_2$)$_3$ | H | 4-PhO—Ph | O | 4-Zb |
| 8-20 | Me | (CH$_2$)$_3$ | H | 3-PhS—Ph | O | 4-Zb |
| 8-21 | Me | (CH$_2$)$_3$ | H | 4-PhS—Ph | O | 4-Zb |
| 8-22 | Me | (CH$_2$)$_3$ | H | 3-PhSO$_2$—Ph | O | 4-Zb |
| 8-23 | Me | (CH$_2$)$_3$ | H | 4-PhSO$_2$—Ph | O | 4-Zb |
| 8-24 | Me | (CH$_2$)$_3$ | H | 3-(Imid-1)Ph | O | 4-Zb |
| 8-25 | Me | (CH$_2$)$_3$ | H | 4-(Imid-1)Ph | O | 4-Zb |
| 8-26 | Me | (CH$_2$)$_3$ | H | 3-(Imid-4)Ph | O | 4-Zb |
| 8-27 | Me | (CH$_2$)$_3$ | H | 4-(Imid-4)Ph | O | 4-Zb |
| 8-28 | Me | (CH$_2$)$_3$ | H | 3-(Fur-2)Ph | O | 4-Zb |
| 8-29 | Me | (CH$_2$)$_3$ | H | 4-(Fur-2)Ph | O | 4-Zb |
| 8-30 | Me | (CH$_2$)$_3$ | H | 3-(Thi-2)Ph | O | 4-Zb |
| 8-31 | Me | (CH$_2$)$_3$ | H | 4-(Thi-2)Ph | O | 4-Zb |
| 8-32 | Me | (CH$_2$)$_3$ | H | 3-(Thi-3)Ph | O | 4-Zb |
| 8-33 | Me | (CH$_2$)$_3$ | H | 4-(Thi-3)Ph | O | 4-Zb |
| 8-34 | Me | (CH$_2$)$_3$ | H | 3-(Pyr-2)Ph | O | 4-Zb |
| 8-35 | Me | (CH$_2$)$_3$ | H | 4-(Pyr-2)Ph | O | 4-Zb |
| 8-36 | Me | (CH$_2$)$_3$ | H | 3-(Pyr-3)Ph | O | 4-Zb |
| 8-37 | Me | (CH$_2$)$_3$ | H | 4-(Pyr-3)Ph | O | 4-Zb |
| 8-38 | Me | (CH$_2$)$_3$ | H | 3-(Pyr-4)Ph | O | 4-Zb |
| 8-39 | Me | (CH$_2$)$_3$ | H | 4-(Pyr-4)Ph | O | 4-Zb |
| 8-40 | Me | (CH$_2$)$_3$ | H | 3-(Oxa-2)Ph | O | 4-Zb |
| 8-41 | Me | (CH$_2$)$_3$ | H | 4-(Oxa-2)Ph | O | 4-Zb |
| 8-42 | Me | (CH$_2$)$_3$ | H | 3-(Oxa-4)Ph | O | 4-Zb |
| 8-43 | Me | (CH$_2$)$_3$ | H | 4-(Oxa-4)Ph | O | 4-Zb |
| 8-44 | Me | (CH$_2$)$_3$ | H | 3-(Oxa-5)Ph | O | 4-Zb |
| 8-45 | Me | (CH$_2$)$_3$ | H | 4-(Oxa-5)Ph | O | 4-Zb |
| 8-46 | Me | (CH$_2$)$_3$ | H | 3-(Thiz-2)Ph | O | 4-Zb |
| 8-47 | Me | (CH$_2$)$_3$ | H | 4-(Thiz-2)Ph | O | 4-Zb |
| 8-48 | Me | (CH$_2$)$_3$ | H | 3-(Thiz-4)Ph | O | 4-Zb |

TABLE 8-continued

| Cpd. No. | R¹ | R² | R³ | X | Y | Z |
|---|---|---|---|---|---|---|
| 8-49 | Me | (CH$_2$)$_3$ | H | 4-(Thiz-4)Ph | O | 4-Zb |
| 8-50 | Me | (CH$_2$)$_3$ | H | 3-(Thiz-5)Ph | O | 4-Zb |
| 8-51 | Me | (CH$_2$)$_3$ | H | 4-(Thiz-5)Ph | O | 4-Zb |
| 8-52 | Me | (CH$_2$)$_3$ | H | 1-Me-Pyrr-2 | O | 4-Zb |
| 8-53 | Me | (CH$_2$)$_3$ | H | 1-Ph-Pyrr-2 | O | 4-Zb |
| 8-54 | Me | (CH$_2$)$_3$ | H | 1-Bz-Pyrr-2 | O | 4-Zb |
| 8-55 | Me | (CH$_2$)$_3$ | H | 5-Me-Fur-2 | O | 4-Zb |
| 8-56 | Me | (CH$_2$)$_3$ | H | 5-Ph-Fur-2 | O | 4-Zb |
| 8-57 | Me | (CH$_2$)$_3$ | H | 5-Me-Thi-2 | O | 4-Zb |
| 8-58 | Me | (CH$_2$)$_3$ | H | 5-Ph-Thi-2 | O | 4-Zb |
| 8-59 | Me | (CH$_2$)$_3$ | H | 5-Me-Thi-3 | O | 4-Zb |
| 8-60 | Me | (CH$_2$)$_3$ | H | 5-Ph-Thi-3 | O | 4-Zb |
| 8-61 | Me | (CH$_2$)$_3$ | H | 1-Me-Pyza-3 | O | 4-Zb |
| 8-62 | Me | (CH$_2$)$_3$ | H | 1-Ph-Pyza-3 | O | 4-Zb |
| 8-63 | Me | (CH$_2$)$_3$ | H | 1-Me-Imid-2 | O | 4-Zb |
| 8-64 | Me | (CH$_2$)$_3$ | H | 1-Ph-Imid-2 | O | 4-Zb |
| 8-65 | Me | (CH$_2$)$_3$ | H | 1-Me-Imid-4 | O | 4-Zb |
| 8-66 | Me | (CH$_2$)$_3$ | H | 1-Ph-Imid-4 | O | 4-Zb |
| 8-67 | Me | (CH$_2$)$_3$ | H | Oxa-4 | O | 4-Zb |
| 8-68 | Me | (CH$_2$)$_3$ | H | Oxa-5 | O | 4-Zb |
| 8-69 | Me | (CH$_2$)$_3$ | H | 2-Me-Oxa-4 | O | 4-Zb |
| 8-70 | Me | (CH$_2$)$_3$ | H | 2-Ph-Oxa-4 | O | 4-Zb |
| 8-71 | Me | (CH$_2$)$_3$ | H | 2-Me-Oxa-5 | O | 4-Zb |
| 8-72 | Me | (CH$_2$)$_3$ | H | 2-Ph-Oxa-5 | O | 4-Zb |
| 8-73 | Me | (CH$_2$)$_3$ | H | 4-Me-2-Ph-Oxa-5 | O | 4-Zb |
| 8-74 | Me | (CH$_2$)$_3$ | H | 5-Me-2-Ph-Oxa-4 | O | 4-Zb |
| 8-75 | Me | (CH$_2$)$_3$ | H | Thiz-4 | O | 4-Zb |
| 8-76 | Me | (CH$_2$)$_3$ | H | Thiz-5 | O | 4-Zb |
| 8-77 | Me | (CH$_2$)$_3$ | H | 2-Me-Thiz-4 | O | 4-Zb |
| 8-78 | Me | (CH$_2$)$_3$ | H | 2-Ph-Thiz-4 | O | 4-Zb |
| 8-79 | Me | (CH$_2$)$_3$ | H | 2-Me-Thiz-5 | O | 4-Zb |
| 8-80 | Me | (CH$_2$)$_3$ | H | 2-Ph-Thiz-5 | O | 4-Zb |
| 8-81 | Me | (CH$_2$)$_3$ | H | 4-Me-2-Ph-Thiz-5 | O | 4-Zb |
| 8-82 | Me | (CH$_2$)$_3$ | H | 5-Me-2-Ph-Thiz-4 | O | 4-Zb |
| 8-83 | Me | (CH$_2$)$_3$ | H | 1-Me-Pyza-4 | O | 4-Zb |
| 8-84 | Me | (CH$_2$)$_3$ | H | 1-Ph-Pyza-4 | O | 4-Zb |
| 8-85 | Me | (CH$_2$)$_3$ | H | 2-Me-Isox-4 | O | 4-Zb |
| 8-86 | Me | (CH$_2$)$_3$ | H | 2-Ph-Isox-4 | O | 4-Zb |
| 8-87 | Me | (CH$_2$)$_3$ | H | Pyr-2 | O | 4-Zb |
| 8-88 | Me | (CH$_2$)$_3$ | H | Pyr-3 | O | 4-Zb |
| 8-89 | Me | (CH$_2$)$_3$ | H | Pyr-4 | O | 4-Zb |
| 8-90 | Me | (CH$_2$)$_3$ | H | 3-Me-Pyr-5 | O | 4-Zb |
| 8-91 | Me | (CH$_2$)$_3$ | H | 3-Et-Pyr-5 | O | 4-Zb |
| 8-92 | Me | (CH$_2$)$_3$ | H | 3-Ph-Pyr-5 | O | 4-Zb |
| 8-93 | Me | (CH$_2$)$_3$ | H | 2-Me-Pyr-5 | O | 4-Zb |
| 8-94 | Me | (CH$_2$)$_3$ | H | 2-Et-Pyr-5 | O | 4-Zb |
| 8-95 | Me | (CH$_2$)$_3$ | H | 2-Ph-Pyr-5 | O | 4-Zb |
| 8-96 | Me | (CH$_2$)$_3$ | H | 2-MeO-Pyr-5 | O | 4-Zb |
| 8-97 | Me | (CH$_2$)$_3$ | H | 2-EtO-Pyr-5 | O | 4-Zb |
| 8-98 | Me | (CH$_2$)$_3$ | H | 2-iPrO-Pyr-5 | O | 4-Zb |
| 8-99 | Me | (CH$_2$)$_3$ | H | 2-MeS-Pyr-5 | O | 4-Zb |
| 8-100 | Me | (CH$_2$)$_3$ | H | 2-EtS-Pyr-5 | O | 4-Zb |
| 8-101 | Me | (CH$_2$)$_3$ | H | 2-iPrS-Pyr-5 | O | 4-Zb |
| 8-102 | Me | (CH$_2$)$_3$ | H | 2-MeSO$_2$-Pyr-5 | O | 4-Zb |
| 8-103 | Me | (CH$_2$)$_3$ | H | 2-EtSO$_2$-Pyr-5 | O | 4-Zb |
| 8-104 | Me | (CH$_2$)$_3$ | H | 2-iPrSO$_2$-Pyr-5 | O | 4-Zb |
| 8-105 | Me | (CH$_2$)$_3$ | H | 2-Bz-Pyr-5 | O | 4-Zb |
| 8-106 | Me | (CH$_2$)$_3$ | H | 2-PhO-Pyr-5 | O | 4-Zb |
| 8-107 | Me | (CH$_2$)$_3$ | H | 2-PhS-Pyr-5 | O | 4-Zb |
| 8-108 | Me | (CH$_2$)$_3$ | H | 2-PhSO$_2$-Pyr-5 | O | 4-Zb |
| 8-109 | Me | (CH$_2$)$_3$ | H | 3-Me-Pyr-6 | O | 4-Zb |
| 8-110 | Me | (CH$_2$)$_3$ | H | 3-Ph-Pyr-6 | O | 4-Zb |
| 8-111 | Me | (CH$_2$)$_3$ | H | 2-Me-Pyr-6 | O | 4-Zb |
| 8-112 | Me | (CH$_2$)$_3$ | H | 2-Ph-Pyr-6 | O | 4-Zb |
| 8-113 | Me | (CH$_2$)$_3$ | H | 2-Me-Pym-4 | O | 4-Zb |
| 8-114 | Me | (CH$_2$)$_3$ | H | 2-Ph-Pym-4 | O | 4-Zb |
| 8-115 | Me | (CH$_2$)$_3$ | H | 2-MeO-Pym-4 | O | 4-Zb |
| 8-116 | Me | (CH$_2$)$_3$ | H | 2-EtO-Pym-4 | O | 4-Zb |
| 8-117 | Me | (CH$_2$)$_3$ | H | 2-iPrO-Pym-4 | O | 4-Zb |
| 8-118 | Me | (CH$_2$)$_3$ | H | 2-MeS-Pym-4 | O | 4-Zb |
| 8-119 | Me | (CH$_2$)$_3$ | H | 2-EtS-Pym-4 | O | 4-Zb |
| 8-120 | Me | (CH$_2$)$_3$ | H | 2-iPrS-Pym-4 | O | 4-Zb |
| 8-121 | Me | (CH$_2$)$_3$ | H | 6-MeS-Pym-4 | O | 4-Zb |
| 8-122 | Me | (CH$_2$)$_3$ | H | 6-EtS-Pym-4 | O | 4-Zb |
| 8-123 | Me | (CH$_2$)$_3$ | H | 6-iPrS-Pym-4 | O | 4-Zb |
| 8-124 | Me | (CH$_2$)$_3$ | H | 2-PhS-Pym-4 | O | 4-Zb |
| 8-125 | Me | (CH$_2$)$_3$ | H | 2-MeSO$_2$-Pym-4 | O | 4-Zb |
| 8-126 | Me | (CH$_2$)$_3$ | H | 2-EtSO$_2$-Pym-4 | O | 4-Zb |
| 8-127 | Me | (CH$_2$)$_3$ | H | 2-iPrSO$_2$-Pym-4 | O | 4-Zb |
| 8-128 | Me | (CH$_2$)$_3$ | H | 2-PhSO$_2$-Pym-4 | O | 4-Zb |
| 8-129 | Me | (CH$_2$)$_3$ | H | 2-Me-Pym-5 | O | 4-Zb |
| 8-130 | Me | (CH$_2$)$_3$ | H | 2-Ph-Pym-5 | O | 4-Zb |
| 8-131 | Me | (CH$_2$)$_3$ | H | 2-MeO-Pym-5 | O | 4-Zb |
| 8-132 | Me | (CH$_2$)$_3$ | H | 2-EtO-Pym-5 | O | 4-Zb |
| 8-133 | Me | (CH$_2$)$_3$ | H | 2-iPrO-Pym-5 | O | 4-Zb |
| 8-134 | Me | (CH$_2$)$_3$ | H | 2-MeS-Pym-5 | O | 4-Zb |
| 8-135 | Me | (CH$_2$)$_3$ | H | 2-EtS-Pym-5 | o | 4-Zb |
| 8-136 | Me | (CH$_2$)$_3$ | H | 2-iPrS-Pym-5 | O | 4-Zb |
| 8-137 | Me | (CH$_2$)$_3$ | H | 2-PhS-Pym-5 | O | 4-Zb |
| 8-138 | Me | (CH$_2$)$_3$ | H | 2-MeSO$_2$-Pym-5 | O | 4-Zb |
| 8-139 | Me | (CH$_2$)$_3$ | H | 2-EtSO$_2$-Pym-5 | O | 4-Zb |
| 8-140 | Me | (CH$_2$)$_3$ | H | 2-iPrSO$_2$-Pym-5 | O | 4-Zb |
| 8-141 | Me | (CH$_2$)$_3$ | H | 2-PhSO$_2$-Pym-5 | O | 4-Zb |
| 8-142 | Me | (CH$_2$)$_3$ | H | Ind-2 | O | 4-Zb |
| 8-143 | Me | (CH$_2$)$_3$ | H | Ind-3 | O | 4-Zb |
| 8-144 | Me | (CH$_2$)$_3$ | H | 1-Me-Ind-2 | O | 4-Zb |
| 8-145 | Me | (CH$_2$)$_3$ | H | 1-Me-Ind-3 | O | 4-Zb |
| 8-146 | Me | (CH$_2$)$_3$ | H | Bimid-2 | O | 4-Zb |
| 8-147 | Me | (CH$_2$)$_3$ | H | Boxa-2 | O | 4-Zb |
| 8-148 | Me | (CH$_2$)$_3$ | H | Bthiz-2 | O | 4-Zb |
| 8-149 | Me | (CH$_2$)$_3$ | H | Quin-2 | O | 4-Zb |
| 8-150 | Me | (CH$_2$)$_3$ | H | Quin-3 | O | 4-Zb |
| 8-151 | Me | (CH$_2$)$_3$ | H | Quin-4 | O | 4-Zb |
| 8-152 | Me | (CH$_2$)$_3$ | H | iQuin-1 | O | 4-Zb |
| 8-153 | Me | (CH$_2$)$_3$ | H | iQuin-3 | O | 4-Zb |
| 8-154 | Me | (CH$_2$)$_3$ | H | iQuin-4 | O | 4-Zb |
| 8-155 | Me | (CH$_2$)$_3$ | H | 3-MeO-Ph | O | 4-Zb |
| 8-156 | Me | (CH$_2$)$_3$ | H | 4-MeO-PH | O | 4-Zb |
| 8-157 | Me | (CH$_2$)$_3$ | H | 3-EtO-Ph | O | 4-Zb |
| 8-158 | Me | (CH$_2$)$_3$ | H | 4-EtO-Ph | O | 4-Zb |
| 8-159 | Me | (CH$_2$)$_3$ | H | 3-iPrO-Ph | O | 4-Zb |
| 8-160 | Me | (CH$_2$)$_3$ | H | 4-iPrO-Ph | O | 4-Zb |
| 8-161 | Me | (CH$_2$)$_3$ | H | 3-MeS-Ph | O | 4-Zb |
| 8-162 | Me | (CH$_2$)$_3$ | H | 4-MeS-Ph | O | 4-Zb |
| 8-163 | Me | (CH$_2$)$_3$ | H | 3-EtS-Ph | O | 4-Zb |
| 8-164 | Me | (CH$_2$)$_3$ | H | 4-EtS-Ph | O | 4-Zb |
| 8-165 | Me | (CH$_2$)$_3$ | H | 3-iPrS-Ph | O | 4-Zb |
| 8-166 | Me | (CH$_2$)$_3$ | H | 4-iPrS-Ph | O | 4-Zb |
| 8-167 | Me | (CH$_2$)$_3$ | H | 3-MeSO$_2$-Ph | O | 4-Zb |
| 8-168 | Me | (CH$_2$)$_3$ | H | 4-MeSO$_2$-Ph | O | 4-Zb |
| 8-169 | Me | (CH$_2$)$_3$ | H | 3-EtSO$_2$-Ph | O | 4-Zb |
| 8-170 | Me | (CH$_2$)$_3$ | H | 4-EtSO$_2$-Ph | O | 4-Zb |
| 8-171 | Me | (CH$_2$)$_3$ | H | 3-iPrSO$_2$-Ph | O | 4-Zb |
| 8-172 | Me | (CH$_2$)$_3$ | H | 4-iPrSO$_2$-Ph | O | 4-Zb |
| 8-173 | Me | (CH$_2$)$_3$ | H | 3-(1-Me-Imid-4)Ph | O | 4-Zb |
| 8-174 | Me | (CH$_2$)$_3$ | H | 4-(1-Me-Imid-4)Ph | O | 4-Zb |
| 8-175 | Me | (CH$_2$)$_3$ | H | 1-Me-2-Ph-Imid-4 | O | 4-Zb |
| 8-176 | Me | (CH$_2$)$_3$ | H | 1,4-diMe-2-Ph-Imid-5 | O | 4-Zb |
| 8-177 | Me | (CH$_2$)$_3$ | H | 1,5-diMe-2-Ph-Imid-4 | O | 4-Zb |
| 8-178 | Me | (CH$_2$)$_3$ | H | 3,4-MdO-Ph | O | 4-Zb |
| 8-179 | Me | (CH$_2$)$_3$ | H | 4-(4-MeO-Ph)Ph | O | 4-Zb |
| 8-180 | Me | (CH$_2$)$_3$ | H | 4-(3,4-MdO-Ph)Ph | O | 4-Zb |
| 8-181 | Me | (CH$_2$)$_3$ | H | 4-[PhSO$_2$N(Me)]Ph | O | 4-Zb |
| 8-182 | Me | (CH$_2$)$_3$ | H | 4-[(Pyr-3)SO$_2$-N(Me)]Ph | O | 4-Zb |
| 8-183 | Me | (CH$_2$)$_3$ | H | 4-(PhSO$_2$-NH)Ph | O | 4-Zb |
| 8-184 | Me | (CH$_2$)$_3$ | H | 4-[(Pyr-3)SO$_2$-NH]Ph | O | 4-Zb |
| 8-185 | Me | (CH$_2$)$_3$ | H | 4-[(Pyr-2)- | O | 4-Zb |

TABLE 8-continued

| Cpd. No. | R¹ | R² | R³ | X | Y | Z |
|---|---|---|---|---|---|---|
| 8-186 | Me | (CH₂)₃ | H | 4-[(Pyr-3)-SO₂]Ph | O | 4-Zb |
| 8-187 | Me | (CH₂)₃ | H | 4-[(Pyr-2)SO₂—N(Me)]Ph | O | 4-Zb |
| 8-188 | Me | (CH₂)₃ | H | 4-[(Pyr-2)SO₂—NH]Ph | O | 4-Zb |
| 8-189 | Me | (CH₂)₃ | H | 4-(4-Me—Ph)Ph | O | 4-Zb |
| 8-190 | Me | (CH₂)₃ | H | 4-(4-F—Ph)Ph | O | 4-Zb |
| 8-191 | Me | (CH₂)₃ | H | 4-(4-CF₃—Ph)Ph | O | 4-Zb |
| 8-192 | Me | (CH₂)₃ | H | 2-[4-Me—PhSO₂—N(Me)]Pyr-5 | O | 4-Zb |
| 8-193 | Me | (CH₂)₃ | H | 2-HO—Pyr-5 | O | 4-Zb |
| 8-194 | Me | (CH₂)₃ | H | 2-BzO—Pyr-5 | O | 4-Zb |
| 8-195 | Me | (CH₂)₃ | H | 4-[(Pyr-4)SO₂]Ph | O | 4-Zb |
| 8-196 | Me | (CH₂)₃ | H | 4-(2,4-diMeO—Ph)Ph | O | 4-Zb |
| 8-197 | Me | (CH₂)₃ | H | 4-(2,5-diMeO—Ph)Ph | O | 4-Zb |
| 8-198 | Me | (CH₂)₃ | H | 3-HO—Ph | O | 4-Zb |
| 8-199 | Me | (CH₂)₃ | H | 4-HO—Ph | O | 4-Zb |
| 8-200 | Me | (CH₂)₃ | H | 5-AcO-2-HO-3,4,6-triMe—Ph | O | 4-Zb |
| 8-201 | Me | (CH₂)₃ | H | 4-HO-3,5-diMe—Ph | O | 4-Zb |
| 8-202 | Me | (CH₂)₃ | H | 3-AcO—Ph | O | 4-Zb |
| 8-203 | Me | (CH₂)₃ | H | 4-AcO—Ph | O | 4-Zb |

TABLE 9

| Cpd. No. | R¹ | R² | R³ | X | Y | Z |
|---|---|---|---|---|---|---|
| 9-1 | H | CH(Me)CH₂ | H | Ph | O | 4-Zb |
| 9-2 | H | CH(Me)CH₂ | H | Np-1 | O | 4-Zb |
| 9-3 | H | CH(Me)CH₂ | H | Np-2 | O | 4-Zb |
| 9-4 | H | CH(Me)CH₂ | H | 4-Me-Ph | O | 4-Zb |
| 9-5 | H | CH(Me)CH₂ | H | 4-Et-Ph | O | 4-Zb |
| 9-6 | H | CH(Me)CH₂ | H | 3-iPr-Ph | O | 4-Zb |
| 9-7 | H | CH(Me)CH₂ | H | 4-iPr-Ph | O | 4-Zb |
| 9-8 | H | CH(Me)CH₂ | H | 3-tBu-Ph | O | 4-Zb |
| 9-9 | H | CH(Me)CH₂ | H | 4-tBu-Ph | O | 4-Zb |
| 9-10 | H | CH(Me)CH₂ | H | 3-Cl-Ph | O | 4-Zb |
| 9-11 | H | CH(Me)CH₂ | H | 4-Cl-Ph | O | 4-Zb |
| 9-12 | H | CH(Me)CH₂ | H | 3-Br-Ph | O | 4-Zb |
| 9-13 | H | CH(Me)CH₂ | H | 4-Br-Ph | O | 4-Zb |
| 9-14 | H | CH(Me)CH₂ | H | 3-Ph-Ph | O | 4-Zb |
| 9-15 | H | CH(Me)CH₂ | H | 4-Ph-Ph | O | 4-Zb |
| 9-16 | H | CH(Me)CH₂ | H | 3-Bz-Ph | O | 4-Zb |
| 9-17 | H | CH(Me)CH₂ | H | 4-Bz-Ph | O | 4-Zb |
| 9-18 | H | CH(Me)CH₂ | H | 3-PhO-Ph | O | 4-Zb |
| 9-19 | H | CH(Me)CH₂ | H | 4-PhO-Ph | O | 4-Zb |
| 9-20 | H | CH(Me)CH₂ | H | 3-PhS-Ph | O | 4-Zb |
| 9-21 | H | CH(Me)CH₂ | H | 4-PhS-Ph | O | 4-Zb |
| 9-22 | H | CH(Me)CH₂ | H | 3-PhSO₂-Ph | O | 4-Zb |
| 9-23 | H | CH(Me)CH₂ | H | 4-PhSO₂-Ph | O | 4-Zb |
| 9-24 | H | CH(Me)CH₂ | H | 3-(Imid-1)Ph | O | 4-Zb |
| 9-25 | H | CH(Me)CH₂ | H | 4-(Imid-1)Ph | O | 4-Zb |
| 9-26 | H | CH(Me)CH₂ | H | 3-(Imid-4)Ph | O | 4-Zb |
| 9-27 | H | CH(Me)CH₂ | H | 4-(Imid-4)Ph | O | 4-Zb |
| 9-28 | H | CH(Me)CH₂ | H | 3-(Fur-2)Ph | O | 4-Zb |
| 9-29 | H | CH(Me)CH₂ | H | 4-(Fur-2)Ph | O | 4-Zb |
| 9-30 | H | CH(Me)CH₂ | H | 3-(Thi-2)Ph | O | 4-Zb |
| 9-31 | H | CH(Me)CH₂ | H | 4-(Thi-2)Ph | O | 4-Zb |
| 9-32 | H | CH(Me)CH₂ | H | 3-(Thi-3)Ph | O | 4-Zb |
| 9-33 | H | CH(Me)CH₂ | H | 4-(Thi-3)Ph | O | 4-Zb |
| 9-34 | H | CH(Me)CH₂ | H | 3-(Pyr-2)Ph | O | 4-Zb |
| 9-35 | H | CH(Me)CH₂ | H | 4-(Pyr-2)Ph | O | 4-Zb |
| 9-36 | H | CH(Me)CH₂ | H | 3-(Pyr-3)Ph | O | 4-Zb |
| 9-37 | H | CH(Me)CH₂ | H | 4-(Pyr-3)Ph | O | 4-Zb |
| 9-38 | H | CH(Me)CH₂ | H | 3-(Pyr-4)Ph | O | 4-Zb |
| 9-39 | H | CH(Me)CH₂ | H | 4-(Pyr-4)Ph | O | 4-Zb |
| 9-40 | H | CH(Me)CH₂ | H | 3-(Oxa-2)Ph | O | 4-Zb |
| 9-41 | H | CH(Me)CH₂ | H | 4-(Oxa-2)Ph | O | 4-Zb |
| 9-42 | H | CH(Me)CH₂ | H | 3-(Oxa-4)Ph | O | 4-Zb |
| 9-43 | H | CH(Me)CH₂ | H | 4-(Oxa-4)Ph | O | 4-Zb |
| 9-44 | H | CH(Me)CH₂ | H | 3-(Oxa-5)Ph | O | 4-Zb |
| 9-45 | H | CH(Me)CH₂ | H | 4-(Oxa-5)Ph | O | 4-Zb |
| 9-46 | H | CH(Me)CH₂ | H | 3-(Thiz-2)Ph | O | 4-Zb |
| 9-47 | H | CH(Me)CH₂ | H | 4-(Thiz-2)Ph | O | 4-Zb |
| 9-48 | H | CH(Me)CH₂ | H | 3-(Thiz-4)Ph | O | 4-Zb |
| 9-49 | H | CH(Me)CH₂ | H | 4-(Thiz-4)Ph | O | 4-Zb |
| 9-50 | H | CH(Me)CH₂ | H | 3-(Thiz-5)Ph | O | 4-Zb |
| 9-51 | H | CH(Me)CH₂ | H | 4-(Thiz-5)Ph | O | 4-Zb |
| 9-52 | H | CH(Me)CH₂ | H | 1-Me-Pyrr-2 | O | 4-Zb |
| 9-53 | H | CH(Me)CH₂ | H | 1-Ph-Pyrr-2 | O | 4-Zb |
| 9-54 | H | CH(Me)CH₂ | H | 1-Bz-Pyrr-2 | O | 4-Zb |
| 9-55 | H | CH(Me)CH₂ | H | 5-Me-Fur-2 | O | 4-Zb |
| 9-56 | H | CH(Me)CH₂ | H | 5-Ph-Fur-2 | O | 4-Zb |
| 9-57 | H | CH(Me)CH₂ | H | 5-Me-Thi-2 | O | 4-Zb |
| 9-58 | H | CH(Me)CH₂ | H | 5-Ph-Thi-2 | O | 4-Zb |
| 9-59 | H | CH(Me)CH₂ | H | 5-Me-Thi-3 | O | 4-Zb |
| 9-60 | H | CH(Me)CH₂ | H | 5-Ph-Thi-3 | O | 4-Zb |
| 9-61 | H | CH(Me)CH₂ | H | 1-Me-Pyza-3 | O | 4-Zb |
| 9-62 | H | CH(Me)CH₂ | H | 1-Ph-Pyza-3 | O | 4-Zb |
| 9-63 | H | CH(Me)CH₂ | H | 1-Me-Imid-2 | O | 4-Zb |
| 9-64 | H | CH(Me)CH₂ | H | 1-Ph-Imid-2 | O | 4-Zb |
| 9-65 | H | CH(Me)CH₂ | H | 1-Me-Imid-4 | O | 4-Zb |
| 9-66 | H | CH(Me)CH₂ | H | 1-Ph-Imid-4 | O | 4-Zb |
| 9-67 | H | CH(Me)CH₂ | H | Oxa-4 | O | 4-Zb |
| 9-68 | H | CH(Me)CH₂ | H | Oxa-5 | O | 4-Zb |
| 9-69 | H | CH(Me)CH₂ | H | 2-Me-Oxa-4 | O | 4-Zb |
| 9-70 | H | CH(Me)CH₂ | H | 2-Ph-Oxa-4 | O | 4-Zb |
| 9-71 | H | CH(Me)CH₂ | H | 2-Me-Oxa-5 | O | 4-Zb |
| 9-72 | H | CH(Me)CH₂ | H | 2-Ph-Oxa-5 | O | 4-Zb |
| 9-73 | H | CH(Me)CH₂ | H | 4-Me-2-Ph-Oxa-5 | O | 4-Zb |
| 9-74 | H | CH(Me)CH₂ | H | 5-Me-2-Ph-Oxa-4 | O | 4-Zb |
| 9-75 | H | CH(Me)CH₂ | H | Thiz-4 | O | 4-Zb |
| 9-76 | H | CH(Me)CH₂ | H | Thiz-5 | O | 4-Zb |
| 9-77 | H | CH(Me)CH₂ | H | 2-Me-Thiz-4 | O | 4-Zb |
| 9-78 | H | CH(Me)CH₂ | H | 2-Ph-Thiz-4 | O | 4-Zb |
| 9-79 | H | CH(Me)CH₂ | H | 2-Me-Thiz-5 | O | 4-Zb |
| 9-80 | H | CH(Me)CH₂ | H | 2-Ph-Thiz-5 | O | 4-Zb |
| 9-81 | H | CH(Me)CH₂ | H | 4-Me-2-Ph-Thiz-5 | O | 4-Zb |
| 9-82 | H | CH(Me)CH₂ | H | 5-Me-2-Ph-Thiz-4 | O | 4-Zb |
| 9-83 | H | CH(Me)CH₂ | H | 1-Me-Pyza-4 | O | 4-Zb |
| 9-84 | H | CH(Me)CH₂ | H | 1-Ph-Pyza-4 | O | 4-Zb |
| 9-85 | H | CH(Me)CH₂ | H | 2-Me-Isox-4 | O | 4-Zb |
| 9-86 | H | CH(Me)CH₂ | H | 2-Ph-Isox-4 | O | 4-Zb |
| 9-87 | H | CH(Me)CH₂ | H | Pyr-2 | O | 4-Zb |
| 9-88 | H | CH(Me)CH₂ | H | Pyr-3 | O | 4-Zb |
| 9-89 | H | CH(Me)CH₂ | H | Pyr-4 | O | 4-Zb |
| 9-90 | H | CH(Me)CH₂ | H | 3-Me-Pyr-5 | O | 4-Zb |
| 9-91 | H | CH(Me)CH₂ | H | 3-Et-Pyr-5 | O | 4-Zb |
| 9-92 | H | CH(Me)CH₂ | H | 3-Ph-Pyr-5 | O | 4-Zb |
| 9-93 | H | CH(Me)CH₂ | H | 2-Me-Pyr-5 | O | 4-Zb |
| 9-94 | H | CH(Me)CH₂ | H | 2-Et-Pyr-5 | O | 4-Zb |
| 9-95 | H | CH(Me)CH₂ | H | 2-Ph-Pyr-5 | O | 4-Zb |
| 9-96 | H | CH(Me)CH₂ | H | 2-MeO-Pyr-5 | O | 4-Zb |
| 9-97 | H | CH(Me)CH₂ | H | 2-EtO-Pyr-5 | O | 4-Zb |
| 9-98 | H | CH(Me)CH₂ | H | 2-iPrO-Pyr-5 | O | 4-Zb |
| 9-99 | H | CH(Me)CH₂ | H | 2-MeS-Pyr-5 | O | 4-Zb |
| 9-10 | H | CH(Me)CH₂ | H | 2-EtS-Pyr-5 | O | 4-Zb |
| 9-101 | H | CH(Me)CH₂ | H | 2-iPrS-Pyr-5 | O | 4-Zb |
| 9-102 | H | CH(Me)CH₂ | H | 2-MeSO₂-Pyr-5 | O | 4-Zb |
| 9-103 | H | CH(Me)CH₂ | H | 2-EtSO₂-Pyr-5 | O | 4-Zb |
| 9-104 | H | CH(Me)CH₂ | H | 2-iPrSO₂-Pyr-5 | O | 4-Zb |
| 9-105 | H | CH(Me)CH₂ | H | 2-Bz-Pyr-5 | O | 4-Zb |
| 9-106 | H | CH(Me)CH₂ | H | 2-PhO-Pyr-5 | O | 4-Zb |
| 9-107 | H | CH(Me)CH₂ | H | 2-PhS-Pyr-5 | O | 4-Zb |
| 9-108 | H | CH(Me)CH₂ | H | 2-PhSO₂-Pyr-5 | O | 4-Zb |
| 9-109 | H | CH(Me)CH₂ | H | 3-Me-Pyr-6 | O | 4-Zb |
| 9-110 | H | CH(Me)CH₂ | H | 3-Ph-Pyr-6 | O | 4-Zb |
| 9-111 | H | CH(Me)CH₂ | H | 2-Me-Pyr-6 | O | 4-Zb |
| 9-112 | H | CH(Me)CH₂ | H | 2-Ph-Pyr-6 | O | 4-Zb |
| 9-113 | H | CH(Me)CH₂ | H | 2-Me-Pym-4 | O | 4-Zb |
| 9-114 | H | CH(Me)CH₂ | H | 2-Ph-Pym-4 | O | 4-Zb |
| 9-115 | H | CH(Me)CH₂ | H | 2-MeO-Pym-4 | O | 4-Zb |
| 9-116 | H | CH(Me)CH₂ | H | 2-EtO-Pym-4 | O | 4-Zb |

TABLE 9-continued

| Cpd. No. | R¹ | R² | R³ | X | Y | Z |
|---|---|---|---|---|---|---|
| 9-117 | H | CH(Me)CH₂ | H | 2-iPrO-Pym-4 | O | 4-Zb |
| 9-118 | H | CH(Me)CH₂ | H | 2-MeS-Pym-4 | O | 4-Zb |
| 9-119 | H | CH(Me)CH₂ | H | 2-EtS-Pym-4 | O | 4-Zb |
| 9-120 | H | CH(Me)CH₂ | H | 2-iPrS-Pym-4 | O | 4-Zb |
| 9-121 | H | CH(Me)CH₂ | H | 6-MeS-Pym-4 | O | 4-Zb |
| 9-122 | H | CH(Me)CH₂ | H | 6-EtS-Pym-4 | O | 4-Zb |
| 9-123 | H | CH(Me)CH₂ | H | 6-iPrS-Pym-4 | O | 4-Zb |
| 9-124 | H | CH(Me)CH₂ | H | 2-PhS-Pym-4 | O | 4-Zb |
| 9-125 | H | CH(Me)CH₂ | H | 2-MeSO₂-Pym-4 | O | 4-Zb |
| 9-126 | H | CH(Me)CH₂ | H | 2-EtSO₂-Pym-4 | O | 4-Zb |
| 9-127 | H | CH(Me)CH₂ | H | 2-iPrSO₂-Pym-4 | O | 4-Zb |
| 9-128 | H | CH(Me)CH₂ | H | 2-PhSO₂-Pym-4 | O | 4-Zb |
| 9-129 | H | CH(Me)CH₂ | H | 2-Me-Pym-5 | O | 4-Zb |
| 9-130 | H | CH(Me)CH₂ | H | 2-Ph-Pym-5 | O | 4-Zb |
| 9-131 | H | CH(Me)CH₂ | H | 2-MeO-Pym-5 | O | 4-Zb |
| 9-132 | H | CH(Me)CH₂ | H | 2-EtO-Pym-5 | O | 4-Zb |
| 9-133 | H | CH(Me)CH₂ | H | 2-iPrO-Pym-5 | O | 4-Zb |
| 9-134 | H | CH(Me)CH₂ | H | 2-MeS-Pym-5 | O | 4-Zb |
| 9-135 | H | CH(Me)CH₂ | H | 2-EtS-Pym-5 | O | 4-Zb |
| 9-136 | H | CH(Me)CH₂ | H | 2-iPrS-Pym-5 | O | 4-Zb |
| 9-137 | H | CH(Me)CH₂ | H | 2-PhS-Pym-5 | O | 4-Zb |
| 9-138 | H | CH(Me)CH₂ | H | 2-MeSO₂-Pym-5 | O | 4-Zb |
| 9-139 | H | CH(Me)CH₂ | H | 2-EtSO₂-Pym-5 | O | 4-Zb |
| 9-140 | H | CH(Me)CH₂ | H | 2-iPrSO₂-Pym-5 | O | 4-Zb |
| 9-141 | H | CH(Me)CH₂ | H | 2-PhSO₂-Pym-5 | O | 4-Zb |
| 9-142 | H | CH(Me)CH₂ | H | Ind-2 | O | 4-Zb |
| 9-143 | H | CH(Me)CH₂ | H | Ind-3 | O | 4-Zb |
| 9-144 | H | CH(Me)CH₂ | H | 1-Me-Ind-2 | O | 4-Zb |
| 9-145 | H | CH(Me)CH₂ | H | 1-Me-Ind-3 | O | 4-Zb |
| 9-146 | H | CH(Me)CH₂ | H | Bimid-2 | O | 4-Zb |
| 9-147 | H | CH(Me)CH₂ | H | Boxa-2 | O | 4-Zb |
| 9-148 | H | CH(Me)CH₂ | H | Bthiz-2 | O | 4-Zb |
| 9-149 | H | CH(Me)CH₂ | H | Quin-2 | O | 4-Zb |
| 9-150 | H | CH(Me)CH₂ | H | Quin-3 | O | 4-Zb |
| 9-151 | H | CH(Me)CH₂ | H | Quin-4 | O | 4-Zb |
| 9-152 | H | CH(Me)CH₂ | H | iQuin-1 | O | 4-Zb |
| 9-153 | H | CH(Me)CH₂ | H | iQuin-3 | O | 4-Zb |
| 9-154 | H | CH(Me)CH₂ | H | iQuin-4 | O | 4-Zb |
| 9-155 | H | CH(Me)CH₂ | H | 3-MeO-Ph | O | 4-Zb |
| 9-156 | H | CH(Me)CH₂ | H | 4-MeO-Ph | O | 4-Zb |
| 9-157 | H | CH(Me)CH₂ | H | 3-EtO-Ph | O | 4-Zb |
| 9-158 | H | CH(Me)CH₂ | H | 4-EtO-Ph | O | 4-Zb |
| 9-159 | H | CH(Me)CH₂ | H | 3-iPrO-Ph | O | 4-Zb |
| 9-160 | H | CH(Me)CH₂ | H | 4-iPrO-Ph | O | 4-Zb |
| 9-161 | H | CH(Me)CH₂ | H | 3-MeS-Ph | O | 4-Zb |
| 9-162 | H | CH(Me)CH₂ | H | 4-MeS-Ph | O | 4-Zb |
| 9-163 | H | CH(Me)CH₂ | H | 3-EtS-Ph | O | 4-Zb |
| 9-164 | H | CH(Me)CH₂ | H | 4-EtS-Ph | O | 4-Zb |
| 9-165 | H | CH(Me)CH₂ | H | 3-iPrS-Ph | O | 4-Zb |
| 9-166 | H | CH(Me)CH₂ | H | 4-iPrS-Ph | O | 4-Zb |
| 9-167 | H | CH(Me)CH₂ | H | 3-MeSO₂-Ph | O | 4-Zb |
| 9-168 | H | CH(Me)CH₂ | H | 4-MeSO₂-Ph | O | 4-Zb |
| 9-169 | H | CH(Me)CH₂ | H | 3-EtSO₂-Ph | O | 4-Zb |
| 9-170 | H | CH(Me)CH₂ | H | 4-EtSO₂-Ph | O | 4-Zb |
| 9-171 | H | CH(Me)CH₂ | H | 3-iPrSO₂-Ph | O | 4-Zb |
| 9-172 | H | CH(Me)CH₂ | H | 4-iPrSO₂-Ph | O | 4-Zb |
| 9-173 | H | CH(Me)CH₂ | H | 3-(1-Me-Imid-4)Ph | O | 4-Zb |
| 9-174 | H | CH(Me)CH₂ | H | 4-(1-Me-Imid-4)Ph | O | 4-Zb |
| 9-175 | H | CH(Me)CH₂ | H | 1-Me-2-Ph-Imid-4 | O | 4-Zb |
| 9-176 | H | CH(Me)CH₂ | H | 1,4-diMe-2-Ph-Imid-5 | O | 4-Zb |
| 9-177 | H | CH(Me)CH₂ | H | 1,5-diMe-2-Ph-Imid-4 | O | 4-Zb |
| 9-178 | H | CH(Me)CH₂ | H | 3,4-MdO-Ph | O | 4-Zb |
| 9-179 | H | CH(Me)CH₂ | H | 4-(4-MeO-Ph)Ph | O | 4-Zb |
| 9-180 | H | CH(Me)CH₂ | H | 4-(3,4-MdO-Ph)Ph | O | 4-Zb |
| 9-181 | H | CH(Me)CH₂ | H | 4-[PhSO₂—N(Me)]Ph | O | 4-Zb |
| 9-182 | H | CH(Me)CH₂ | H | 4-[(Pyr-3)SO₂—N(Me)]Ph | O | 4-Zb |
| 9-183 | H | CH(Me)CH₂ | H | 4-(PhSO₂—NH)Ph | O | 4-Zb |
| 9-184 | H | 2H(Me)CH₂ | H | 4-[(Pyr-3)SO₂—NH]Ph | O | 4-Zb |
| 9-185 | H | CH(Me)CH₂ | H | 4-[(Pyr-2)-SO₂]Ph | O | 4-Zb |
| 9-186 | H | CH(Me)CH₂ | H | 4-[(Pyr-3)-SO₂]Ph | O | 4-Zb |
| 9-187 | H | CH(Me)CH₂ | H | 4-[(Pyr-2)SO₂—N(Me)]Ph | O | 4-Zb |
| 9-188 | H | CH(Me)CH₂ | H | 4-[(Pyr-2)SO₂—NH]Ph | O | 4-Zb |
| 9-189 | H | CH(Me)CH₂ | H | 4-(4-Me-Ph)Ph | O | 4-Zb |
| 9-190 | H | CH(Me)CH₂ | H | 4-(4-F-Ph)Ph | O | 4-Zb |
| 9-191 | H | CH(Me)CH₂ | H | 4-(4-CF₃-Ph)Ph | O | 4-Zb |
| 9-192 | H | CH(Me)CH₂ | H | 2-[4-Me-PhSO₂—N(Me)]-Pyr-5 | O | 4-Zb |
| 9-193 | H | CH(Me)CH₂ | H | 2-HO-Pyr-5 | O | 4-Zb |
| 9-194 | H | CH(Me)CH₂ | H | 2-BzO-Pyr-5 | O | 4-Zb |
| 9-195 | H | CH(Me)CH₂ | H | 4-[(Pyr-4)SO₂]Ph | O | 4-Zb |
| 9-196 | H | CH(Me)CH₂ | H | 4-(2,4-diMeO-Ph)Ph | O | 4-Zb |
| 9-197 | H | CH(Me)CH₂ | H | 4-(2,5-diMeO-Ph)Ph | O | 4-Zb |
| 9-198 | H | CH(Me)CH₂ | H | 3-HO-Ph | O | 4-Zb |
| 9-199 | H | CH(Me)CH₂ | H | 4-HO-Ph | O | 4-Zb |
| 9-200 | H | CH(Me)CH₂ | H | 5-AcO-2-HO-3,4,6-triMe-Ph | O | 4-Zb |
| 9-201 | H | CH(Me)CH₂ | H | 4-HO-3,5-diMe-Ph | O | 4-Zb |
| 9-202 | H | CH(Me)CH₂ | H | 3-AcO-Ph | O | 4-Zb |
| 9-203 | H | CH(Me)CH₂ | H | 4-AcO-Ph | O | 4-Zb |

TABLE 10

| Cpd. No. | R¹ | R² | R³ | X | Y | Z |
|---|---|---|---|---|---|---|
| 10-1 | Me | CH(Me)CH₂ | H | Ph | O | 4-Zb |
| 10-2 | Me | CH(Me)CH₂ | H | Np-1 | O | 4-Zb |
| 10-3 | Me | CH(Me)CH₂ | H | Np-2 | O | 4-Zb |
| 10-4 | Me | CH(Me)CH₂ | H | 4-Me-Ph | O | 4-Zb |
| 10-5 | Me | CH(Me)CH₂ | H | 4-Et-Ph | O | 4-Zb |
| 10-6 | Me | CH(Me)CH₂ | H | 3-iPr-Ph | O | 4-Zb |
| 10-7 | Me | CH(Me)CH₂ | H | 4-iPr-Ph | O | 4-Zb |
| 10-8 | Me | CH(Me)CH₂ | H | 3-tBu-Ph | O | 4-Zb |
| 10-9 | Me | CH(Me)CH₂ | H | 4-tBu-Ph | O | 4-Zb |
| 10-10 | Me | CH(Me)CH₂ | H | 3-Cl-Ph | O | 4-Zb |
| 10-11 | Me | CH(Me)CH₂ | H | 4-Cl-Ph | O | 4-Zb |
| 10-12 | Me | CH(Me)CH₂ | H | 3-Br-Ph | O | 4-Zb |
| 10-13 | Me | CH(Me)CH₂ | H | 4-Br-Ph | O | 4-Zb |
| 10-14 | Me | CH(Me)CH₂ | H | 3-Ph-Ph | O | 4-Zb |
| 10-15 | Me | CH(Me)CH₂ | H | 4-Ph-Ph | O | 4-Zb |
| 10-16 | Me | CH(Me)CH₂ | H | 3-Bz-Ph | O | 4-Zb |
| 10-17 | Me | CH(Me)CH₂ | H | 4-Bz-Ph | O | 4-Zb |
| 10-18 | Me | CH(Me)CH₂ | H | 3-PhO-Ph | O | 4-Zb |
| 10-19 | Me | CH(Me)CH₂ | H | 4-PhO-Ph | O | 4-Zb |
| 10-20 | Me | CH(Me)CH₂ | H | 3-PhS-Ph | O | 4-Zb |
| 10-21 | Me | CH(Me)CH₂ | H | 4-PhS-Ph | O | 4-Zb |
| 10-22 | Me | CH(Me)CH₂ | H | 3-PhSO₂-Ph | O | 4-Zb |
| 10-23 | Me | CH(Me)CH₂ | H | 4-PhSO₂-Ph | O | 4-Zb |
| 10-24 | Me | CH(Me)CH₂ | H | 3-(Imid-1)Ph | O | 4-Zb |
| 10-25 | Me | CH(Me)CH₂ | H | 4-(Imid-1)Ph | O | 4-Zb |
| 10-26 | Me | CH(Me)CH₂ | H | 3-(Imid-4)Ph | O | 4-Zb |
| 10-27 | Me | CH(Me)CH₂ | H | 4-(Imid-4)Ph | O | 47Zb |
| 10-28 | Me | CH(Me)CH₂ | H | 3-(Fur-2)Ph | O | 4-Zb |
| 10-29 | Me | CH(Me)CH₂ | H | 4-(Fur-2)Ph | O | 4-Zb |
| 10-30 | Me | CH(Me)CH₂ | H | 3-(Thi-2)Ph | O | 4-Zb |
| 10-31 | Me | CH(Me)CH₂ | H | 4-(Thi-2)Ph | O | 4-Zb |
| 10-32 | Me | CH(Me)CH₂ | H | 3-(Thi-3)Ph | O | 4-Zb |
| 10-33 | Me | CH(Me)CH₂ | H | 4-(Thi-3)Ph | O | 4-Zb |
| 10-34 | Me | CH(Me)CH₂ | H | 3-(Pyr-2)Ph | O | 4-Zb |
| 10-35 | Me | CH(Me)CH₂ | H | 4-(Pyr-2)Ph | O | 4-Zb |
| 10-36 | Me | CH(Me)CH₂ | H | 3-(Pyr-3)Ph | O | 4-Zb |
| 10-37 | Me | CH(Me)CH₂ | H | 4-(Pyr-3)Ph | O | 4-Zb |
| 10-38 | Me | CH(Me)CH₂ | H | 3-(Pyr-4)Ph | O | 4-Zb |
| 10-39 | Me | CH(Me)CH₂ | H | 4-(Pyr-4)Ph | O | 4-Zb |
| 10-40 | Me | CH(Me)CH₂ | H | 3-(Oxa-2)Ph | O | 4-Zb |
| 10-41 | Me | CH(Me)CH₂ | H | 4-(Oxa-2)Ph | O | 4-Zb |
| 10-42 | Me | CH(Me)CH₂ | H | 3-(Oxa-4)Ph | O | 4-Zb |
| 10-43 | Me | CH(Me)CH₂ | H | 4-(Oxa-4)Ph | O | 4-Zb |
| 10-44 | Me | CH(Me)CH₂ | H | 3-(Oxa-5)Ph | O | 4-Zb |
| 10-45 | Me | CH(Me)CH₂ | H | 4-(Oxa-5)Ph | O | 4-Zb |
| 10-46 | Me | CH(Me)CH₂ | H | 3-(Thiz-2)Ph | O | 4-Zb |
| 10-47 | Me | CH(Me)CH₂ | H | 4-(Thiz-2)Ph | O | 4-Zb |
| 10-48 | Me | CH(Me)CH₂ | H | 3-(Thiz-4)Ph | O | 4-Zb |
| 10-49 | Me | CH(Me)CH₂ | H | 4-(Thiz-4)Ph | O | 4-Zb |
| 10-50 | Me | CH(Me)CH₂ | H | 3-(Thiz-5)Ph | O | 4-Zb |
| 10-51 | Me | CH(Me)CH₂ | H | 4-(Thiz-5)Ph | O | 4-Zb |
| 10-52 | Me | CH(Me)CH₂ | H | 1-Me-Pyrr-2 | O | 4-Zb |
| 10-53 | Me | CH(Me)CH₂ | H | 1-Ph-Pyrr-2 | O | 4-Zb |
| 10-54 | Me | CH(Me)CH₂ | H | 1-Bz-Pyrr-2 | O | 4-Zb |
| 10-55 | Me | CH(Me)CH₂ | H | 5-Me-Fur-2 | O | 4-Zb |

TABLE 10-continued

| Cpd. No. | R¹ | R² | R³ | X | Y | Z |
|---|---|---|---|---|---|---|
| 10-56 | Me | CH(Me)CH₂ | H | 5-Ph-Fur-2 | O | 4-Zb |
| 10-57 | Me | CH(Me)CH₂ | H | 5-Me-Thi-2 | O | 4-Zb |
| 10-58 | Me | CH(Me)CH₂ | H | 5-Ph-Thi-2 | O | 4-Zb |
| 10-59 | Me | CH(Me)CH₂ | H | 5-Me-Thi-3 | O | 4-Zb |
| 10-60 | Me | CH(Me)CH₂ | H | 5-Ph-Thi-3 | O | 4-Zb |
| 10-61 | Me | CH(Me)CH₂ | H | 1-Me-Pyza-3 | O | 4-Zb |
| 10-62 | Me | CH(Me)CH₂ | H | 1-Ph-Pyza-3 | O | 4-Zb |
| 10-63 | Me | CH(Me)CH₂ | H | 1-Me-Imid-2 | O | 4-Zb |
| 10-64 | Me | CH(Me)CH₂ | H | 1-Ph-Imid-2 | O | 4-Zb |
| 10-65 | Me | CH(Me)CH₂ | H | 1-Me-Imid-4 | O | 4-Zb |
| 10-66 | Me | CH(Me)CH₂ | H | 1-Ph-Imid-4 | O | 4-Zb |
| 10-67 | Me | CH(Me)CH₂ | H | Oxa-4 | O | 4-Zb |
| 10-68 | Me | CH(Me)CH₂ | H | Oxa-5 | O | 4-Zb |
| 10-69 | Me | CH(Me)CH₂ | H | 2-Me-Oxa-4 | O | 4-Zb |
| 10-70 | Me | CH(Me)CH₂ | H | 2-Ph-Oxa-4 | O | 4-Zb |
| 10-71 | Me | CH(Me)CH₂ | H | 2-Me-Oxa-5 | O | 4-Zb |
| 10-72 | Me | CH(Me)CH₂ | H | 2-Ph-Oxa-5 | O | 4-Zb |
| 10-73 | Me | CH(Me)CH₂ | H | 4-Me-2-Ph-Oxa-5 | O | 4-Zb |
| 10-74 | Me | CH(Me)CH₂ | H | 5-Me-2-Ph-Oxa-4 | O | 4-Zb |
| 10-75 | Me | CH(Me)CH₂ | H | Thiz-4 | O | 4-Zb |
| 10-76 | Me | CH(Me)CH₂ | H | Thiz-5 | O | 4-Zb |
| 10-77 | Me | CH(Me)CH₂ | H | 2-Me-Thiz-4 | O | 4-Zb |
| 10-78 | Me | CH(Me)CH₂ | H | 2-Ph-Thiz-4 | O | 4-Zb |
| 10-79 | Me | CH(Me)CH₂ | H | 2-Me-Thiz-5 | O | 4-Zb |
| 10-80 | Me | CH(Me)CH₂ | H | 2-Ph-Thiz-5 | O | 4-Zb |
| 10-81 | Me | CH(Me)CH₂ | H | 4-Me-2-Ph-Thiz-5 | O | 4-Zb |
| 10-82 | Me | CH(Me)CH₂ | H | 5-Me-2-Ph-Thiz-5 | O | 4-Zb |
| 10-83 | Me | CH(Me)CH₂ | H | 1-Me-Pyza-4 | O | 4-Zb |
| 10-84 | Me | CH(Me)CH₂ | H | 1-Ph-Pyza-4 | O | 4-Zb |
| 10-85 | Me | CH(Me)CH₂ | H | 2-Me-Isox-4 | O | 4-Zb |
| 10-86 | Me | CH(Me)CH₂ | H | 2-Ph-Isox-4 | O | 4-Zb |
| 10-87 | Me | CH(Me)CH₂ | H | Pyr-2 | O | 4-Zb |
| 10-88 | Me | CH(Me)CH₂ | H | Pyr-3 | O | 4-Zb |
| 10-89 | Me | CH(Me)CH₂ | H | Pyr-4 | O | 4-Zb |
| 10-90 | Me | CH(Me)CH₂ | H | 3-Me-Pyr-5 | O | 4-Zb |
| 10-91 | Me | CH(Me)CH₂ | H | 3-Et-Pyr-5 | O | 4-Zb |
| 10-92 | Me | CH(Me)CH₂ | H | 3-Ph-Pyr-5 | O | 4-Zb |
| 10-93 | Me | CH(Me)CH₂ | H | 2-Me-Pyr-5 | O | 4-Zb |
| 10-94 | Me | CH(Me)CH₂ | H | 2-Et-Pyr-5 | O | 4-Zb |
| 10-95 | Me | CH(Me)CH₂ | H | 2-Ph-Pyr-5 | O | 4-Zb |
| 10-96 | Me | CH(Me)CH₂ | H | 2-MeO-Pyr-5 | O | 4-Zb |
| 10-97 | Me | CH(Me)CH₂ | H | 2-EtO-Pyr-5 | Q | 4-Zb |
| 10-98 | Me | CH(Me)CH₂ | H | 2-iPrO-Pyr-5 | O | 4-Zb |
| 10-99 | Me | CH(Me)CH₂ | H | 2-MeS-Pyr-5 | O | 4-Zb |
| 10-100 | Me | CH(Me)CH₂ | H | 2-EtS-Pyr-5 | O | 4-Zb |
| 10-101 | Me | CH(Me)CH₂ | H | 2-iPrS-Pyr-5 | O | 4-Zb |
| 10-102 | Me | CH(Me)CH₂ | H | 2-MeSO₂-Pyr-5 | O | 4-Zb |
| 10-103 | Me | CH(Me)CH₂ | H | 2-EtSO₂-Pyr-5 | O | 4-Zb |
| 10-104 | Me | CH(Me)CH₂ | H | 2-iPrSO₂-Pyr-5 | O | 4-Zb |
| 10-105 | Me | CH(Me)CH₂ | H | 2-Bz-Pyr-5 | O | 4-Zb |
| 10-106 | Me | CH(Me)CH₂ | H | 2-PhO-Pyr-5 | O | 4-Zb |
| 10-107 | Me | CH(Me)CH₂ | H | 2-PhS-Pyr-5 | O | 4-Zb |
| 10-108 | Me | CH(Me)CH₂ | H | 2-PhSO₂-Pyr-5 | O | 4-Zb |
| 10-109 | Me | CH(Me)CH₂ | H | 3-Me-Pyr-6 | O | 4-Zb |
| 10-110 | Me | CH(Me)CH₂ | H | 3-Ph-Pyr-6 | O | 4-Zb |
| 10-111 | Me | CH(Me)CH₂ | H | 2-Me-Pyr-6 | O | 4-Zb |
| 10-112 | Me | CH(Me)CH₂ | H | 2-Ph-Pyr-6 | O | 4-Zb |
| 10-113 | Me | CH(Me)CH₂ | H | 2-Me-Pym-4 | O | 4-Zb |
| 10-114 | Me | CH(Me)CH₂ | H | 2-Ph-Pym-4 | O | 4-Zb |
| 10-115 | Me | CH(Me)CH₂ | H | 2-MeO-Pym-4 | O | 4-Zb |
| 10-116 | Me | CH(Me)CH₂ | H | 2-EtO-Pym-4 | O | 4-Zb |
| 10-117 | Me | CH(Me)CH₂ | H | 2-iPrO-Pym-4 | O | 4-Zb |
| 10-118 | Me | CH(Me)CH₂ | H | 2-MeS-Pym-4 | O | 4-Zb |
| 10-119 | Me | CH(Me)CH₂ | H | 2-EtS-Pym-4 | O | 4-Zb |
| 10-120 | Me | CH(Me)CH₂ | H | 2-iPrS-Pym-4 | O | 4-Zb |
| 10-121 | Me | CH(Me)CH₂ | H | 6-MeS-Pym-4 | O | 4-Zb |
| 10-122 | Me | CH(Me)CH₂ | H | 6-EtS-Pym-4 | O | 4-Zb |
| 10-123 | Me | CH(Me)CH₂ | H | 6-iPrS-Pym-4 | O | 4-Zb |
| 10-124 | Me | CH(Me)CH₂ | H | 2-PhS-Pym-4 | O | 4-Zb |
| 10-125 | Me | CH(Me)CH₂ | H | 2-MeSO₂-Pym-4 | O | 4-Zb |
| 10-126 | Me | CH(Me)CH₂ | H | 2-EtSO₂-Pym-4 | O | 4-Zb |
| 10-127 | Me | CH(Me)CH₂ | H | 2-iPrSO₂-Pym-4 | O | 4-Zb |
| 10-128 | Me | CH(Me)CH₂ | H | 2-PhSO₂-Pym-4 | O | 4-Zb |
| 10-129 | Me | CH(Me)CH₂ | H | 2-Me-Pym-5 | O | 4-Zb |
| 10-130 | Me | CH(Me)CH₂ | H | 2-Ph-Pym-5 | O | 4-Zb |
| 10-131 | Me | CH(Me)CH₂ | H | 2-MeO-Pym-5 | O | 4-Zb |
| 10-132 | Me | CH(Me)CH₂ | H | 2-EtO-Pym-5 | O | 4-Zb |
| 10-133 | Me | CH(Me)CH₂ | H | 2-iPrO-Pym-5 | O | 4-Zb |
| 10-134 | Me | CH(Me)CH₂ | H | 2-MeS-Pym-5 | O | 4-Zb |
| 10-135 | Me | CH(Me)CH₂ | H | 2-EtS-Pym-5 | O | 4-Zb |
| 10-136 | Me | CH(Me)CH₂ | H | 2-iPrS-Pym-5 | O | 4-Zb |
| 10-137 | Me | CH(Me)CH₂ | H | 2-PhS-Pym-5 | O | 4-Zb |
| 10-138 | Me | CH(Me)CH₂ | H | 2-MeSO₂-Pym-5 | O | 4-Zb |
| 10-139 | Me | CH(Me)CH₂ | H | 2-EtSO₂-Pym-5 | O | 4-Zb |
| 10-140 | Me | CH(Me)CH₂ | H | 2-iPrSO₂-Pym-5 | O | 4-Zb |
| 10-141 | Me | CH(Me)CH₂ | H | 2-PhSO₂-Pym-5 | O | 4-Zb |
| 10-142 | Me | CH(Me)CH₂ | H | Ind-2 | O | 4-Zb |
| 10-143 | Me | CH(Me)CH₂ | H | Ind-3 | O | 4-Zb |
| 10-144 | Me | CH(Me)CH₂ | H | 1-Me-Ind-2 | O | 4-Zb |
| 10-145 | Me | CH(Me)CH₂ | H | 1-Me-Ind-3 | O | 4-Zb |
| 10-146 | Me | CH(Me)CH₂ | H | Bimid-2 | O | 4-Zb |
| 10-147 | Me | CH(Me)CH₂ | H | Boxa-2 | O | 4-Zb |
| 10-148 | Me | CH(Me)CH₂ | H | Bthiz-2 | O | 4-Zb |
| 10-149 | Me | CH(Me)CH₂ | H | Quin-2 | O | 4-Zb |
| 10-150 | Me | CH(Me)CH₂ | H | 3-Quin | O | 4-Zb |
| 10-151 | Me | CH(Me)CH₂ | H | 4-Quin | O | 4-Zb |
| 10-152 | Me | CH(Me)CH₂ | H | 1-iQuin | O | 4-Zb |
| 10-153 | Me | CH(Me)CH₂ | H | 3-iQuin | O | 4-Zb |
| 10-154 | Me | CH(Me)CH₂ | H | 4-iQuin | O | 4-Zb |
| 10-155 | Me | CH(Me)CH₂ | H | 3-MeO-Ph | O | 4-Zb |
| 10-156 | Me | CH(Me)CH₂ | H | 4-MeO-Ph | O | 4-Zb |
| 10-157 | Me | CH(Me)CH₂ | H | 3-EtO-Ph | O | 4-Zb |
| 10-158 | Me | CH(Me)CH₂ | H | 4-EtO-Ph | O | 4-Zb |
| 10-159 | Me | CH(Me)CH₂ | H | 3-iPrO-Ph | O | 4-Zb |
| 10-160 | Me | CH(Me)CH₂ | H | 4-iPrO-Ph | O | 4-Zb |
| 10-161 | Me | CH(Me)CH₂ | H | 3-MeS-Ph | O | 4-Zb |
| 10-162 | Me | CH(Me)CH₂ | H | 4-MeS-Ph | O | 4-Zb |
| 10-163 | Me | CH(Me)CH₂ | H | 3-EtS-Ph | O | 4-Zb |
| 10-164 | Me | CH(Me)CH₂ | H | 4-EtS-Ph | O | 4-Zb |
| 10-165 | Me | CH(Me)CH₂ | H | 3-iPrS-Ph | O | 4-Zb |
| 10-166 | Me | CH(Me)CH₂ | H | 4-iPrS-Ph | O | 4-Zb |
| 10-167 | Me | CH(Me)CH₂ | H | 3-MeSO₂-Ph | O | 4-Zb |
| 10-168 | Me | CH(Me)CH₂ | H | 4-MeSO₂-Ph | O | 4-Zb |
| 10-169 | Me | CH(Me)CH₂ | H | 3-EtSO₂-Ph | O | 4-Zb |
| 10-170 | Me | CH(Me)CH₂ | H | 4-EtSO₂-Ph | O | 4-Zb |
| 10-171 | Me | CH(Me)CH₂ | H | 3-iPrSO₂-Ph | O | 4-Zb |
| 10-172 | Me | CH(Me)CH₂ | H | 4-iPrSO₂-Ph | O | 4-Zb |
| 10-173 | Me | CH(Me)CH₂ | H | 3-(1-Me-Imid-4)Ph | O | 4-Zb |
| 10-174 | Me | CH(Me)CH₂ | H | 4-(1-Me-Imid-4)Ph | O | 4-Zb |
| 10-175 | Me | CH(Me)CH₂ | H | 1-Me-2-Ph-Imid-4 | O | 4-Zb |
| 10-176 | Me | CH(Me)CH₂ | H | 1,4-diMe-2-Ph-Imid-5 | O | 4-Zb |
| 10-177 | Me | CH(Me)CH₂ | H | 1,5-diMe-2-Ph-Imid-4 | O | 4-Zb |
| 10-178 | Me | CH(Me)CH₂ | H | 3,4-MdO-Ph | O | 4-Zb |
| 10-179 | Me | CH(Me)CH₂ | H | 4-(4-MeO-Ph)Ph | O | 4-Zb |
| 10-180 | Me | CH(Me)CH₂ | H | 4-(3,4-MdO-Ph)Ph | O | 4-Zb |
| 10-181 | Me | CH(Me)CH₂ | H | 4-[PhSO₂-N(Me)]Ph | O | 4-Zb |
| 10-182 | Me | CH(Me)CH₂ | H | 4-[(Pyr-3)SO₂-N(Me)]Ph | O | 4-Zb |
| 10-183 | Me | CH(Me)CH₂ | H | 4-(PhSO₂NH)-Ph | O | 4-Zb |
| 10-184 | Me | CH(Me)CH₂ | H | 4-[(Pyr-3)SO₂-NH]Ph | O | 4-Zb |
| 10-185 | Me | CH(Me)CH₂ | H | 4-[(Pyr-2)-SO₂]Ph | O | 4-Zb |
| 10-186 | Me | CH(Me)CH₂ | H | 4-[(Pyr-3)-SO₂]Ph | O | 4-Zb |
| 10-187 | Me | CH(Me)CH₂ | H | 4-[(Pyr-2)SO₂-N(Me)]Ph | O | 4-Zb |
| 10-188 | Me | CH(Me)CH₂ | H | 4-[(Pyr-2)SO₂-NH]Ph | O | 4-Zb |
| 10-189 | Me | CH(Me)CH₂ | H | 4-(4-Me-Ph)Ph | O | 4-Zb |
| 10-190 | Me | CH(Me)CH₂ | H | 4-(4-F-Ph)Ph | O | 4-Zb |
| 10-191 | Me | CH(Me)CH₂ | H | 4-(4-CF₃-Ph)Ph | O | 4-Zb |
| 10-192 | Me | CH(Me)CH₂ | H | 2-[4-Me-PhSO₂-N(Me)]Pyr-5 | O | 4-Zb |
| 10-193 | Me | CH(Me)CH₂ | H | 2-HO-Pyr-5 | O | 4-Zb |
| 10-194 | Me | CH(Me)CH₂ | H | 2-BzO-Pyr-5 | O | 4-Zb |
| 10-195 | Me | CH(Me)CH₂ | H | 4-[(Pyr-4)SO₂]Ph | O | 4-Zb |
| 10-196 | Me | CH(Me)CH₂ | H | 4-(2,4-diMeO-Ph)Ph | O | 4-Zb |
| 10-197 | Me | CH(Me)CH₂ | H | 4-(2,5-diMeO-Ph)Ph | O | 4-Zb |
| 10-198 | Me | CH(Me)CH₂ | H | 3-HO-Ph | O | 4-Zb |
| 10-199 | Me | CH(Me)CH₂ | H | 4-HO-Ph | O | 4-Zb |
| 10-200 | Me | CH(Me)CH₂ | H | 5-AcO-2-HO-3,4,6-triMe-Ph | O | 4-Zb |
| 10-201 | Me | CH(Me)CH₂ | H | 4-HO-3,5-diMe-Ph | O | 4-Zb |
| 10-202 | Me | CH(Me)CH₂ | H | 3-AcO-Ph | O | 4-Zb |
| 10-203 | Me | CH(Me)CH₂ | H | 4-AcO-Ph | O | 4-Zb |

TABLE 11

| Cpd. No. | R¹ | R² | R³ | X | Y | Z |
|---|---|---|---|---|---|---|
| 11-1 | H | C(Me)₂CH₂ | H | 4-Et-Ph | O | 4-Zb |
| 11-2 | H | C(Me)₂CH₂ | H | 4-iPr-Ph | O | 4-Zb |
| 11-3 | H | C(Me)₂CH₂ | H | 3-Ph-Ph | O | 4-Zb |
| 11-4 | H | C(Me)₂CH₂ | H | 4-Ph-Ph | O | 4-Zb |
| 11-5 | H | C(Me)₂CH₂ | H | Pyr-3 | O | 4-Zb |
| 11-6 | H | C(Me)₂CH₂ | H | 5-Me-Pyr-3 | O | 4-Zb |
| 11-7 | H | C(Me)₂CH₂ | H | 5-Et-Pyr-3 | O | 4-Zb |
| 11-8 | H | C(Me)₂CH₂ | H | 5-Ph-Pyr-3 | O | 4-Zb |
| 11-9 | H | C(Me)₂CH₂ | H | 6-Me-Pyr-3 | O | 4-Zb |
| 11-10 | H | C(Me)₂CH₂ | H | 6-Et-Pyr-3 | O | 4-Zb |
| 11-11 | H | C(Me)₂CH₂ | H | 6-Ph-Pyr-3 | O | 4-Zb |
| 11-12 | H | C(Me)₂CH₂ | H | 6-MeO-Pyr-3 | O | 4-Zb |
| 11-13 | H | C(Me)₂CH₂ | H | 6-EtO-Pyr-3 | O | 4-Zb |
| 11-14 | H | C(Me)₂CH₂ | H | 6-iPrO-Pyr-3 | O | 4-Zb |
| 11-15 | H | C(Me)₂CH₂ | H | 6-MeS-Pyr-3 | O | 4-Zb |
| 11-16 | H | C(Me)₂CH₂ | H | 6-EtS-Pyr-3 | O | 4-Zb |
| 11-17 | H | C(Me)₂CH₂ | H | 6-iPrS-Pyr-3 | O | 4-Zb |
| 11-18 | H | C(Me)₂CH₂ | H | 6-MeSO₂-Pyr-3 | O | 4-Zb |
| 11-19 | H | C(Me)₂CH₂ | H | 6-EtSO₂-Pyr-3 | O | 4-Zb |
| 11-20 | H | C(Me)₂CH₂ | H | 6-iPrSO₂-Pyr-3 | O | 4-Zb |
| 11-21 | H | C(Me)₂CH₂ | H | 6-Bz-Pyr-3 | O | 4-Zb |
| 11-22 | H | C(Me)₂CH₂ | H | 6-PhO-Pyr-3 | O | 4-Zb |
| 11-23 | H | C(Me)₂CH₂ | H | 6-PhS-Pyr-3 | O | 4-Zb |
| 11-24 | H | C(Me)₂CH₂ | H | 6-PhSO₂-Pyr-3 | O | 4-Zb |
| 11-25 | H | C(Me)₂CH₂ | H | Quin-2 | O | 4-Zb |
| 11-26 | H | C(Me)₂CH₂ | H | 4-MeO-Ph | O | 4-Zb |
| 11-27 | H | C(Me)₂CH₂ | H | 4-EtO-Ph | O | 4-Zb |
| 11-28 | H | C(Me)₂CH₂ | H | 4-iPrO-Ph | O | 4-Zb |
| 11-29 | H | C(Me)₂CH₂ | H | 4-MeS-Ph | O | 4-Zb |
| 11-30 | H | C(Me)₂CH₂ | H | 4-EtS-Ph | O | 4-Zb |
| 11-31 | H | C(Me)₂CH₂ | H | 4-iPrS-Ph | O | 4-Zb |
| 11-32 | H | C(Me)₂CH₂ | H | 4-MeSO₂-Ph | O | 4-Zb |
| 11-33 | H | C(Me)₂CH₂ | H | 4-EtSO₂-Ph | O | 4-Zb |
| 11-34 | H | C(Me)₂CH₂ | H | 4-iPrSO₂-Ph | O | 4-Zb |

TABLE 12

| Cpd. No. | R¹ | R² | R³ | X | Y | Z |
|---|---|---|---|---|---|---|
| 12-1 | Me | H(Me)₂CH₂ | H | 4-Et-Ph | O | 4-Zb |
| 12-2 | Me | C(Me)₂CH₂ | H | 4-iPr-Ph | O | 4-Zb |
| 12-3 | Me | C(Me)₂CH₂ | H | 3-Ph-Ph | O | 4-Zb |
| 12-4 | Me | C(Me)₂CH₂ | H | 4-Ph-Ph | O | 4-Zb |
| 12-5 | Me | C(Me)₂CH₂ | H | Pyr-3 | O | 4-Zb |
| 12-6 | Me | C(Me)₂CH₂ | H | 5-Me-Pyr-3 | O | 4-Zb |
| 12-7 | Me | C(Me)₂CH₂ | H | 5-Et-Pyr-3 | O | 4-Zb |
| 12-8 | Me | C(Me)₂CH₂ | H | 5-Ph-Pyr-3 | O | 4-Zb |
| 12-9 | Me | C(Me)₂CH₂ | H | 6-Me-Pyr-3 | O | 4-Zb |
| 12-10 | Me | C(Me)₂CH₂ | H | 6-Et-Pyr-3 | O | 4-Zb |
| 12-11 | Me | C(Me)₂CH₂ | H | 6-Ph-Pyr-3 | O | 4-Zb |
| 12-12 | Me | C(Me)₂CH₂ | H | 6-MeO-Pyr-3 | O | 4-Zb |
| 12-13 | Me | C(Me)₂CH₂ | H | 6-EtO-Pyr-3 | O | 4-Zb |
| 12-14 | Me | C(Me)₂CH₂ | H | 6-iPrO-Pyr-3 | O | 4-Zb |
| 12-15 | Me | C(Me)₂CH₂ | H | 6-MeS-Pyr-3 | O | 4-Zb |
| 12-16 | Me | C(Me)₂CH₂ | H | 6-EtS-Pyr-3 | O | 4-Zb |
| 12-17 | Me | C(Me)₂CH₂ | H | 6-iPrS-Pyr-3 | O | 4-Zb |
| 12-18 | Me | C(Me)₂CH₂ | H | 6-MeSO₂-Pyr-3 | O | 4-Zb |
| 12-19 | Me | C(Me)₂CH₂ | H | 6-EtSO₂-Pyr-3 | O | 4-Zb |
| 12-20 | Me | C(Me)₂CH₂ | H | 6-iPrSO₂-Pyr-3 | O | 4-Zb |
| 12-21 | Me | C(Me)₂CH₂ | H | 6-Bz-Pyr-3 | O | 4-Zb |
| 12-22 | Me | C(Me)₂CH₂ | H | 6-PhO-Pyr-3 | O | 4-Zb |
| 12-23 | Me | C(Me)₂CH₂ | H | 6-PhS-Pyr-3 | O | 4-Zb |
| 12-24 | Me | C(Me)₂CH₂ | H | 6-PhSO₂-Pyr-3 | O | 4-Zb |
| 12-25 | Me | C(Me)₂CH₂ | H | Quin-2 | O | 4-Zb |
| 12-26 | Me | C(Me)₂CH₂ | H | 4-MeO-Ph | O | 4-Zb |
| 12-27 | Me | C(Me)₂CH₂ | H | 4-EtO-Ph | O | 4-Zb |
| 12-28 | Me | C(Me)₂CH₂ | H | 4-iPrO-Ph | O | 4-Zb |
| 12-29 | Me | C(Me)₂CH₂ | H | 4-MeS-Ph | O | 4-Zb |
| 12-30 | Me | C(Me)₂CH₂ | H | 4-EtS-Ph | O | 4-Zb |
| 12-31 | Me | C(Me)₂CH₂ | H | 4-iPrS-Ph | O | 4-Zb |
| 12-32 | Me | C(Me)₂CH₂ | H | 4-MeSO₂-Ph | O | 4-Zb |
| 12-33 | Me | C(Me)₂CH₂ | H | 4-EtSO₂-Ph | O | 4-Zb |
| 12-34 | Me | C(Me)₂CH₂ | H | 4-iPrSO₂-Ph | O | 4-Zb |

TABLE 13

| Cpd. No. | R¹ | R² | R³ | X | Y | Z |
|---|---|---|---|---|---|---|
| 13-1 | H | CH₂CH(Me) | H | 4-Et-Ph | O | 4-Zb |
| 13-2 | H | CH₂CH(Me) | H | 4-iPr-Ph | O | 4-Zb |
| 13-3 | H | CH₂CH(Me) | H | 3-Ph-Ph | O | 4-Zb |
| 13-4 | H | CH₂CH(Me) | H | 4-Ph-Ph | O | 4-Zb |
| 13-5 | H | CH₂CH(Me) | H | Pyr-3 | O | 4-Zb |
| 13-6 | H | CH₂CH(Me) | H | 5-Me-Pyr-3 | O | 4-Zb |
| 13-7 | H | CH₂CH(Me) | H | 5-Et-Pyr-3 | O | 4-Zb |
| 13-8 | H | CH₂CH(Me) | H | 5-Ph-Pyr-3 | O | 4-Zb |
| 13-9 | H | CH₂CH(Me) | H | 6-Me-Pyr-3 | O | 4-Zb |
| 13-10 | H | CH₂CH(Me) | H | 6-Et-Pyr-3 | O | 4-Zb |
| 13-11 | H | CH₂CH(Me) | H | 6-Ph-Pyr-3 | O | 4-Zb |
| 13-12 | H | CH₂CH(Me) | H | 6-MeO-Pyr-3 | O | 4-Zb |
| 13-13 | H | CH₂CH(Me) | H | 6-EtO-Pyr-3 | O | 4-Zb |
| 13-14 | H | CH₂CH(Me) | H | 6-iPrO-Pyr-3 | O | 4-Zb |
| 13-15 | H | CH₂CH(Me) | H | 6-MeS-Pyr-3 | O | 4-Zb |
| 13-16 | H | CH₂CH(Me) | H | 6-EtS-Pyr-3 | O | 4-Zb |
| 13-17 | H | CH₂CH(Me) | H | 6-iPrS-Pyr-3 | O | 4-Zb |
| 13-18 | H | CH₂CH(Me) | H | 6-MeSO₂-Pyr-3 | O | 4-Zb |
| 13-19 | H | CH₂CH(Me) | H | 6-EtSO₂-Pyr-3 | O | 4-Zb |
| 13-20 | H | CH₂CH(Me) | H | 6-iPrSO₂-Pyr-3 | O | 4-Zb |
| 13-21 | H | CH₂CH(Me) | H | 6-Bz-Pyr-3 | O | 4-Zb |
| 13-22 | H | CH₂CH(Me) | H | 6-PhO-Pyr-3 | O | 4-Zb |
| 13-23 | H | CH₂CH(Me) | H | 6-PhS-Pyr-3 | O | 4-Zb |
| 13-24 | H | CH₂CH(Me) | H | 6-PhSO₂-Pyr-3 | O | 4-Zb |
| 13-25 | H | CH₂CH(Me) | H | Quin-2 | O | 4-Zb |
| 13-26 | H | CH₂CH(Me) | H | 4-MeO-Ph | O | 4-Zb |
| 13-27 | H | CH₂CH(Me) | H | 4-EtO-Ph | O | 4-Zb |
| 13-28 | H | CH₂CH(Me) | H | 4-iPrO-Ph | O | 4-Zb |
| 13-29 | H | CH₂CH(Me) | H | 4-MeS-Ph | O | 4-Zb |
| 13-30 | H | CH₂CH(Me) | H | 4-EtS-Ph | O | 4-Zb |
| 13-31 | H | CH₂CH(Me) | H | 4-iPrS-Ph | O | 4-Zb |
| 13-32 | H | CH₂CH(Me) | H | 4-MeSO₂-Ph | O | 4-Zb |
| 13-33 | H | CH₂CH(Me) | H | 4-EtSO₂-Ph | O | 4-Zb |
| 13-34 | H | CH₂CH(Me) | H | 4-iPrSO₂-Ph | O | 4-Zb |

TABLE 14

| Cpd. No. | R¹ | R² | R³ | X | Y | Z |
|---|---|---|---|---|---|---|
| 14-1 | Me | CH₂CH(Me) | H | 4-Et-Ph | O | 4-Zb |
| 14-2 | Me | CH₂CH(Me) | H | 4-iPr-Ph | O | 4-Zb |
| 14-3 | Me | CH₂CH(Me) | H | 3-Ph-Ph | O | 4-Zb |
| 14-4 | Me | CH₂CH(Me) | H | 4-Ph-Ph | O | 4-Zb |
| 14-5 | Me | CH₂CH(Me) | H | Pyr-3 | O | 4-Zb |
| 14-6 | Me | CH₂CH(Me) | H | 5-Me-Pyr-3 | O | 4-Zb |
| 14-7 | Me | CH₂CH(Me) | H | 5-Et-Pyr-3 | O | 4-Zb |
| 14-8 | Me | CH₂CH(Me) | H | 5-Ph-Pyr-3 | O | 4-Zb |
| 14-9 | Me | CH₂CH(Me) | H | 6-Me-Pyr-3 | O | 4-Zb |
| 14-10 | Me | CH₂CH(Me) | H | 6-Et-Pyr-3 | O | 4-Zb |
| 14-11 | Me | CH₂CH(Me) | H | 6-Ph-Pyr-3 | O | 4-Zb |
| 14-12 | Me | CH₂CH(Me) | H | 6-MeO-Pyr-3 | O | 4-Zb |
| 14-13 | Me | CH₂CH(Me) | H | 6-EtO-Pyr-3 | O | 4-Zb |
| 14-14 | Me | CH₂CH(Me) | H | 6-iPrO-Pyr-3 | O | 4-Zb |
| 14-15 | Me | CH₂CH(Me) | H | 6-MeS-Pyr-3 | O | 4-Zb |
| 14-16 | Me | CH₂CH(Me) | H | 6-EtS-Pyr-3 | O | 4-Zb |
| 14-17 | Me | CH₂CH(Me) | H | 6-iPrS-Pyr-3 | O | 4-Zb |
| 14-18 | Me | CH₂CH(Me) | H | 6-MeSO₂-Pyr-3 | O | 4-Zb |
| 14-19 | Me | CH₂CH(Me) | H | 6-EtSO₂-Pyr-3 | O | 4-Zb |
| 14-20 | Me | CH₂CH(Me) | H | 6-iPrSO₂-Pyr-3 | O | 4-Zb |
| 14-21 | Me | CH₂CH(Me) | H | 6-Bz-Pyr-3 | O | 4-Zb |
| 14-22 | Me | CH₂CH(Me) | H | 6-PhO-Pyr-3 | O | 4-Zb |

TABLE 14-continued

| Cpd. No. | R¹ | R² | R³ | X | Y | Z |
|---|---|---|---|---|---|---|
| 14-23 | Me | CH₂CH(Me) | H | 6-PhS-Pyr-3 | O | 4-Zb |
| 14-24 | Me | CH₂CH(Me) | H | 6-PhSO₂-Pyr-3 | O | 4-Zb |
| 14-25 | Me | CH₂CH(Me) | H | Quin-2 | O | 4-Zb |
| 14-26 | Me | CH₂CH(Me) | H | 4-MeO-Ph | O | 4-Zb |
| 14-27 | Me | CH₂CH(Me) | H | 4-EtO-Ph | O | 4-Zb |
| 14-28 | Me | CH₂CH(Me) | H | 4-iPrO-Ph | O | 4-Zb |
| 14-29 | Me | CH₂CH(Me) | H | 4-MeS-Ph | O | 4-Zb |
| 14-30 | Me | CH₂CH(Me) | H | 4-EtS-Ph | O | 4-Zb |
| 14-31 | Me | CH₂CH(Me) | H | 4-iPrS-Ph | O | 4-Zb |
| 14-32 | Me | CH₂CH(Me) | H | 4-MeSO₂-Ph | O | 4-Zb |
| 14-33 | Me | CH₂CH(Me) | H | 4-EtSO₂-Ph | O | 4-Zb |
| 14-34 | Me | CH₂CH(Me) | H | 4-iPrSO₂-Ph | O | 4-Zb |

TABLE 15

| Cpd. No. | R¹ | R² | R³ | X | Y | Z |
|---|---|---|---|---|---|---|
| 15-1 | H | CH(Me)CH(Me) | H | 4-Et-Ph | O | 4-Zb |
| 15-2 | H | CH(Me)CH(Me) | H | 4-iPr-Ph | O | 4-Zb |
| 15-3 | H | CH(Me)CH(Me) | H | 3-Ph-Ph | O | 4-Zb |
| 15-4 | H | CH(Me)CH(Me) | H | 4-Ph-Ph | O | 4-Zb |
| 15-5 | H | CH(Me)CH(Me) | H | Pyr-3 | O | 4-Zb |
| 15-6 | H | CH(Me)CH(Me) | H | 5-Me-Pyr-3 | O | 4-Zb |
| 15-7 | H | CH(Me)CH(Me) | H | 5-Et-Pyr-3 | O | 4-Zb |
| 15-8 | H | CH(Me)CH(Me) | H | 5-Ph-Pyr-3 | O | 4-Zb |
| 15-9 | H | CH(Me)CH(Me) | H | 6-Me-Pyr-3 | O | 4-Zb |
| 15-10 | H | CH(Me)CH(Me) | H | 6-Et-Pyr-3 | O | 4-Zb |
| 15-11 | H | CH(Me)CH(Me) | H | 6-Ph-Pyr-3 | C | 4-Zb |
| 15-12 | H | CH(Me)CH(Me) | H | 6-MeO-Pyr-3 | O | 4-Zb |
| 15-13 | H | CH(Me)CH(Me) | H | 6-EtO-Pyr-3 | O | 4-Zb |
| 15-14 | H | CH(Me)CH(Me) | H | 6-iPrO-Pyr-3 | O | 4-Zb |
| 15-15 | H | CH(Me)CH(Me) | H | 6-MeS-Pyr-3 | O | 4-Zb |
| 15-16 | H | CH(Me)CH(Me) | H | 6-EtS-Pyr-3 | O | 4-Zb |
| 15-17 | H | CH(Me)CH(Me) | H | 6-iPrS-Pyr-3 | O | 4-Zb |
| 15-18 | H | CH(Me)CH(Me) | H | 6-MeSO₂-Pyr-3 | O | 4-Zb |
| 15-19 | H | CH(Me)CH(Me) | H | 6-EtSO₂-Pyr-3 | O | 4-Zb |
| 15-20 | H | CH(Me)CH(Me) | H | 6-iPrSO₂-Pyr-3 | O | 4-Zb |
| 15-21 | H | CH(Me)CH(Me) | H | 6-Bz-Pyr-3 | O | 4-Zb |
| 15-22 | H | CH(Me)CH(Me) | H | 6-PhO-Pyr-3 | O | 4-Zb |
| 15-23 | H | CH(Me)CH(Me) | H | 6-PhS-Pyr-3 | O | 4-Zb |
| 15-24 | H | CH(Me)CH(Me) | H | 6-PhSO₂-Pyr-3 | O | 4-Zb |
| 15-25 | H | CH(Me)CH(Me) | H | Quin-2 | O | 4-Zb |
| 15-26 | H | CH(Me)CH(Me) | H | 4-MeO-Ph | O | 4-Zb |
| 15-27 | H | CH(Me)CH(Me) | H | 4-EtO-Ph | O | 4-Zb |
| 15-28 | H | CH(Me)CH(Me) | H | 4-iPrO-Ph | O | 4-Zb |
| 15-29 | H | CH(Me)CH(Me) | H | 4-MeS-Ph | O | 4-Zb |
| 15-30 | H | CH(Me)CH(Me) | H | 4-EtS-Ph | O | 4-Zb |
| 15-31 | H | CH(Me)CH(Me) | H | 4-iPrS-Ph | O | 4-Zb |
| 15-32 | H | CH(Me)CH(Me) | H | 4-MeSO₂-Ph | O | 4-Zb |
| 15-33 | H | CH(Me)CH(Me) | H | 4-EtSO₂-Ph | O | 4-Zb |
| 15-34 | H | CH(Me)CH(Me) | H | 4-iPrSO₂-Ph | O | 4-Zb |

TABLE 16

| Cpd. No. | R¹ | R² | R³ | X | Y | Z |
|---|---|---|---|---|---|---|
| 16-1 | Me | CH(Me)CH(Me) | H | 4-Et—Ph | O | 4-Zb |
| 16-2 | Me | CH(Me)CH(Me) | H | 4-iPr—Ph | O | 4-Zb |
| 16-3 | Me | CH(Me)CH(Me) | H | 3-Ph—Ph | O | 4-Zb |
| 16-4 | Me | CH(Me)CH(Me) | H | 4-Ph—Ph | O | 4-Zb |
| 16-5 | Me | CH(Me)CH(Me) | H | Pyr-3 | O | 4-Zb |
| 16-6 | Me | CH(Me)CH(Me) | H | 5-Me—Pyr-3 | O | 4-Zb |
| 16-7 | Me | CH(Me)CH(Me) | H | 5-Et—Pyr-3 | O | 4-Zb |
| 16-8 | Me | CH(Me)CH(Me) | H | 5-Ph—Pyr-3 | O | 4-Zb |
| 16-9 | Me | CH(Me)CH(Me) | H | 6-Me—Pyr-3 | O | 4-Zb |
| 16-10 | Me | CH(Me)CH(Me) | H | 6-Et—Pyr-3 | O | 4-Zb |
| 16-11 | Me | CH(Me)CH(Me) | H | 6-Ph—Pyr-3 | O | 4-Zb |
| 16-12 | Me | CH(Me)CH(Me) | H | 6-MeO—Pyr-3 | O | 4-Zb |
| 16-13 | Me | CH(Me)CH(Me) | H | 6-EtO—Pyr-3 | O | 4-Zb |
| 16-14 | Me | CH(Me)CH(Me) | H | 6-iPrO—Pyr-3 | O | 4-Zb |
| 16-15 | Me | CH(Me)CH(Me) | H | 6-MeS—Pyr-3 | O | 4-Zb |
| 16-16 | Me | CH(Me)CH(Me) | H | 6-EtS—Pyr-3 | O | 4-Zb |
| 16-17 | Me | CH(Me)CH(Me) | H | 6-iPrS—Pyr-3 | O | 4-Zb |
| 16-18 | Me | CH(Me)CH(Me) | H | 6-MeSO₂-Pyr-3 | O | 4-Zb |
| 16-19 | Me | CH(Me)CH(Me) | H | 6-EtSO₂—Pyr-3 | O | 4-Zb |
| 16-20 | Me | CH(Me)CH(Me) | H | 6-iPrSO₂—Pyr-3 | O | 4-Zb |
| 16-21 | Me | CH(Me)CH(Me) | H | 6-Bz—Pyr-3 | O | 4-Zb |
| 16-22 | Me | CH(Me)CH(Me) | H | 6-PhO—Pyr-3 | O | 4-Zb |
| 16-23 | Me | CH(Me)CH(Me) | H | 6-PhS—Pyr-3 | O | 4-Zb |
| 16-24 | Me | CH(Me)CH(Me) | H | 6-PhSO₂—Pyr-3 | O | 4-Zb |
| 16-25 | Me | CH(Me)CH(Me) | H | Quin-2 | O | 4-Zb |
| 16-26 | Me | CH(Me)CH(Me) | H | 4-MeO—Ph | O | 4-Zb |
| 16-27 | Me | CH(Me)CH(Me) | H | 4-EtO—Ph | O | 4-Zb |
| 16-28 | Me | CH(Me)CH(Me) | H | 4-iPrO—Ph | O | 4-Zb |
| 16-29 | Me | CH(Me)CH(Me) | H | 4-MeS—Ph | O | 4-Zb |
| 16-30 | Me | CH(Me)CH(Me) | H | 4-EtS—Ph | O | 4-Zb |
| 16-31 | Me | CH(Me)CH(Me) | H | 4-iPrS—Ph | O | 4-Zb |
| 16-32 | Me | CH(Me)CH(Me) | H | 4-MeSO₂—Ph | O | 4-Zb |
| 16-33 | Me | CH(Me)CH(Me) | H | 4-EtSO₂—Ph | O | 4-Zb |
| 16-34 | Me | CH(Me)CH(Me) | H | 4-iPrSO₂—Ph | O | 4-Zb |

TABLE 17

| Cpd. No. | R¹ | R² | R³ | X | Y | Z |
|---|---|---|---|---|---|---|
| 17-1 | Me | (CH₂)₂ | H | 4-Et—Ph | S | 4-Zb |
| 17-2 | Me | (CH₂)₂ | H | 4-iPr—Ph | S | 4-Zb |
| 17-3 | Me | (CH₂)₂ | H | 3-Ph—Ph | S | 4-Zb |
| 17-4 | Me | (CH₂)₂ | H | 4-Ph—Ph | S | 4-Zb |
| 17-5 | Me | (CH₂)₂ | H | Pyr-3 | S | 4-Zb |
| 17-6 | Me | (CH₂)₂ | H | 5-Me—Pyr-3 | S | 4-Zb |
| 17-7 | Me | (CH₂)₂ | H | 5-Et—Pyr-3 | S | 4-Zb |
| 17-8 | Me | (CH₂)₂ | H | 5-Ph—Pyr-3 | S | 4-Zb |
| 17-9 | Me | (CH₂)₂ | H | 6-Me—Pyr-3 | S | 4-Zb |
| 17-10 | Me | (CH₂)₂ | H | 6-Et—Pyr-3 | S | 4-Zb |
| 17-11 | Me | (CH₂)₂ | H | 6-Ph—Pyr-3 | S | 4-Zb |
| 17-12 | Me | (CH₂)₂ | H | 6-MeO—Pyr-3 | S | 4-Zb |
| 17-13 | Me | (CH₂)₂ | H | 6-EtO—Pyr-3 | S | 4-Zb |
| 17-14 | Me | (CH₂)₂ | H | 6-iPrO—Pyr-3 | S | 4-Zb |
| 17-15 | Me | (CH₂)₂ | H | 6-MeS—Pyr-3 | S | 4-Zb |
| 17-16 | Me | (CH₂)₂ | H | 6-EtS—Pyr-3 | S | 4-Zb |
| 17-17 | Me | (CH₂)₂ | H | 6-iPrS—Pyr-3 | S | 4-Zb |
| 17-18 | Me | (CH₂)₂ | H | 6-MeSO₂—Pyr-3 | S | 4-Zb |
| 17-19 | Me | (CH₂)₂ | H | 6-EtSO₂—Pyr-3 | S | 4-Zb |
| 17-20 | Me | (CH₂)₂ | H | 6-iPrSO₂—Pyr-3 | S | 4-Zb |
| 17-21 | Me | (CH₂)₂ | H | 6-Bz—Pyr-3 | S | 4-Zb |
| 17-22 | Me | (CH₂)₂ | H | 6-PhO—Pyr-3 | S | 4-Zb |
| 17-23 | Me | (CH₂)₂ | H | 6-PhS—Pyr-3 | S | 4-Zb |
| 17-24 | Me | (CH₂)₂ | H | 6-PhSO₂—Pyr-3 | S | 4-Zb |
| 17-25 | Me | (CH₂)₂ | H | Quin-2 | S | 4-Zb |
| 17-26 | Me | (CH₂)₂ | H | 4-MeO—Ph | S | 4-Zb |
| 17-27 | Me | (CH₂)₂ | H | 4-EtO—Ph | S | 4-Zb |
| 17-28 | Me | (CH₂)₂ | H | 4-iPrO—Ph | S | 4-Zb |
| 17-29 | Me | (CH₂)₂ | H | 4-MeS—Ph | S | 4-Zb |
| 17-30 | Me | (CH₂)₂ | H | 4-EtS—Ph | S | 4-Zb |
| 17-31 | Me | (CH₂)₂ | H | 4-iPrS—Ph | S | 4-Zb |
| 17-32 | Me | (CH₂)₂ | H | 4-MeSO₂—Ph | S | 4-Zb |
| 17-33 | Me | (CH₂)₂ | H | 4-EtSO₂—Ph | S | 4-Zb |
| 17-34 | Me | (CH₂)₂ | H | 4-iPrSO₂—Ph | S | 4-Zb |

TABLE 18

| Cpd. No. | R¹ | R² | R³ | X | Y | Z |
|---|---|---|---|---|---|---|
| 18-1 | Me | (CH₂)₂ | H | 4-Et-Ph | NMe | 4-Zb |
| 18-2 | Me | (CH₂)₂ | H | 4-iPr-Ph | NMe | 4-Zb |

TABLE 18-continued

| Cpd. No. | R¹ | R² | R³ | X | Y | Z |
|---|---|---|---|---|---|---|
| 18-3 | Me | (CH₂)₂ | H | 3-Ph-Ph | NMe | 4-Zb |
| 18-4 | Me | (CH₂)₂ | H | 4-Ph-Ph | NMe | 4-Zb |
| 18-5 | Me | (CH₂)₂ | H | Pyr-3 | NMe | 4-Zb |
| 18-6 | Me | (CH₂)₂ | H | 5-Me-Pyr-3 | NMe | 4-Zb |
| 18-7 | Me | (CH₂)₂ | H | 5-Et-Pyr-3 | NMe | 4-Zb |
| 18-8 | Me | (CH₂)₂ | H | 5-Ph-Pyr-3 | NMe | 4-Zb |
| 18-9 | Me | (CH₂)₂ | H | 6-Me-Pyr-3 | NMe | 4-Zb |
| 18-10 | Me | (CH₂)₂ | H | 6-Et-Pyr-3 | NMe | 4-Zb |
| 18-11 | Me | (CH₂)₂ | H | 6-Ph-Pyr-3 | NMe | 4-Zb |
| 18-12 | Me | (CH₂)₂ | H | 6-MeO-Pyr-3 | NMe | 4-Zb |
| 18-13 | Me | (CH₂)₂ | H | 6-EtO-Pyr-3 | NMe | 4-Zb |
| 18-14 | Me | (CH₂)₂ | H | 6-iPrO-Pyr-3 | NMe | 4-Zb |
| 18-15 | Me | (CH₂)₂ | H | 6-MeS-Pyr-3 | NMe | 4-Zb |
| 18-16 | Me | (CH₂)₂ | H | 6-EtS-Pyr-3 | NMe | 4-Zb |
| 18-17 | Me | (CH₂)₂ | H | 6-iPrS-Pyr-3 | NMe | 4-Zb |
| 18-18 | Me | (CH₂)₂ | H | 6-MeSO₂-Pyr-3 | NMe | 4-Zb |
| 18-19 | Me | (CH₂)₂ | H | 6-EtSO₂-Pyr-3 | NMe | 4-Zb |
| 18-20 | Me | (CH₂)₂ | H | 6-iPrSO₂-Pyr-3 | NMe | 4-Zb |
| 18-21 | Me | (CH₂)₂ | H | 6-Bz-Pyr-3 | NMe | 4-Zb |
| 18-22 | Me | (CH₂)₂ | H | 6-PhO-Pyr-3 | NMe | 4-Zb |
| 18-23 | Me | (CH₂)₂ | H | 6-PhS-Pyr-3 | NMe | 4-Zb |
| 18-24 | Me | (CH₂)₂ | H | 6-PhSO₂-Pyr-3 | NMe | 4-Zb |
| 18-25 | Me | (CH₂)₂ | H | Quin-2 | NMe | 4-Zb |
| 18-26 | Me | (CH₂)₂ | H | 4-MeO-Ph | NMe | 4-Zb |
| 18-27 | Me | (CH₂)₂ | H | 4-EtO-Ph | NMe | 4-Zb |
| 18-28 | Me | (CH₂)₂ | H | 4-iPrO-Ph | NMe | 4-Zb |
| 18-29 | Me | (CH₂)₂ | H | 4-MeS-Ph | NMe | 4-Zb |
| 18-30 | Me | (CH₂)₂ | H | 4-EtS-Ph | NMe | 4-Zb |
| 18-31 | Me | (CH₂)₂ | H | 4-iPrS-Ph | NMe | 4-Zb |
| 18-32 | Me | (CH₂)₂ | H | 4-MeSO₂-Ph | NMe | 4-Zb |
| 18-33 | Me | (CH₂)₂ | H | 4-EtSO₂-Ph | NMe | 4-Zb |
| 18-34 | Me | (CH₂)₂ | H | 4-iPrSO₂-Ph | NMe | 4-Zb |

TABLE 19

| Cpd. No. | R¹ | R² | R³ | X | Y | Z |
|---|---|---|---|---|---|---|
| 19-1 | Me | (CH₂)₂ | H | 4-Et-Ph | NAc | 4-Zb |
| 19-2 | Me | (CH₂)₂ | H | 4-iPr-Ph | NAc | 4-Zb |
| 19-3 | Me | (CH₂)₂ | H | 3-Ph-Ph | NAc | 4-Zb |
| 19-4 | Me | (CH₂)₂ | H | 4-Ph-Ph | NAc | 4-Zb |
| 19-5 | Me | (CH₂)₂ | H | Pyr-3 | NAc | 4-Zb |
| 19-6 | Me | (CH₂)₂ | H | 5-Me-Pyr-3 | NAc | 4-Zb |
| 19-7 | Me | (CH₂)₂ | H | 5-Et-Pyr-3 | NAc | 4-Zb |
| 19-8 | Me | (CH₂)₂ | H | 5-Ph-Pyr-3 | NAc | 4-Zb |
| 19-9 | Me | (CH₂)₂ | H | 6-Me-Pyr-3 | NAc | 4-Zb |
| 19-10 | Me | (CH₂)₂ | H | 6-Et-Pyr-3 | NAc | 4-Zb |
| 19-11 | Me | (CH₂)₂ | H | 6-Ph-Pyr-3 | NAc | 4-Zb |
| 19-12 | Me | (CH₂)₂ | H | 6-MeO-Pyr-3 | NAc | 4-Zb |
| 19-13 | Me | (CH₂)₂ | H | 6-EtO-Pyr-3 | NAc | 4-Zb |
| 19-14 | Me | (CH₂)₂ | H | 6-iPrO-Pyr-3 | NAc | 4-Zb |
| 19-15 | Me | (CH₂)₂ | H | 6-MeS-Pyr-3 | NAc | 4-Zb |
| 19-16 | Me | (CH₂)₂ | H | 6-EtS-Pyr-3 | NAc | 4-Zb |
| 19-17 | Me | (CH₂)₂ | H | 6-iPrS-Pyr-3 | NAc | 4-Zb |
| 19-18 | Me | (CH₂)₂ | H | 6-MeSO₂-Pyr-3 | NAc | 4-Zb |
| 19-19 | Me | (CH₂)₂ | H | 6-EtSO₂-Pyr-3 | NAc | 4-Zb |
| 19-20 | Me | (CH₂)₂ | H | 6-iPrSO₂-Pyr-3 | NAc | 4-Zb |
| 19-21 | Me | (CH₂)₂ | H | 6-Bz-Pyr-3 | NAc | 4-Zb |
| 19-22 | Me | (CH₂)₂ | H | 6-PhO-Pyr-3 | NAc | 4-Zb |
| 19-23 | Me | (CH₂)₂ | H | 6-PhS-Pyr-3 | NAc | 4-Zb |
| 19-24 | Me | (CH₂)₂ | H | 6-PhSO₂-Pyr-3 | NAc | 4-Zb |
| 19-25 | Me | (CH₂)₂ | H | Quin-2 | NAc | 4-Zb |
| 19-26 | Me | (CH₂)₂ | H | 4-MeO-Ph | NAc | 4-Zb |
| 19-27 | Me | (CH₂)₂ | H | 4-EtO-Ph | NAc | 4-Zb |
| 19-28 | Me | (CH₂)₂ | H | 4-iPrO-Ph | NAc | 4-Zb |
| 19-29 | Me | (CH₂)₂ | H | 4-MeS-Ph | NAc | 4-Zb |
| 19-30 | Me | (CH₂)₂ | H | 4-EtS-Ph | NAc | 4-Zb |
| 19-31 | Me | (CH₂)₂ | H | 4-iPrS-Ph | NAc | 4-Zb |
| 19-32 | Me | (CH₂)₂ | H | 4-MeSO₂-Ph | NAc | 4-Zb |
| 19-33 | Me | (CH₂)₂ | H | 4-EtSO₂-Ph | NAc | 4-Zb |
| 19-34 | Me | (CH₂)₂ | H | 4-iPrSO₂-Ph | NAc | 4-Zb |

TABLE 20

| Cpd. No. | R¹ | R² | R³ | X | Y | Z |
|---|---|---|---|---|---|---|
| 20-1 | Me | (CH₂)₂ | 2-Cl | 4-Et-Ph | O | 4-Zb |
| 20-2 | Me | (CH₂)₂ | 2-Cl | 4-iPr-Ph | O | 4-Zb |
| 20-3 | Me | (CH₂)₂ | 2-Cl | 3-Ph-Ph | O | 4-Zb |
| 20-4 | Me | (CH₂)₂ | 2-Cl | 4-Ph-Ph | O | 4-Zb |
| 20-5 | Me | (CH₂)₂ | 2-Cl | Pyr-3 | O | 4-Zb |
| 20-6 | Me | (CH₂)₂ | 2-Cl | 5-Me-Pyr-3 | O | 4-Zb |
| 20-7 | Me | (CH₂)₂ | 2-Cl | 5-Et-Pyr-3 | O | 4-Zb |
| 20-8 | Me | (CH₂)₂ | 2-Cl | 5-Ph-Pyr-3 | O | 4-Zb |
| 20-9 | Me | (CH₂)₂ | 2-Cl | 6-Me-Pyr-3 | O | 4-Zb |
| 20-10 | Me | (CH₂)₂ | 2-Cl | 6-Et-Pyr-3 | O | 4-Zb |
| 20-11 | Me | (CH₂)₂ | 2-Cl | 6-Ph-Pyr-3 | O | 4-Zb |
| 20-12 | Me | (CH₂)₂ | 2-Cl | 6-MeO-Pyr-3 | O | 4-Zb |
| 20-13 | Me | (CH₂)₂ | 2-Cl | 6-EtO-Pyr-3 | O | 4-Zb |
| 20-14 | Me | (CH₂)₂ | 2-Cl | 6-iPrO-Pyr-3 | O | 4-Zb |
| 20-15 | Me | (CH₂)₂ | 2-Cl | 6-MeS-Pyr-3 | O | 4-Zb |
| 20-16 | Me | (CH₂)₂ | 2-Cl | 6-EtS-Pyr-3 | O | 4-Zb |
| 20-17 | Me | (CH₂)₂ | 2-Cl | 6-iPrS-Pyr-3 | O | 4-Zb |
| 20-18 | Me | (CH₂)₂ | 2-Cl | 6-MeSO₂-Pyr-3 | O | 4-Zb |
| 20-19 | Me | (CH₂)₂ | 2-Cl | 6-EtSO₂-Pyr-3 | O | 4-Zb |
| 20-20 | Me | (CH₂)₂ | 2-Cl | 6-iPrSO₂-Pyr-3 | O | 4-Zb |
| 20-21 | Me | (CH₂)₂ | 2-Cl | 6-Bz-Pyr-3 | O | 4-Zb |
| 20-22 | Me | (CH₂)₂ | 2-Cl | 6-PhO-Pyr-3 | O | 4-Zb |
| 20-23 | Me | (CH₂)₂ | 2-Cl | 6-PhS-Pyr-3 | O | 4-Zb |
| 20-24 | Me | (CH₂)₂ | 2-Cl | 6-PhSO₂-Pyr-3 | O | 4-Zb |
| 20-25 | Me | (CH₂)₂ | 2-Cl | Quin-2 | O | 4-Zb |
| 20-26 | Me | (CH₂)₂ | 2-Cl | 4-MeO-Ph | O | 4-Zb |
| 20-27 | Me | (CH₂)₂ | 2-Cl | 4-EtO-Ph | O | 4-Zb |
| 20-28 | Me | (CH₂)₂ | 2-Cl | 4-iPrO-Ph | O | 4-Zb |
| 20-29 | Me | (CH₂)₂ | 2-Cl | 4-MeS-Ph | O | 4-Zb |
| 20-30 | Me | (CH₂)₂ | 2-Cl | 4-EtS-Ph | O | 4-Zb |
| 20-31 | Me | (CH₂)₂ | 2-Cl | 4-iPrS-Ph | O | 4-Zb |
| 20-32 | Me | (CH₂)₂ | 2-Cl | 4-MeSO₂-Ph | O | 4-Zb |
| 20-33 | Me | (CH₂)₂ | 2-Cl | 4-EtSO₂-Ph | O | 4-Zb |
| 20-34 | Me | (CH₂)₂ | 2-Cl | 4-iPrSO₂-Ph | O | 4-Zb |

TABLE 21

| Cpd. No. | R¹ | R² | R³ | X | Y | Z |
|---|---|---|---|---|---|---|
| 21-1 | Me | (CH₂)₂ | 3-Cl | 4-Et-Ph | O | 4-Zb |
| 21-2 | Me | (CH₂)₂ | 3-Cl | 4-iPr-Ph | O | 4-Zb |
| 21-3 | Me | (CH₂)₂ | 3-Cl | 3-Ph-Ph | O | 4-Zb |
| 21-4 | Me | (CH₂)₂ | 3-Cl | 4-Ph-Ph | O | 4-Zb |
| 21-5 | Me | (CH₂)₂ | 3-Cl | Pyr-3 | O | 4-Zb |
| 21-6 | Me | (CH₂)₂ | 3-Cl | 5-Me-Pyr-3 | O | 4-Zb |
| 21-7 | Me | (CH₂)₂ | 3-Cl | 5-Et-Pyr-3 | O | 4-Zb |
| 21-8 | Me | (CH₂)₂ | 3-Cl | 5-Ph-Pyr-3 | O | 4-Zb |
| 21-9 | Me | (CH₂)₂ | 3-Cl | 6-Me-Pyr-3 | O | 4-Zb |
| 21-10 | Me | (CH₂)₂ | 3-Cl | 6-Et-Pyr-3 | O | 4-Zb |
| 21-11 | Me | (CH₂)₂ | 3-Cl | 6-Ph-Pyr-3 | O | 4-Zb |
| 21-12 | Me | (CH₂)₂ | 3-Cl | 6-MeO-Pyr-3 | O | 4-Zb |
| 21-13 | Me | (CH₂)₂ | 3-Cl | 6-BtO-Pyr-3 | O | 4-Zb |
| 21-14 | Me | (CH₂)₂ | 3-Cl | 6-iPrO-Pyr-3 | O | 4-Zb |
| 21-15 | Me | (CH₂)₂ | 3-Cl | 6-MeS-Pyr-3 | O | 4-Zb |
| 21-16 | Me | (CH₂)₂ | 3-Cl | 6-EtS-Pyr-3 | O | 4-Zb |
| 21-17 | Me | (CH₂)₂ | 3-Cl | 6-iPrS-Pyr-3 | O | 4-Zb |
| 21-18 | Me | (CH₂)₂ | 3-Cl | 6-MeSO₂-Pyr-3 | O | 4-Zb |
| 21-19 | Me | (CH₂)₂ | 3-Cl | 6-EtSO₂-Pyr-3 | O | 4-Zb |
| 21-20 | Me | (CH₂)₂ | 3-Cl | 6-iPrSO₂-Pyr-3 | O | 4-Zb |
| 21-21 | Me | (CH₂)₂ | 3-Cl | 6-Bz-Pyr-3 | O | 4-Zb |
| 21-22 | Me | (CH₂)₂ | 3-Cl | 6-PhO-Pyr-3 | O | 4-Zb |
| 21-23 | Me | (CH₂)₂ | 3-Cl | 6-PhS-Pyr-3 | O | 4-Zb |
| 21-24 | Me | (CH₂)₂ | 3-Cl | 6-PhSO₂-Pyr-3 | O | 4-Zb |
| 21-25 | Me | (CH₂)₂ | 3-Cl | Quin-2 | O | 4-Zb |
| 21-26 | Me | (CH₂)₂ | 3-Cl | 4-MeO-Ph | O | 4-Zb |
| 21-27 | Me | (CH₂)₂ | 3-Cl | 4-EtO-Ph | O | 4-Zb |
| 21-28 | Me | (CH₂)₂ | 3-Cl | 4-iPrO-Ph | O | 4-Zb |
| 21-29 | Me | (CH₂)₂ | 3-Cl | 4-MeS-Ph | O | 4-Zb |
| 21-30 | Me | (CH₂)₂ | 3-Cl | 4-EtS-Ph | O | 4-Zb |
| 21-31 | Me | (CH₂)₂ | 3-Cl | 4-iPrS-Ph | O | 4-Zb |

TABLE 21-continued

| Cpd. No. | R¹ | R² | X | Y | | Z |
|---|---|---|---|---|---|---|
| 21-32 | Me | (CH₂)₂ | 3-Cl | 4-MeSO₂-Ph | O | 4-Zb |
| 21-33 | Me | (CH₂)₂ | 3-Cl | 4-EtSO₂-Ph | O | 4-Zb |
| 21-34 | Me | (CH₂)₂ | 3-Cl | 4-iPrSO₂-Ph | O | 4-Zb |

TABLE 22

| Cpd. No. | R¹ | R² | X | Y | | Z |
|---|---|---|---|---|---|---|
| 22-1 | Me | (CH₂)₂ | 2-MeO | 4-Et-Ph | O | 4-Zb |
| 22-2 | Me | (CH₂)₂ | 2-MeO | 4-iPr-Ph | O | 4-Zb |
| 22-3 | Me | (CH₂)₂ | 2-MeO | 3-Ph-Ph | O | 4-Zb |
| 22-4 | Me | (CH₂)₂ | 2-MeO | 4-Ph-Ph | O | 4-Zb |
| 22-5 | Me | (CH₂)₂ | 2-MeO | Pyr-3 | O | 4-Zb |
| 22-6 | Me | (CH₂)₂ | 2-MeO | 5-Me-Pyr-3 | O | 4-Zb |
| 22-7 | Me | (CH₂)₂ | 2-MeO | 5-Et-Pyr-3 | O | 4-Zb |
| 22-8 | Me | (CH₂)₂ | 2-MeO | 5-Ph-Pyr-3 | O | 4-Zb |
| 22-9 | Me | (CH₂)₂ | 2-MeO | 6-Me-Pyr-3 | O | 4-Zb |
| 22-10 | Me | (CH₂)₂ | 2-MeO | 6-Et-Pyr-3 | O | 4-Zb |
| 22-11 | Me | (CH₂)₂ | 2-MeO | 6-Ph-Pyr-3 | O | 4-Zb |
| 22-12 | Me | (CH₂)₂ | 2-MeO | 6-MeO-Pyr-3 | O | 4-Zb |
| 22-13 | Me | (CH₂)₂ | 2-MeO | 6-EtO-Pyr-3 | O | 4-Zb |
| 22-14 | Me | (CH₂)₂ | 2-MeO | 6-iPrO-Pyr-3 | O | 4-Zb |
| 22-15 | Me | (CH₂)₂ | 2-MeO | 6-MeS-Pyr-3 | O | 4-Zb |
| 22-16 | Me | (CH₂)₂ | 2-MeO | 6-EtS-Pyr-3 | O | 4-Zb |
| 22-17 | Me | (CH₂)₂ | 2-MeO | 6-iPrS-Pyr-3 | O | 4-Zb |
| 22-18 | Me | (CH₂)₂ | 2-MeO | 6-MeSO₂-Pyr-3 | O | 4-Zb |
| 22-19 | Me | (CH₂)₂ | 2-MeO | 6-EtSO₂-Pyr-3 | O | 4-Zb |
| 22-20 | Me | (CH₂)₂ | 2-MeO | 6-iPrSO₂-Pyr-3 | O | 4-Zb |
| 22-21 | Me | (CH₂)₂ | 2-MeO | 6-Bz-Pyr-3 | O | 4-Zb |
| 22-22 | Me | (CH₂)₂ | 2-MeO | 6-PhO-Pyr-3 | O | 4-Zb |
| 22-23 | Me | (CH₂)₂ | 2-MeO | 6-PhS-Pyr-3 | O | 4-Zb |
| 22-24 | Me | (CH₂)₂ | 2-MeO | 6-PhSO₂-Pyr-3 | O | 4-Zb |
| 22-25 | Me | (CH₂)₂ | 2-MeO | Quin-2 | O | 4-Zb |
| 22-26 | Me | (CH₂)₂ | 2-MeO | 4-MeO-Ph | O | 4-Zb |
| 22-27 | Me | (CH₂)₂ | 2-MeO | 4-EtO-Ph | O | 4-Zb |
| 22-28 | Me | (CH₂)₂ | 2-MeO | 4-iPrO-Ph | O | 4-Zb |
| 22-29 | Me | (CH₂)₂ | 2-MeO | 4-MeS-Ph | O | 4-Zb |
| 22-30 | Me | (CH₂)₂ | 2-MeO | 4-EtS-Ph | O | 4-Zb |
| 22-31 | Me | (CH₂)₂ | 2-MeO | 4-iPrS-Ph | O | 4-Zb |
| 22-32 | Me | (CH₂)₂ | 2-MeO | 4-MeSO₂-Ph | O | 4-Zb |
| 22-33 | Me | (CH₂)₂ | 2-MeO | 4-EtSO₂-Ph | O | 4-Zb |
| 22-34 | Me | (CH₂)₂ | 2-MeO | 4-iPrSO₂-Ph | O | 4-Zb |

TABLE 23

| Cpd. No. | R¹ | R² | X | Y | | Z |
|---|---|---|---|---|---|---|
| 23-1 | Me | (CH₂)₂ | 3-MeO | 4-Et-Ph | O | 4-Zb |
| 23-2 | Me | (CH₂)₂ | 3-MeO | 4-iPr-Ph | O | 4-Zb |
| 23-3 | Me | (CH₂)₂ | 3-MeO | 3-Ph-Ph | O | 4-Zb |
| 23-4 | Me | (CH₂)₂ | 3-MeO | 4-Ph-Ph | O | 4-Zb |
| 23-5 | Me | (CH₂)₂ | 3-MeO | Pyr-3 | O | 4-Zb |
| 23-6 | Me | (CH₂)₂ | 3-MeO | 5-Me-Pyr-3 | O | 4-Zb |
| 23-7 | Me | (CH₂)₂ | 3-MeO | 5-Et-Pyr-3 | O | 4-Zb |
| 23-8 | Me | (CH₂)₂ | 3-MeO | 5-Ph-Pyr-3 | O | 4-Zb |
| 23-9 | Me | (CH₂)₂ | 3-MeO | 6-Me-Pyr-3 | O | 4-Zb |
| 23-10 | Me | (CH₂)₂ | 3-MeO | 6-Et-Pyr-3 | O | 4-Zb |
| 23-11 | Me | (CH₂)₂ | 3-MeO | 6-Ph-Pyr-3 | O | 4-Zb |
| 23-12 | Me | (CH₂)₂ | 3-MeO | 6-MeO-Pyr-3 | O | 4-Zb |
| 23-13 | Me | (CH₂)₂ | 3-MeO | 6-EtO-Pyr-3 | O | 4-Zb |
| 23-14 | Me | (CH₂)₂ | 3-MeO | 6-iPrO-Pyr-3 | O | 4-Zb |
| 23-15 | Me | (CH₂)₂ | 3-MeO | 6-MeS-Pyr-3 | O | 4-Zb |
| 23-16 | Me | (CH₂)₂ | 3-MeO | 6-EtS-Pyr-3 | O | 4-Zb |
| 23-17 | Me | (CH₂)₂ | 3-MeO | 6-iPrS-Pyr-3 | O | 4-Zb |
| 23-18 | Me | (CH₂)₂ | 3-MeO | 6-MeSO₂-Pyr-3 | O | 4-Zb |
| 23-19 | Me | (CH₂)₂ | 3-MeO | 6-EtSO₂-Pyr-3 | O | 4-Zb |
| 23-20 | Me | (CH₂)₂ | 3-MeO | 6-PrSO₂-Pyr-3 | O | 4-Zb |
| 23-21 | Me | (CH₂)₂ | 3-MeO | 6-Bz-Pyr-3 | O | 4-Zb |
| 23-22 | Me | (CH₂)₂ | 3-MeO | 6-PhO-Pyr-3 | O | 4-Zb |

TABLE 23-continued

| Cpd. No. | R¹ | R² | X | Y | | Z |
|---|---|---|---|---|---|---|
| 23-23 | Me | (CH₂)₂ | 3-MeO | 6-PhS-Pyr-3 | O | 4-Zb |
| 23-24 | Me | (CH₂)₂ | 3-MeO | 6-PhSO₂-Pyr-3 | O | 4-Zb |
| 23-25 | Me | (CH₂)₂ | 3-MeO | Quin-2 | O | 4-Zb |
| 23-26 | Me | (CH₂)₂ | 3-MeO | 4-MeO-Ph | O | 4-Zb |
| 23-27 | Me | (CH₂)₂ | 3-MeO | 4-EtO-Ph | O | 4-Zb |
| 23-28 | Me | (CH₂)₂ | 3-MeO | 4-iPrO-Ph | O | 4-Zb |
| 23-29 | Me | (CH₂)₂ | 3-MeO | 4-MeS-Ph | O | 4-Zb |
| 23-30 | Me | (CH₂)₂ | 3-MeO | 4-EtS-Ph | O | 4-Zb |
| 23-31 | Me | (CH₂)₂ | 3-MeO | 4-iPrS-Ph | O | 4-Zb |
| 23-32 | Me | (CH₂)₂ | 3-MeO | 4-MeSO₂-Ph | O | 4-Zb |
| 23-33 | Me | (CH₂)₂ | 3-MeO | 4-EtSO₂-Ph | O | 4-Zb |
| 23-34 | Me | (CH₂)₂ | 3-MeO | 4-iPrSO₂-Ph | O | 4-Zb |

TABLE 24

| Cpd. No. | R¹ | R² | R³ | X | Y | Z |
|---|---|---|---|---|---|---|
| 24-1 | Me | (CH₂)₂ | H | 4-Et-Ph | O | 4-Za |
| 24-2 | Me | (CH₂)₂ | H | 4-iPr-Ph | O | 4-Za |
| 24-3 | Me | (CH₂)₂ | H | 3-Ph-Ph | O | 4-Za |
| 24-4 | Me | (CH₂)₂ | H | 4-Ph-Ph | O | 4-Za |
| 24-5 | Me | (CH₂)₂ | H | Pyr-3 | O | 4-Za |
| 24-6 | Me | (CH₂)₂ | H | 5-Me-Pyr-3 | O | 4-Za |
| 24-7 | Me | (CH₂)₂ | H | 5-Et-Pyr-3 | O | 4-Za |
| 24-8 | Me | (CH₂)₂ | H | 5-Ph-Pyr-3 | O | 4-Za |
| 24-9 | Me | (CH₂)₂ | H | 6-Me-Pyr-3 | O | 4-Za |
| 24-10 | Me | (CH₂)₂ | H | 6-Et-Pyr-3 | O | 4-Za |
| 24-11 | Me | (CH₂)₂ | H | 6-Ph-Pyr-3 | O | 4-Za |
| 24-12 | Me | (CH₂)₂ | H | 6-MeO-Pyr-3 | O | 4-Za |
| 24-13 | Me | (CH₂)₂ | H | 6-EtO-Pyr-3 | O | 4-Za |
| 24-14 | Me | (CH₂)₂ | H | 6-iPrO-Pyr-3 | O | 4-Za |
| 24-15 | Me | (CH₂)₂ | H | 6-MeS-Pyr-3 | O | 4-Za |
| 24-16 | Me | (CH₂)₂ | H | 6-EtS-Pyr-3 | O | 4-Za |
| 24-17 | Me | (CH₂)₂ | H | 6-iPrS-Pyr-3 | O | 4-Za |
| 24-18 | Me | (CH₂)₂ | H | 6-MeSO₂-Pyr-3 | O | 4-Za |
| 24-19 | Me | (CH₂)₂ | H | 6-EtSO₂-Pyr-3 | O | 4-Za |
| 24-20 | Me | (CH₂)₂ | H | 6-iPrSO₂-Pyr-3 | O | 4-Za |
| 24-21 | Me | (CH₂)₂ | H | 6-Bz-Pyr-3 | O | 4-Za |
| 24-23 | Me | (CH₂)₂ | H | 6-PhO-Pyr-3 | O | 4-Za |
| 24-23 | Me | (CH₂)₂ | H | 6-PhS-Pyr-3 | O | 4-Za |
| 24-24 | Me | (CH₂)₂ | H | 6-PhSO₂-Pyr-3 | O | 4-Za |
| 24-25 | Me | (CH₂)₂ | H | Quin-2 | O | 4-Za |
| 24-26 | Me | (CH₂)₂ | H | 4-MeO-Ph | O | 4-Za |
| 24-27 | Me | (CH₂)₂ | H | 4-EtO-Ph | O | 4-Za |
| 24-28 | Me | (CH₂)₂ | H | 4-iPrO-Ph | O | 4-Za |
| 24-29 | Me | (CH₂)₂ | H | 4-MeS-Ph | O | 4-Za |
| 24-30 | Me | (CH₂)₂ | H | 4-EtS-Ph | O | 4-Za |
| 24-31 | Me | (CH₂)₂ | H | 4-iPrS-Ph | O | 4-Za |
| 24-32 | Me | (CH₂)₂ | H | 4-MeSO₂-Ph | O | 4-Za |
| 24-33 | Me | (CH₂)₂ | H | 4-EtSO₂-Ph | O | 4-Za |
| 24-34 | Me | (CH₂)₂ | H | 4-iPrSO₂-Ph | O | 3-Za |

TABLE 25

| Cpd. No. | R¹ | R² | R³ | X | Y | Z |
|---|---|---|---|---|---|---|
| 25-1 | Me | (CH₂)₂ | H | 4-Et—Ph | O | 4-Zd |
| 25-2 | Me | (CH₂)₂ | H | 4-iPr—Ph | O | 4-Zd |
| 25-3 | Me | (CH₂)₂ | H | 3-Ph—Ph | O | 4-Zd |
| 25-4 | Me | (CH₂)₂ | H | 4-Ph—Ph | O | 4-Zd |
| 25-5 | Me | (CH₂)₂ | H | Pyr-3 | O | 4-Zd |
| 25-6 | Me | (CH₂)₂ | H | 4-Me—Pyr-3 | O | 4-Zd |
| 25-7 | Me | (CH₂)₂ | H | 5-Et—Pyr-3 | O | 4-Zd |
| 25-8 | Me | (CH₂)₂ | H | 5-Ph—Pyr-3 | O | 4-Zd |
| 25-9 | Me | (CH₂)₂ | H | 6-Me—Pyr-3 | O | 4-Zd |
| 25-10 | Me | (CH₂)₂ | H | 6-Et—Pyr-3 | O | 4-Zd |
| 25-11 | Me | (CH₂)₂ | H | 6-Ph—Pyr-3 | O | 4-Zd |
| 25-12 | Me | (CH₂)₂ | H | 6-MeO—Pyr-3 | O | 4-Zd |
| 25-13 | Me | (CH₂)₂ | H | 6-EtO—Pyr-3 | O | 4-Zd |

TABLE 25-continued

| Cpd. No. | R¹ | R² | R³ | X | Y | Z |
|---|---|---|---|---|---|---|
| 25-14 | Me | (CH₂)₂ | H | 6-iPrO—Pyr-3 | O | 4-Zd |
| 25-15 | Me | (CH₂)₂ | H | 6-MeS—Pyr-3 | O | 4-Zd |
| 25-16 | Me | (CH₂)₂ | H | 6-EtS—Pyr-3 | O | 4-Zd |
| 25-17 | Me | (CH₂)₂ | H | 6-iPrS—Pyr-3 | O | 4-Zd |
| 25-18 | Me | (CH₂)₂ | H | 6-MeSO₂—Pyr-3 | O | 4-Zd |
| 25-19 | Me | (CH₂)₂ | H | 6-EtSO₂—Pyr-3 | O | 4-Zd |
| 25-20 | Me | (CH₂)₂ | H | 6-iPrSO₂—Pyr-3 | O | 4-Zd |
| 25-21 | Me | (CH₂)₂ | H | 6-Bz—Pyr-3 | O | 4-Zd |
| 25-22 | Me | (CH₂)₂ | H | 6-PhO—Pyr-3 | O | 4-Zd |
| 25-23 | Me | (CH₂)₂ | H | 6-PhS—Pyr-3 | O | 4-Zd |
| 25-24 | Me | (CH₂)₂ | H | 6-PhSO₂—Pyr-3 | O | 4-Zd |
| 25-25 | Me | (CH₂)₂ | H | Quin-2 | O | 4-Zd |
| 25-26 | Me | (CH₂)₂ | H | 4-MeO—Ph | O | 4-Zd |
| 25-27 | Me | (CH₂)₂ | H | 4-EtO—Ph | O | 4-Zd |
| 25-28 | Me | (CH₂)₂ | H | 4-iPrO—Ph | O | 4-Zd |
| 25-29 | Me | (CH₂)₂ | H | 4-MeS—Ph | O | 4-Zd |
| 25-30 | Me | (CH₂)₂ | H | 4-EtS—Ph | O | 4-Zd |
| 25-31 | Me | (CH₂)₂ | H | 4-iPrS—Ph | O | 4-Zd |
| 25-32 | Me | (CH₂)₂ | H | 4-MeSO₂—Ph | O | 4-Zd |
| 25-33 | Me | (CH₂)₂ | H | 4-EtSO₂—Ph | O | 4-Zd |
| 25-34 | Me | (CH₂)₂ | H | 4-iPrSO₂—Ph | O | 4-Zd |

TABLE 26

| Cpd. No. | R¹ | R² | R³ | X | Y | Z |
|---|---|---|---|---|---|---|
| 26-1 | Me | (CH₂)₂ | H | 4-Et—Ph | O | 3-Zb |
| 26-2 | Me | (CH₂)₂ | H | 4-iPr—Ph | O | 3-Zb |
| 26-3 | Me | (CH₂)₂ | H | 3-Ph—Ph | O | 3-Zb |
| 26-4 | Me | (CH₂)₂ | H | 4-Ph—Ph | O | 3-Zb |
| 26-5 | Me | (CH₂)₂ | H | Pyr-3 | O | 3-Zb |
| 26-6 | Me | (CH₂)₂ | H | 4-Me—Pyr-3 | O | 3-Zb |
| 26-7 | Me | (CH₂)₂ | H | 5-Et—Pyr-3 | O | 3-Zb |
| 26-8 | Me | (CH₂)₂ | H | 5-Ph—Pyr-3 | O | 3-Zb |
| 26-9 | Me | (CH₂)₂ | H | 6-Me—Pyr-3 | O | 3-Zb |
| 26-10 | Me | (CH₂)₂ | H | 6-Et—Pyr-3 | O | 3-Zb |
| 26-11 | Me | (CH₂)₂ | H | 6-Ph—Pyr-3 | O | 3-Zb |
| 26-12 | Me | (CH₂)₂ | H | 6-MeO—Pyr-3 | O | 3-Zb |
| 26-13 | Me | (CH₂)₂ | H | 6-EtO—Pyr-3 | O | 3-Zb |
| 26-14 | Me | (CH₂)₂ | H | 6-iPrO—Pyr-3 | O | 3-Zb |
| 26-15 | Me | (CH₂)₂ | H | 6-MeS—Pyr-3 | O | 3-Zb |
| 26-16 | Me | (CH₂)₂ | H | 6-EtS—Pyr-3 | O | 3-Zb |
| 26-17 | Me | (CH₂)₂ | H | 6-iPrS—Pyr-3 | O | 3-Zb |
| 26-18 | Me | (CH₂)₂ | H | 6-MeSO₂—Pyr-3 | O | 3-Zb |
| 26-19 | Me | (CH₂)₂ | H | 6-EtSO₂—Pyr-3 | O | 3-Zb |
| 26-20 | Me | (CH₂)₂ | H | 6-iPrSO₂—Pyr-3 | O | 3-Zb |
| 26-21 | Me | (CH₂)₂ | H | 6-Bz—Pyr-3 | O | 3-Zb |
| 26-22 | Me | (CH₂)₂ | H | 6-PhO—Pyr-3 | O | 3-Zb |
| 26-23 | Me | (CH₂)₂ | H | 6-PhS—Pyr-3 | O | 3-Zb |
| 26-24 | Me | (CH₂)₂ | H | 6-PhSO₂—Pyr-3 | O | 3-Zb |
| 26-25 | Me | (CH₂)₂ | H | Quin-2 | O | 3-Zb |
| 26-26 | Me | (CH₂)₂ | H | 4-MeO—Ph | O | 3-Zb |
| 26-27 | Me | (CH₂)₂ | H | 4-EtO—Ph | O | 3-Zb |
| 26-28 | Me | (CH₂)₂ | H | 4-iPrO—Ph | O | 3-Zb |
| 26-29 | Me | (CH₂)₂ | H | 4-MeS—Ph | O | 3-Zb |
| 26-30 | Me | (CH₂)₂ | H | 4-EtS—Ph | O | 3-Zb |
| 26-31 | Me | (CH₂)₂ | H | 4-iPrS—Ph | O | 3-Zb |
| 26-32 | Me | (CH₂)₂ | H | 4-MeSO₂—Ph | O | 3-Zb |
| 26-33 | Me | (CH₂)₂ | H | 4-EtSO₂—Ph | O | 3-Zb |
| 26-34 | Me | (CH₂)₂ | H | 4-iPrSO₂—Ph | O | 3-Zb |

Of the compounds listed in the above Tables, (1) Preferred compounds are Compounds No. 1-1, 1-2, 1-3, 1-4, 1-5, 1-7, 1-10, 1-11, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-53, 1-56, 1-58, 1-60, 1-66, 1-70, 1-72, 1-78, 1-80, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-144, 1-145, 1-146, 1-147, 1-148, 1-149, 1-150, 1-155, 1-156, 1-157, 1-158, 1-161, 1-162, 1-163, 1-164, 1-165, 1-166, 1-167, 1-168, 1-169, 1-170, 1-171, 1-172, 1-175, 1-176, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 2-1, 2-2, 2-3, 2-4, 2-5, 2-7, 2-10, 2-11, 2-14, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-53, 2-56, 2-58, 2-60, 2-66, 2-70, 2-72, 2-78, 2-80, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-111, 2-112, 2-144, 2-145, 2-146, 2-147, 2-148, 2-149, 2-150, 2-155, 2-156, 2-157, 2-158, 2-161, 2-162, 2-163, 2-164, 2-165, 2-166, 2-167, 2-168, 2-169, 2-170, 2-171, 2-172, 2-175, 2-176, 2-180, 2-181, 2-182, 2-183, 2-184, 2-185, 2-186, 2-187, 2-188, 2-189, 2-190, 2-191, 2-192, 2-193, 2-194, 2-195, 2-196, 2-197, 2-198, 2-199, 2-200, 2-201, 2-202, 2-203, 3-1, 3-2, 3-3, 3-4, 3-5, 3-7, 3-10, 3-11, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 3-37, 3-38, 3-39, 3-40, 3-41, 3-42, 3-43, 3-44, 3-45, 3-53, 3-56, 3-58, 3-60, 3-66, 3-70, 3-72, 3-78, 3-80, 3-87, 3-88, 3-89, 3-90, 3-91, 3-92, 3-93, 3-94, 3-95, 3-96, 3-97, 3-98, 3-99, 3-100, 3-101, 3-102, 3-103, 3-104, 3-105, 3-106, 3-107, 3-108, 3-109, 3-110, 3-111, 3-112, 3-144, 3-145, 3-146, 3-147, 3-148, 3-149, 3-150, 3-155, 3-156, 3-157, 3-158, 3-161, 3-162, 3-163, 3-164, 3-165, 3-166, 3-167, 3-168, 3-169, 3-170, 3-171, 3-172, 3-175, 3-176, 3-180, 3-181, 3-182, 3-183, 3-184, 3-185, 3-186, 3-187, 3-188, 3-189, 3-190, 3-191, 3-192, 3-193, 3-194, 3-195, 3-196, 3-197, 3-198, 3-199, 3-200, 3-201, 3-202, 3-203, 4-1, 4-2, 4-3, 4-4, 4-5, 4-7, 4-10, 4-11, 4-14, 4-15, 4-16, 4-17, 4-18, 4-19, 4-20, 4-21, 4-22, 4-23, 4-24, 4-25, 4-26, 4-27, 4-28, 4-29, 4-30, 4-31, 4-32, 4-33, 4-34, 4-35, 4-36, 4-37, 4-38, 4-39, 4-40, 4-41, 4-42, 4-43, 4-44, 4-45, 4-53, 4-56, 4-58, 4-60, 4-66, 4-70, 4-72, 4-78, 4-80, 4-87, 4-88, 4-89, 4-90, 4-91, 4-92, 4-93, 4-94, 4-95, 4-96, 4-97, 4-98, 4-99, 4-100, 4-101, 4-102, 4-103, 4-104, 4-105, 4-106, 4-107, 4-108, 4-109, 4-110, 4-111, 4-112, 4-144, 4-145, 4-146, 4-147, 4-148, 4-149, 4-150, 4-155, 4-156, 4-157, 4-158, 4-161, 4-162, 4-163, 4-164, 4-165, 4-166, 4-167, 4-168, 4-169, 4-170, 4-171, 4-172, 4-175, 4-176, 4-180, 4-181, 4-182, 4-183, 4-184, 4-185, 4-186, 4-187, 4-188, 4-189, 4-190, 4-191, 4-192, 4-193, 4-194, 4-195, 4-196, 4-197, 4-198, 4-199, 4-200, 4-201, 4-202, 4-203, 5-1, 5-2, 5-3, 5-4, 5-5, 5-7, 5-10, 5-11, 5-14, 5-15, 5-16, 5-17, 5-18, 5-19, 5-20, 5-21, 5-22, 5-23, 5-24, 5-25, 5-26, 5-27, 5-28, 5-29, 5-30, 5-31, 5-32, 5-33, 5-34, 5-35, 5-36, 5-37, 5-38, 5-39, 5-40, 5-41, 5-42, 5-43, 5-44, 5-45, 5-53, 5-56, 5-58, 5-60, 5-66, 5-70, 5-72, 5-78, 5-80, 5-87, 5-88, 5-89, 5-90, 5-91, 5-92, 5-93, 5-94, 5-95, 5-96, 5-97, 5-98, 5-99, 5-100, 5-101, 5-102, 5-103, 5-104, 5-105, 5-106, 5-107, 5-108, 5-109, 5-110, 5-111, 5-112, 5-144, 5-145, 5-146, 5-147, 5-148, 5-149, 5-150, 5-155, 5-156, 5-157, 5-158, 5-161, 5-162, 5-163, 5-164, 5-165, 5-166, 5-167, 5-168, 5-169, 5-170, 5-171, 5-172, 5-175, 5-176, 5-180, 5-181, 5-182, 5-183, 5-184, 5-185, 5-186, 5-187, 5-188, 5-189, 5-190, 5-191, 5-192, 5-193, 5-194, 5-195, 5-196, 5-197, 5-198, 5-199, 5-200, 5-201, 5-202, 5-203, 6-1, 6-2, 6-3, 6-4, 6-5, 6-7, 6-10, 6-11, 6-14, 6-15, 6-16, 6-17, 6-18, 6-19, 6-20, 6-21, 6-22, 6-23, 6-24, 6-25, 6-26, 6-27, 6-28, 6-29, 6-30, 6-31, 6-32, 6-33, 6-34, 6-35, 6-36, 6-37, 6-38, 6-39, 6-40, 6-41, 6-42, 6-43, 6-44, 6-45, 6-53, 6-56, 6-58, 6-60, 6-66, 6-70, 6-72, 6-78, 6-80, 6-87, 6-88, 6-89, 6-90, 6-91, 6-92, 6-93, 6-94, 6-95, 6-96, 6-97, 6-98, 6-99, 6-100, 6-101, 6-102, 6-103, 6-104, 6-105, 6-106, 6-107, 6-108, 6-109, 6-110, 6-111, 6-112, 6-144, 6-145, 6-146, 6-147, 6-148, 6-149, 6-150, 6-155, 6-156, 6-157, 6-158, 6-161, 6-162, 6-163, 6-164, 6-165, 6-166, 6-167, 6-168, 6-169, 6-170, 6-171, 6-172, 6-175, 6-176, 6-180, 6-181, 6-182, 6-183, 6-184, 6-185, 6-186, 6-187, 6-188, 6-189, 6-190, 6-191, 6-192, 6-193, 6-194, 6-195, 6-196, 6-197, 6-198, 6-199, 6-200, 6-201, 6-202, 6-203, 7-1, 7-2, 7-3, 7-4, 7-5, 7-7, 7-10, 7-11, 7-14, 7-15, 7-16, 7-17, 7-18, 7-19, 7-20, 7-21, 7-22, 7-23, 7-24, 7-25, 7-26, 7-27, 7-28, 7-29, 7-30, 7-31, 7-32, 7-33, 7-34, 7-35, 7-36, 7-37, 7-38, 7-39, 7-40, 7-41, 7-42, 7-43, 7-44, 7-45, 7-53, 7-56, 7-58, 7-60, 7-66, 7-70, 7-72, 7-78, 7-80, 7-87, 7-88, 7-89, 7-90, 7-91, 7-92, 7-93, 7-94, 7-95, 7-96, 7-97, 7-98, 7-99, 7-100, 7-101, 7-102, 7-103, 7-104, 7-105, 7-106, 7-107, 7-108, 7-109, 7-110, 7-111, 7-112, 7-144, 7-145, 7-146, 7-147, 7-148, 7-149, 7-150, 7-155, 7-156, 7-157, 7-158, 7-161, 7-162, 7-163, 7-164, 7-165, 7-166, 7-167, 7-168, 7-169, 7-170, 7-171, 7-172, 7-175, 7-176, 7-180, 7-181, 7-182, 7-183, 7-184, 7-185, 7-186, 7-187, 7-188, 7-189, 7-190, 7-191, 7-192, 7-193, 7-194, 7-195, 7-196, 7-197, 7-198, 7-199, 7-200, 7-201, 7-202, 7-203, 8-1, 8-2, 8-3, 8-4, 8-5, 8-7, 8-10, 8-11, 8-14, 8-15, 8-16, 8-17, 8-18, 8-19, 8-20, 8-21, 8-22, 8-23, 8-24, 8-25, 8-26, 8-27, 8-28, 8-29, 8-30, 8-31, 8-32, 8-33, 8-34, 8-35, 8-36, 8-37, 8-38, 8-39, 8-40, 8-41, 8-42, 8-43, 8-44, 8-45, 8-53, 8-56, 8-58, 8-60, 8-66, 8-70, 8-72, 8-78, 8-80, 8-87, 8-88, 8-89, 8-90, 8-91, 8-92, 8-93, 8-94, 8-95, 8-96, 8-97, 8-98, 8-99, 8-100, 8-101, 8-102, 8-103, 8-104, 8-105, 8-106, 8-107, 8-108, 8-109, 8-110, 8-111, 8-112, 8-144, 8-145, 8-146, 8-147, 8-148, 8-149, 8-150, 8-155, 8-156, 8-157, 8-158, 8-161, 8-162, 8-163, 8-164, 8-165, 8-166, 8-167, 8-168, 8-169, 8-170, 8-171, 8-172, 8-175, 8-176, 8-180, 8-181, 8-182, 8-183, 8-184, 8-185, 8-186, 8-187, 8-188, 8-189, 8-190, 8-191, 8-192, 8-193, 8-194, 8-195, 8-196, 8-197, 8-198, 8-199, 8-200, 8-201, 8-202, 8-203, 9-1, 9-2, 9-3, 9-4, 9-5, 9-7, 9-10, 9-11, 9-14, 9-15, 9-16, 9-17, 9-18, 9-19, 9-20, 9-21, 9-22, 9-23, 9-24, 9-25, 9-26, 9-27, 9-28, 9-29, 9-30, 9-31, 9-32, 9-33, 9-34, 9-35, 9-36, 9-37, 9-38, 9-39, 9-40, 9-41, 9-42, 9-43, 9-44, 9-45, 9-53, 9-56, 9-58, 9-60, 9-66, 9-70, 9-72, 9-78, 9-80, 9-87, 9-88, 9-89, 9-90, 9-91, 9-92, 9-93, 9-94, 9-95, 9-96, 9-97, 9-98, 9-99, 9-100, 9-101, 9-102, 9-103, 9-104, 9-105, 9-106, 9-107, 9-108, 9-109, 9-110, 9-111, 9-112, 9-144, 9-145, 9-146, 9-147, 9-148, 9-149, 9-150, 9-155, 9-156, 9-157, 9-158, 9-161, 9-162, 9-163, 9-164, 9-165, 9-166, 9-167, 9-168, 9-169, 9-170, 9-171, 9-172, 9-175, 9-176, 9-180, 9-181, 9-182, 9-183, 9-184, 9-185, 9-186, 9-187, 9-188, 9-189, 9-190, 9-191, 9-192, 9-193, 9-194, 9-195, 9-196, 9-197, 9-198, 9-199, 9-200, 9-201, 9-202, 9-203, 10-1, 10-2, 10-3, 10-4, 10-5, 10-7, 10-10, 10-11, 10-14, 10-15, 10-16, 10-17, 10-18, 10-19, 10-20, 10-21, 10-22, 10-23, 10-24, 10-25, 10-26, 10-27, 10-28, 10-29, 10-30, 10-31, 10-32, 10-33, 10-34, 10-35, 10-36, 10-37, 10-38, 10-39, 10-40, 10-41, 10-42, 10-43, 10-44, 10-45, 10-53, 10-56, 10-58, 10-60, 10-66, 10-70, 10-72, 10-78, 10-80, 10-87, 10-88, 10-89, 10-90, 10-91, 10-92, 10-93, 10-94, 10-95, 10-96, 10-97, 10-98, 10-99, 10-100, 10-101, 10-102, 10-103, 10-104, 10-105, 10-106, 10-107, 10-108, 10-109, 10-110, 10-111, 10-112, 10-144, 10-145, 10-146, 10-147, 10-148, 10-149, 10-150, 10-155, 10-156, 10-157, 10-158, 10-161, 10-162, 10-163, 10-164, 10-165, 10-166, 10-167, 10-168, 10-169, 10-170, 10-171, 10-172, 10-175, 10-176, 10-180, 10-181, 10-182, 10-183, 10-184, 10-185, 10-186, 10-187, 10-188, 10-189, 10-190, 10-191, 10-192, 10-193, 10-194, 10-195, 10-196, 10-197, 10-198, 10-199, 10-200, 10-201, 10-202 and 10-203.

(2) More preferred compounds are Compounds No. 1-1, 1-2, 1-3, 1-10, 1-11, 1-14, 1-15, 1-16, 1-17, 1-18, 1-19, 1-20, 1-21, 1-22, 1-23, 1-25, 1-29, 1-31, 1-33, 1-34, 1-35, 1-36, 1-37, 1-38, 1-39, 1-41, 1-43, 1-45, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-149, 1-150, 1-156, 1-158, 1-162, 1-164, 1-166, 1-168, 1-170, 1-172, 1-175, 1-176, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 2-1, 2-2, 2-3, 2-10, 2-11, 2-14, 2-15, 2-16, 2-17, 2-18, 2-19, 2-20, 2-21, 2-22, 2-23, 2-25, 2-29, 2-31, 2-33, 2-34, 2-35, 2-36, 2-37, 2-38, 2-39, 2-41, 2-43, 2-45, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-111, 2-112, 2-149, 2-150, 2-156, 2-158, 2-162, 2-164, 2-166, 2-168, 2-170, 2-172, 2-175, 2-176, 2-180, 2-181, 2-182, 2-183, 2-184, 2-185, 2-186, 2-187, 2-188, 2-189, 2-190, 2-191, 2-192, 2-193, 2-194, 2-195, 2-196, 2-197, 2-198, 2-199, 2-200, 2-201, 2-202, 2-203, 3-1, 3-2, 3-3, 3-10, 3-11, 3-14, 3-15, 3-16, 3-17, 3-18, 3-19, 3-20, 3-21, 3-22, 3-23, 3-25, 3-29, 3-31, 3-33, 3-34, 3-35, 3-36, 3-37, 3-38, 3-39, 3-41, 3-43, 3-45, 3-87, 3-88, 3-89, 3-90, 3-91, 3-92, 3-93, 3-94, 3-95, 3-96, 3-97, 3-98, 3-99, 3-100, 3-101, 3-102, 3-103, 3-104, 3-105, 3-106, 3-107, 3-108, 3-109, 3-110, 3-111, 3-112, 3-149, 3-150, 3-156, 3-158, 3-162, 3-164, 3-166, 3-168, 3-170, 3-172, 3-175, 3-176, 3-180, 3-181, 3-182, 3-183, 3-184, 3-185, 3-186, 3-187, 3-188, 3-189, 3-190, 3-191, 3-192, 3-193, 3-194, 3-195, 3-196, 3-197, 3-198, 3-199, 3-200, 3-201, 3-202, 3-203, 6-1, 6-2, 6-3, 6-10, 6-11, 6-14, 6-15, 6-16, 6-17, 6-18, 6-19, 6-20, 6-21, 6-22, 6-23, 6-25, 6-29, 6-31, 6-33, 6-34, 6-35, 6-36, 6-37, 6-38, 6-39, 6-41, 6-43, 6-45, 6-87, 6-88, 6-89, 6-90, 6-91, 6-92, 6-93, 6-94, 6-95, 6-96, 6-97, 6-98, 6-99, 6-100, 6-101, 6-102, 6-103, 6-104, 6-105, 6-106, 6-107, 6-108, 6-109, 6-110, 6-111, 6-112, 6-149, 6-150, 6-156, 6-158, 6-162, 6-164, 6-166, 6-168, 6-170, 6-172, 6-175, 6-176, 6-180, 6-181, 6-182, 6-183, 6-184, 6-185, 6-186, 6-187, 6-188, 6-189, 6-190, 6-191, 6-192, 6-193, 6-194, 6-195, 6-196, 6-197, 6-198, 6-199, 6-200, 6-201, 6-202, 6-203, 8-1, 8-2, 8-3, 8-10, 8-11, 8-14, 8-15, 8-16, 8-17, 8-18, 8-19, 8-20, 8-21, 8-22, 8-23, 8-25, 8-29, 8-31, 8-33, 8-34, 8-35, 8-36, 8-37, 8-38, 8-39, 8-41, 8-43, 8-45, 8-87, 8-88, 8-89, 8-90, 8-91, 8-92, 8-93, 8-94, 8-95, 8-96, 8-97, 8-98, 8-99, 8-100, 8-101, 8-102, 8-103, 8-104, 8-105, 8-106, 8-107, 8-108, 8-109, 8-110, 8-111, 8-112, 8-149, 8-150, 8-156, 8-158, 8-162, 8-164, 8-166, 8-168, 8-170, 8-172, 8-175, 8-176, 8-180, 8-181, 8-182, 8-183, 8-184, 8-185, 8-186, 8-187, 8-188, 8-189, 8-190, 8-191, 8-192, 8-193, 8-194, 8-195, 8-196, 8-197, 8-198, 8-199, 8-200, 8-201, 8-202, 8-203, 10-1, 10-2, 10-3, 10-10, 10-11, 10-14, 10-15, 10-16, 10-17, 10-18, 10-19, 10-20, 10-21, 10-22, 10-23, 10-25, 10-29, 10-31, 10-33, 10-34, 10-35, 10-36, 10-37, 10-38, 10-39, 10-41, 10-43, 10-45, 10-87, 10-88, 10-89, 10-90, 10-91, 10-92, 10-93, 10-94, 10-95, 10-96, 10-97, 10-98, 10-99, 10-100, 10-101, 10-102, 10-103, 10-104, 10-105, 10-106, 10-107, 10-108, 10-109, 10-110, 10-111, 10-112, 10-149, 10-150, 10-156, 10-158, 10-162, 10-164, 10-166, 10-168, 10-170, 10-172, 10-175, 10-176, 10-180, 10-181, 10-182, 10-183, 10-184, 10-185, 10-186, 10-187, 10-188, 10-189, 10-190, 10-191, 10-192, 10-193, 10-194, 10-195, 10-196, 10-197, 10-198, 10-199, 10-200, 10-201, 10-202, 10-203.

(3) Still more preferred compounds are Compounds No. 1-14, 1-15, 1-16, 1-17, 1-18, 1-19, 1-20, 1-21, 1-22, 1-23, 1-29, 1-31, 1-33, 1-34, 1-35, 1-36, 1-37, 1-38, 1-39, 1-41, 1-43, 1-45, 1-88, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-181, 1-182, 1-183, 1-184, 1-185, 1-186, 1-187, 1-188, 1-189, 1-192, 1-193, 1-195, 2-14, 2-15, 2-16, 2-17, 2-18, 2-19, 2-20, 2-21, 2-22, 2-23, 2-29, 2-31, 2-33, 2-34, 2-35, 2-36, 2-37, 2-38, 2-39, 2-41, 2-43, 2-45, 2-88, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-181, 2-182, 2-183, 2-184, 2-185, 2-186, 2-187, 2-188, 2-189, 2-192, 2-193, 2-195, 3-14, 3-15, 3-16, 3-17, 3-18, 3-19, 3-20, 3-21, 3-22, 3-23, 3-29, 3-31, 3-33, 3-34, 3-35, 3-36, 3-37, 3-38, 3-39, 3-41, 3-43, 3-45, 3-88, 3-90, 3-91, 3-92, 3-93, 3-94, 3-95, 3-96, 3-97, 3-98, 3-99, 3-100, 3-101, 3-102, 3-103, 3-104, 3-105, 3-106, 3-107, 3-108, 3-109, 3-110, 3-181, 3-182, 3-183, 3-184, 3-185, 3-186, 3-187, 3-188, 3-189, 3-192, 3-193 and 3-195.

(4) Even more preferred compounds are Compounds No. 1-15, 1-17, 1-19, 1-21, 1-23, 1-35, 1-37, 1-39, 1-95, 1-96, 1-97, 1-98, 1-99, 1-100, 1-101, 1-102, 1-103, 1-104, 1-105, 1-108, 1-183, 1-185, 1-187, 1-189, 1-195, 2-15, 2-17, 2-19, 2-21, 2-23, 2-35, 2-37, 2-39, 2-95, 2-96, 2-97, 2-98, 2-99, 2-100, 2-101, 2-102, 2-103, 2-104, 2-105, 2-108, 2-183, 2-185, 2-187, 2-189, 2-195, 3-15, 3-17, 3-19, 3-21, 3-23, 3-35, 3-37, 3-39, 3-95, 3-96, 3-97, 3-98, 3-99, 3-100, 3-101, 3-102, 3-103, 3-104, 3-105, 3-108, 3-183, 3-185, 3-187, 3-189 and 3-195.

(5) Yet more preferred compounds are Compounds No. 2-15, 2-17, 2-19, 2-21, 2-23, 2-35, 2-37, 2-39, 2-95, 2-96, 2-97, 2-98, 2-99, 2-100, 2-101, 2-102, 2-103, 2-104, 2-105, 2-108, 2-183, 2-185, 2-187, 2-189, 2-195, 3-15, 3-17, 3-19, 3-21, 3-23, 3-35, 3-37, 3-39, 3-95, 3-96, 3-97, 3-98, 3-99, 3-100, 3-101, 3-102, 3-103, 3-104, 3-105; 3-108, 3-183, 3-185, 3-187, 3-189 and 3-195.

(6) Still more preferred compounds are Compounds No. 2-15, 2-23, 2-35, 2-37, 2-39, 2-95, 2-96, 2-97, 2-98, 2-105, 3-15, 3-23, 3-35, 3-37, 3-39, 3-95, 3-96, 3-97, 3-98 and 3-105.

(7) The most preferred compounds are Compounds No.

2-15. 5-(4-{2-[1-(4-Biphenylyl)ethylideneaminooxy]ethoxy}benzyl)thiazolidine-2,4-dione;

2-23. 5-(4-{2-[1-(4-Phenylsulfonylphenyl)ethylideneaminooxy]ethoxy}benzyl)thiazolidine-2,4-dione;

2-35. 5-(4-{2-[1-(4-2'-Pyridylphenyl)ethylideneaminooxy]ethoxy}benzyl)thiazolidine-2,4-dione;

2-37. 5-(4-{2-[1-(4-3'-Pyridylphenyl)ethylideneaminooxy]ethoxy}benzyl)thiazolidine-2,4-dione;

2-39. 5-(4-{2-[1-(4-4'-Pyridylphenyl)ethylideneaminooxy]ethoxy}benzyl)thiazolidine-2,4-dione;

2-95. 5-(4-{2-[1-(2-Phenyl-5-pyridyl)ethylideneaminooxy]ethoxy}benzyl)thiazolidine-2,4-dione;

2-96. 5-(4-{2-[1-(2-Methoxy-5-pyridyl)ethylideneaminooxy]ethoxy}benzyl)thiazolidine-2,4-dione;

2-97. 5-(4-{2-[1-(2-Ethoxy-5-pyridyl)ethylideneaminooxy]ethoxy}benzyl)thiazolidine-2,4-dione;

2-98. 5-(4-{2-[1-(2-Isopropoxy-5-pyridyl)ethylideneaminooxy]ethoxy}benzyl)thiazolidine-2,4-dione; and;

2-105. 5-(4-{2-[1-(2-Benzyl-5-pyridyl)ethylideneaminooxy]ethoxy}benzyl)thiazolidine-2,4-dione.

The compounds of the present invention may be prepared by a variety of processes well known in the art for the preparation of compounds of this general type. For example they may be prepared by the following Reaction Schemes A, B and C:

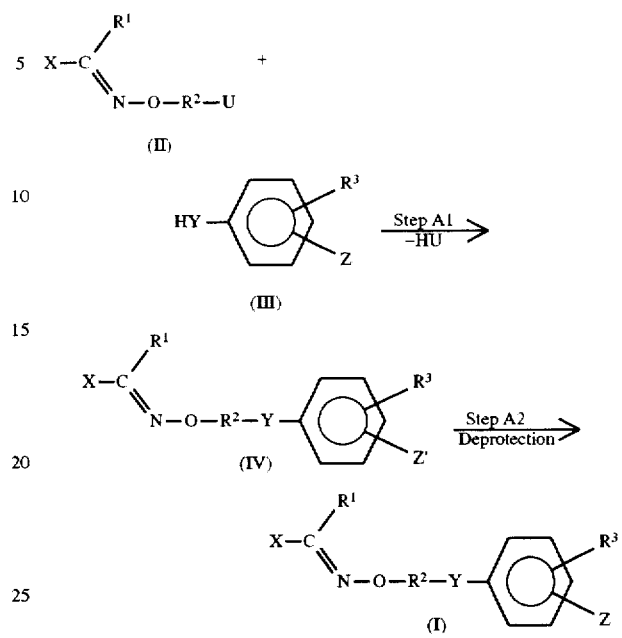

Reaction Scheme A:

In the above formulae:

$R^1$, $R^2$, $R^3$, X, Y and Z are as defined above;

U represents a hydroxy group, a halogen atom (preferably a chlorine, bromine or iodine atom) or a group of formula —O—SO$_2$—R$^5$ (in which R$^5$ represents: an alkyl group having from 1 to 6 carbon atoms, such as a methyl or ethyl group; a halogenated alkyl group having from 1 to 4 carbon atoms, such as those exemplified above in relation to substituent α, especially a trifluoromethyl group; or a carbocyclic aryl group having from 6 to 10 carbon atoms, which is unsubstituted or is substituted by at least one substituent selected from the group consisting of alkyl groups having from 1 to 4 carbon atoms, nitro groups or halogen atoms, such as the phenyl, p-tolyl, p-nitrophenyl and p-bromophenyl groups); and Z' represents any of those groups represented by Z [i.e. a group of formula (Za), (Zb), (Zc) or (Zd)] in which a group of formula >NH is protected, e.g. by conversion to a group of formula >N—CPh$_3$ [i.e. protected by a triphenylmethyl group (hereinafter referred to as a trityl group)].

Step A1

In Step A1, a compound of formula (IV) is prepared by reacting a compound of formula (II) with a compound of formula (III).

Where U represents a hydroxy group, the reaction of this step may be carried out by the conventional procedure known as a Mitsunobu reaction [O. Mitsunobu, Synthesis, 1(1981)].

The reaction is usually carried out in a solvent in the presence of at least one azo compound and at least one phosphine.

There is no particular restriction on the nature of the azo compounds used, and any azo compounds commonly used in this type of reaction may equally be employed here used. Examples of such azo compounds include diethyl azodicarboxylate and 1,1'-(azodicarbonyl)dipiperidine. There is likewise no particular restriction on the nature of the phosphines used, and examples include triphenylphosphine and tributylphosphine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride, carbon tetrachloride or 1,2-dichloroethane; ethers, such as diethyl ether, tetrahydrofuran or dioxane; amides, such as dimethylformamide, dimethylacetamide or hexamethylphosphoric triamide; and mixtures of any two or more of these solvents.

The reaction can take place over a wide range of temperatures, and the precise reaction temperature is not critical to the invention. In general, we find it convenient to carry out the reaction at a temperature of from 10° C. to 100° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 1 hour to 3 days, more preferably from 5 hours to 3 days, will usually suffice.

Where U represents a halogen atom or a group —O—SO$_2$—R$^5$, the reaction may be carried out in an inert solvent and in the presence of a base.

There is no particular restriction on the nature of the base employed in this reaction and any base commonly used in conventional reactions of this type may equally be used here. However, examples of preferred bases include: alkali metal carbonates, such as sodium carbonate or potassium carbonate; alkali metal hydrides, such as sodium hydride, potassium hydride or lithium hydride; alkali metal alkoxides, such as sodium methoxide, sodium ethoxide, potassium t-butoxide or lithium methoxide; alkyllithium compounds, such as butyllithium or methyllithium; lithium amides, such as lithium diethylamide, lithium diisopropylamide or lithium bis(trimethylsilyl)amide; alkali metal hydrogencarbonates, such as sodium hydrogencarbonate or potassium hydrogencarbonate; and tertiary organic amines, such as 1,5-diazabicyclo[4.3.0]non-5-ene, 1,8-diazabicyclo[5.4.0] undec-7-ene or N,N-diisopropylethylamine. Of these, we prefer the alkali metal carbonates, alkali metal hydrides and alkali metal alkoxides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene or toluene; ethers, such as tetrahydrofuran or dioxane; alcohols, such as methanol, ethanol or t-butanol; amides, such as dimethylformamide, dimethylacetamide or N-methylpyrrolidinone; ketones, such as acetone or 2-butanone; nitriles, such as acetonitrile; sulfoxides, such as dimethyl sulfoxide; and mixtures of any two or more of these solvents. Of these, we prefer the ethers, amides, ketones or sulfoxides.

Where the reaction is carried out in the presence of a phase transfer catalyst such as benzyltriethylammonium iodide or tetrabutylammonium iodide, it can be carried out using as the base an alkali metal hydroxide, such as sodium hydroxide or potassium hydroxide, in a two-layer solvent system consisting of water and one or more halogenated hydrocarbon, such as methylene chloride or chloroform.

The reaction can take place over a wide range of temperatures, and the precise reaction temperature is not critical to the invention. In general, we find it convenient to carry out the reaction at a temperature of from −10° C. to 120° C., more preferably from 10° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 16 hours, will usually suffice.

Step A2

In Step A2, a compound of formula (I) is prepared by removing the protecting trityl group from the compound of formula (IV).

The reaction in this step may be carried out by reacting the compound of formula (IV) with an acid, such as formic acid, acetic acid, trifluoroacetic acid, methanesulfonic acid, benzenesulfonic acid, p-toluenesulfonic acid, trifluoromethanesulfonic acid, hydrochloric acid or sulfuric acid, in the presence or absence of a solvent.

Where this reaction is carried out in the presence of a solvent, there is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride or carbon tetrachloride; ethers, such as diethyl ether, tetrahydrofuran or dioxane; alcohols, such as methanol or ethanol; amides, such as dimethylformamide, dimethylacetamide or hexamethylphosphoric triamide; esters, such as methyl acetate or ethyl acetate; water; and mixtures of any two or more of these solvents.

The reaction can take place over a wide range of temperatures, and the precise reaction temperature is not critical to the invention. In general, we find it convenient to carry out the reaction at a temperature of from −10° C. to 120° C., more preferably from 0° C. to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 16 hours, will usually suffice.

Alternatively, the reaction in this step may be carried out by subjecting the compound of formula (IV) to catalytic hydrogenation. Examples of suitable catalysts include: for example, palladium-on-charcoal, palladium black, platinum oxide or platinum black, preferably palladium-on-charcoal.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride or carbon tetrachloride; ethers, such as diethyl ether, tetrahydrofuran or dioxane; alcohols, such as methanol, ethanol or isopropanol; amides, such as dimethylformamide, dimethylacetamide or hexamethylphosphoric triamide; carboxylic acids, such as formic acid or acetic acid; and mixtures of any two or more of these solvents.

The reaction can take place over a wide range of temperatures, and the precise reaction temperature is not critical to the invention. In general, we find it convenient to carry out the reaction at a temperature of from 10° C. to 140° C., more preferably from 20° C. to 120° C. The time required for the reaction may also vary widely, depending on many factors, notably the reaction temperature, the nature of the reagents and solvent employed and other factors. However, provided that the reaction is effected under the preferred conditions outlined above, a period of from 30 minutes to 3 days, more preferably from one hour to one day, will usually suffice.

In some instances, the reaction may be accelerated by adding a carboxylic acid, such as formic acid, acetic acid or trifluoroacetic acid, or a mineral acid, such as hydrochloric acid or sulfuric acid, to the reaction mixture.

Reaction Scheme B

The compound of formula (IV), an intermediate used in Reaction Scheme A, can also be prepared by the following Reaction Scheme B:

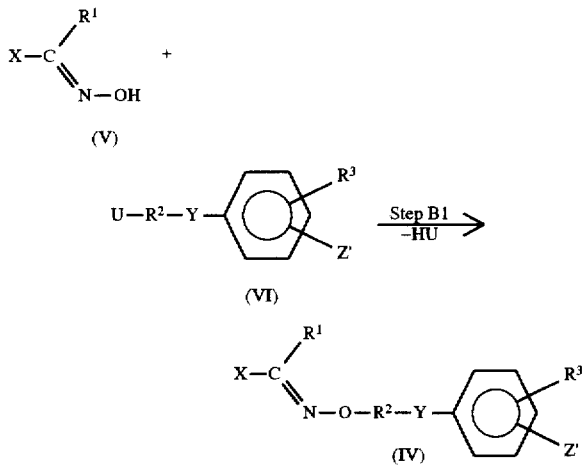

In the above formulae, $R^1$, $R^2$, $R^3$, U, X, Y and Z' are as defined above.

Step B1

In Step B1, a compound of formula (IV) is prepared by reacting a compound of formula (V) with a compound of formula (VI).

This reaction is essentially the same as that described in Step A1 of Reaction Scheme A, and may be carried out using the same reagents and reaction conditions.

Reaction Scheme C

The compounds of formula (I), which are the compounds of the present invention, and the intermediate of formula (IV) can also be prepared by the following Reaction Scheme C.

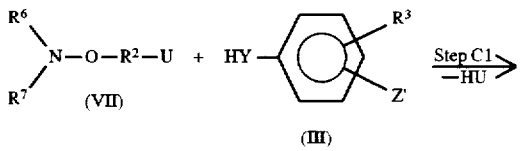

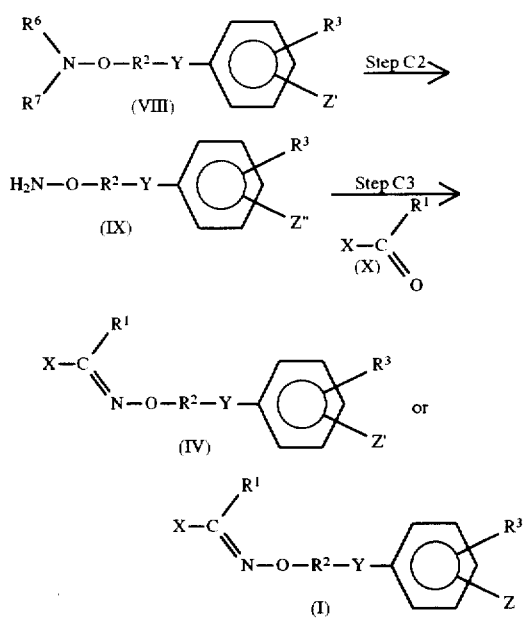

In the above formulae:

$R^1$, $R^2$, $R^3$, U, X, Y, Z and Z' are as defined above;

$R^6$ and $R^7$ are the same or different and each represents a hydrogen atom or an amino-protecting group; and Z" represents Z or Z'.

The amino-protecting groups which may be represented by $R^6$ and/or $R^7$ are well-known in organic synthetic chemistry, and their nature is not critical to the present invention. Examples of such protecting groups include: aralkyl groups, such as the benzyl, diphenylmethyl and trityl groups; aliphatic acyl groups, such as the formyl and trifluoroacetyl groups; alkoxycarbonyl groups, such as the t-butoxycarbonyl group; aralkyloxycarbonyl groups, such as the benzyloxycarbonyl and p-nitrobenzyloxycarbonyl groups; and the phthaloyl group. Of these, we prefer the benzyl, trityl, trifluoroacetyl, t-butoxycarbonyl, benzyloxycarbonyl and phthaloyl groups.

Step C1

In Step C1, a compound of formula (VIII) is prepared by reacting a compound of formula (VII) with a compound of formula (III).

This reaction is essentially the same as that described in Step A1 of Reaction Scheme A, and may be carried out using the same reagents and reaction conditions.

Step C2

In Step C2, a compound of formula (IX) is prepared by removing the amino-protecting group represented by $R^6$ and/or $R^7$ in the compound of formula (VIII) and, if desired, by removing the protecting group of Z' to produce Z.

The removal reaction(s) employed will, of course, depend on the nature of the protecting group used, as is well known in the art, and is not critical to the present invention.

For example, where the protecting group represented by $R^6$ is an aralkyl or aralkyloxycarbonyl group, it can be removed by catalytic reduction. Alternatively, where it is a trityl or t-butoxycarbonyl group, it can be removed by treatment with an acid. These reactions are essentially the same as those described in Step A2 of Reaction Scheme A, and may be carried out using the same reagents and reaction conditions. When preparing an intermediate of formula (IV), it is necessary that the reaction conditions employed should not result also in the elimination of the trityl group of Z'.

Where the protecting group represented by $R^6$ is an aliphatic acyl group, such as a formyl or trifluoroacetyl group, it can be removed by treatment under basic conditions.

The nature of the base employed is not critical to the invention, and any base commonly used in reactions of this type may equally be used here. Examples of suitable bases include: alkali metal hydroxides, such as sodium hydroxide, potassium hydroxide or lithium hydroxide; and alkali metal carbonates, such as sodium carbonate or potassium carbonate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; water; ethers, such as tetrahydrofuran or dioxane; and mixtures of any two or more of these solvents.

The reaction can take place over a wide range of temperatures, and the precise reaction temperature is not critical to the invention. In general, we find it convenient to carry out the reaction at a temperature of from 0° C. to 100° C., more preferably from 10° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

Where the protecting group represented by $R^6$ and/or $R^7$ is a phthaloyl group, it can be removed by treatment with a hydrazine or a primary amine.

Examples of suitable hydrazines include, for example, hydrazine, methylhydrazine and phenylhydrazine. Examples of suitable primary amines include, for example, methylamine, ethylamine, propylamine, butylamine, isobutylamine, pentylamine and hexylamine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; halogenated hydrocarbons, such as methylene chloride or chloroform; and mixtures of any two or more of these solvents.

The reaction can take place over a wide range of temperatures, and the precise reaction temperature is not critical to the invention. In general, we find it convenient to carry out the reaction at a temperature of from 0° C. to 100° C., more preferably from 10° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

Moreover, if desired, the protecting group in Z' can be removed to produce a group Z. This reaction is essentially the same as that described in Step A2 of Reaction Scheme A, and may be carried out using the same reagents and reaction conditions.

Step C3

In Step C3, a compound of formula (IV) is prepared by a dehydration-condensation reaction of an amino compound of formula (IX) with an carbonyl compound of formula (X).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, benzene or xylene; halogenated hydrocarbons, such as methylene chloride, chloroform or 1,2-dichloroethane; ethers, such as tetrahydrofuran or dioxane; alcohols, such as methanol or ethanol; esters, such as ethyl acetate or butyl acetate; and amides, such as dimethylformamide or dimethylacetamide. Of these, we prefer the hydrocarbons, halogenated hydrocarbons, ethers or alcohols.

The reaction can take place over a wide range of temperatures, and the precise reaction temperature is not critical to the invention. In general, we find it convenient to carry out the reaction at a temperature of from 0° C. to 120° C., more preferably from 10° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

Reaction Scheme D

A compound of formula (II), which is one of the starting materials in Reaction Scheme A, can be prepared by, for example, the following Reaction Scheme D.

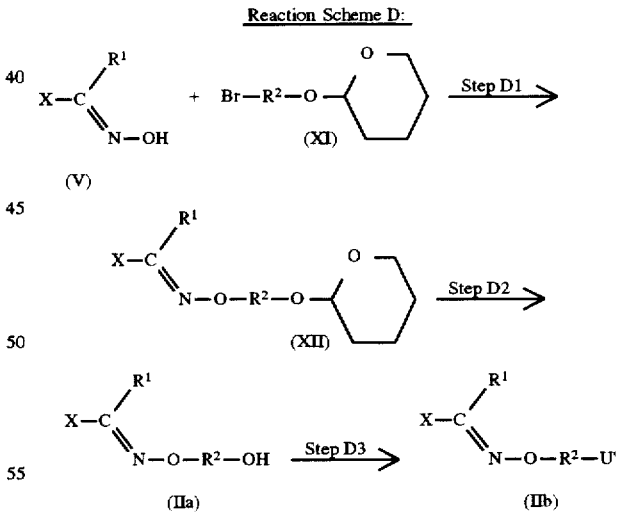

In the formulae $R^1$, $R^2$ and X are as defined above; and U' represents a halogen atom or a group of formula $-O-SO_2-R^5$ (in which $R^5$ is as defined above) included in the definition of the group U.

The compound of formula (IIa) which may be prepared by this reaction scheme is a compound of formula (II) in which U represents a hydroxy group. The compound of formula (IIb) is a compound of formula (II) in which U represents a halogen atom or a group of formula $-O-SO_2-R^5$.

Step D1

In Step D1, a compound of formula (XII) is prepared by reacting a compound of formula (V) with a compound of formula (XI).

This reaction is essentially the same as that described in Step A1 of Reaction Scheme A, where U represents a halogen atom or a group of formula —O—SO$_2$—R$^5$, and may be carried out using the same reagents and reaction conditions.

Step D2

In Step D2, a compound of formula (IIa) is prepared by removing a tetrahydropyranyl group from the compound of formula (XII).

This reaction is essentially the same as that described in Step A2 of Reaction Scheme A, and may be carried out using an acid (as exemplified in that Step) and the same reaction conditions.

Step D3

In Step D3, a compound of formula (IIb) is prepared by converting the hydroxy group in the compound of formula (IIa) to a halogen atom or to a group of formula —O—SO$_2$—R$^5$.

Where U' represents a halogen atom, the reaction may be carried out by reacting the compound of formula (IIa) with a halogenating agent in the presence of a solvent.

The nature of the halogenating agent used in this reaction is not critical to the invention, and examples of such halogenating agents include: thionyl halides, such as thionyl chloride or thionyl bromide; phosphorus pentahalides, such as phosphorus pentachloride or phosphorus pentabromide; phosphorus oxyhalides, such as phosphorus oxychloride or phosphorus oxybromide; and oxalyl chloride. Of these, we prefer the thionyl halides or oxalyl chloride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, benzene, toluene or xylene; halogenated hydrocarbons, such as methylene chloride, chloroform or 1,2-dichloroethane; ethers, such as tetrahydrofuran or dioxane; and esters, such as ethyl acetate or butyl acetate. Of these, we prefer the halogenated hydrocarbons or ethers.

The reaction can take place over a wide range of temperatures, and the precise reaction temperature is not critical to the invention. In general, we find it convenient to carry out the reaction at a temperature of from −10° C. to 100° C., more preferably from 10° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

Alternatively, the reaction in this step may be carried out by reacting the compound of formula (IIa) with a halogenating agent, such as carbon tetrachloride, carbon tetrabromide, N-bromosuccinimide or N-chlorosuccinimide, in the presence of a phosphine, such as triphenylphospine or tributylphosphine. The reaction conditons employed in this reaction are similar to those of the Mitsunobu reaction described in Step A1 of Reaction Scheme A.

Where U' represents a group of formula —O—SO$_2$—R$^5$ in the compound of formula (IIa), the reaction may be carried out by reacting the compound of formula (IIa) with a compound of formula R$^5$—SO$_2$—Cl (in which R$^5$ is as defined above) or with a compound of formula (R$_5$—SO$_2$)$_2$O (in which R$^5$ is as defined above) in an inert solvent in the presence of a base.

The nature of the base used in this reaction is not critical to the invention, and examples of such bases include tertiary amines, such as triethylamine, N-methylmorpholine and N,N-diisopropylethylamine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, benzene, toluene or xylene; halogenated hydrocarbons, such as methylene chloride, chloroform or 1,2-dichloroethane; ethers, such as tetrahydrofuran or dioxane; and esters, such as ethyl acetate or butyl acetate. Of these, we prefer the halogenated hydrocarbons or ethers.

The reaction can take place over a wide range of temperatures, and the precise reaction temperature is not critical to the invention. In general, we find it convenient to carry out the reaction at a temperature of from −10° C. to 100° C., preferably 0° C. to 60° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

In each of the aforesaid steps, after completion of the reaction, the desired compound may be recovered from the reaction mixture and, if necessary, may be purified by conventional means, for example, by column chromatography, recrystallization, reprecipitation and similar methods. An example of one such technique comprises: extracting the compound by adding an organic solvent to the reaction mixture; distilling off the solvent from the extract; and finally purifying the compound by column chromatography through silica gel or the like to afford a pure specimen of the desired compound.

BIOLOGICAL ACTIVITY

The compounds of formula (I) and salts thereof possess the ability to lower blood glucose levels, to relieve obesity, to alleviate impaired glucose tolerance, to inhibit hepatic gluconeogenesis, to lower blood lipid levels and to inhibit aldose reductase. They are thus useful for the prevention and/or therapy of hyperglycemia, obesity, impaired glucose tolerance (IGT), insulin resistant non-IGT (NGT), non-diagnostic glucose tolerance, insulin resistance, hyperlipidemia, diabetic complications (including retinopathy, nephropathy, neuropathy, cataracts and coronary artery disease) and arteriosclerosis and furthermore for essential hypertension, cachexia, psoriasis and osteoporosis. In addition, they are useful for the treatment and prevention of polycystic ovary syndrome, fatty liver and gestational diabetes mellitus (GDM).

The compounds of the present invention can be administered in various forms, depending on the disorder to be treated and the age, condition and body weight of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drip infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The preparation of various of the compounds of the present invention is further illustrated by the following non-limiting Examples. The preparation of certain of the intermediates used in these Examples is illustrated by the subsequent Preparations, and pharmaceutical compositions containing the compounds of the present invention are illustrated by the subsequent Formulations.

EXAMPLE 1

5-[4-(2-Benzylideneaminooxyethoxy)benzyl] thiazolidine-2,4-dione (Compound No. 1-1)

1(a) 5-[4-(2-Benzylideneaminooxyethoxy)benzyl]-3-tritylthiazolidine-2,4-dione

A solution of 450 mg of diethyl azodicarboxylate in 4 ml of tetrahydrofuran was added dropwise at room temperature to a solution of 383 mg of 2-(benzylideneaminooxy)ethanol (prepared as described in Preparation 1), 1.00 g of 5-(4-hydroxybenzyl)-3-tritylthiazolidine-2,4-dione and 629 mg of triphenylphosphine in 10 ml of tetrahydrofuran, and the resulting mixture was stirred at room temperature for 16 hours. At the end of this time, the reaction product was purified by column chromatography through silica gel, using a 3:1 by volume mixture of hexane and ethyl acetate as the eluent, to give 0.53 g of the title compound as a gum.

$^1$H Nuclear Magnetic Resonance Spectrum (CDCl$_3$, 270 MHz, using tetramethylsilane as the internal standard), δ ppm:

3.07 (1H, doublet of doublets, J=8.5 & 14 Hz);

3.44 (1H, doublet of doublets, J=4 & 14 Hz);

4.26 (2H, triplet, J=4.5 Hz);

4.36 (1H, doublet of doublets, J=4 & 8.5 Hz);

4.52 (2H, triplet, J=4.5 Hz);

6.88 (2H, doublet, J=8.5 Hz);

7.12 (2H, doublet, J=8.5 Hz);

7.17–7.59 (20H, multiplet);

8.14 (1H, singlet).

1(b) 5-[4-(2-Benzylideneaminooxyethoxy)benzyl] thiazolidine-2,4-dione

A solution of 0.53 g of 5-[4-(2-benzylideneaminooxyethoxy|benzyl]-3-tritylthiazolidine-2,4-dione [prepared as described in step (a) above] in a mixture of 10 ml of dioxane, 7 ml of acetic acid and 3 ml of water was stirred at 80° C. for 2 hours. At the end of this time, the reaction mixture was concentrated by evaporation under reduced pressure, and then the remaining acetic acid and water were removed by distillation as a toluene azeotrope. The residue thus obtained was purified by column chromatography through silica gel, using a gradient elution method, with mixtures of hexane and ethyl acetate ranging from 2:1 to 1:1 by volume as the eluent, to give a product as a crystalline powder. This powder was suspended in diisopropyl ether and then collected by filtration, to give 215 mg of the title compound, melting at 126°–129° C.

$^1$H Nuclear Magnetic Resonance Spectrum (CDCl$_3$, 270 MHz, using tetramethylsilane as the internal standard), δ ppm:

3.10 (1H, doublet of doublets, J=9 & 14 Hz);

3.45 (1H, doublet of doublets, J=4 & 14 Hz);

4.26 (2H, triplet, J=4.5 Hz);

4.47–4.53 (3H, multiplet);

6.90 (2H, doublet, J=8.5 Hz);

7.14 (2H, doublet, J=8.5 Hz);

7.36–7.38 (3H, multiplet);

7.56–7.59 (2H, multiplet);

8.02 (1H, broad singlet);

8.14 (1H, singlet).

EXAMPLE 2

5-{4-[2-(2-Quinolylmethyleneaminooxy)ethoxy] benzyl}thiazolidine-2,4-dione (Compound No. 1-149)

2(a) 5-{4-[2-(2-Quinolylmethyleneaminooxy)ethoxy| benzyl}-3-tritylthiazolidine-2,4-dione Following a procedure similar to that described in Example 1(a), but using 478 mg of 2-(2-quinolylmethyleneaminooxy)ethanol (prepared as described in Preparation 2), 1.00 g of 5-(4-hydroxybenzyl)-3-tritylthiazolidine-2,4-dione, 638 mg of triphenylphosphine and 423 mg of diethyl azodicarboxylate, 1.12 g of the title compound were obtained as a crystalline powder, melting at 127°–130° C.

$^1$H Nuclear Magnetic Resonance Spectrum (CDCl$_3$, 270 MHz, using tetramethylsilane as the internal standard), δ ppm:

3.06 (1H, doublet of doublets, J=8.5 & 14 Hz);

3.41 (1H, doublet of doublets, J=4 & 14 Hz);

4.29–4.38 (3H, multiplet);

4.61 (2H, triplet, J=4.5 Hz);

6.90 (2H, doublet, J=8.5 Hz);

7.11–7.44 (17H, multiplet);

7.56 (1H, triplet, J=8 Hz);

7.72 (1H, triplet, J=8 Hz);

7.82 (1H, doublet, J=8 Hz);

7.96 (1H, doublet, J=8.5 Hz);

8.09 (1H, doublet, J=8.5 Hz);

8.13 (1H, doublet, J=8 Hz);

8.39 (1H, singlet).

2(b) 5-{4-[2-(2-Quinolylmethyleneaminooxy)ethoxy| benzyl}thiazolidine-2,4-dione

Following a procedure similar to that described in Example 1(b), but using 1.00 g of 5-{4-[2-(2-quinolylmethyleneaminooxy)ethoxy|benzyl}-3-tritylthiazolidine-2,4-dione [prepared as described in step (a) above], 522 mg of the title compound were obtained as a crystalline powder, melting at 164°–166° C.

Nuclear Magnetic Resonance Spectrum (hexadeuterated dimethyl sulfoxide, 270 MHz, using tetramethylsilane as the internal standard), δ ppm:

3.06 (1H, doublet of doublets, J=9 & 14 Hz);

3.31 (1H, doublet of doublets, J=4.5 & 14 Hz);

4.30 (2H, triplet, J=4.5 Hz);

4.56 (2H, triplet, J=4.5 Hz);
4.87 (1H, doublet of doublets, J=4.5 & 9 Hz);
6.94 (2H, doublet, J=8.5 Hz);
7.17 (2H, doublet, J=8.5 Hz);
7.66 (1H, triplet, J=8 Hz);
7.80 (1H, triplet, J=8 Hz);
7.95–8.06 (3H, multiplet);
8.37 (1H, singlet);
8.42 (1H, doublet, J=8.5 Hz).

EXAMPLE 3

5-{4-[2-(3-Quinolylmethyleneaminooxy)ethoxy] benzyl}thiazolidine-2,4-dione (Compound No. 1-150)

3(a) 5-{4-[2-(3-Quinolylmethyleneaminooxy)ethoxy] benzyl}-3-tritylthiazolidine-2,4-dione A solution of 0.73 g of 1,1'-(azodicarbonyl)dipiperazine in 10 ml of toluene was added dropwise at room temperature to a suspension of 0.60 g of 2-(3-quinolylmethyleneaminooxy)ethanol (prepared as described in Preparation 3), 1.10 g of 5-(4-hydroxybenzyl)-3-tritylthiazolidine-2,4-dione and 0.72 ml of tributylphosphine in 30 ml of tetrahydrofuran, and the resulting mixture was stirred for 16 hours. At the end of this time, the reaction product was purified by column chromatography through silica gel, using a 1:1 by volume mixture of hexane and ethyl acetate as the eluent, to give 1.45 g of the title compound as a crystalline powder, melting at 127°–130° C.

Nuclear Magnetic Resonance Spectrum (CDCl$_3$, 270 MHz, using tetramethylsilane as the internal standard), δ ppm:

3.07 (1H, doublet of doublets, J=9 & 14 Hz);
3.41 (1H, doublet of doublets, J=4 & 14 Hz);
4.30 (2H, triplet, J=4.5 Hz);
4.36 (1H, doublet of doublets, J=4 & 9 Hz);
4.60 (2H, triplet, J=4.5 Hz);
6.91 (2H, doublet, J=8.5 Hz);
7.12–7.44 (17H, multiplet);
7.57 (1H, triplet, J=7.5 Hz);
7.75 (1H, triplet, J=7.5 Hz);
7.83 (1H, doublet, J=8.5 Hz);
8.12 (1H, doublet, J=8.5 Hz);
8.18 (1H, singlet);
8.27 (1H, singlet);
9.21 (1H, singlet).

3(b) 5-{4-[2-(3-Quinolylmethyleneaminooxy)ethoxy] benzyl}thiazolidine-2,4-dione

Following a procedure similar to that described in Example 1(b), but using 0.89 g of 5-{4-[2-(3-quinolylmethyleneaminooxy)ethoxy|benzyl}-3-tritylthiazolidine-2,4-dione [prepared as described in step (a) above], 0.47 g of the title compound was obtained as a crystalline powder, melting at 182°–184° C.

Nuclear Magnetic Resonance Spectrum (hexadeuterated dimethyl sulfoxide, 270 MHz, using tetramethylsilane as the internal standard), δ ppm:

3.06 (1H, doublet of doublets, J=9 & 14 Hz);
3.31 (1H, doublet of doublets, J=4 & 14 Hz);
4.28 (2H, triplet, J=4.5 Hz);
4.52 (2H, triplet, J=4.5 Hz);
4.87 (1H, doublet of doublets, J=4 & 9 Hz);
6.94 (2H, doublet, J=8.5 Hz);
7.17 (2H, doublet, J=8.5 Hz);
7.66 (1H, triplet, J=7.5 Hz);
7.81 (1H, triplet, J=7.5 Hz);
8.05 (2H, doublet, J=8.5 Hz);
8.53 (2H, singlet);
9.18 (1H, singlet).

EXAMPLE 4

5-{4-[2-(2-Pyridylmethyleneaminooxy)ethoxy] benzyl}thiazolidine-2,4-dione (Compound No. 1-87)

4(a) 5-{4-[2-(2-Pyridylmethyleneaminooxy)ethoxy] benzyl}-3-tritylthiazolidine-2,4-dione Following a procedure similar to that described in Example 3(a), but using 498 mg of 2-(2-pyridylmethyleneaminooxy)ethanol (prepared as described in Preparation 4), 1.13 g of 5-(4-hydroxybenzyl)-3-tritylthiazolidine-2,4-dione, 0.75 ml of tributylphosphine and 693 mg of 1,1'-(azodicarbonyl)dipiperazine, 0.82 g of the title compound was obtained as a foam-like solid.

$^1$H Nuclear Magnetic Resonance Spectrum (CDCl$_3$, 270 MHz, using tetramethylsilane as the internal standard), δ ppm:

3.06 (1H, doublet of doublets, J=9 & 14 Hz);
3.42 (1H, doublet of doublets, J=4 & 14 Hz);
4.27 (2H, triplet, J=5 Hz);
4.37 (1H, doublet of doublets, J=4 & 9 Hz);
4.58 (2H, triplet, J=5 Hz);
6.89 (2H, doublet, J=8.5 Hz);
7.11–7.33 (18H, multiplet);
7.69–7.77 (2H, multiplet);
8.24 (1H, singlet);
8.63 (1H, doublet, J=5 Hz).

4(b) 5-{4-[2-(2-Pyridylmethyleneaminooxy)ethoxy] benzyl}thiazolidine-2,4-dione

Following a procedure similar to that described in Example 1(b), but using 0.82 g of 5-{4-[2-(2-pyridylmethyleneaminooxy)ethoxy|benzyl}-3-tritylthiazolidine-2,4-dione [prepared as described in step (a) above], 0.42 g of the title compound was obtained as a crystalline powder, melting at 161°–163° C.

Nuclear Magnetic Resonance Spectrum (hexadeuterated dimethyl sulfoxide, 270 MHz, using tetramethylsilane as the internal standard), δ ppm:

3.06 (1H, doublet of doublets, J=9 & 14 Hz);
3.31 (1H, doublet of doublets, J=4 & 14 Hz);
4.26 (2H, triplet, J=4.5 Hz);
4.49 (2H, triplet, J=4.5 Hz);
4.88 (1H, doublet of doublets, J=4 & 9 Hz);
6.92 (2H, doublet, J=8.5 Hz);
7.16 (2H, doublet, J=8.5 Hz);
7.40–7.45 (1H, multiplet);
7.79–7.89 (2H, multiplet);
8.22 (1H, singlet);
8.61 (1H, doublet, J=5 Hz);
11.98 (1H, singlet).

EXAMPLE 5

5-{4-[2-(3-Pyridylmethyleneaminooxy)ethoxy] benzyl}-thiazolidine-2,4-dione (Compound No. 1-88)

5(a) 5-{4-[2-(3-Pyridylmethyleneaminooxyethoxy|benzyl}-3-tritylthiazolidine-2,4-dione Following a procedure similar to that described in Example 3(a), but using 0.90 g of 2-(3-pyridylmethyleneaminooxy)ethanol (prepared as described in Preparation 5), 2.00 g of 5-(4-hydroxybenzyl)-3-tritylthiazolidine-2,4-dione, 1.32 ml of tributylphosphine and 1.23 g of 1,1'-(azodicarbonyl)dipiperazine, 1.37 g of the title compound were obtained as a crystalline powder, melting at 155°–157° C.

¹H Nuclear Magnetic Resonance Spectrum (CDCl₃, 270 MHz, using tetramethylsilane as the internal standard), δ ppm:

3.07 (1H, doublet of doublets, J=9 & 14 Hz);
3.41 (1H, doublet of doublets, J=4 & 14 Hz);
4.26 (2H, triplet, J=4.5 Hz);
4.36 (1H, doublet of doublets, J=4 & 9 Hz);
4.54 (2H, triplet, J=4.5 Hz);
6.88 (2H, doublet, J=8.5 Hz);
7.11–7.37 (18H, multiplet);
7.93 (1H, doublet, J=8 Hz);
8.13 (1H, singlet);
8.60 (1H, doublet of doublets, J=1.5 & 5 Hz);
8.73 (1H, doublet, J=2 Hz).

5(b) 5-{4-[2-(3-Pyridylmethyleneaminooxy)ethoxy] benzyl}thiazolidine-2,4-dione

Following a procedure similar to that described in Example 1(b), but using 1.27 g of 5-{4-[2-(3-pyridylmethyleneaminooxy)ethoxy|benzyl}-3-tritylthiazolidine-2,4-dione [prepared as described in step (a) above], 0.75 g of the title compound was obtained as a crystalline powder, melting at 157°–159° C.

Nuclear Magnetic Resonance Spectrum (hexadeuterated dimethyl sulfoxide, 270 MHz, using tetramethylsilane as the internal standard), δ ppm:

3.06 (1H, doublet of doublets, J=9 & 14 Hz);
4.32 (1H, doublet of doublets, J=4 & 14 Hz);
4.24 (2H, triplet, J=4.5 Hz);
4.46 (2H, triplet, J=4.5 Hz);
4.87 (1H, doublet of doublets, J=4 & 9 Hz);
6.92 (2H, doublet, J=8.5 Hz);
7.16 (2H, doublet, J=8.5 Hz);
7.45 (1H, doublet of doublets, J=5 & 8 Hz);
8.02 (1H, doublet, J=8 Hz);
8.37 (1H, singlet);
8.60 (1H, doublet, J=5 Hz);
8.78 (1H, singlet).

EXAMPLE 6

5-{4-[2-(4-Pyridylmethyleneaminooxy)ethoxy] benzyl}thiazolidine-2,4-dione (Compound No. 1-89)

6(a) 5-{4-[2-(4-Pyridylmethyleneaminooxy)ethoxy] benzyl}-3-tritylthiazolidine-2,4-dione Following a procedure similar to that described in Example 3(a), but using 0.88 g of 2-(4-pyridylmethyleneaminooxy)ethanol (prepared as described in Preparation 6), 2.00 g of 5-(4-hydroxybenzyl)-3-tritylthiazolidine-2,4-dione, 1.32 ml of tributylphosphine and 1.23 g of 1,1'-(azodicarbonyl)dipiperazine, 1.10 g of the title compound were obtained as a foam-like solid.

¹H Nuclear Magnetic Resonance Spectrum (CDCl₃, 270 MHz, using tetramethylsilane as the internal standard), δ ppm:

3.08 (1H, doublet of doublets, J=9 & 14 Hz);
3.40 (1H, doublet of doublets, J=4 & 14 Hz);
4.26 (2H, triplet, J=4.5 Hz);
4.37 (1H, doublet of doublets, J=4 & 9 Hz);
4.57 (2H, triplet, J=4.5 Hz);
6.88 (2H, doublet, J=8.5 Hz);
7.13 (2H, doublet, J=8.5 Hz);
7.17–7.33 (15H, multiplet);
7.43 (1H, doublet, J=6 Hz);
8.07 (1H, singlet);
8.62 (1H, doublet, J=6 Hz).

6(b) 5-{4-[2-(4-Pyridylmethyleneaminooxy)ethoxy] benzyl}thiazolidine-2,4-dione

Following a procedure similar to that described in Example 1(b), but using 1.10 g of 5-{4-[2-(4-pyridylmethyleneaminooxyethoxy|benzyl}-3-tritylthiazolidine-2,4-dione [prepared as described in step (a) above], 0.42 g of the title compound was obtained as a crystalline powder, melting at 221° C.

Nuclear Magnetic Resonance Spectrum (hexadeuterated dimethyl sulfoxide, 270 MHz, using tetramethylsilane as the internal standard), δ ppm:

3.06 (1H, doublet of doublets, J=9 & 14 Hz);
3.32 (1H, doublet of doublets, J=4 & 14 Hz);
4.25 (2H, triplet, J=4.5 Hz);
4.50 (2H, triplet, J=4.5 Hz);
4.87 (1H, doublet of doublets, J=4 & 9 Hz);
6.92 (2H, doublet, J=8.5 Hz);
7.16 (2H, doublet, J=8.5 Hz);
7.57 (2H, doublet, J=6 Hz);
8.35 (1H, singlet);
8.63 (2H, doublet, J=6 Hz).

EXAMPLE 7

5-{4-[2-(2-Naphthylmethyleneaminooxy)ethoxy] benzyl}thiazolidine-2,4-dione (Compound No. 1-3)

7(a) 5-{4-[2-(2-Naphthylmethyleneaminooxy)ethoxy] benzyl}-3-tritylthiazolidine-2,4-dione Following a procedure similar to that described in Example 1(a), but using 430 mg of 2-(2-naphthylmethyleneaminooxy)ethanol (prepared as described in Preparation 7), 716 mg of 5-(4-hydroxybenzyl)-3-tritylthiazolidine-2,4-dione, 525 mg of triphenylphosphine and 348 mg of diethyl azodicarboxylate, 712 mg of the title compound were obtained as a foam-like solid.

¹H Nuclear Magnetic Resonance Spectrum (CDCl₃, 270 MHz, using tetramethylsilane as the internal standard), δ ppm:

3.07 (1H, doublet of doublets, J=9 & 14 Hz);
3.40 (1H, doublet of doublets, J=4 & 14 Hz);
4.29 (2H, triplet, J=4.5 Hz);
4.36 (1H, doublet of doublets, J=4 & 9 Hz);
4.56 (2H, triplet, J=4.5 Hz);
6.91 (2H, doublet, J=8.5 Hz);
7.11–7.32 (17H, multiplet);
7.46–7.54 (2H, multiplet);
7.79–7.87 (5H, multiplet);
8.28 (1H, singlet).

7(b) 5-{4-[2-(2-Naphthylmethyleneaminooxy)ethoxy] benzyl}thiazolidine-2,4-dione

Following a procedure similar to that described in Example 1(b), but using 712 mg of 5-{4-[2-(2- naphthylmethyleneaminooxy)ethoxy|benzyl}-3-tritylthiazolidine-2,4-dione [prepared as described in step (a) above], 374 mg of the title compound were obtained as a foam-like solid, melting at 108°–111° C.

¹H Nuclear Magnetic Resonance Spectrum (CDCl₃, 270 MHz, using tetramethylsilane as the internal standard), δ ppm:

3.09 (1H, doublet of doublets, J=9.5 & 14 Hz);
3.45 (1H, doublet of doublets, J=4 & 14 Hz);
4.29 (2H, triplet, J=4.5 Hz);
4.49 (1H, doublet of doublets, J=4 & 9.5 Hz);
4.56 (2H, triplet, J=4.5 Hz);
6.92 (2H, doublet, J=8.5 Hz);
7.14 (2H, doublet, J=8.5 Hz);
7.47–7.54 (2H, multiplet);
7.80–7.89 (5H, multiplet);
8.29 (1H, singlet).

EXAMPLE 8

5-{4-[2-(3-Phenylbenzylideneaminooxy)ethoxy]benzyl}thiazolidine-2,4-dione (Compound No. 1-14)

8(a) 5-{4-[2-(3-Phenylbenzylideneaminooxy)ethoxy]benzyl}-3-tritylthiazolidine-2,4-dione Following a procedure similar to that described in Example 1(a), but using 483 mg of 2-(3-phenylbenzylideneaminooxy)ethanol (prepared as described in Preparation 8), 716 mg of 5-(4-hydroxybenzyl)-3-tritylthiazolidine-2,4-dione, 525 mg of triphenylphosphine and 348 mg of diethyl azodicarboxylate, 807 mg of the title compound were obtained as a foam-like solid.

¹H Nuclear Magnetic Resonance Spectrum (CDCl₃, 270 MHz, using tetramethylsilane as the internal standard), δ ppm:

3.06 (1H, doublet of doublets, J=9 & 14 Hz);
3.41 (1H, doublet of doublets, J=4 & 14 Hz);
4.27 (2H, triplet, J=4.5 Hz);
4.36 (1H, doublet of doublets, J=4 & 9 Hz);
4.54 (2H, triplet, J=4.5 Hz);
6.90 (2H, doublet, J=8.5 Hz);
7.11–7.61 (25H, multiplet);
7.80 (1H, singlet);
8.20 (1H, singlet).

8(b) 5-{4-[2-(3-Phenylbenzylideneaminooxy)ethoxy]benzyl}thiazolidine-2,4-dione

Following a procedure similar to that described in Example 1(b), but using 800 mg of 5-{4-[2-(3-phenylbenzylideneaminooxy)ethoxy|benzyl}-3-tritylthiazolidine-2,4-dione [prepared as described in step (a) above], 344 mg of the title compound were obtained as a crystalline powder, melting at 128° C.

¹H Nuclear Magnetic Resonance Spectrum (CDCl₃, 270 MHz, using tetramethylsilane as the internal standard), δ ppm:

3.09 (1H, doublet of doublets, J=9 & 14 Hz);
3.44 (1H, doublet of doublets, J=4 & 14 Hz);
4.27 (2H, triplet, J=4.5 Hz);
4.49 (1H, doublet of doublets, J=4 & 9 Hz);
4.53 (2H, triplet, J=4.5 Hz);
6.91 (2H, doublet, J=8.5 Hz);
7.14 (2H, doublet, J=8.5 Hz);
7.34–7.61 (8H, multiplet);
7.81 (1H, singlet);
8.20 (1H, singlet).

EXAMPLE 9

5-{4-[2-(4-Phenylbenzylideneaminooxy)ethoxy]benzyl}thiazolidine-2,4-dione (Compound No. 1-15)

9(a) 5-{4-[2-(4-Phenylbenzylideneaminooxy)ethoxy]benzyl}-3-tritylthiazolidine-2,4-dione Following a procedure similar to that described in Example 1(a), but using 483 mg of 2-(4-phenylbenzylideneaminooxy)ethanol (prepared as described in Preparation 9), 716 mg of 5-(4-hydroxybenzyl)-3-tritylthiazolidine-2,4-dione, 525 mg of triphenylphosphine and 348 mg of diethyl azodicarboxylate, 914 mg of the title compound were obtained as a crystalline powder, melting at 157°–159° C.

¹H Nuclear Magnetic Resonance Spectrum (CDCl₃, 270 MHz, using tetramethylsilane as the internal standard), δ ppm:

3.08 (1H, doublet of doublets, J=9 & 14 Hz);
3.42 (1H, doublet of doublets, J=4 & 14 Hz);
4.29 (2H, triplet, J=4.5 Hz);
4.37 (1H, doublet of doublets, J=4 & 9 Hz);
4.55 (2H, triplet, J=4.5 Hz);
6.91 (2H, doublet, J=8.5 Hz);
7.12–7.68 (26H), 8.19 (1H, singlet).

9(b) 5-{4-[2-(4-Phenylbenzylideneaminooxy)ethoxy]benzyl}thiazolidine-2,4-dione

Following a procedure similar to that described in Example 1(b), but using 907 mg of 5-{4-[2-(4-phenylbenzylideneaminooxy)ethoxy|benzyl}-3-tritylthiazolidine- 2,4-dione [prepared as described in step (a) above], 442 mg of the title compound were obtained as a crystalline powder, melting at 124°–127° C.

¹H Nuclear Magnetic Resonance Spectrum (CDCl₃, 270 MHz, using tetramethylsilane as the internal standard), δ ppm:

3.11 (1H, doublet of doublets, J=9 & 14 Hz);
3.45 (1H, doublet of doublets, J=4 & 14 Hz);
4.28 (2H, triplet, J=4.5 Hz);
4.50 (1H, doublet of doublets, J=4 & 9 Hz);
4.53 (2H, triplet, J=4.5 Hz);
6.92 (2H, doublet, J=8.5 Hz);
7.15 (2H, doublet, J=8.5 Hz);
7.27–7.68 (9H, multiplet);
8.18 (1H, singlet).

EXAMPLE 10

5-{4-[2-(2-Phenyl-5-pyridylmethyleneaminooxy)ethoxy|benzyl}thiazolidine-2,4-dione (Compound No. 1-95)

10(a) 5-{4-[2-(2-Phenyl-5-pyridylmethyleneaminooxy)ethoxy|benzyl}-3-tritylthiazolidine-2,4-dione Following a procedure similar to that described in Example 1(a), but using 390 mg of 2-(2-phenyl-5-pyridylmethyleneaminooxy)ethanol (prepared as described in Preparation 10), 576 mg of 5-(4-hydroxybenzyl)-3-tritylthiazolidine-2,4-dione, 422 mg of triphenylphosphine and 280 mg of diethyl azodicarboxylate, 671 mg of the title compound were obtained as a crystalline powder, melting at 146°–148° C.

¹H Nuclear Magnetic Resonance Spectrum (CDCl₃, 270 MHz, using tetramethylsilane as the internal standard), δ ppm:

3.08 (1H, doublet of doublets, J=9 & 14 Hz);
3.41 (1H, doublet of doublets, J=4 & 14 Hz);
4.28 (2H, triplet, J=4.5 Hz);
4.37 (1H, doublet of doublets, J=4 & 9 Hz);
4.56 (2H, triplet, J=4.5 Hz);
6.90 (2H, doublet, J=8.5 Hz);
7.12–7.33 (17H, multiplet);
7.44–7.53 (3H, multiplet);
7.74 (1H, doublet, J=8.5 Hz);
7.99–8.03 (3H, multiplet);
8.18 (1H, singlet);
8.77 (1H, doublet, J=2 Hz).

10(b) 5-{4-[2-(2-Phenyl-5-pyridylmethyleneaminooxy)ethoxy]benzyl}thiazolidine-2,4-dione Following a procedure similar to that described in Example 1(b), but using 600 mg of 5-{4-[2-(2-phenyl-5-pyridylmethyleneaminooxy)ethoxy]benzyl}-3-tritylthiazolidine-2,4-dione [prepared as described in step (a) above], 312 mg of the title compound were obtained as a crystalline powder, melting at 102°–104° C.

¹H Nuclear Magnetic Resonance Spectrum (CDCl₃, 270 MHz, using tetramethylsilane as the internal standard), δ ppm:

3.14 (1H, doublet of doublets, J=9 & 14 Hz);
3.42 (1H, doublet of doublets, J=4 & 14 Hz);
4.29 (2H, triplet, J=4.5 Hz);
4.48–4.58 (3H, multiplet);
6.91 (2H, doublet, J=8.5 Hz);
7.16 (2H, doublet, J=8.5 Hz);
7.44–7.53 (3H, multiplet);
7.75 (1H, doublet, J=8.5 Hz);
8.00–8.03 (3H, multiplet);
8.18 (1H, singlet);
8.43 (1H, broad singlet);
8.76 (1H, doublet, J=2 Hz).

EXAMPLE 11

5-{4-[2-(3-Phenyl-5-pyridylmethyleneaminooxy)ethoxy]benzyl}thiazolidine-2,4-dione (Compound No. 1-92)

11(a) 5-{4-[2-(3-Phenyl-5-pyridylmethyleneaminooxy)ethoxy]benzyl}-3-tritylthiazolidine-2,4-dione Following a procedure similar to that described in Example 1(a), but using 354 mg of 2-(3-phenyl-5-pyridylmethyleneaminooxy)ethanol (prepared as described in Preparation 11), 510 mg of 5-(4-hydroxybenzyl)-3-tritylthiazolidine-2,4-dione, 383 mg of triphenylphosphine and 255 mg of diethyl azodicarboxylate, 550 mg of the title compound were obtained as a foam-like solid.

¹H Nuclear Magnetic Resonance Spectrum (CDCl₃, 270 MHz, using tetramethylsilane as the internal standard), δ ppm:

3.07 (1H, doublet of doublets, J=9 & 14 Hz);
3.41 (1H, doublet of doublets, J=4 & 14 Hz);
4.28 (2H, triplet, J=4.5 Hz);
4.36 (1H, doublet of doublets, J=4 & 9 Hz);
4.57 (2H, triplet, J=4.5 Hz);
6.89 (2H, doublet, J=8.5 Hz);
7.11–7.33 (17H, multiplet);
7.40–7.53 (3H, multiplet);
7.59–7.62 (2H, multiplet);
8.12 (1H, triplet, J=2 Hz);
8.20 (1H, singlet);
8.69 (1H, doublet, J=2 Hz);
8.84 (1H, doublet, J=2 Hz).

11(b) 5-{4-[2-(3-Phenyl-5-pyridylmethyleneaminooxy)ethoxy]benzyl}thiazolidine-2,4-dione Following a procedure similar to that described in Example 1(b), but using 550 mg of 5-{4-[2-(3-phenyl-5-pyridylmethyleneaminooxy)ethoxy]benzyl}-3-tritylthiazolidine-2,4-dione [prepared as described in step (a) above], 287 mg of the title compound were obtained as a crystalline powder, melting at 160°–161° C.

¹H Nuclear Magnetic Resonance Spectrum (a mixture of CDCl₃ with a small amount of hexadeuterated dimethyl sulfoxide, 270 MHz, using tetramethylsilane as the internal standard), δ ppm:

3.05 (1H, doublet of doublets, J=9 & 14 Hz);
3.44 (1H, doublet of doublets, J=4 & 14 Hz);
4.28 (2H, triplet, J=4.5 Hz);
4.44 (1H, doublet of doublets, J=4 & 9 Hz);
4.56 (2H, triplet, J=4.5 Hz);
6.90 (2H, doublet, J=8.5 Hz);
7.15 (2H, doublet, J=8.5 Hz);
7.43–7.53 (3H, multiplet);
7.61–7.64 (2H, multiplet);
8.15 (1H, triplet, J=2 Hz);
8.23 (1H, singlet);
8.70 (1H, doublet, J=2 Hz);
8.83 (1H, doublet, J=2 Hz).

EXAMPLE 12

5-{4-[2-(2-Ethoxy-5-pyridylmethyleneaminooxy)ethoxy]benzyl}thiazolidine-2,4-dione (Compound No. 1-97)

12(a) 5-{4-[2-(2-Ethoxy-5-pyridylmethyleneaminooxy)ethoxy]benzyl}-3-tritylthiazolidine-2,4-dione Following a procedure similar to that described in Example 1(a), but using 570 mg of 2-(2-ethoxy-5-pyridylmethyleneaminooxy)ethanol (prepared as described in Preparation 12), 1.20 g of 5-(4-hydroxybenzyl)-3-tritylthiazolidine-2,4-dione, 695 mg of triphenylphosphine and 462 mg of diethyl azodicarboxylate, 1.27 g of the title compound were obtained as a foam-like solid.

¹H Nuclear Magnetic Resonance Spectrum (CDCl₃, 270 MHz, using tetramethylsilane as the internal standard), δ ppm:

1.40 (3H, triplet, J=7 Hz);
3.07 (1H, doublet of doublets, J=9 & 14 Hz);
3.42 (1H, doublet of doublets, J=4 & 14 Hz);
4.25 (2H, triplet, J=4.5 Hz);
4.36 (1H, doublet of doublets, J=4 & 9 Hz);
4.38 (2H, quartet, J=7 Hz);
4.49 (2H, triplet, J=4.5 Hz);
6.72 (1H, doublet, J=8.5 Hz);
6.89 (2H, doublet, J=8.5 Hz);
7.11–7.53 (17H, multiplet);
7.90 (1H, doublet of doublets, J=2 & 8.5 Hz);
8.08 (1H, singlet);

8.17 (1H, doublet, J=2 Hz).

12(b) 5-{4-[2-(2-Ethoxy-5-pyridylmethyleneaminooxy)ethoxy]benzyl}thiazolidine-2,4-dione Following a procedure similar to that described in Example 1(b), but using 1.27 g of 5-{4-[2-(2-ethoxy-5-pyridylmethyleneaminooxy)ethoxy]benzyl}-3-tritylthiazolidine-2,4-dione [prepared as described in step (a) above], 572 mg of the title compound were obtained as a crystalline powder, melting at 127°–129° C.

Nuclear Magnetic Resonance Spectrum (hexadeuterated dimethyl sulfoxide, 270 MHz, using tetramethylsilane as the internal standard), δ ppm:

1.32 (3H, triplet, J=7 Hz);
3.05 (1H, doublet of doublets, J=9 & 14 Hz);
3.31 (1H, doublet of doublets, J=4 & 14 Hz);
4.22 (2H, triplet, J=4.5 Hz);
4.33 (2H, quartet, J=7 Hz);
4.41 (2H, triplet, J=4.5 Hz);
4.87 (1H, doublet of doublets, J=4 & 9 Hz);
6.84 (1H, doublet, J=8.5 Hz);
6.91 (2H, doublet, J=8.5 Hz);
7.15 (2H, doublet, J=8.5 Hz);
7.95 (1H, doublet of doublets, J=2 & 8.5 Hz);
8.28 (1H, singlet);
8.31 (1H, doublet, J=2 Hz);
12.00 (1H, broad singlet).

EXAMPLE 13

5-(4-{2-[1-(2-Naphthyl)ethylideneaminooxy]ethoxy}benzyl)thiazolidine-2,4-dione (Compound No. 2-3)

13(a) 5-(4-{2-[1-(2-Naphthyl)ethylideneaminooxy]ethoxy}benzyl)-3-tritylthiazolidine-2,4-dione Following a procedure similar to that described in Example 1(a), but using 459 mg of 2-[1-(2-naphthyl)ethylideneaminooxy]ethanol (prepared as described in Preparation 13), 716 mg of 5-(4-hydroxybenzyl)-3-tritylthiazolidine-2,4-dione, 525 mg of triphenylphosphine and 348 mg of diethyl azodicarboxylate, 858 mg of the title compound were obtained as a foam-like solid.

$^1$H Nuclear Magnetic Resonance Spectrum (CDCl$_3$, 270 MHz, using tetramethylsilane as the internal standard), δ ppm:

2.35 (3H, singlet);
3.07 (1H, doublet of doublets, J=9 & 14 Hz);
3.41 (1H, doublet of doublets, J=4 & 14 Hz);
4.31 (2H, triplet, J=5 Hz);
4.36 (1H, doublet of doublets, J=4 & 9 Hz);
4.59 (2H, triplet, J=5 Hz);
6.91 (2H, doublet, J=8.5 Hz);
7.11–7.33 (17H, multiplet);
7.46–7.52 (2H, multiplet);
7.79–7.93 (4H, multiplet);
7.99 (1H, singlet).

13(b) 5-(4-{2-[1-(2-Naphthyl)ethylideneaminooxy]ethoxy}benzyl)thiazolidine-2,4-dione Following a procedure similar to that described in Example 1(b), but using 854 mg of 5-(4-{2-[1-(2-naphthyl)ethylideneaminooxy]ethoxy}benzyl)-3-tritylthiazolidine-2,4-dione [prepared as described in step (a) above], 442 mg of the title compound were obtained as a crystalline powder, melting at 138°–139° C.

$^1$H Nuclear Magnetic Resonance Spectrum (CDCl$_3$, 270 MHz, using tetramethylsilane as the internal standard), δ ppm:

2.36 (3H, singlet);
3.10 (1H, doublet of doublets, J=9 & 14 Hz);
3.45 (1H, doublet of doublets, J=4 & 14 Hz);
4.31 (2H, triplet, J=5 Hz);
4.50 (1H, doublet of doublets, J=4 & 9 Hz);
4.58 (2H, triplet, J=5 Hz);
6.93 (2H, doublet, J=8.5 Hz);
7.15 (2H, doublet, J=8.5 Hz);
7.46–7.53 (2H, multiplet);
7.80–7.93 (4H, multiplet);
8.00 (1H, singlet);
8.12 (1H, broad singlet).

EXAMPLE 14

5-(4-{2-[1-(2-Quinolyl)ethylideneaminooxy]ethoxy}benzyl)thiazolidine-2,4-dione (Compound No. 2-149)

14(a) 5-(4-{2-[1-(2-Quinolyl)ethylideneaminooxy]ethoxy}benzyl)-3-tritylthiazolidine-2,4-dione Following a procedure similar to that described in Example 1(a), but using 461 mg of 2-[1-(2-quinolyl)ethylideneaminooxy]ethanol (prepared as described in Preparation 14), 716 mg of 5-(4-hydroxybenzyl)-3-tritylthiazolidine-2,4-dione, 525 mg of triphenylphosphine and 348 mg of diethyl azodicarboxylate, 911 mg of the title compound were obtained as a foam-like solid.

$^1$H Nuclear Magnetic Resonance Spectrum (CDCl$_3$, 270 MHz, using tetramethylsilane as the internal standard), δ ppm:

2.49 (3H, singlet);
3.06 (1H, doublet of doublets, J=9 & 14 Hz);
3.41 (1H, doublet of doublets, J=4 & 14 Hz);
4.32 (2H, triplet, J=4.5 Hz);
4.36 (1H, doublet of doublets, J=4 & 9 Hz);
4.62 (2H, triplet, J=4.5 Hz);
6.90 (2H, doublet, J=8.5 Hz);
7.11–7.33 (17H, multiplet);
7.51 (1H, doublet of triplets, J=1 & 7.5 Hz);
7.70 (1H, doublet of triplets, J=1.5 & 7 Hz);
7.80 (1H, doublet of doublets, J=1 & 7.5 Hz);
8.06 (2H, singlet);
8.10 (1H, doublet, J=8 Hz).

14(b) 5-(4-{2-[1-(2-Quinolyl)ethylideneaminooxy]ethoxy}benzyl)thiazolidine-2,4-dione Following a procedure similar to that described in Example 1(b), but using 904 mg of 5-(4-{2-(1-(2-quinolyl)ethylideneaminooxy]ethoxy}benzyl)-3-tritylthiazolidine-2,4-dione [prepared as described in step (a) above], 402 mg of the title compound were obtained as a crystalline powder, melting at 162°–163° C.

$^1$H Nuclear Magnetic Resonance Spectrum (CDCl$_3$, 270 MHz, using tetramethylsilane as the internal standard), δ ppm:

2.46 (3H, singlet);
3.11 (1H, doublet of doublets, J=9 & 14 Hz);
3.43 (1H, doublet of doublets, J=4 & 14 Hz);
4.32 (2H, triplet, J=4.5 Hz);
4.50 (1H, doublet of doublets, J=4 & 9 Hz);

4.62 (2H, triplet, J=4.5 Hz);
6.92 (2H, doublet, J=8.5 Hz);
7.14 (2H, doublet, J=8.5 Hz);
7.54 (1H, triplet, J=7.5 Hz);
7.70 (1H, triplet, J=7.5 Hz);
7.80 (1H, doublet, J=8 Hz);
8.04–8.11 (3H, multiplet).

EXAMPLE 15

5-(4-{2-|1-(4-Biphenylyl)ethylideneaminooxy|ethoxy}benzyl)thiazolidine-2,4-dione (Compound No. 2-15)

15(a) 5-(4-{2-|1-(4-Biphenylyl)ethylideneaminooxy|ethoxy}benzyl)-3-tritylthiazolidine-2,4-dione Following a procedure similar to that described in Example 1(a), but using 170 mg of 2-|1-(4-biphenylyl)ethylideneaminooxy|ethanol (prepared as described in Preparation 15), 238 mg of 5-(4-hydroxybenzyl)-3-tritylthiazolidine-2,4-dione, 175 mg of triphenylphosphine and 116 mg of diethyl azodicarboxylate, 257 mg of the title compound were obtained as a crystalline powder, melting at 145° C.

$^1$H Nuclear Magnetic Resonance Spectrum (CDCl$_3$, 270 MHz, using tetramethylsilane as the internal standard), δ ppm:

2.27 (3H, singlet);
3.07 (1H, doublet of doublets, J=9 & 14 Hz);
3.41 (1H, doublet of doublets, J=4 & 14 Hz);
4.29 (2H, triplet, J=4.5 Hz);
4.36 (1H, doublet of doublets, J=4 & 9 Hz);
4.55 (2H, doublet, J=4.5 Hz);
6.90 (2H, doublet, J=8.5 Hz);
7.11–7.48 (20H, multiplet);
7.58–7.62 (4H, multiplet);
7.72 (2H, doublet, J=8.5 Hz).

15(b) 5-(4-{2-|1-(4-Biphenylyl)ethylideneaminooxy|ethoxy}benzyl)thiazolidine-2,4-dione Following a procedure similar to that described in Example 1(b), but using 254 mg of 5-(4-{2-[1-(4-biphenylyl)ethylideneaminooxy|ethoxy}benzyl)-3-tritylthiazolidine-2,4-dione [prepared as described in step (a) above], 139 mg of the title compound were obtained as a crystalline powder, melting at 164°–166° C.

$^1$H Nuclear Magnetic Resonance Spectrum (CDCl$_3$, 270 MHz, using tetramethylsilane as the internal standard), δ ppm:

2.28 (3H, singlet);
3.10 (1H, doublet of doublets, J=9 & 14 Hz);
3.45 (1H, doublet of doublets, J=4 & 14 Hz);
4.29 (2H, triplet, J=4.5 Hz);
4.50 (1H, doublet of doublets, J=4 & 9 Hz);
4.55 (2H, triplet, J=4.5 Hz);
6.92 (2H, doublet, J=8.5 Hz);
7.15 (2H, doublet, J=8.5 Hz);
7.33–7.48 (3H, multiplet);
7.60 (4H, doublet of doublets, J=2 & 8.5 Hz);
7.73 (2H, doublet, J=8.5 Hz);
8.05 (1H, broad singlet).

EXAMPLE 16

5-(4-{2-|1-(3-Biphenylyl)ethylideneaminooxy|ethoxy}benzyl)thiazolidine-2,4-dione (Compound No. 2-14)

16(a) 5-(4-{2-|1-(3-Biphenylyl)ethylideneaminooxy|ethoxy}benzyl)-3-tritylthiazolidine-2,4-dione Following a procedure similar to that described in Example 1(a), but using 511 mg of 2-|1-(3-biphenylyl)ethylideneaminooxy|ethanol (prepared as described in Preparation 16), 716 mg of 5-(4-hydroxybenzyl)-3-tritylthiazolidine-2,4-dione, 525 mg of triphenylphosphine and 348 mg of diethyl azodicarboxylate, 916 mg of the title compound were obtained as an amorphous solid.

$^1$H Nuclear Magnetic Resonance Spectrum (CDCl$_3$, 270 MHz, using tetramethylsilane as the internal standard), δ ppm:

2.29 (3H, singlet);
3.06 (1H, doublet of doublets, J=9 & 14 Hz);
3.41 (1H, doublet of doublets, J=4 & 14 Hz);
4.28 (2H, triplet, J=4.5 Hz);
4.36 (1H, doublet of doublets, J=4 & 9 Hz);
4.55 (2H, doublet, J=4.5 Hz);
6.90 (2H, doublet, J=8.5 Hz);
7.10–7.39 (17H, multiplet);
7.41–7.48 (3H, multiplet);
7.58–7.63 (4H, multiplet);
7.85 (2H, doublet, J=8.5 Hz).

16(b) 5-(4-{2-|1-(3-Biphenylyl)ethylideneaminooxy|ethoxy}benzyl)thiazolidine-2,4-dione Following a procedure similar to that described in Example 1(b), but using 912 mg of 5-(4-{2-|1-(3-biphenylyl)ethylideneaminooxy|ethoxy}benzyl)-3-tritylthiazolidine-2,4-dione |prepared as described in step (a) above| and subsequently purifying the crude product by column chromatography through silica gel, using a 2:1 by volume mixture of hexane and ethyl acetate as the eluent, 540 mg of the title compound were obtained as a gum.

$^1$H Nuclear Magnetic Resonance Spectrum (CDCl$_3$, 270 MHz, using tetramethylsilane as the internal standard), δ ppm:

2.29 (3H, singlet);
3.11 (1H, doublet of doublets, J=9.5 & 14 Hz);
3.45 (1H, doublet of doublets, J=4 & 14 Hz);
4.28 (2H, triplet, J=5 Hz);
4.49 (1H, doublet of doublets, J=4 & 9.5 Hz);
4.55 (2H, triplet, J=5 Hz);
6.92 (2H, doublet, J=8.5 Hz);
7.14 (2H, doublet, J=8.5 Hz);
7.34–7.48 (4H, multiplet);
7.57–7.63 (4H, multiplet);
7.85 (2H, doublet, J=2 Hz);
8.07 (1H, broad singlet).

EXAMPLE 17

5-(4-{2-|1-(2-Phenyl-5-pyridyl)ethylideneaminooxy|ethoxy}benzyl)thiazolidine-2,4-dione (Compound No. 2-95)

17(a) 5-(4-{2-|1-(2-Phenyl-5-pyridyl)ethylideneaminooxy|ethoxy}benzyl)-3-tritylthiazolidine-2,4-dione Following a procedure similar to that described in Example 1(a), but using 384 mg of 2-[1-(2-phenyl-5-pyridyl)ethylideneaminooxy|ethanol (prepared as described in Preparation 17), 537 mg of 5-(4-hydroxybenzyl)-3-tritylthiazolidine-2,4-dione, 393 mg of triphenylphosphine and 261 mg of diethyl azodicarboxylate, 698 mg of the title compound were obtained as a foam-like solid.

$^1$H Nuclear Magnetic Resonance Spectrum (CDCl$_3$, 270 MHz, using tetramethylsilane as the internal standard), δ ppm:

2.29 (3H, singlet);
3.07 (1H, doublet of doublets, J=9 & 14 Hz);
3.41 (1H, doublet of doublets, J=4 & 14 Hz);
4.29 (2H, triplet, J=4.5 Hz);
4.37 (1H, doublet of doublets, J=4 & 9 Hz);
4.57 (2H, doublet, J=4.5 Hz);
6.90 (2H, doublet, J=8.5 Hz);
7.12–7.36 (17H, multiplet);
7.43–7.52 (3H, multiplet);
7.72 (1H, doublet, J=8 Hz);
8.00–8.04 (3H, multiplet);
8.94 (1H, doublet, J=2.5 Hz).

17(b) 5-(4-{2-[1-(2-Phenyl-5-pyridyl)ethylideneaminooxy]ethoxy}benzyl)thiazolidine-2,4-dione Following a procedure similar to that described in Example 1(b), but using 695 mg of 5-(4-{2-[1-(2-phenyl-5-pyridyl)ethylideneaminooxy]ethoxy}benzyl)-3-tritylthiazolidine-2,4-dione [prepared as described in step (a) above], 380 mg of the title compound were obtained as a crystalline powder, melting at 186°–187° C.

¹H Nuclear Magnetic Resonance Spectrum (CDCl₃, 270 MHz, using tetramethylsilane as the internal standard), δ ppm:

2.29 (3H, singlet);
3.16 (1H, doublet of doublets, J=9 & 14 Hz);
3.40 (1H, doublet of doublets, J=4 & 14 Hz);
4.31 (2H, triplet, J=4.5 Hz);
4.49–4.59 (3H, multiplet);
6.91 (2H, doublet, J=8.5 Hz);
7.16 (2H, doublet, J=8.5 Hz);
7.43–7.52 (3H, multiplet);
7.73 (1H, doublet, J=8.5 Hz);
7.99–8.03 (3H, multiplet);
8.87 (1H, doublet, J=2 Hz).

EXAMPLE 18

5-(4-{2-[1-(3-Phenyl-5-pyridyl)ethylideneaminooxy]ethoxy}benzyl)thiazolidine-2,4-dione (Compound No. 2-92)

18(a) 5-(4-{2-[1-(3-Phenyl-5-pyridyl)ethylideneaminooxy]ethoxy}benzyl)-3-tritylthiazolidine-2,4-dione Following a procedure similar to that described in Example 1(a), but using 419 mg of 2-[1-(3-phenyl-5-pyridyl)ethylideneaminooxy]ethanol (prepared as described in Preparation 18), 585 mg of 5-(4-hydroxybenzyl)-3-tritylthiazolidine-2,4-dione, 429 mg of triphenylphosphine and 285 mg of diethyl azodicarboxylate, 522 mg of the title compound were obtained as a foam-like solid.

¹H Nuclear Magnetic Resonance Spectrum (CDCl₃, 270 MHz, using tetramethylsilane as the internal standard), δ ppm:

2.30 (3H, singlet);
3.06 (1H, doublet of doublets, J=9 & 14 Hz);
3.40 (1H, doublet of doublets, J=4 & 14 Hz);
4.28 (2H, triplet, J=4.5 Hz);
4.35 (1H, doublet of doublets, J=4 & 9 Hz);
4.57 (2H, triplet, J=4.5 Hz);
6.88 (2H, doublet, J=8.5 Hz);
7.10–7.32 (17H, multiplet);
7.41–7.51 (3H, multiplet);
7.58–7.61 (2H, multiplet);
8.12 (1H, triplet, J=2 Hz);
8.88–8.90 (2H, multiplet).

18(b) 5-(4-{2-[1-(3-Phenyl-5-pyridyl)ethylideneaminooxy]ethoxy}benzyl)thiazolidine-2,4-dione Following a procedure similar to that described in Example 1(b), but using 516 mg of 5-(4-{2-[1-(3-phenyl-5-pyridyl)ethylideneaminooxy]ethoxy}benzyl)-3-tritylthiazolidine-2,4-dione [prepared as described in step (a) above], 303 mg of the title compound were obtained as a crystalline powder, melting at 150°–153° C.

¹H Nuclear Magnetic Resonance Spectrum (a mixture of CDCl₃ with a small amount of hexadeuterated dimethyl sulfoxide, 270 MHz, using tetramethylsilane as the internal standard), δ ppm:

2.31 (3H, singlet);
3.06 (1H, doublet of doublets, J=9 & 14 Hz);
3.45 (1H, doublet of doublets, J=4 & 14 Hz);
4.29 (2H, triplet, J=4.5 Hz);
4.43 (1H, doublet of doublets, J=4 & 9 Hz);
4.57 (2H, triplet, J=4.5 Hz);
6.90 (2H, doublet, J=8.5 Hz);
7.15 (2H, doublet, J=8.5 Hz);
7.43–7.53 (3H, multiplet);
7.60–7.63 (2H, multiplet);
8.13 (1H, triplet, J=2 Hz);
8.82 (2H, doublet, J=2 Hz).

EXAMPLE 19

5-(4-{2-[1-(2-Ethoxy-5-pyridyl)ethylideneaminooxy]ethoxy}benzyl)thiazolidine-2,4-dione (Compound No. 2-97)

19(a) 5-(4-{2-[1-(2-Ethoxy-5-pyridyl)ethylideneaminooxy]ethoxy}benzyl)-3-tritylthiazolidine-2,4-dione Following a procedure similar to that described in Example 1(a), but using 410 mg of 2-[1-(2-ethoxy-5-pyridyl)ethylideneaminooxy]ethanol (prepared as described in Preparation 19), 655 mg of 5-(4-hydroxybenzyl)-3-tritylthiazolidine-2,4-dione, 480 mg of triphenylphosphine and 319 mg of diethyl azodicarboxylate, 763 mg of the title compound were obtained as a foam-like solid.

¹H Nuclear Magnetic Resonance Spectrum (CDCl₃, 270 MHz, using tetramethylsilane as the internal standard), δ ppm:

1.40 (3H, triplet, J=7 Hz);
2.21 (3H, singlet);
3.07 (1H, doublet of doublets, J=9 & 14 Hz);
3.41 (1H, doublet of doublets, J=4 & 14 Hz);
4.25 (2H, triplet, J=4.5 Hz);
4.33–4.41 (3H, multiplet);
4.51 (2H, triplet, J=4.5 Hz);
6.70 (1H, doublet, J=9 Hz);
6.88 (2H, doublet, J=8.5 Hz);
7.11–7.33 (17H, multiplet);
7.91 (1H, doublet of doublets, J=2.5 & 9 Hz);
8.35 (1H, doublet, J=2.5 Hz).

19(b) 5-(4-{2-[1-(2-Ethoxy-5-pyridyl)ethylideneaminooxy]ethoxy}benzyl)thiazolidine-2,4-dione Following a procedure similar to that described in Example 1(b), but using 508 mg of 5-(4-{2-[1-(2-ethoxy-5-pyridyl)ethylideneaminooxy]ethoxy}benzyl)-3- tritylthiazolidine-2,4-dione [prepared as described in step (a) above], 219 mg of the title compound were obtained as a crystalline powder, melting at 135°–138° C.

$^1$H Nuclear Magnetic Resonance Spectrum (CDCl$_3$, 270 MHz, using tetramethylsilane as the internal standard), δ ppm:

1.40 (3H, triplet, J=7 Hz);
2.21 (3H, singlet);
3.13 (1H, doublet of doublets, J=9 & 14 Hz);
3.43 (1H, doublet of doublets, J=4 & 14 Hz);
4.27 (2H, triplet, J=4.5 Hz);
4.37 (2H, quartet, J=7 Hz);
4.48–4.53 (3H, multiplet);
6.71 (1H, doublet, J=9 Hz);
6.90 (2H, doublet, J=8.5 Hz);
7.15 (2H, doublet, J=8.5 Hz);
7.91 (1H, doublet of doublets, J=2.5 & 9 Hz);
8.32 (1H, doublet, J=2.5 Hz).

EXAMPLE 20

5-(4-{2-[1-(4-1'-Imidazolylphenyl)ethylideneaminooxy]ethoxy}benzyl)thiazolidine-2,4-dione (Compound No. 2-25)

20(a) 5-(4-{2-[1-(4-1'-Imidazolylphenyl)ethylideneaminooxy]ethoxy}benzyl)-3-tritylthiazolidine-2,4-dione Following a procedure similar to that described in Example 1(a), but using 490 mg of 2-[1-(4-1'-imidazolylphenyl)ethylideneaminooxy]ethanol (prepared as described in Preparation 20), 907 mg of 5-(4-hydroxybenzyl)-3-tritylthiazolidine-2,4-dione, 550 mg of triphenylphosphine and 365 mg of diethyl azodicarboxylate, 830 mg of the title compound were obtained as an amorphous solid.

$^1$H Nuclear Magnetic Resonance Spectrum (CDCl$_3$, 270 MHz, using tetramethylsilane as the internal standard), δ ppm:

2.26 (3H, singlet);
3.08 (1H, doublet of doublets, J=9 & 14 Hz);
3.40 (1H, doublet of doublets, J=4 & 14 Hz);
4.28 (2H, triplet, J=5 Hz);
4.37 (1H, doublet of doublets, J=4 & 9 Hz);
4.56 (2H, triplet, J=5 Hz);
6.89 (2H, doublet, J=8.5 Hz);
7.10–7.39 (21H, multiplet);
7.75 (2H, doublet, J=8.5 Hz);
7.87 (1H, singlet).

20(b) 5-(4-{2-[1-(4-1'-Imidazolylphenyl)ethylideneaminooxy]ethoxy}benzyl)thiazolidine-2,4-dione Following a procedure similar to that described in Example 1(b), but using 830 mg of 5-(4-{2-[1-(4-1'-imidazolylphenyl)ethylideneaminooxy]ethoxy}benzyl)-3-tritylthiazolidine-2,4-dione [prepared as described in step (a) above], 465 mg of the title compound were obtained as a crystalline powder, melting at 192°–200° C.

Nuclear Magnetic Resonance Spectrum (hexadeuterated dimethyl sulfoxide, 270 MHz, using tetramethylsilane as the internal standard), δ ppm:

2.22 (3H, singlet);
3.06 (1H, doublet of doublets, J=9 & 14 Hz);
3.31 (1H, doublet of doublets, J=4.5 & 14 Hz);
4.27 (2H, triplet, J=4.5 Hz);
4.47 (2H, triplet, J=4.5 Hz);
4.87 (1H, doublet of doublets, J=4.5 & 9 Hz);
6.93 (2H, doublet, J=8.5 Hz);
7.13 (1H, singlet);
7.16 (2H, doublet, J=8.5 Hz);
7.71 (2H, doublet, J=8.5 Hz);
7.80 (2H, doublet, J=8.5 Hz);
7.81 (1H, singlet);
8.33 (1H, singlet).

EXAMPLE 21

5-(4-{2-[1-(4-2'-Pyridylphenyl)ethylideneaminooxy]ethoxy}benzyl)thiazolidine-2,4-dione (Compound No. 2-35)

21(a) 5-(4-{2-[1-(4-2'-Pyridylphenyl)ethylideneaminooxy]ethoxy}benzyl)-3-tritylthiazolidine-2,4-dione Following a procedure similar to that described in Example 1(a), but using 7.00 g of 2-[1-(4-2'-pyridylphenyl)ethylideneaminooxy]ethanol (prepared as described in Preparation 21), 12.39 g of 5-(4-hydroxybenzyl)-3-tritylthiazolidine-2,4-dione, 7.51 g of triphenylphosphine and 4.99 g of diethyl azodicarboxylate, 16.15 g of the title compound were obtained as a crystalline powder, melting at 117°–119° C.

$^1$H Nuclear Magnetic Resonance Spectrum (CDCl$_3$, 270 MHz, using tetramethylsilane as the internal standard), δ ppm:

2.29 (3H, singlet);
3.07 (1H, doublet of doublets, J=9 & 14 Hz);
3.41 (1H, doublet of doublets, J=4 & 14 Hz);
4.29 (2H, triplet, J=4.5 Hz);
4.37 (1H, doublet of doublets, J=4 & 9 Hz);
4.56 (2H, triplet, J=4.5 Hz);
6.90 (2H, doublet, J=8.5 Hz);
7.11–7.34 (18H, multiplet);
7.75–7.78 (3H, multiplet);
8.01 (2H, doublet, J=8.5 Hz);
8.71 (1H, doublet, J=5 Hz).

21(b) 5-(4-{2-[1-(4-2'-Pyridylphenyl)ethylideneaminooxy]ethoxy}benzyl)thiazolidine-2,4-dione Following a procedure similar to that described in Example 1(b), but using 16.00 g of 5-(4-{2-[1-(4-2'-pyridylphenyl)ethylideneaminooxy]ethoxy}benzyl)-3-tritylthiazolidine-2,4-dione [prepared as described in step (a) above], 9.17 g of the title compound were obtained as a crystalline powder, melting at 176°–179° C.

$^1$H Nuclear Magnetic Resonance Spectrum (CDCl$_3$, 270 MHz, using tetramethylsilane as the internal standard), δ ppm:

2.28 (3H, singlet);
3.13 (1H, doublet of doublets, J=9 & 14 Hz);
3.44 (1H, doublet of doublets, J=4 & 14 Hz);
4.30 (2H, triplet, J=5 Hz);
4.51 (1H, doublet of doublets, J=4 & 14 Hz);
4.56 (2H, triplet, J=5 Hz);
6.92 (2H, doublet, J=8.5 Hz);
7.15 (2H, doublet, J=8.5 Hz);
7.23–7.28 (1H, multiplet);
7.74–7.81 (4H, multiplet);
7.99 (2H, doublet, J=8.5 Hz);
8.70 (1H, doublet, J=4.5 Hz).

21(c) 5-(4-{2-[1-(4-2'-Pyridylphenyl)ethylideneaminooxy] ethoxy}benzyl)thiazolidine-2,4-dione hydrochloride 1 ml of a 4N solution of hydrogen chloride in dioxane was added to a solution of 500 mg of 5-(4-{2-[1-(4-2'-pyridylphenyl)ethylideneaminooxy]ethoxy}benzyl) thiazolidine-2,4-dione [prepared as described in step (b) above] in a mixture of 20 ml of ethyl acetate and 20 ml of dioxane, and the resulting mixture was concentrated by evaporation under reduced pressure. The crystalline powder thus obtained was suspended in a mixture of ethyl acetate and diethyl ether and then collected by filtration, to give 540 mg of the hydrochloride of the title compound as a crystalline powder, melting at 187.5° C.

Nuclear Magnetic Resonance Spectrum (hexadeuterated dimethyl sulfoxide, 270 MHz, using tetramethylsilane as the internal standard), δ ppm:

2.25 (3H, singlet);
3.06 (1H, doublet of doublets, J=9 & 14 Hz);
3.31 (1H, doublet of doublets, J=4.5 & 14 Hz);
4.28 (2H, triplet, J=4.5 Hz);
4.50 (2H, triplet, J=4.5 Hz);
4.88 (1H, doublet of doublets, J=4.5 & 9 Hz);
6.94 (2H, doublet, J=8.5 Hz);
7.17 (2H, doublet, J=8.5 Hz);
7.67 (1H, doublet of doublets, J=2 & 6 Hz);
7.87 (2H, doublet, J=8.5 Hz);
8.15 (2H, doublet, J=8.5 Hz);
8.20–8.28 (2H, multiplet);
8.79 (1H, doublet, J=5 Hz).

EXAMPLE 22

5-(4-{2-[1-(4-3'-Pyridylphenyl)ethylideneaminooxy] ethoxy}benzyl)thiazolidine-2,4-dione (Compound No. 2-37)

22(a) 5-(4-{2-[1-(4-3'-Pyridylphenyl)ethylideneaminooxy] ethoxy}benzyl)-3-tritylthiazolidine-2,4-dione Following a procedure similar to that described in Example 1(a), but using 512 mg of 2-[1-(4-3'-pyridylphenyl) ethylideneaminooxy]ethanol (prepared as described in Preparation 22), 907 mg of 5-(4-hydroxybenzyl)-3-tritylthiazolidine-2,4-dione, 550 mg of triphenylphosphine and 365 mg of diethyl azodicarboxylate, 1.16 g of the title compound were obtained as a foam-like solid.

¹H Nuclear Magnetic Resonance Spectrum (CDCl₃, 270 MHz, using tetramethylsilane as the internal standard), δ ppm:

2.28 (3H, singlet);
3.07 (1H, doublet of doublets, J=9 & 14 Hz);
3.41 (1H, doublet of doublets, J=4 & 14 Hz);
4.29 (2H, triplet, J=4.5 Hz);
4.37 (1H, doublet of doublets, J=4 & 9 Hz);
4.56 (2H, triplet, J=4.5 Hz);
6.90 (2H, doublet, J=8.5 Hz);
7.11–7.41 (18H, multiplet);
7.58 (2H, doublet, J=8.5 Hz);
7.76 (2H, doublet, J=8.5 Hz);
7.88 (1H, doublet of triplets, J=1.5 & 8 Hz);
8.61 (1H, doublet of doublets, J=2 & 5 Hz);
8.86 (1H, doublet, J=1.5 Hz).

22(b) 5-(4-{2-[1-(4-3'-Pyridylphenyl)ethylideneaminooxy] ethoxy}benzyl)thiazolidine-2,4-dione Following a procedure similar to that described in Example 1(b), but using 1.16 g of 5-(4-{2-[1-(4-3'-pyridylphenyl)ethylideneaminooxy]ethoxy}benzyl)-3-tritylthiazolidine-2,4-dione [prepared as described in step (a) above], 696 mg of the title compound were obtained as a crystalline powder, melting at 182° C.

Nuclear Magnetic Resonance Spectrum (hexadeuterated dimethyl sulfoxide, 270 MHz, using tetramethylsilane as the internal standard), δ ppm:

2.23 (3H, singlet);
3.06 (1H, doublet of doublets, J=9 & 14 Hz);
3.30 (1H, doublet of doublets, J=4.5 & 14 Hz);
4.27 (2H, triplet, J=4.5 Hz);
4.48 (2H, triplet, J=4.5 Hz);
4.87 (1H, doublet of doublets, J=4.5 & 9 Hz);
6.93 (2H, doublet, J=8.5 Hz);
7.16 (2H, doublet, J=8.5 Hz);
7.51 (1H, doublet of doublets, J=5 & 8 Hz);
7.80 (4H, singlet);
8.12 (1H, doublet of triplets, J=2 & 8 Hz);
8.59 (1H, doublet of doublets, J=1.5 & 5 Hz);
8.94 (1H, doublet, J=2 Hz).

EXAMPLE 23

5-(4-{2-[1-(4-4'-Pyridylphenyl)ethylideneaminooxy] ethoxy}benzyl)thiazolidine-2,4-dione (Compound No. 2-39)

23(a) 5-(4-{2-[1-(4-4'-Pyridylphenyl)ethylideneaminooxy] ethoxy}benzyl)-3-tritylthiazolidine-2,4-dione Following a procedure similar to that described in Example 1(a), but using 769 mg of 2-[1-(4-4'-pyridylphenyl) ethylideneaminooxy]ethanol (prepared as described in Preparation 23), 1.53 g of 5-(4-hydroxybenzyl)-3-tritylthiazolidine-2,4-dione, 866 mg of triphenylphosphine and 575 mg of diethyl azodicarboxylate, 2.00 g of the title compound were obtained as a foam-like solid.

¹H Nuclear Magnetic Resonance Spectrum (CDCl₃, 270 MHz, using tetramethylsilane as the internal standard), δ ppm:

2.28 (3H, singlet);
3.08 (1H, doublet of doublets, J=9 & 14 Hz);
3.41 (1H, doublet of doublets, J=4 & 14 Hz);
4.29 (2H, triplet, J=5 Hz);
4.37 (1H, doublet of doublets, J=4 & 9 Hz);
4.57 (1H, triplet, J=5 Hz);
6.90 (2H, doublet, J=8.5 Hz);
7.11–7.33 (17H, multiplet);
7.51 (2H, doublet of doublets, J=1.5 & 4.5 Hz);
7.64 (2H, doublet, J=8.5 Hz);
7.77 (2H, doublet, J=8.5 Hz);
8.67 (2H, doublet of doublets, J=1.5 & 4.5 Hz).

23(b) 5-(4-{2-[1-(4-4'-Pyridylphenyl)ethylideneaminooxy] ethoxy}benzyl)thiazolidine-2,4-dione Following a procedure similar to that described in Example 1(b), but using 1.34 g of 5-(4-{2-[1-(4-4'-pyridylphenyl)ethylideneaminooxy]ethoxy}benzyl)-3-tritylthiazolidine-2,4-dione [prepared as described in step (a) above], 630 mg of the title compound were obtained as a crystalline powder, melting at 234°–235° C.

Nuclear Magnetic Resonance Spectrum (hexadeuterated dimethyl sulfoxide, 270 MHz, using tetramethylsilane as the internal standard), δ ppm:

2.23 (3H, singlet);
3.06 (1H, doublet of doublets, J=9 & 14 Hz);
4.31 (1H, doublet of doublets, J=4 & 14 Hz);
4.27 (2H, triplet, J=4.5 Hz);
4.48 (2H, triplet, J=4.5 Hz);
4.88 (1H, doublet of doublets, J=4 & 9 Hz);
6.93 (2H, doublet, J=8.5 Hz);
7.16 (2H, doublet, J=8.5 Hz);
7.75 (2H, doublet, J=6 Hz);
7.82 (2H, doublet, J=8.5 Hz);
7.86 (2H, doublet, J=8.5 Hz);
8.66 (2H, doublet, J=6 Hz).

EXAMPLE 24

5-{4-[2-(1,4-Dimethyl-2-phenylimidazol-5-ylmethyleneaminooxy)ethoxy|benzyl}thiazolidine-2,4-dione (Compound No. 1-176)

24(a) 5-{4-[2-(1,4-Dimethyl-2-phenylimidazol-5-ylmethyleneaminooxy)ethoxy|benzyl}-3-tritylthiazolidine-2,4-dione Following a procedure similar to that described in Example 1(a), but using 420 mg of 2-(1,4-dimethyl-2-phenylimidazol-5-ylmethyleneaminooxy)ethanol (prepared as described in Preparation 24), 580 mg of 5-(4-hydroxybenzyl)-3-tritylthiazolidine-2,4-dione, 425 mg of triphenylphosphine and 282 mg of diethyl azodicarboxylate, 646 mg of the title compound were obtained as a foam-like solid.

$^1$H Nuclear Magnetic Resonance Spectrum (CDCl$_3$, 270 MHz, using tetramethylsilane as the internal standard), δ ppm:

2.33 (3H, singlet);
3.08 (1H, doublet of doublets, J=9 & 14 Hz);
3.41 (1H, doublet of doublets, J=4 & 14 Hz);
3.76 (3H, singlet);
4.26 (2H, triplet, J=5 Hz);
4.37 (1H, doublet of doublets, J=4 & 9 Hz);
4.49 (2H, doublet, J=5 Hz);
6.90 (2H, doublet, J=8.5 Hz);
7.13–7.32 (18H, multiplet);
7.42–7.47 (3H, multiplet);
7.56–7.60 (2H, multiplet);
8.22 (1H, singlet).

24(b) 5-{4-[2-(1,4-Dimethyl-2-phenylimidazol-5-ylmethyleneaminooxy)ethoxy|benzyl}-thiazolidine-2,4-dione Following a procedure similar to that described in Example 1(b), but using 640 mg of 5-{4-[2-(1,4-dimethyl-2-phenylimidazol-5-ylmethyleneaminooxy)ethoxy|benzyl}-3-tritylthiazolidine-2,4-dione [prepared as described in step (a) above], 354 mg of the title compound were obtained as an amorphous powder.

$^1$H Nuclear Magnetic Resonance Spectrum (CDCl$_3$, 270 MHz, using tetramethylsilane as the internal standard), δ ppm:

2.32 (3H, singlet);
3.11 (1H, doublet of doublets, J=9 & 14 Hz);
3.43 (1H, doublet of doublets, J=4 & 14 Hz);
3.83 (3H, singlet);
4.25 (2H, triplet, J=5 Hz);
4.46–4.51 (3H, multiplet);
6.90 (2H, doublet, J=8.5 Hz);
7.15 (2H, doublet, J=8.5 Hz);
7.43–7.50 (3H, multiplet);
7.58–7.62 (2H, multiplet);
8.21 (1H, singlet).

EXAMPLE 25

5-(4-{2-[1-(1-Methyl-2-phenylimidazol-4-yl)ethylideneaminooxy|ethoxy}benzyl)thiazolidine-2,4-dione (Compound No. 2-175)

25(a) 5-(4-{2-[1-(1-Methyl-2-phenylimidazol-4-yl)ethylideneaminooxy|ethoxy}benzyl)-3-tritylthiazolidine-2,4-dione Following a procedure similar to that described in Example 1(a), but using 396 mg of 2-[1-(1-methyl-2-phenylimidazol-4-yl)ethylideneaminooxy|ethanol (prepared as described in Preparation 25), 694 mg of 5-(4-hydroxybenzyl)-3-tritylthiazolidine-2,4-dione, 440 mg of triphenylphosphine and 292 mg of diethyl azodicarboxylate, 866 mg of the title compound were obtained as a foam-like solid.

$^1$H Nuclear Magnetic Resonance Spectrum (CDCl$_3$, 270 MHz, using tetramethylsilane as the internal standard), δ ppm:

2.27 (3H, singlet);
3.06 (1H, doublet of doublets, J=9 & 14 Hz);
3.42 (1H, doublet of doublets, J=4 & 14 Hz);
3.70 (3H, singlet);
4.25 (2H, triplet, J=5 Hz);
4.36 (1H, doublet of doublets, J=4 & 9 Hz);
4.52 (2H, doublet, J=5 Hz);
6.89 (2H, doublet, J=8.5 Hz);
7.12 (2H, doublet, J=8.5 Hz);
7.15–7.34 (15H, multiplet);
7.41–7.49 (3H, multiplet);
7.59–7.64 (2H, multiplet).

25(b) 5-(4-{2-[1-(1-Methyl-2-phenylimidazol-4-yl)ethylideneaminooxy|ethoxy}benzyl)thiazolidine-2,4-dione Following a procedure similar to that described in Example 1(b), but using 866 mg of 5-(4-{2-[1-(1-methyl-2-phenylimidazol-4-yl)ethylideneaminooxy|ethoxy}benzyl)-3-tritylthiazolidine-2,4-dione [prepared as described in step (a) above], 444 mg of the title compound were obtained as an amorphous powder.

Nuclear Magnetic Resonance Spectrum (hexadeuterated dimethyl sulfoxide, 270 MHz, using tetramethylsilane as the internal standard), δ ppm:

2.15 (3H, singlet);
3.06 (1H, doublet of doublets, J=9 & 14 Hz);
3.31 (1H, doublet of doublets, J=4.5 & 14 Hz);
3.75 (3H, singlet);
4.22 (2H, triplet, J=4.5 Hz);
4.37 (2H, doublet, J=4.5 Hz);
4.88 (1H, doublet of doublets, J=4.5 & 9 Hz);
6.93 (2H, doublet, J=8.5 Hz);
7.16 (2H, doublet, J=8.5 Hz);
7.46–7.53 (3H, multiplet);
7.63–7.72 (2H, multiplet).

EXAMPLE 26

5-(4-{2-[1-(4'-Methylbiphenyl-4-yl)ethylideneaminooxy|ethoxy}benzyl)thiazolidine-2,4-dione (Compound No. 2-189)

26(a) 5-(4-{2-[1-(4'-Methylbiphenyl-4-yl)ethylideneaminooxy|ethoxy}benzyl)-3-tritylthiazolidine-2,4-dione Following a procedure similar to that described in Example 1(a), but using 539 mg of 2-|1-(4'-methylbiphenyl-4-yl)ethylideneaminooxy|ethanol (prepared as described in Preparation 26), 931 mg of 5-(4-hydroxybenzyl)-3-tritylthiazolidine-2,4-dione, 577 mg of triphenylphosphine and 366 mg of diethyl azodicarboxylate, 1.24 g of the title compound were obtained as a foam-like solid.

$^1$H Nuclear Magnetic Resonance Spectrum (CDCl$_3$, 270 MHz, using tetramethylsilane as the internal standard), δ ppm:

2.27 (3H, singlet);
2.40 (3H, singlet);
3.07 (1H, doublet of doublets, J=9 & 14 Hz);
3.41 (1H, doublet of doublets, J=4 & 14 Hz);
4.28 (2H, triplet, J=4.5 Hz);
4.36 (1H, doublet of doublets, J=4 & 9 Hz);
4.55 (2H, triplet, J=4.5 Hz);
6.90 (2H, doublet, J=8.5 Hz);
7.11-7.33 (19H, multiplet);
7.50 (2H, doublet, J=8 Hz);
7.57 (2H, doublet, J=8.5 Hz);
7.70 (2H, doublet, J=8.5 Hz).

26(b) 5-(4-{2-|1-(4'-Methylbiphenyl-4-yl)ethylideneaminooxy|ethoxy}benzyl)thiazolidine-2,4-dione Following a procedure similar to that described in Example 1(b), but using 1.24 g of 5-(4-{2-|1-(4'-methylbiphenyl-4-yl)ethylideneaminooxy|ethoxy}benzyl)-3-tritylthiazolidine-2,4-dione [prepared as described in step (a) above], 670 mg of the title compound were obtained as a crystalline powder, melting at 184°-186° C.

$^1$H Nuclear Magnetic Resonance Spectrum (a mixture of CDCl$_3$ with a small amount of hexadeuterated dimethyl sulfoxide, 270 MHz, using tetramethylsilane as the internal standard), δ ppm:

2.27 (3H, singlet);
2.40 (3H, singlet);
3.06 (1H, doublet of doublets, J=9 & 14 Hz);
3.46 (1H, doublet of doublets, J=4 & 14 Hz);
4.28 (2H, triplet, J=4.5 Hz) 4.43 (1H, doublet of doublets, J=4 & 9 Hz);
4.54 (2H, triplet, J=4.5 Hz);
6.90 (2H, doublet, J=8.5 Hz);
7.15 (2H, doublet, J=8.5 Hz);
7.26 (2H, doublet, J=8 Hz);
7.50 (2H, doublet, J=8 Hz);
7.58 (2H, doublet, J=8.5 Hz);
7.71 (2H, doublet, J=8.5 Hz).

EXAMPLE 27

5-(4-{2-|1-(4'-Fluorobiphenyl-4-yl)ethylideneaminooxy|ethoxy}benzyl)thiazolidine-2,4-dione (Compound No. 2-190)

27(a) 5-(4-{2-|1-(4'-Fluorobiphenyl-4-yl)ethylideneaminooxy|ethoxy}benzyl)-3-tritylthiazolidine-2,4-dione Following a procedure similar to that described in Example 1(a), but using 547 mg of 2-|1-(4'-fluorobiphenyl-4-yl)ethylideneaminooxy|ethanol (prepared as described in Preparation 27), 931 mg of 5-(4-hydroxybenzyl)-3-tritylthiazolidine-2,4-dione, 577 mg of triphenylphosphine and 366 mg of diethyl azodicarboxylate, 1.29 g of the title compound were obtained as a foam-like solid.

$^1$H Nuclear Magnetic Resonance Spectrum (CDCl$_3$, 270 MHz, using tetramethylsilane as the internal standard), δ ppm:

2.27 (3H, singlet);
3.07 (1H, doublet of doublets, J=9 & 14 Hz);
3.41 (1H, doublet of doublets, J=4 & 14 Hz);
4.28 (2H, triplet, J=5 Hz);
4.36 (1H, doublet of doublets, J=4 & 9 Hz);
4.55 (2H, triplet, J=5 Hz);
6.90 (2H, doublet, J=8.5 Hz);
7.10-7.33 (19H, multiplet);
7.52-7.58 (4H, multiplet);
7.71 (2H, doublet, J=8.5 Hz).

27(b) 5-(4-{2-|1-(4'-Fluorobiphenyl-4-yl)ethylideneaminooxy|-ethoxy}benzyl)thiazolidine-2,4-dione Following a procedure similar to that described in Example 1(b), but using 1.29 g of 5-(4-{2-|1-(4'-fluorobiphenyl-4-yl)ethylideneaminooxy|ethoxy}benzyl)-3-tritylthiazolidine-2,4-dione [prepared as described in step (a) above], 695 mg of the title compound were obtained as a crystalline powder, melting at 155°-156° C.

$^1$H Nuclear Magnetic Resonance Spectrum (CDCl$_3$, 270 MHz, using tetramethylsilane as the internal standard), δ ppm:

2.27 (3H, singlet);
3.11 (1H, doublet of doublets, J=9 & 14 Hz);
3.45 (1H, doublet of doublets, J=4 & 14 Hz);
4.29 (2H, triplet, J=5 Hz);
4.50 (1H, doublet of doublets, J=4 & 9 Hz);
4.55 (2H, triplet, J=5 Hz);
6.92 (2H, doublet, J=8.5 Hz);
7.14 (2H, triplet, J=8.5 Hz);
7.15 (2H, doublet, J=8.5 Hz);
7.53-7.60 (4H, multiplet);
7.72 (2H, doublet, J=8.5 Hz).

EXAMPLE 28

5-(4-{2-|1-(4'-Trifluoromethylbiphenyl-4-yl)ethylideneaminooxy|ethoxy}benzyl)thiazolidine-2,4-dione (Compound No. 2-191)

28(a) 5-(4-{2-|1-(4'-Trifluoromethylbiphenyl-4-yl)ethylideneaminooxy|ethoxy}benzyl)-3-tritylthiazolidine-2,4-dione Following a procedure similar to that described in Example 1(a), but using 647 mg of 2-|1-(4'-trifluoromethylbiphenyl-4-yl)ethylideneaminooxy|ethanol (prepared as described in Preparation 28), 931 mg of 5-(4-hydroxybenzyl)-3-tritylthiazolidine-2,4-dione, 577 mg of triphenylphosphine and 366 mg of diethyl azodicarboxylate, 1.35 g of the title compound were obtained as a foam-like solid.

$^1$H Nuclear Magnetic Resonance Spectrum (CDCl$_3$, 270 MHz, using tetramethylsilane as the internal standard), δ ppm:

2.28 (3H, singlet);
3.07 (1H, doublet of doublets, J=9 & 14 Hz);
3.41 (1H, doublet of doublets, J=4 & 14 Hz);
4.28 (2H, triplet, J=5 Hz);
4.36 (1H, doublet of doublets, J=4 & 9 Hz);
4.56 (2H, triplet, J=5 Hz);
6.90 (2H, doublet, J=8.5 Hz);

7.11–7.33 (17H, multiplet);

7.59 (2H, doublet, J=8.5 Hz);

7.70 (4H, singlet);

7.75 (2H, doublet, J=8.5 Hz).

28(b) 5-(4-{2-[1-(4'-Trifluoromethylbiphenyl-4-yl)ethylideneaminooxy]ethoxy}benzyl)thiazolidine-2,4-dione Following a procedure similar to that described in Example 1(b), but using 1.35 g of 5-(4-{2-[1-(4'-trifluoromethylbiphenyl-4-yl)ethylideneaminooxy]ethoxy}benzyl)-3-tritylthiazolidine-2,4-dione [prepared as described in step (a) above], 781 mg of the title compound were obtained as a crystalline powder, melting at 165°–166° C.

$^1$H Nuclear Magnetic Resonance Spectrum (a mixture of CDCl$_3$ with a small amount of hexadeuterated dimethyl sulfoxide, 270 MHz, using tetramethylsilane as the internal standard), δ ppm:

2.28 (3H, singlet);

3.05 (1H, doublet of doublets, J=9 & 14 Hz);

3.46 (1H, doublet of doublets, J=4 & 14 Hz);

4.29 (2H, triplet, J=5 Hz);

4.43 (1H, doublet of doublets, J=4 & 9 Hz);

4.55 (2H, triplet, J=5 Hz);

6.90 (2H, doublet, J=8.5 Hz);

7.15 (2H, triplet, J=8.5 Hz);

7.61 (2H, doublet, J=8.5 Hz);

7.71 (4H, singlet);

7.76 (2H, doublet, J=8.5 Hz).

EXAMPLE 29

5-(4-{2-[1-(4-Ethoxyphenyl)ethylideneaminooxy]ethoxy}benzyl)thiazolidine-2,4-dione (Compound No. 2-158)

29(a) 5-(4-{2-[1-(4-Ethoxyphenyl)ethylideneaminooxy]ethoxy}benzyl)-3-tritylthiazolidine-2,4-dione Following a procedure similar to that described in Example 1(a), but using 447 mg of 2-[1-(4-ethoxyphenyl)ethylideneaminooxy]ethanol (prepared as described in Preparation 29), 931 mg of 5-(4-hydroxybenzyl)-3-tritylthiazolidine-2,4-dione, 577 mg of triphenylphosphine and 366 mg of diethyl azodicarboxylate, 1.34 g of the title compound were obtained as a foam-like solid.

$^1$H Nuclear Magnetic Resonance Spectrum (CDCl$_3$, 270 MHz, using tetramethylsilane as the internal standard), δ ppm:

1.41 (3H, triplet, J=7 Hz);

2.21 (3H, singlet);

3.06 (1H, doublet of doublets, J=9 & 14 Hz);

3.41 (1H, doublet of doublets, J=4 & 14 Hz);

4.04 (2H, quartet, J=7 Hz);

4.26 (2H, triplet, J=5 Hz);

4.36 (1H, doublet of doublets, J=4 & 9 Hz);

4.50 (2H, triplet, J=5 Hz);

6.87 (2H, doublet, J=9 Hz);

6.89 (2H, doublet, J=8.5 Hz);

7.10–7.33 (17H, multiplet);

7.57 (2H, doublet, J=9 Hz).

29(b) 5-(4-{2-[1-(4-Ethoxyphenyl)ethylideneaminooxy]ethoxy}benzyl)thiazolidine-2,4-dione Following a procedure similar to that described in Example 1(b), but using 1.34 g of 5-(4-{2-[1-(4-ethoxyphenyl)ethylideneaminooxy]ethoxy}benzyl)-3-tritylthiazolidine-2,4-dione [prepared as described in step (a) above], 517 mg of the title compound were obtained as a crystalline powder, melting at 128°–131° C.

$^1$H Nuclear Magnetic Resonance Spectrum (CDCl$_3$, 270 MHz, using tetramethylsilane as the internal standard), δ ppm:

1.42 (3H, triplet, J=7 Hz);

2.21 (3H, singlet);

3.10 (1H, doublet of doublets, J=9 & 14 Hz);

3.46 (1H, doublet of doublets, J=4 & 14 Hz);

4.05 (2H, quartet, J=7 Hz);

4.26 (2H, triplet, J=5 Hz);

4.49 (1H, doublet of doublets, J=4 & 9 Hz);

4.51 (2H, triplet, J=5 Hz);

6.88 (2H, doublet, J=8.5 Hz);

6.91 (2H, triplet, J=8.5 Hz);

7.41 (2H, doublet, J=8.5 Hz);

7.58 (2H, doublet, J=9 Hz).

EXAMPLE 30

5-(4-{2-[1-(3',4'-Methylenedioxybiphenyl-4-yl)ethylideneaminooxy]ethoxy}benzyl)thiazolidine-2,4-dione (Compound No. 2-180)

30(a) 5-(4-{2-[1-(3',4'-Methylenedioxybiphenyl-4-yl)ethylideneaminooxy]ethoxy}benzyl)-3-tritylthiazolidine-2,4-dione Following a procedure similar to that described in Example 1(a), but using 600 mg of 2-(1-(3',4'-methylenedioxybiphenyl-4-yl)ethylideneaminooxy]ethanol (prepared as described in Preparation 30), 907 mg of 5-(4-hydroxybenzyl)-3-tritylthiazolidine-2,4-dione, 550 mg of triphenylphosphine and 365 mg of diethyl azodicarboxylate, 1.12 g of the title compound were obtained as a foam-like solid.

$^1$H Nuclear Magnetic Resonance Spectrum (CDCl$_3$, 270 MHz, using tetramethylsilane as the internal standard), δ ppm:

2.26 (3H, singlet);

3.07 (1H, doublet of doublets, J=9 & 14 Hz);

3.41 (1H, doublet of doublets, J=4 & 14 Hz);

4.28 (2H, triplet, J=5 Hz);

4.37 (1H, doublet of doublets, J=4 & 9 Hz);

4.55 (2H, triplet, J=5 Hz);

6.01 (2H, singlet);

6.89 (2H, doublet, J=8.5 Hz);

6.90 (1H, doublet, J=8.5 Hz);

7.06–7.33 (19H, multiplet);

7.51 (2H, doublet, J=8.5 Hz);

7.68 (2H, doublet, J=8.5 Hz).

30(b) 5-(4-{2-[1-(3',4'-Methylenedioxybiphenyl-4-yl)ethylideneaminooxy]ethoxy}benzyl)thiazolidine-2,4-dione Following a procedure similar to that described in Example 1(b), but using 1.12 g of 5-(4-{2-[1-(3',4'-methylenedioxybiphenyl-4-yl)ethylideneaminooxy]ethoxy}benzyl)-3-tritylthiazolidine-2,4-dione [prepared as described in step (a) above], 646 mg of the title compound were obtained as a crystalline powder, melting at 137°–139° C.

$^1$H Nuclear Magnetic Resonance Spectrum (CDCl$_3$, 270 MHz, using tetramethylsilane as the internal standard), δ ppm:

2.26 (3H, singlet);
3.10 (1H, doublet of doublets, J=9 & 14 Hz);
3.45 (1H, doublet of doublets, J=4 & 14 Hz);
4.28 (2H, triplet, J=5 Hz);
4.47–4.56 (3H, multiplet);
6.01 (2H, singlet);
6.89 (1H, doublet, J=8.5 Hz);
6.92 (2H, doublet, J=8.5 Hz);
7.06–7.09 (2H, multiplet);
7.14 (2H, doublet, J=8.5 Hz);
7.52 (2H, doublet, J=8.5 Hz);
7.69 (2H, doublet, J=8.5 Hz).

EXAMPLE 31

5-(4-{2-[1-(2-Methoxy-5-pyridyl)
ethylideneaminooxy]ethoxy}benzyl)thiazolidine-2,4-
dione (Compound No. 2-96)

31(a)  5-(4-{2-[1-(2-Methoxy-5-pyridyl)
ethylideneaminooxy]ethoxy}benzyl)-3-tritylthiazolidine-2,
4-dione Following a procedure similar to that described in Example 1(a), but using 346 mg of 2-[1-(2-methoxy-5-pyridyl)ethylideneaminooxy]ethanol (prepared as described in Preparation 31), 766 mg of 5-(4-hydroxybenzyl)-3-tritylthiazolidine-2,4-dione, 475 mg of triphenylphosphine and 301 mg of diethyl azodicarboxylate, 846 mg of the title compound were obtained as a foam-like solid.

$^1$H Nuclear Magnetic Resonance Spectrum (CDCl$_3$, 270 MHz, using tetramethylsilane as the internal standard), δ ppm:

2.21 (3H, singlet);
3.05 (1H, doublet of doublets, J=9 & 14 Hz);
3.41 (1H, doublet of doublets, J=4 & 14 Hz);
3.95 (3H, singlet);
4.25 (2H, triplet, J=5 Hz);
4.36 (1H, doublet of doublets, J=4 & 9 Hz);
4.51 (2H, triplet, J=5 Hz);
6.72 (1H, doublet, J=8.5 Hz);
6.88 (2H, doublet, J=8.5 Hz);
7.11–7.33 (17H, multiplet);
7.92 (1H, doublet of doublets, J=2.5 & 8.5 Hz);
8.37 (1H, doublet, J=2 Hz).

31(b)  5-(4-{2-[1-(2-Methoxy-5-pyridyl)
ethylideneaminooxy]ethoxy}benzyl)thiazolidine-2,4-dione Following a procedure similar to that described in Example 1(b), but using 840 mg of 5-(4-{2-[1-(2-methoxy-5-pyridyl)ethylideneaminooxy]ethoxy}benzyl)-3-tritylthiazolidine-2,4-dione [prepared as described in step (a) above], 436 mg of the title compound were obtained as a crystalline powder, melting at 148°–149° C.

$^1$H Nuclear Magnetic Resonance Spectrum (CDCl$_3$, 270 MHz, using tetramethylsilane as the internal standard), δ ppm:

2.22 (3H, singlet);
3.09 (1H, doublet of doublets, J=9 & 14 Hz);
3.45 (1H, doublet of doublets, J=4 & 14 Hz);
3.95 (3H, singlet);
4.26 (2H, triplet, J=5 Hz);
4.45 (1H, doublet of doublets, J=4 & 9 Hz);
4.51 (2H, triplet, J=5 Hz);
6.73 (1H, doublet, J=9 Hz);
6.89 (2H, doublet, J=8.5 Hz);
7.15 (2H, doublet, J=8.5 Hz);
7.93 (1H, doublet of doublets, J=2.5 & 9 Hz);
8.36 (1H, doublet, J=2.5 Hz).

EXAMPLE 32

5-(4-{2-[1-(2-Isopropoxy-5-pyridyl)
ethylideneaminooxy]ethoxy}benzyl)thiazolidine-2,4-
dione (Compound No. 2-98)

32(a)  5-(4-{2-[1-(2-Isopropoxy-5-pyridyl)
ethylideneaminooxy]ethoxy}benzyl)-3-tritylthiazolidine-2,
4-dione Following a procedure similar to that described in Example 1(a), but using 1.02 g of 2-[1-(2-isopropoxy-5-pyridyl)ethylideneaminooxy]ethanol (prepared as described in Preparation 32), 2.00 g of 5-(4-hydroxybenzyl)-3-tritylthiazolidine-2,4-dione, 1.24 g of triphenylphosphine and 784 mg of diethyl azodicarboxylate, 2.39 g of the title compound were obtained as a foam-like solid.

$^1$H Nuclear Magnetic Resonance Spectrum (CDCl$_3$, 270 MHz, using tetramethylsilane as the internal standard), δ ppm:

1.35 (6H, doublet, J=6 Hz);
2.21 (3H, singlet);
3.06 (1H, doublet of doublets, J=9 & 14 Hz);
3.41 (1H, doublet of doublets, J=4 & 14 Hz);
4.25 (2H, triplet, J=5 Hz);
4.36 (1H, doublet of doublets, J=4 & 9 Hz);
4.51 (2H, triplet, J=5 Hz);
5.32 (1H, septet, J=6 Hz);
6.65 (1H, doublet, J=8.5 Hz);
6.88 (2H, doublet, J=8.5 Hz);
7.11–7.33 (17H, multiplet);
7.89 (1H, doublet of doublets, J=2.5 & 8.5 Hz);
8.35 (1H, doublet, J=2.5 Hz).

32(b)  5-(4-{2-[1-(2-Isopropoxy-5-pyridyl)
ethylideneaminooxy]ethoxy}benzyl)thiazolidine-2,4-dione Following a procedure similar to that described in Example 1(b), but using 2.39 g of 5-(4-{2-[1-(2-isopropoxy-5-pyridyl)ethylideneaminooxy]ethoxy}benzyl)-3-tritylthiazolidine-2,4-dione [prepared as described in step (a) above], 1.32 g of the title compound were obtained as a crystalline powder, melting at 143°–144° C.

$^1$H Nuclear Magnetic Resonance Spectrum (CDCl$_3$, 270 MHz, using tetramethylsilane as the internal standard), δ ppm:

1.35 (6H, doublet, J=6 Hz);
2.21 (3H, singlet);
3.12 (1H, doublet of doublets, J=9 & 14 Hz);
3.44 (1H, doublet of doublets, J=4 & 14 Hz);
4.27 (2H, triplet, J=5 Hz);
4.48–4.52 (3H, multiplet);
5.30 (1H, septet, J=6 Hz);
6.67 (1H, doublet, J=9 Hz);
6.90 (2H, doublet, J=8.5 Hz);
7.15 (2H, doublet, J=8.5 Hz);
7.89 (1H, doublet of doublets, J=2.5 & 9 Hz);
8.33 (1H, doublet, J=2.5 Hz).

EXAMPLE 33

5-(4-{2-[1-(2-Phenylsulfonyl-5-pyridyl)
ethylideneaminooxy]ethoxy}benzyl)thiazolidine-2,4-
dione (Compound No. 2-108)

33(a)  5-(4-{2-[1-(2-Phenylsulfonyl-5-pyridyl)
ethylideneaminooxy]ethoxy}benzyl)-3-tritylthiazolidine-2,
4-dione Following a procedure similar to that described in Example 1(a), but using 640 mg of 2-|1-(2-phenylsulfonyl-5-pyridyl)ethylideneaminooxy|ethanol (prepared as described in Preparation 33), 907 mg of 5-(4-hydroxybenzyl)-3-tritylthiazolidine-2,4-dione, 550 mg of triphenylphosphine and 365 mg of diethyl azodicarboxylate, 500 mg of the title compound were obtained as a foam-like solid.

$^1$H Nuclear Magnetic Resonance Spectrum (CDCl$_3$, 270 MHz, using tetramethylsilane as the internal standard), δ ppm:

2.22 (3H, singlet);
3.06 (1H, doublet of doublets, J=9 & 14 Hz);
3.39 (1H, doublet of doublets, J=4 & 14 Hz);
4.24 (2H, triplet, J=5 Hz);
4.35 (1H, doublet of doublets, J=4 & 9 Hz);
4.55 (2H, triplet, J=5 Hz);
6.85 (2H, doublet, J=8.5 Hz);
7.09–7.33 (17H, multiplet);
7.39–7.63 (3H, multiplet);
8.04–8.16 (4H, multiplet);
8.89 (1H, doublet, J=1.5 Hz).

33(b) 5-(4-{2-|1-(2-Phenylsulfonyl-5-pyridyl) ethylideneaminooxy|ethoxy}benzyl)thiazolidine-2,4-dione Following a procedure similar to that described in Example 1(b), but using 500 mg of 5-(4-{2-|1-(2-phenylsulfonyl-5-pyridyl)ethylideneaminooxy| ethoxy}benzyl)-3-tritylthiazolidine-2,4-dione [prepared as described in step (a) above], 260 mg of the title compound were obtained as a crystalline powder.

$^1$H Nuclear Magnetic Resonance Spectrum (CDCl$_3$, 270 MHz, using tetramethylsilane as the internal standard), δ ppm:

2.23 (3H, singlet);
3.14 (1H, doublet of doublets, J=9 & 14 Hz);
3.41 (1H, doublet of doublets, J=4 & 14 Hz);
4.25 (2H, triplet, J=5 Hz);
4.50 (1H, doublet of doublets, J=4 & 9 Hz);
4.55 (2H, triplet, J=5 Hz);
6.87 (2H, doublet, J=8.5 Hz);
7.14 (2H, doublet, J=8.5 Hz);
7.51–7.65 (3H, multiplet);
8.05–8.20 (4H, multiplet);
8.88 (1H, doublet, J=2 Hz).

EXAMPLE 34

5-{4-|2-(1-{2-[N-(4-Methylphenylsulfonyl)-N-methylamino|pyridin-5-yl}ethylideneaminooxy) ethoxy|benzyl}thiazolidine-2,4-dione (Compound No. 2-192)

34(a) 5-{4-|2-(1-{2-[N-(4-Methylphenylsulfonyl)-N-methylamino|pyridin-5-yl}ethylideneaminooxy)ethoxy| benzyl}-3-tritylthiazolidine-2,4-dione Following a procedure similar to that described in Example 1(a), but using 1.22 g of 2-(1-{2-|N-(4-methylphenylsulfonyl)-N-methylamino|pyridin-5-yl}ethylideneaminooxy)ethanol (prepared as described in Preparation 34), 1.52 g of 5-(4-hydroxybenzyl)-3-tritylthiazolidine-2,4-dione, 0.97 g of triphenylphosphine and 0.63 g of diethyl azodicarboxylate, 2.33 g of the title compound were obtained as a foam-like solid.

$^1$H Nuclear Magnetic Resonance Spectrum (CDCl$_3$, 270 MHz, using tetramethylsilane as the internal standard), δ ppm:

2.22 (3H, singlet);
2.38 (3H, singlet);
3.07 (1H, doublet of doublets, J=9 & 14 Hz);
3.29 (3H, singlet);
3.41 (1H, doublet of doublets, J=4 & 14 Hz);
4.27 (2H, triplet, J=5 Hz);
4.37 (1H, doublet of doublets, J=4 & 9 Hz);
4.54 (2H, triplet, J=5 Hz);
6.88 (2H, doublet, J=8.5 Hz);
7.11–7.36 (19H, multiplet);
7.48 (2H, triplet, J=8 Hz);
7.71 (1H, doublet, J=8.5 Hz);
7.96 (1H, doublet of doublets, J=2.5 & 8.5 Hz);
8.51 (1H, doublet, J=2.5 Hz).

34(b) 5-{4-|2-(1-{2-|N-(4-Methylphenylsulfonyl)-N-methylamino|-pyridin-5-yl}ethylideneaminooxy)ethoxy| benzyl}thiazolidine-2,4-dione Following a procedure similar to that described in Example 1(b), but using 2.33 g of 5-{4-|2-(1-{2-|N-(4-methylphenylsulfonyl)-N-methylamino|pyridin-5-yl}-ethylideneaminooxy)ethoxy|benzyl}-3-tritylthiazolidine-2, 4-dione |prepared as described in step (a) above], 1.48 g of the title compound were obtained as a foam-like solid.

$^1$H Nuclear Magnetic Resonance Spectrum (CDCl$_3$, 270 MHz, using tetramethylsilane as the internal standard), δ ppm:

2.22 (3H, singlet);
2.39 (3H, singlet);
3.13 (1H, doublet of doublets, J=9 & 14 Hz);
3.28 (3H, singlet);
3.43 (1H, doublet of doublets, J=4 & 14 Hz);
4.27 (2H, triplet, J=5 Hz);
4.50 (1H, doublet of doublets, J=4 & 9 Hz);
4.53 (2H, triplet, J=5 Hz);
6.89 (2H, doublet, J=8.5 Hz);
7.15 (2H, doublet, J=8.5 Hz);
7.22 (2H, doublet, J=8 Hz);
7.49 (2H, doublet, J=8 Hz);
7.71 (1H, doublet, J=8.5 Hz);
7.96 (1H, doublet of doublets, J=2.5 & 8.5 Hz);
8.49 (1H, doublet, J=2.5 Hz).

EXAMPLE 35

5-(4-{2-|1-(4-Phenylsulfonylphenyl) ethylideneaminooxy|ethoxy}benzyl)thiazolidine-2,4-dione (Compound No. 2-23)

35(a) 5-(4-{2-|1-(4-Phenylsulfonylphenyl) ethylideneaminooxy|ethoxy}benzyl)-3-tritylthiazolidine-2, 4-dione Following a procedure similar to that described in Example 1(a), but using 1.006 g of 2-|1-(4-phenylsulfonylphenyl)ethylideneaminooxy|ethanol (prepared as described in Preparation 35), 1.40 g of 5-(4-hydroxybenzyl)-3-tritylthiazolidine-2,4-dione, 866 mg of triphenylphosphine and 549 mg of diethyl azodicarboxylate, 2.05 g of the title compound were obtained as a foam-like solid.

$^1$H Nuclear Magnetic Resonance Spectrum (CDCl$_3$, 270 MHz, using tetramethylsilane as the internal standard), δ ppm:

2.22 (3H, singlet);

3.06 (1H, doublet of doublets, J=9 & 14 Hz);

3.37 (1H, doublet of doublets, J=4 & 14 Hz);

4.24 (2H, triplet, J=5 Hz);

4.36 (1H, doublet of doublets, J=4 & 9 Hz);

4.54 (2H, triplet, J=5 Hz);

6.86 (2H, doublet, J=8.5 Hz);

7.10–7.33 (17H, multiplet);

7.46–7.56 (3H, multiplet);

7.74 (2H, doublet, J=8.5 Hz);

7.90–7.95 (4H, multiplet).

35(b) 5-(4-{2-[1-(4-Phenylsulfonylphenyl) ethylideneaminooxy]ethoxy}benzyl)thiazolidine-2,4-dione Following a procedure similar to that described in Example 1(b), but using 2.04 g of 5-(4-{2-[1-(4-phenylsulfonylphenyl)ethylideneaminooxy]ethoxy}benzyl)-3-tritylthiazolidine-2,4-dione [prepared as described in step (a) above], 1.09 g of the title compound were obtained as a foam-like solid.

¹H Nuclear Magnetic Resonance Spectrum (CDCl₃, 270 MHz, using tetramethylsilane as the internal standard), δ ppm:

2.23 (3H, singlet);

3.11 (1H, doublet of doublets, J=9 & 14 Hz);

3.44 (1H, doublet of doublets, J=4 & 14 Hz);

4.25 (2H, triplet, J=5 Hz);

4.50 (1H, doublet of doublets, J=4 & 9 Hz);

4.54 (2H, triplet, J=5 Hz);

6.88 (2H, doublet, J=8.5 Hz);

7.14 (2H, doublet, J=8.5 Hz);

7.47–7.60 (2H, doublet, J=8.5 Hz);

7.47–7.60 (3H, singlet);

7.76 (2H, doublet, J=8.5 Hz);

7.92–7.97 (4H, multiplet).

EXAMPLE 36

5-(4-{2-[1-(4-Phenylthiophenyl) ethylideneaminooxy]ethoxy}benzyl)thiazolidine-2,4-dione (Compound No. 2-21)

36(a) 5-(4-{2-[1-(4-Phenylthiophenyl)ethylideneaminooxy] ethoxy}benzyl)-3-tritylthiazolidine-2,4-dione Following a procedure similar to that described in Example 1(a), but using 862 mg of 2-[1-(4-phenylthiophenyl)ethylideneaminooxy]ethanol (prepared as described in Preparation 36), 1.40 g of 5-(4-hydroxybenzyl)-3-tritylthiazolidine-2,4-dione, 866 mg of triphenylphosphine and 549 mg of diethyl azodicarboxylate, 1.95 g of the title compound were obtained as a foam-like solid.

¹H Nuclear Magnetic Resonance Spectrum (CDCl₃, 270 MHz, using tetramethylsilane as the internal standard), δ ppm:

2.21 (3H, singlet);

3.07 (1H, doublet of doublets, J=9 & 14 Hz);

3.40 (1H, doublet of doublets, J=4 & 14 Hz);

4.25 (2H, triplet, J=5 Hz);

4.36 (1H, doublet of doublets, J=4 & 9 Hz);

4.52 (2H, triplet, J=5 Hz);

6.88 (2H, doublet, J=8.5 Hz);

7.10–7.46 (24H, multiplet);

7.56 (2H, doublet, J=8.5 Hz).

36(b) 5-(4-{2-[1-(4-Phenylthiophenyl)ethylideneaminooxy] ethoxy}benzyl)thiazolidine-2,4-dione Following a procedure similar to that described in Example 1(b), but using 1.95 g of 5-(4-{2-[1-(4-phenylthiophenyl)ethylideneaminooxy]ethoxy}benzyl)-3-tritylthiazolidine-2,4-dione [prepared as described in step (a) above], 1.24 g of the title compound were obtained as a glass.

¹H Nuclear Magnetic Resonance Spectrum (CDCl₃, 270 MHz, using tetramethylsilane as the internal standard), δ ppm:

2.21 (3H, singlet);

3.09 (1H, doublet of doublets, J=9 & 14 Hz);

3.45 (1H, doublet of doublets, J=4 & 14 Hz);

4.25 (2H, triplet, J=5 Hz);

4.46–4.53 (3H, multiplet);

6.89 (2H, doublet, J=8.5 Hz);

7.13 (2H, doublet, J=8.5 Hz);

7.26–7.40 (7H, multiplet);

7.56 (2H, doublet, J=8.5 Hz).

EXAMPLE 37

5-{4-[2-(1-{4-[N-(Phenylsulfonyl)-N-methylamino] phenyl}ethylideneaminooxy)ethoxy] benzyl}thiazolidine-2,4-dione (Compound No. 2-181)

37(a) 5-{4-[2-(1-{4-[N-(Phenylsulfonyl)-N-methylamino] phenyl}ethylideneaminooxy)ethoxy]benzyl}-3-tritylthiazolidine-2,4-dione Following a procedure similar to that described in Example 1(a), but using 667 mg of 2-(1-{4-[N-(phenylsulfonyl)-N-methylamino]phenyl}ethylideneaminooxy)ethanol (prepared as described in Preparation 37), 1.02 g of 5-(4-hydroxybenzyl)-3-tritylthiazolidine-2,4-dione, 577 mg of triphenylphosphine and 383 mg of diethyl azodicarboxylate, 554 mg of the title compound were obtained as a crystalline powder, melting at 143°–145° C.

¹H Nuclear Magnetic Resonance Spectrum (CDCl₃, 270 MHz, using tetramethylsilane as the internal standard), δ ppm:

2.22 (3H, singlet);

3.07 (1H, doublet of doublets, J=9 & 14 Hz);

3.17 (3H, singlet);

3.41 (1H, doublet of doublets, J=4 & 14 Hz);

4.26 (2H, triplet, J=4.5 Hz);

4.37 (1H, doublet of doublets, J=4 & 9 Hz);

4.53 (2H, triplet, J=5 Hz);

6.88 (2H, doublet, J=8.5 Hz);

7.06–7.33 (21H, multiplet);

7.44 (1H, triplet, J=8 Hz);

7.54–7.60 (4H, multiplet).

37(b) 5-{4-[2-(1-{4-[N-(Phenylsulfonyl)-N-methylamino] phenyl}ethylideneaminooxy)ethoxy]benzyl}thiazolidine-2,4-dione Following a procedure similar to that described in Example 1(b), but using 554 mg of 5-{4-[2-(1-{4-[N-(phenylsulfonyl)-N-methylamino] phenyl}ethylideneaminooxy)ethoxy]benzyl}-3-tritylthiazolidine-2,4-dione [prepared as described in step (a) above], 266 mg of the title compound were obtained as an amorphous powder.

¹H Nuclear Magnetic Resonance Spectrum (CDCl₃, 270 MHz, using tetramethylsilane as the internal standard), δ ppm:

2.23 (3H, singlet);
3.12 (1H, doublet of doublets, J=9 & 14 Hz);
3.18 (3H, singlet);
3.45 (1H, doublet of doublets, J=4 & 14 Hz);
4.26 (2H, triplet, J=5 Hz);
4.48–4.54 (3H, multiplet);
6.90 (2H, doublet, J=8.5 Hz);
7.11 (2H, doublet, J=8.5 Hz);
7.15 (2H, doublet, J=8.5 Hz);
7.46 (2H, triplet, J=8 Hz);
7.51–7.65 (5H, multiplet).

EXAMPLE 38

5-(4-{2-|1-(4-Biphenylyl)propylideneaminooxy| ethoxy}benzyl)thiazolidine-2,4-dione (Compound No. 3-31)

38(a) 5(4-{2-|1-(4-Biphenylyl)propylideneaminooxy| ethoxy}benzyl)-3-tritylthiazolidine-2,4-dione Following a procedure similar to that described in Example 1(a), but using 539 mg of 2-|1-(4-biphenylyl) propylideneaminooxy|ethanol (prepared as described in Preparation 38), 1.02 g of 5-(4-hydroxybenzyl)-3-tritylthiazolidine-2,4-dione, 577 mg of triphenylphosphine and 383 mg of diethyl azodicarboxylate, 1.09 g of the title compound were obtained as a foam-like solid.

¹H Nuclear Magnetic Resonance Spectrum (CDCl₃, 270 MHz, using tetramethylsilane as the internal standard), δ ppm:

1.22 (3H, triplet, J=7.5 Hz);
2.86 (2H, quartet, J=7.5 Hz);
3.13 (1H, doublet of doublets, J=9 & 14 Hz);
3.48 (1H, doublet of doublets, J=4 & 14 Hz);
4.34 (2H, triplet, J=5 Hz);
4.43 (1H, doublet of doublets, J=4 & 9 Hz);
4.61 (2H, triplet, J=5 Hz);
6.96 (2H, doublet, J=8.5 Hz);
7.18–7.54 (20H, multiplet);
7.65–7.74 (4H, multiplet);
7.78 (2H, doublet, J=8.5 Hz).

38(b) 5-(4-{2-|1-(4-Biphenylyl)proplylideneaminooxy| ethoxy}benzyl)thiazolidine-2,4-dione Following a procedure similar to that described in Example 1(b), but using 1.09 g of 5-(4-{2-|1-(4-biphenylyl) propylideneaminooxy|ethoxy}benzyl)-3-tritylthiazolidine-2,4-dione [prepared as described in step (a) above], 585 mg of the title compound were obtained as a crystalline powder, melting at 162°–164° C.

Nuclear Magnetic Resonance Spectrum (hexadeuterated dimethyl sulfoxide, 270 MHz, using tetramethylsilane as the internal standard), δ ppm:

1.06 (3H, triplet, J=7.5 Hz);
2.74 (2H, quartet, J=7.5 Hz);
3.05 (1H, doublet of doublets, J=9 & 14 Hz);
3.31 (1H, doublet of doublets, J=4 & 14 Hz);
4.26 (2H, triplet, J=5 Hz);
4.46 (2H, triplet, J=5 Hz);
4.87 (1H, doublet of doublets, J=4 & 9 Hz);
6.93 (2H, doublet, J=8.5 Hz);
7.16 (2H, doublet, J=8.5 Hz);
7.39 (1H, doublet, J=8.5 Hz);
7.49 (2H, triplet, J=7.5 Hz);
7.69–7.78 (6H, multiplet).

EXAMPLE 39

5-(4-{2-|1-(5-Phenyl-2-pyridyl)ethylideneaminooxy| ethoxy}benzyl)thiazolidine-2,4-dione (Compound No. 2-110)

39(a) 5-(4-{2-|1-(5-Phenyl-2-pyridyl)ethylideneaminooxy| ethoxy}benzyl)-3-tritylthiazolidine-2,4-dione Following a procedure similar to that described in Example 1(a), but using 513 mg of 2-|1-(5-phenyl-2-pyridyl)ethylideneaminooxy|ethanol (prepared as described in Preparation 39), 1.02 g of 5-(4-hydroxybenzyl)-3-tritylthiazolidine-2,4-dione, 577 mg of triphenylphosphine and 383 mg of diethyl azodicarboxylate, 1.40 g of the title compound were obtained as a foam-like solid.

¹H Nuclear Magnetic Resonance Spectrum (CDCl₃, 270 MHz, using tetramethylsilane as the internal standard), δ ppm:

2.39 (3H, singlet);
3.07 (1H, doublet of doublets, J=9 & 14 Hz);
3.41 (1H, doublet of doublets, J=4 & 14 Hz);
4.30 (2H, triplet, J=5 Hz);
4.36 (1H, doublet of doublets, J=4 & 9 Hz);
4.59 (2H, doublet, J=5 Hz);
6.90 (2H, doublet, J=8.5 Hz);
7.12–7.33 (17H, multiplet);
7.38–7.55 (3H, multiplet);
7.60 (2H, doublet, J=8 Hz);
7.84 (1H, doublet of doublets, J=2 & 8 Hz);
7.96 (1H, doublet, J=8 Hz);
8.83 (1H, doublet, J=2 Hz).

39(b) 5-(4-{2-|1-(5-Phenyl-2-pyridyl)ethylideneaminooxy| ethoxy}benzyl)thiazolidine-2,4-dione Following a procedure similar to that described in Example 1(b), but using 1.40 g of 5-(4-{2-|1-(5-phenyl-2-pyridyl)ethylideneaminooxy|ethoxy}benzyl)-3-tritylthiazolidine-2,4-dione [prepared as described in step (a) above], 590 mg of the title compound were obtained as a crystalline powder, melting at 136°–138° C.

¹H Nuclear Magnetic Resonance Spectrum (CDCl₃, 270 MHz, using tetramethylsilane as the internal standard), δ ppm:

2.35 (3H, singlet);
3.13 (1H, doublet of doublets, J=9 & 14 Hz);
3.43 (1H, doublet of doublets, J=4 & 14 Hz);
4.30 (2H, triplet, J=5 Hz);
4.50 (1H, doublet of doublets, J=4 & 9 Hz);
4.58 (2H, triplet, J=5 Hz);
6.91 (2H, doublet, J=8.5 Hz);
7.15 (2H, doublet, J=8.5 Hz);
7.39–7.52 (3H, multiplet);
7.61 (2H, doublet, J=8.5 Hz);
7.87 (1H, doublet of doublets, J=2.5 & 8.5 Hz);
7.97 (1H, doublet, J=8.5 Hz);
8.28 (1H, broad singlet);
8.83 (1H, doublet, J=2.5 Hz).

EXAMPLE 40

5-(4-{2-|1-(2-Hydroxy-5-pyridyl) ethylideneaminooxy|ethoxy}benzyl)thiazolidine-2,4-dione (Compound No. 2-193)

40(a) N-|2-(Tetrahydropyran-2-yloxy)ethoxy|phthalimide

A suspension of 10.8 g of 2-(2-bromoethoxy) tetrahydropyran, 7.0 g of N-hydroxyphthalimide and 11.1 g of potassium carbonate in 100 ml of dimethylformamide was stirred at 80° C. for 2.5 hours. Ethyl acetate and water were then added to the reaction mixture to make a solution. The ethyl acetate layer was then separated and dried over anhydrous magnesium sulfate. The solvent was then removed by distillation under reduced pressure, after which the resulting residue was purified by column chromatography through silica gel, using a 2:1 by volume mixture of hexane and ethyl acetate as the eluent, to give 8.62 g of the title compound as a syrup.

$^1$H Nuclear Magnetic Resonance Spectrum (CDCl$_3$, 270 MHz, using tetramethylsilane as the internal standard), δ ppm:

1.35–1.73 (6H, multiplet);
3.46–3.53 (1H, multiplet);
3.80–3.89 (2H, multiplet);
4.00–4.08 (1H, multiplet);
4.51–4.35 (2H, multiplet);
4.66 (1H, broad singlet);
7.72–7.78 (2H, multiplet);
7.81–7.87 (2H, multiplet).

40(b) N-(2-Hydroxyethoxy)phthalimide 0.56 g of p-toluenesulfonic acid monohydrate was added to a solution of 8.62 g of N-[2-(tetrahydropyran-2-yloxy)ethoxy]phthalimide [prepared as described in step (a) above] in 86 ml of methanol, and the resulting mixture was stirred at room temperature for 2 hours. At the end of this time, the reaction mixture was concentrated by evaporation under reduced pressure, and then the resulting residue was dissolved in a mixture of ethyl acetate and water and neutralyzed with sodium hydrogen carbonate. The ethyl acetate layer was separated and dried over anhydrous magnesium sulfate. The solvent was removed by distillation under reduced pressure, giving the title compound as a crystalline powder. This was washed with diisopropyl ether to give 4.10 g of the pure compound, melting at 82°–85° C.

$^1$H Nuclear Magnetic Resonance Spectrum (CDCl$_3$, 270 MHz, using tetramethylsilane as the internal standard), δ ppm:

3.48 (1H, triplet, J=6 Hz);
3.78–3.84 (2H, multiplet);
4.30–4.33 (2H, multiplet);
7.74–7.82 (2H, multiplet);
7.85–7.91 (2H, multiplet).

40(c) 5-[4-(2-Phthalimidooxyethoxy)benzyl]-3-tritylthiazolidine-2,4-dione

Following a procedure similar to that described in Example 1(a), but using 2.0 g of N-(2-hydroxyethoxy) phthalimide [prepared as described in step (a) above], 4.4 g of 5-(4-hydroxybenzyl)-3-tritylthiazolidine-2,4-dione, 2.53 g of triphenylphosphine and 1.68 g of diethyl azodicarboxylate, 5.00 g of the title compound were obtained as a foam-like solid.

$^1$H Nuclear Magnetic Resonance Spectrum (CDCl$_3$, 270 MHz, using tetramethylsilane as the internal standard), δ ppm:

3.03 (1H, doublet of doublets, J=9 & 14 Hz);
3.41 (1H, doublet of doublets, J=4 & 14 Hz);
4.31–4.38 (3H, multiplet);
4.56–4.60 (2H, multiplet);
6.77 (2H, doublet, J=8.5 Hz);
7.09 (2H, doublet, J=8.5 Hz);
7.15–7.34 (15H, multiplet);
7.72–7.78 (2H, multiplet);
7.80–7.86 (2H, multiplet).

40(d) 5-[4-(2-Phthalimidooxyethoxy)benzyl]thiazolidine-2,4-dione

Following a procedure similar to that described in Example 1(b), but using 5.00 g of 5-[4-(2-phthalimidooxyethoxy)benzyl]-3-tritylthiazolidine-2,4-dione [prepared as described in step (c) above], 2.74 g of the title compound were obtained as a crystalline powder, melting at 146°–147° C.

$^1$H Nuclear Magnetic Resonance Spectrum (CDCl$_3$, 270 MHz, using tetramethylsilane as the internal standard), δ ppm:

3.10 (1H, doublet of doublets, J=9 & 14 Hz);
3.44 (1H, doublet of doublets, J=4 & 14 Hz);
4.33–4.36 (2H, multiplet);
4.49 (1H, doublet of doublets, J=4 & 9 Hz);
4.56–4.60 (2H, multiplet);
6.79 (1H, doublet, J=8.5 Hz);
7.12 (2H, doublet, J=8.5 Hz);
7.74–7.80 (2H, multiplet);
7.81–7.86 (2H, multiplet);
8.08 (1H, broad singlet).

40(e) 5-[4-(2-Aminooxyethoxy)benzyl]thiazolidine-2,4-dione hydrochloride 0.32 ml of hydrazine monohydrate was added to a suspension of 2.64 g of 5-[4-(2-phthalimidooxyethoxy)benzyl] thiazolidine-2,4-dione [prepared as described in step (d) above] in 30 ml of ethanol, and the resulting mixture was stirred at 80° C. for 2 hours. At the end of this time, the reaction mixture was cooled and the precipitated phthalhydrazide was filtered off. The filtrate was concentrated by evaporation under reduced pressure, and the concentrate was purified by column chromatography through silica gel, using a 1:20 by volume mixture of methanol and methylene chloride as the eluent, to give 1.93 g of 5-[4-(2-aminooxyethoxy)benzyl]thiazolidine-2,4-dione as a syrup.

$^1$H Nuclear Magnetic Resonance Spectrum (CDCl$_3$, 270 MHz, using tetramethylsilane as the internal standard), δ ppm:

3.10 (1H, doublet of doublets, J=9 & 14 Hz);
3.44 (1H, doublet of doublets, J=4 & 14 Hz);
4.02 (2H, triplet, J=5 Hz);
4.15 (2H, triplet, J=5 Hz);
4.49 (1H, doublet of doublets, J=4 & 9 Hz);
6.89 (2H, doublet, J=8.5 Hz);
7.15 (2H, doublet, J=8.5 Hz).

The whole of this product was dissolved in 20 ml of ethyl acetate, and then 3 ml of a 4N solution of hydrogen chloride in dioxane were added, followed by 20 ml of diethyl ether. The resulting mixture was then stirred for 16 hours. At the end of this time, the precipitate was collected by filtration, to give 1.27 g of the title compound as an amorphous solid.

Nuclear Magnetic Resonance Spectrum (hexadeuterated dimethyl sulfoxide, 270 MHz, using tetramethylsilane as the internal standard), δ ppm:

3.07 (1H, doublet of doublets, J=9 & 14 Hz);
3.31 (1H, doublet of doublets, J=4.5 & 14 Hz);
4.19–4.23 (2H, multiplet);
4.31–4.34 (2H, multiplet);
4.88 (1H, doublet of doublets, J=4.5 & 9 Hz);
6.91 (2H, doublet, J=8.5 Hz);

7.18 (2H, doublet, J=8.5 Hz).

40(f)  5-(4-{2-|1-(2-Hydroxy-5-pyridyl) ethylideneaminooxy|ethoxy}benzyl)thiazolidine-2,4-dione 124 µl of pyridine were added at room temperature to a suspension of 100 mg of 3-acetyl-6-hydroxypyridine and 232 mg of 5-|4-(2-aminooxyethoxy)benzyl|thiazolidine-2,4-dione hydrochloride |prepared as described in step (e) above| in 10 ml of ethanol, and the resulting mixture was stirred and heated under reflux for 1 hour. At the end of this time, the reaction mixture was cooled to room temperature and the precipitate was collected by filtration to give 183 mg of the title compound as a crystalline powder, melting at 240°–242° C.

Nuclear Magnetic Resonance Spectrum (hexadeuterated dimethyl sulfoxide, 270 MHz, using tetramethylsilane as the internal standard), δ ppm:

2.05 (3H, singlet);
3.05 (1H, doublet of doublets, J=9 & 14 Hz);
3.31 (1H, doublet of doublets, J=4 & 14 Hz);
4.22 (2H, triplet, J=5 Hz);
4.38 (2H, triplet, J=5 Hz);
4.86 (1H, doublet of doublets, J=4 & 9 Hz);
6.35 (1H, doublet, J=9.5 Hz);
6.91 (2H, doublet, J=8.5 Hz);
7.15 (2H, doublet, J=8.5 Hz);
7.59 (1H, doublet, J=2.5 Hz);
7.84 (1H, doublet of doublets, J=2.5 & 9.5 Hz).

EXAMPLE 41

5-(4-{2-|1-(2-Benzyloxy-5-pyridyl) ethylideneaminooxy|ethoxybenzyl}thiazolidine-2,4-dione (Compound No. 2-194)

Following a procedure similar to that described in Example 40(f), 130 mg of 5-acetyl-2-benzyloxypyridine were reacted with 182 mg of 5-|4-(2-aminooxyethoxy) benzyl|thiazolidine-2,4-dione hydrochloride [prepared as described in Example 40(e)|. The reaction mixture was concentrated by evaporation under reduced pressure, and the resulting residue was extracted with ethyl acetate. The extract was washed with water and the solvent was removed by distillation under reduced pressure, to give 219 mg of the title compound, melting at 160°–161° C.

Nuclear Magnetic Resonance Spectrum (hexadeuterated dimethyl sulfoxide, 270 MHz, using tetramethylsilane as the internal standard), δ ppm:

2.18 (3H, singlet);
3.05 (1H, doublet of doublets, J=9 & 14 Hz);
3.31 (1H, doublet of doublets, J=4 & 14 Hz);
4.25 (2H, triplet, J=5 Hz);
4.43 (2H, triplet, J=5 Hz);
4.86 (1H, doublet of doublets, J=4 & 9 Hz);
5.39 (2H, singlet);
6.91 (1H, doublet, J=8.5 Hz);
6.92 (2H, doublet, J=8.5 Hz);
7.15 (2H, doublet, J=8.5 Hz);
7.32–7.47 (5H, multiplet);
8.02 (1H, doublet of doublets, J=2.5 & 8.5 Hz);
8.43 (1H, doublet, J=2.5 Hz).

EXAMPLE 42

5-|4-(2-{1-|4-(2-Pyridylsulfonyl)phenyl| ethylideneaminooxy}ethoxy)benzyl|thiazolidine-2,4-dione (Compound No. 2-185)

Following a procedure similar to that described in Example 40(f), 150 mg of 4'-(2-pyridylsulfonyl) acetophenone were reacted with 183 mg of 5-(4-|2-aminooxyethoxy)benzyl|thiazolidine-2,4-dione hydrochloride |prepared as described in Example 40(e)|. The reaction mixture was then concentrated by evaporation under reduced pressure, and the resulting residue was extracted with ethyl acetate. The extract was washed with water and the solvent was removed by distillation under reduced pressure. The residue was purified by column chromatography through silica gel, using a 2:98 by volume mixture of methanol and methylene chloride as the eluent, to give 185 mg of the title compound as a gum.

¹H Nuclear Magnetic Resonance Spectrum (CDCl₃, 270 MHz, using tetramethylsilane as the internal standard), δ ppm:

2.24 (3H, singlet);
3.12 (1H, doublet of doublets, J=9 & 14 Hz);
3.44 (1H, doublet of doublets, J=4 & 14 Hz);
4.25 (2H, triplet, J=5 Hz);
4.50 (1H, doublet of doublets, J=4 & 9 Hz);
4.55 (2H, triplet, J=5 Hz);
6.88 (2H, doublet, J=8.5 Hz);
7.14 (2H, doublet, J=8.5 Hz);
7.44–7.49 (1H, multiplet);
7.80 (2H, doublet, J=8.5 Hz);
7.93 (1H, doublet of triplets, J=1.5 & 8 Hz);
8.06 (2H, doublet, J=8.5 Hz);
8.21 (1H, doublet, J=8 Hz);
8.66–8.69 (1H, multiplet).

EXAMPLE 43

5-|4-(2-{1-|4-(4-Pyridylsulfonyl)phenyl| ethylideneaminooxy}ethoxy)benzyl|thiazolidine-2,4-dione (Compound No. 2-195)

Following a procedure similar to that described in Example 40(f), but using 150 mg of 4'-(4-pyridylsulfonyl) acetophenone and 183 mg of 5-|4-(2-aminooxyethoxy) benzyl|thiazolidine-2,4-dione hydrochloride |prepared as described in Example 40(e)|, 173 mg of the title compound, melting at 213°–215° C., were obtained.

Nuclear Magnetic Resonance Spectrum (hexadeuterated dimethyl sulfoxide, 270 MHz, using tetramethylsilane as the internal standard), δ ppm:

2.20 (3H, singlet);
3.05 (1H, doublet of doublets, J=9 & 14 Hz);
3.30 (1H, doublet of doublets, J=4 & 14 Hz);
4.25 (2H, triplet, J=5 Hz);
4.48 (2H, triplet, J=5 Hz);
4.87 (1H, doublet of doublets, J=4 & 9 Hz);
6.91 (2H, doublet, J=8.5 Hz);
7.14 (2H, doublet, J=8.5 Hz);
7.91–7.94 (4H, multiplet);
8.05 (2H, doublet, J=8.5 Hz);
8.89 (2H, doublet, J=6 Hz).

EXAMPLE 44

5-|4-(2-{1-|4-(Phenylsulfonylamino)phenyl| ethylideneaminooxy}ethoxy)benzyl|thiazolidine-2,4-dione (Compound No. 2-183)

Following a procedure similar to that described in Example 40(f), 170 mg of 4'-(phenylsulfonylamino)

acetophenone were reacted with 197 mg of 5-[4-(2-aminooxyethoxy)benzyl]thiazolidine-2,4-dione hydrochloride [prepared as described in Example 40(e)]. The reaction mixture was then concentrated by evaporation under reduced pressure, and the resulting residue was extracted with ethyl acetate. The extract was washed with water and the solvent was removed by distillation under reduced pressure. The residue was purified by column chromatography through silica gel, using a 2:98 by volume mixture of methanol and methylene chloride as the eluent, to give 170 mg of the title compound, melting at 213°–215° C.

$^1$H Nuclear Magnetic Resonance Spectrum (CDCl$_3$, 270 MHz, using tetramethylsilane as the internal standard), δ ppm:

2.17 (3H, singlet);
3.11 (1H, doublet of doublets, J=9 & 14 Hz);
3.44 (1H, doublet of doublets, J=4 & 14 Hz);
4.24 (2H, triplet, J=5 Hz);
4.48–4.53 (3H, multiplet);
6.89 (2H, doublet, J=8.5 Hz);
7.07 (2H, doublet, J=8.5 Hz);
7.14 (2H, doublet, J=8.5 Hz);
7.42–7.57 (5H, multiplet);
7.78 (2H, doublet, J=8 Hz).

EXAMPLE 45

5-(4-{2-[1-(2',4'-Dimethoxybiphenyl-4-yl)ethylideneaminooxy]ethoxy}benzyl)thiazolidine-2,4-dione (Compound No. 2-196)

Following a procedure similar to that described in Example 40(f), but using 256 mg of 4'-(2,4-dimethoxyphenyl)acetophenone and 382 mg of 5-[4-(2-aminooxyethoxy)benzyl]thiazolidine-2,4-dione hydrochloride [prepared as described in Example 40(e)], 467 mg of the title compound, melting at 186°–188° C., were obtained.

Nuclear Magnetic Resonance Spectrum (hexadeuterated dimethyl sulfoxide, 270 MHz, using tetramethylsilane as the internal standard), δ ppm:

2.20 (3H, singlet);
3.06 (1H, doublet of doublets, J=9 & 14 Hz);
3.31 (1H, doublet of doublets, J=4.5 & 14 Hz);
3.77 (3H, singlet);
3.81 (3H, singlet);
4.26 (2H, triplet, J=4.5 Hz);
4.45 (2H, triplet, J=4.5 Hz);
4.87 (1H, doublet of doublets, J=4.5 & 9 Hz);
6.62 (1H, doublet of doublets, J=2 & 8.5 Hz);
6.67 (1H, doublet, J=2 Hz);
6.93 (2H, doublet, J=8.5 Hz);
7.16 (2H, doublet, J=8.5 Hz);
7.24 (1H, doublet, J=8.5 Hz);
7.47 (2H, doublet, J=8.5 Hz);
7.67 (2H, doublet, J=8.5 Hz);
11.99 (1H, broad singlet).

EXAMPLE 46

5-(4-{2-[1-(2',5'-Dimethoxybiphenyl-4-yl)ethylideneaminooxy]ethoxy}benzyl)thiazolidine-2,4-dione (Compound No. 2-197)

Following a procedure similar to that described in Example 40(f), 256 mg of 4'-(2,5-dimethoxyphenyl)acetophenone were reacted with 382 mg of 5-[4-(2-aminooxyethoxy)benzyl]thiazolidine-2,4-dione hydrochloride [prepared as described in Example 40(e)]. The reaction mixture was then concentrated by evaporation under reduced pressure, and the resulting residue was extracted with ethyl acetate. The extract was washed with water and the solvent was removed by distillation under reduced pressure. The residue was purified by column chromatography through silica gel, using a 2:3 by volume mixture of ethyl acetate and hexane as the eluent, to give 482 mg of the title compound as an amorphous solid, melting at 47°–52° C. (softening point).

Nuclear Magnetic Resonance Spectrum (hexadeuterated dimethyl sulfoxide, 270 MHz, using tetramethylsilane as the internal standard), δ ppm:

2.21 (3H, singlet);
3.06 (1H, doublet of doublets, J=9 & 14 Hz);
3.31 (1H, doublet of doublets, J=4.5 & 14 Hz);
3.70 (3H, singlet);
3.75 (3H, singlet);
4.26 (2H, triplet, J=4.5 Hz);
4.46 (2H, triplet, J=4.5 Hz);
4.87 (1H, doublet of doublets, J=4.5 & 9 Hz);
6.88 (1H, doublet, J=3 Hz);
6.91–6.94 (3H, multiplet);
7.05 (1H, doublet, J=8.5 Hz);
7.16 (2H, doublet, J=8.5 Hz);
7.52 (2H, doublet, J=8.5 Hz);
7.70 (2H, doublet, J=8.5 Hz);
12.00 (1H, broad singlet).

EXAMPLE 47

5-{4-[2-(1-Phenylethylideneaminooxy)ethoxy]benzyl}thiazolidine-2,4-dione (Compound No. 2-1)

Following a procedure similar to that described in Example 40(f), 0.16 ml of acetophenone was reacted with 400 mg of 5-[4-(2-aminooxyethoxy)benzyl]thiazolidine-2,4-dione hydrochloride [prepared as described in Example 40(e)]. The reaction mixture was then concentrated by evaporation under reduced pressure, and the resulting residue was extracted with ethyl acetate. The extract was washed with water and the solvent was removed by distillation under reduced pressure. The residue was mixed with diisopropyl ether and the mixture was stirred. The precipitated powder was collected by filtration, to give 370 mg of the title compound.

Nuclear Magnetic Resonance Spectrum (hexadeuterated dimethyl sulfoxide, 270 MHz, using tetramethylsilane as the internal standard), δ ppm:

2.18 (3H, singlet);
3.07 (1H, doublet of doublets, J=9 & 14 Hz);
3.30 (1H, doublet of doublets, J=4 & 14 Hz);
4.25 (2H, triplet, J=4.5 Hz);
4.45 (2H, triplet, J=4.5 Hz);
4.86 (1H, doublet of doublets, J=4 & 9 Hz);
6.92 (2H, doublet, J=8.5 Hz);
7.16 (2H, doublet, J=8.5 Hz);
7.40–7.68 (5H, multiplet).

EXAMPLE 48

5-(4-{2-[3-(3-Chlorophenyl)ethylideneaminooxy]ethoxy}benzyl)thiazolidine-2,4-dione (Compound No. 2-10)

Following a procedure similar to that described in Example 40(f), 0.18 ml of 3'-chloroacetophenone was reacted with 400 mg of 5-|4-(2-aminooxyethoxy)benzyl| thiazolidine-2,4-dione hydrochloride |prepared as described in Example 40(e)|. The reaction mixture was then concentrated by evaporation under reduced pressure, and the resulting residue was extracted with ethyl acetate. The extract was washed with water and the solvent was removed by distillation under reduced pressure. The residue was mixed with a mixture of diethyl ether, diisopropyl ether and hexane, and stirred. The resulting precipitate was collected by filtration, to give 290 mg of the title compound, melting at 82°–84° C.

Nuclear Magnetic Resonance Spectrum (hexadeuterated dimethyl sulfoxide, 270 MHz, using tetramethylsilane as the internal standard), δ ppm:

2.18 (3H, singlet);
3.06 (1H, doublet of doublets, J=9 & 14 Hz);
3.30 (1H, doublet of doublets, J=4 & 14 Hz);
4.25 (2H, triplet, J=4.5 Hz);
4.47 (2H, triplet, J=4.5 Hz);
4.84 (1H, doublet of doublets, J=4 & 9 Hz);
6.92 (2H, doublet, J=8.5 Hz);
7.16 (2H, doublet, J=8.5 Hz);
7.45–7.69 (4H, multiplet).

EXAMPLE 49

5-(4-{2-|1-(4-Chlorophenyl)ethylideneaminooxy| ethoxy}benzyl)thiazolidine-2,4-dione (Compound No. 2-11)

Following a procedure similar to that described in Example 40(f), 0.18 ml of 4'-chloroacetophenone was reacted with 400 mg of 5-|4-(2-aminooxyethoxy)benzyl| thiazolidine-2,4-dione hydrochloride [prepared as described in Example 40(e)|. The reaction mixture was then concentrated by evaporation under reduced pressure, and the resulting residue was extracted with ethyl acetate. The extract was washed with water and the solvent was removed by distillation under reduced pressure. The residue was mixed with a mixture of diethyl ether, diisopropyl ether and hexane, and the mixture was then stirred. The resulting precipitate was collected by filtration, to give 360 mg of the title compound, melting at 118°–119° C.

Nuclear Magnetic Resonance Spectrum (hexadeuterated dimethyl sulfoxide, 270 MHz, using tetramethylsilane as the internal standard), δ ppm:

2.17 (3H, singlet);
3.07 (1H, doublet of doublets, J=9 & 14 Hz);
3.30 (1H, doublet of doublets, J=4 & 14 Hz);
4.25 (2H, triplet, J=4.5 Hz);
4.45 (2H, triplet, J=4.5 Hz);
4.86 (1H, doublet of doublets, J=4 & 9 Hz);
6.92 (2H, doublet, J=8.5 Hz);
7.15 (2H, doublet, J=8.5 Hz);
7.47 (2H, doublet, J=8.5 Hz);
7.69 (2H, doublet, J=8.5 Hz).

EXAMPLE 50

5-(4-{2-|1-(3-Hydroxyphenyl)ethylideneaminooxy| ethoxy}benzyl)thiazolidine-2,4-dione (Compound No. 2-198)

Following a procedure similar to that described in Example 40(f), but using 0.33 g of 3'-hydroxyacetophenone and 0.70 g of 5-|4-(2-aminooxyethoxy)benzyl|thiazolidine-2,4-dione hydrochloride |prepared as described in Example 40(e)|, 0.74 g of the title compound, melting at 133°–135° C., was obtained.

¹H Nuclear Magnetic Resonance Spectrum (hexadeuterated dimethyl sulfoxide, 270 MHz, using tetramethylsilane as the internal standard), δ ppm:

2.13 (3H, singlet);
3.07 (1H, doublet of doublets, J=9 & 14 Hz);
3.30 (1H, doublet of doublets, J=4 & 14 Hz);
4.24 (2H, triplet, J=4.5 Hz);
4.43 (2H, triplet, J=4.5 Hz);
4.86 (1H, doublet of doublets, J=4 & 14 Hz);
6.79–6.81 (1H, multiplet);
6.92 (2H, doublet, J=8.5 Hz);
7.08–7.23 (5H, multiplet).

EXAMPLE 51

5-(4-{2-|1-(4-Hydroxyphenyl)ethylideneaminooxy| ethoxy}benzyl)thiazolidine-2,4-dione (Compound No. 2-199)

Following a procedure similar to that described in Example 40(f), but using 0.33 g of 4'-hydroxyacetophenone and 0.70 g of 5-|4-(2-aminooxyethoxy)benzyl|thiazolidine-2,4-dione hydrochloride |prepared as described in Example 40(e)|, 0.74 g of the title compound, melting at 157°–159° C., was obtained.

¹H Nuclear Magnetic Resonance Spectrum (hexadeuterated dimethyl sulfoxide, 270 MHz, using tetramethylsilane as the internal standard), δ ppm:

2.12 (3H, singlet);
3.07 (1H, doublet of doublets, J=9 & 14 Hz);
3.30 (1H, doublet of doublets, J=4.5 & 14 Hz);
4.23 (2H, triplet, J=4.5 Hz);
4.39 (2H, triplet, J=4.5 Hz);
4.86 (1H, doublet of doublets, J=4.5 & 9 Hz);
6.80 (2H, doublet, J=8.5 Hz);
6.91 (2H, doublet, J=8.5 Hz);
7.15 (2H, doublet, J=8.5 Hz);
7.50 (2H, doublet, J=8.5 Hz).

EXAMPLE 52

5-(4-{2-|1-(5-Acetoxy-2-hydroxy-3,4,6-trimethylphenyl)ethylideneaminooxy] ethoxy}benzyl)thiazolidine-2,4-dione (Compound No. 2-200)

Following a procedure similar to that described in Example 46, but using 0.32 g of 5'-acetoxy-2'-hydroxy-3', 4',6'-trimethylacetophenone and 0.40 g of 5-[4-(2-aminooxyethoxy)benzyl|thiazolidine-2,4-dione hydrochloride |prepared as described in Example 40(e)|, 0.28 g of the title compound was obtained as an amorphous powder, melting at 60°–75° C. (softening point).

¹H Nuclear Magnetic Resonance Spectrum (hexadeuterated dimethyl sulfoxide, 270 MHz, using tetramethylsilane as the internal standard), δ ppm:

1.85 (3H, singlet);
1.96 (3H, singlet);
2.02 (3H, singlet);
2.09 (3H, singlet);

2.30 (3H, singlet);
3.07 (1H, doublet of doublets, J=9 & 14 Hz);
3.30 (1H, doublet of doublets, J=4.5 & 9 Hz);
4.19 (2H, doublet, J=4.5 Hz);
4.36 (2H, triplet, J=4.5 Hz);
4.87 (1H, doublet of doublets, J=4.5 & 9 Hz);
6.92 (2H, doublet, J=8.5 Hz);
7.16 (2H, doublet, J=8.5 Hz).

EXAMPLE 53

5-(4-{2-[1-(4-Hydroxy-3,5-dimethylphenyl)ethylideneaminooxy]ethoxy}benzyl)thiazolidine-2,4-dione (Compound No. 2-201)

Following a procedure similar to that described in Example 46, but using 0.22 g of 4'-hydroxy-3',5'-dimethylacetophenone and 0.40 g of 5-[4-(2-aminooxyethoxy)benzyl]thiazolidine-2,4-dione hydrochloride [prepared as described in Example 40(e)], 0.30 g of the title compound was obtained as an amorphous powder, melting at 53°–65° C. (softening point).

Nuclear Magnetic Resonance Spectrum (hexadeuterated dimethyl sulfoxide, 270 MHz, using tetramethylsilane as the internal standard), δ ppm:

2.10 (3H, singlet);
2.17 (6H, singlet);
3.06 (1H, doublet of doublets, J=9 & 14 Hz);
3.30 (1H, doublet of doublets, J=4.5 & 14 Hz);
4.22 (2H, triplet, J=4.5 Hz);
4.38 (2H, triplet, J=4.5 Hz);
4.86 (1H, doublet of doublets, J=4.5 & 9 Hz);
6.91 (2H, doublet, J=8.5 Hz);
7.15 (2H, doublet, J=8.5 Hz);
7.24 (2H, singlet).

EXAMPLE 54

5-(4-{2-[1-(3-Acetoxyphenyl)ethylideneaminooxy]ethoxy}benzyl)thiazolidine-2,4-dione (Compound No. 2-202)

A mixture of 0.30 g of 5-(4-{2-[1-(3-hydroxyphenyl)ethylideneaminooxy]ethoxy}benzyl)thiazolidine-2,4-dione (prepared as described in Example 50), 0.092 ml of acetic anhydride and 15 ml of pyridine was stirred at room temperature for 1.5 hours. At the end of this time, the solvent was removed by distillation under reduced pressure, and then the resulting residue was diluted with water and then extracted with ethyl acetate. The extract was washed with 1N aqueous hydrochloric acid and with an aqueous solution of sodium chloride, in that order, after which it was dried over anhydrous magnesium sulfate. The solvent was then removed by distillation under reduced pressure, and the residue was purified by column chromatography through silica gel, using a 1:2 by volume mixture of ethyl acetate and hexane as the eluent, to give 0.23 g of the title compound, melting at 30°–50° C. (softening point).

Nuclear Magnetic Resonance Spectrum (hexadeuterated dimethyl sulfoxide, 270 MHz, using tetramethylsilane as the internal standard), δ ppm:

2.17 (3H, singlet);
2.28 (3H, singlet);
3.07 (1H, doublet of doublets, J=9 & 14 Hz);
3.30 (1H, doublet of doublets, J=4.5 & 14 Hz);
4.25 (2H, triplet, J=4.5 Hz);
4.45 (2H, triplet, J=4.5 Hz);
4.86 (1H, doublet of doublets, J=4.5 & 9 Hz);
6.92 (2H, doublet, J=8.5 Hz);
7.14–7.56 (6H, multiplet).

EXAMPLE 55

5-(4-{2-[1-(4-Acetoxyphenyl)ethylideneaminooxy]ethoxy}benzyl)thiazolidine-2,4-dione (Compound No. 2-203)

Following a procedure similar to that described in Example 54, but using 0.30 g of 5-(4-{2-[1-(4-hydroxyphenyl)ethylideneaminooxy]ethoxy}benzyl)thiazolidine-2,4-dione (prepared as described in Example 51), 0.092 ml of acetic anhydride and 15 ml of pyridine, 0.3 g of the title compound, melting at 133°–135° C., was obtained.

Nuclear Magnetic Resonance Spectrum (hexadeuterated dimethyl sulfoxide, 270 MHz, using tetramethylsilane as the internal standard), δ ppm:

2.18 (3H, singlet);
2.28 (3H, singlet);
3.07 (1H, doublet of doublets, J=9 & 14 Hz);
3.30 (1H, doublet of doublets, J=4.5 & 14 Hz);
4.23 (2H, triplet, J=4.5 Hz);
4.44 (2H, triplet, J=4.5 Hz);
4.86 (1H, doublet of doublets, J=4.5 & 9 Hz);
6.92 (2H, doublet, J=8.5 Hz);
7.14–7.17 (4H, multiplet);
7.70 (2H, doublet, J=8.5 Hz).

EXAMPLE 56

5-(4-{2-[1-(4-Biphenylyl)ethylideneaminooxy]ethoxy}benzyl)oxazolidine-2,4-dione (Compound No. 6-15)

56(a) 5-(4-{2-[1-(4-Biphenylyl)ethylideneaminooxy]ethoxy}benzyl)-3-trityloxazolidine-2,4-dione Following a procedure similar to that described in Example 3(a), but using 0.23 g of 2-[1-(4-biphenylyl)ethylideneaminooxy]ethanol (prepared as described in Preparation 15), 0.40 g of 5-(4-hydroxybenzyl)-3-trityloxazolidine-2,4-dione, 0.40 g of tributylphosphine and 0.50 g of 1,1'-(azodicarbonyl)dipiperazine, 0.31 g of the title compound was obtained as a crystalline powder, melting at 193°–195° C.

Nuclear Magnetic Resonance Spectrum (hexadeuterated dimethyl sulfoxide, 270 MHz, using tetramethylsilane as the internal standard), δ ppm:

2.24 (3H, singlet);
3.03 (1H, doublet of doublets, J=4.5 & 15 Hz);
3.19 (1H, doublet of doublets, J=4.5 & 15 Hz);
4.20–4.30 (2H, multiplet);
4.50 (2H, triplet, J=4.5 Hz);
5.32 (1H, triplet, J=4.5 Hz);
6.98 (2H, doublet, J=8.5 Hz);
7.10–7.20 (17H, multiplet);
7.39 (1H, triplet, J=1.5 Hz);
7.48 (2H, triplet, J=8 Hz);
7.60–7.70 (4H, multiplet);

7.73 (2H, doublet, J=8 Hz).

56(b) 5-(4-{2-[1-(4-Biphenylyl)ethylideneaminooxy]ethoxy}benzyl)oxazolidine-2,4-dione Following a procedure similar to that described in Example 1(b), but using 0.31 g of 5-(4-{2-[1-(4-biphenylyl)ethylideneaminooxy]ethoxy}benzyl)-3-trityloxazolidine-2,4-dione [prepared as described in Example 56(a)], 0.16 g of the title compound was obtained as a crystalline powder, melting at 177°–179° C.

¹H Nuclear Magnetic Resonance Spectrum (a mixture of CDCl₃ with a small amount of hexadeuterated dimethyl sulfoxide, 270 MHz, using tetramethylsilane as the internal standard), δ ppm:

2.28 (3H, singlet);
3.07 (1H, doublet of doublets, J=5.5 & 15 Hz);
3.24 (1H, doublet of doublets, J=4 & 15 Hz);
4.28 (2H, triplet, J=5 Hz);
4.54 (2H, triplet, J=5 Hz);
4.97 (1H, doublet of doublets, J=4 & 5.5 Hz);
6.89 (2H, doublet, J=8.5 Hz);
7.17 (2H, doublet, J=8.5 Hz);
7.30–7.50 (3H, multiplet);
7.60–7.70 (4H, multiplet);
7.74 (2H, doublet, J=8.5 Hz).

EXAMPLE 57

5-(4-{2-[1-(4-2'-Pyridylphenyl)propylideneaminooxy]ethoxy}benzyl)thiazolidine-2,4-dione (Compound No. 3-35)

Following a procedure similar to that described in Example 47, but using 211 mg of 4'-(2-pyridyl)propiophenone and 319 mg of 5-[4-(2-aminooxyethoxy)benzyl]thiazolidine-2,4-dione hydrochloride [prepared as described in Example 40(e)], 239 mg of the title compound were obtained as a crystalline powder, melting at 171°–172.5° C.

Nuclear Magnetic Resonance Spectrum (hexadeuterated dimethyl sulfoxide, 270 MHz, using tetramethylsilane as the internal standard), δ ppm:

1.06 (3H, triplet, J=7.5 Hz);
2.75 (2H, quartet, J=7.5 Hz);
3.05 (1H, doublet of doublets, J=9 & 14 Hz);
3.28 (1H, doublet of doublets, J=4.5 & 14 Hz);
4.26 (2H, triplet, J=4.5 Hz);
4.48 (2H, triplet, J=4.5 Hz);
4.88 (1H, doublet of doublets, J=4.5 & 9 Hz);
6.93 (2H, doublet, J=8.5 Hz);
7.16 (2H, doublet, J=8.5 Hz);
7.39 (1H, doublet of doublets, J=4.5 & 7 Hz);
7.79 (2H, doublet, J=8.5 Hz);
7.91 (1H, doublet of doublets, J=7 & 8 Hz);
8.02 (1H, doublet, J=8 Hz);
8.14 (2H, doublet, J=8.5 Hz);
8.69 (1H, doublet, J=4.5 Hz).

PREPARATION 1

2-(Benzylideneaminooxy)ethanol

1(a) Benzaldehyde oxime O-2-(tetrahydropyran-2-yloxy)ethyl ether 2.5 g of potassium carbonate were added to a solution of 1.2 g of 2-(2-bromoethoxy)tetrahydropyran and 0.36 g of benzaldehyde oxime in 10 ml of dimethylacetamide, and the resulting mixture was stirred at 80° C. for 4 hours. The reaction mixture was then dissolved in a mixture of ethyl acetate and water. The ethyl acetate layer was separated and dried over anhydrous magnesium sulfate, after which the solvent was removed by distillation under reduced pressure. The resulting residue was then purified by column chromatography through silica gel, using a 7:1 by volume mixture of hexane and ethyl acetate as the eluent, to give 0.51 g of the title compound as a syrup.

¹H Nuclear Magnetic Resonance Spectrum (CDCl₃, 270 MHz, using tetramethylsilane as the internal standard), δ ppm:

1.49–1.92 (6H, multiplet);
3.47–3.55 (1H, multiplet);
3.77 (1H, doublet of triplets, J=5 & 11.5 Hz);
3.85–3.94 (1H, multiplet);
4.01 (1H, doublet of triplets, J=5 & 11.5 Hz);
4.36 (2H, triplet, J=5 Hz);
4.68 (1H, triplet, J=3.5 Hz);
7.34–7.38 (3H, multiplet);
7.56–7.60 (2H, multiplet);
8.13 (1H, singlet).

1(b) 2-(Benzylideneaminooxy)ethanol 100 mg of p-toluenesulfonic acid monohydrate were added to a solution of 1.3 g of benzaldehyde oxime O-2-(tetrahydropyran-2-yloxy)ethyl ether [prepared as described in Preparation 1(a)] in 15 ml of methanol, and the resulting mixture was stirred at room temperature for 2 hours, after which it was concentrated by evaporation under reduced pressure. The concentrate was dissolved in ethyl acetate. The resulting solution was washed with an aqueous solution of sodium hydrogen-carbonate and then dried over anhydrous magnesium sulfate. The solvent was then removed by distillation under reduced pressure, and the resulting residue was purified by column chromatography through silica gel, using a 2:1 by volume mixture of hexane and ethyl acetate as the eluent, to give 0.90 g of the title compound as a syrup.

¹H Nuclear Magnetic Resonance Spectrum (CDCl₃, 270 MHz, using tetramethylsilane as the internal standard), δ ppm:

2.34 (1H, triplet, J=6 Hz);
3.93–3.95 (2H, multiplet);
4.28–4.31 (2H, multiplet);
7.38–7.40 (3H, multiplet);
7.56–7.58 (2H, multiplet);
8.13 (1H, singlet).

PREPARATION 2

2-(2-Quinolylmethyleneaminooxy)ethanol

2(a) 2-Quinolinecarboxaldehyde oxime O-2-(tetrahydropyran-2-yloxy)ethyl ether

Following a procedure similar to that described in Preparation 1(a), but using 1.50 g of 2-(2-bromoethoxy)tetrahydropyran, 1.10 g of 2-quinolinecarboxaldehyde oxime and 2.8 g of potassium carbonate, 2.00 g of the title compound were obtained as a syrup.

2(b) 2-(2-Quinolylmethyleneaminooxy)ethanol

Following a procedure similar to that described in Preparation 1(b), but using 2.00 g of 2-quinolinecarboxaldehyde oxime O-2-(tetrahydropyran-2-yloxy)ethyl ether [prepared as described in step (a) above] and 1.50 g of p-toluenesulfonic acid monohydrate, 0.98 g of the title compound, melting at 128° C., was obtained.

¹H Nuclear Magnetic Resonance Spectrum (CDCl₃, 270 MHz, using tetramethylsilane as the internal standard), δ ppm:

2.34 (1H, triplet, J=6 Hz);
3.97–4.01 (2H, multiplet);
4.39–4.43 (2H, multiplet);
7.57 (1H, triplet, J=8 Hz);
7.74 (1H, triplet, J=8 Hz);
7.83 (1H, doublet, J=8.5 Hz);
7.95 (1H, doublet, J=8.5 Hz);
8.10 (1H, doublet, J=8.5 Hz);
8.15 (1H, doublet, J=8.5 Hz);
8.40 (1H, singlet).

PREPARATION 3

2-(3-Quinolylmethyleneaminooxy)ethanol

3(a) 3-Quinolinecarboxaldehyde oxime O-2-(tetrahydropyran-2-yloxy)ethyl ether

Following a procedure similar to that described in Preparation 1(a), but using 4.45 g of 2-(2-bromoethoxy)tetrahydropyran, 2.60 g of 3-quinolinecarboxaldehyde oxime and 7.30 g of potassium carbonate, 4.72 g of the title compound were obtained as a syrup.

3(b) 2-(3-Quinolylmethyleneaminooxy)ethanol

Following a procedure similar to that described in Preparation 1(b), but using 4.72 g of 3-quinolinecarboxaldehyde oxime O-2-(tetrahydropyran-2-yloxy)ethyl ether [prepared as described in step (a) above] and 2.91 g of p-toluenesulfonic acid monohydrate, 1.55 g of the title compound, melting at 129° C., were obtained.

¹H Nuclear Magnetic Resonance Spectrum (CDCl₃, 270 MHz, using tetramethylsilane as the internal standard), δ ppm:

2.17 (1H, broad singlet);
3.97–4.01 (2H, multiplet);
4.36–4.40 (2H, multiplet);
7.59 (1H, triplet, J=8 Hz);
7.76 (1H, doublet of doublets, J=1 & 8 Hz);
7.85 (1H, doublet, J=8 Hz);
8.13 (1H, doublet, J=8.5 Hz);
8.24 (1H, doublet, J=2 Hz);
8.31 (1H, singlet);
9.19 (1H, doublet, J=2 Hz).

PREPARATION 4

2-(2-Pyridylmethyleneaminooxy)ethanol

4(a) 2-Pyridinecarboxaldehyde oxime O-2-(tetrahydropyran-2-yloxy)ethyl ether

Following a procedure similar to that described in Preparation 1(a), but using 4.00 g of 2-(2-bromoethoxy)tetrahydropyran, 1.22 g of 2-pyridinecarboxaldehyde oxime and 6.00 g of potassium carbonate, 2.30 g of the title compound were obtained as a syrup.

4(b) 2-(2-Pyridylmethyleneaminooxy)ethanol

Following a procedure similar to that described in Preparation 1(b), but using 2.30 g of 2-pyridinecarboxaldehyde oxime O-2-(tetrahydropyran-2-yloxy)ethyl ether [prepared as described in step (a) above] and 2.10 g of p-toluenesulfonic acid monohydrate, 1.29 g of the title compound, melting at 45° C., were obtained.

¹H Nuclear Magnetic Resonance Spectrum (CDCl₃, 270 MHz, using tetramethylsilane as the internal standard), δ ppm:

2.34 (1H, broad singlet);
3.93–3.97 (2H, multiplet);
4.35–4.38 (2H, multiplet);
7.27–7.30 (1H, multiplet);
7.68–7.80 (2H, multiplet);
8.24 (1H, singlet);
8.62 (1H, doublet, J=4.5 Hz).

PREPARATION 5

2-(3-Pyridylmethyleneaminooxy)ethanol

5(a) 3-Pyridinecarboxaldehyde oxime O-2-(tetrahydropyran-2-yloxy)ethyl ether

Following a procedure similar to that described in Preparation 1(a), but using 8.00 g of 2-(2-bromoethoxy)tetrahydropyran, 2.44 g of 3-pyridinecarboxaldehyde oxime and 12.00 g of potassium carbonate, 4.18 g of the title compound were obtained as a syrup.

5(b) 2-(3-Pyridylmethyleneaminooxy)ethanol

Following a procedure similar to that described in Preparation 1(b), but using 4.18 g of 3-pyridinecarboxaldehyde oxime O-2-(tetrahydropyran-2-yloxy)ethyl ether [prepared as described in step (a) above] and 3.00 g of p-toluenesulfonic acid monohydrate, 2.00 g of the title compound were obtained as a wax.

¹H Nuclear Magnetic Resonance Spectrum (CDCl₃, 270 MHz, using tetramethylsilane as the internal standard), δ ppm:

2.28 (1H, broad singlet);
3.93–3.97 (2H, multiplet);
4.32–4.35 (2H, multiplet);
7.32 (1H, doublet of doublets, J=5 & 8 Hz);
7.95 (1H, doublet of doublets, J=1 & 5 Hz);
8.14 (1H, singlet);
8.61 (1H, doublet of doublets, J=1.5 & 5 Hz);
8.74 (1H, doublet, J=2 Hz).

PREPARATION 6

2-(4-Pyridylmethyleneaminooxy)ethanol

6(a) 4-Pyridinecarboxaldehyde oxime O-2-(tetrahydropyran-2-yloxy)ethyl ether

Following a procedure similar to that described in Preparation 1(a), but using 4.00 g of 2-(2-bromoethoxy)tetrahydropyran, 1.22 g of 4-pyridinecarboxaldehyde oxime and 6.00 g of potassium carbonate, 2.00 g of the title compound were obtained as a syrup.

6(b) 2-(4-Pyridylmethyleneaminooxy)ethanol

Following a procedure similar to that described in Preparation 1(b), but using 2.10 g of 4-pyridinecarboxaldehyde oxime O-2-(tetrahydropyran-2-yloxy)ethyl ether [prepared as described in step (a) above] and 2.00 g of p-toluenesulfonic acid monohydrate, 1.01 g of the title compound, melting at 78°–80° C., were obtained.

¹H Nuclear Magnetic Resonance Spectrum (CDCl₃, 270 MHz, using tetramethylsilane as the internal standard), δ ppm:

2.18 (1H, broad singlet);
3.93–3.97 (2H, multiplet);
4.34–4.37 (2H, multiplet);
7.45 (2H, doublet of doublets, J=1.5 & 4.5 Hz);
8.09 (1H, singlet);
8.64 (2H, doublet of doublets, J=1.5 & 4.5 Hz).

PREPARATION 7

2-(2-Naphthylmethyleneaminooxy)ethanol

7(a) 2-Naphthaldehyde oxime O-2-(tetrahydropyran-2-yloxy)ethyl ether

Following a procedure similar to that described in Preparation 1(a), but using 4.89 g of 2-(2-bromoethoxy)tetrahydropyran, 2.00 g of 2-naphthaldehyde oxime and 6.46 g of potassium carbonate, 2.39 g of the title compound, melting at 72°–73° C., were obtained.

7(b) 2-(2-Naphthylmethyleneaminooxy)ethanol

Following a procedure similar to that described in Preparation 1(b), but using 2.39 g of 2-naphthaldehyde oxime O-2-(tetrahydropyran-2-yloxy)ethyl ether |prepared as described in step (a) above| and 0.20 g of p-toluenesulfonic acid monohydrate, 1.17 g of the title compound, melting at 87° C., were obtained.

$^1$H Nuclear Magnetic Resonance Spectrum (CDCl$_3$, 270 MHz, using tetramethylsilane as the internal standard), δ ppm:

2.35 (1H, triplet, J=6 Hz);
3.95–4.00 (2H, multiplet);
4.33–4.36 (2H, multiplet);
7.49–7.53 (2H, multiplet);
7.82–7.87 (5H, multiplet);
8.28 (1H, singlet).

PREPARATION 8

2-(3-Phenylbenzylideneaminooxy)ethanol

8(a) 3-Biphenylcarboxaldehyde oxime O-2-(tetrahydropyran-2-yloxy)ethyl ether

Following a procedure similar to that described in Preparation 1(a), but using 4.24 g of 2-(2-bromoethoxy)tetrahydropyran, 2.00 g of 3-biphenylcarboxaldehyde oxime and 5.61 g of potassium carbonate, 2.81 g of the title compound were obtained as a syrup.

8(b) 2-(3-Phenylbenzylideneaminooxy)ethanol

Following a procedure similar to that described in Preparation 1(b), but using 2.14 g of 3-biphenylcarboxaldehyde oxime O-2-(tetrahydropyran-2-yloxy)ethyl ether |prepared as described in step (a) above| and 200 mg of p-toluenesulfonic acid monohydrate, 1.23 g of the title compound were obtained as a syrup.

$^1$H Nuclear Magnetic Resonance Spectrum (CDCl$_3$, 270 MHz, using tetramethylsilane as the internal standard), δ ppm:

2.30 (1H, triplet, J=6 Hz);
3.93–3.98 (2H, multiplet);
4.30–4.34 (2H, multiplet);
7.35–7.48 (4H, multiplet);
7.54–7.63 (4H, multiplet);
7.79 (1H, singlet);
8.20 (1H, singlet).

PREPARATION 9

2-(4-Phenylbenzylideneaminooxy)ethanol

9(a) 4-Biphenylcarboxaldehyde oxime O-2-(tetrahydropyran-2-yloxy)ethyl ether

Following a procedure similar to that described in Preparation 1(a), but using 4.24 g of 2-(2-bromoethoxy)tetrahydropyran, 2.00 g of 4-biphenylcarboxaldehyde oxime and 5.61 g of potassium carbonate, 2.73 g of the title compound were obtained as a syrup.

9(b) 2-(4-Phenylbenzylideneaminooxy)ethanol

Following a procedure similar to that described in Preparation 1(b), but using 2.73 g of 4-biphenylcarboxaldehyde oxime O-2-(tetrahydropyran-2-yloxy)ethyl ether |prepared as described in step (a) above| and 200 mg of p-toluenesulfonic acid monohydrate, 1.78 g of the title compound, melting at 116°–118° C., were obtained.

$^1$H Nuclear Magnetic Resonance Spectrum (CDCl$_3$, 270 MHz, using tetramethylsilane as the internal standard), δ ppm:

2.32 (1H, triplet, J=6 Hz);
3.93–3.98 (2H, multiplet);
4.30–4.33 (2H, multiplet);
7.34–7.49 (3H, multiplet);
7.58–7.67 (6H, multiplet);
8.17 (1H, singlet).

PREPARATION 10

2-(2-Phenyl-5-pyridylmethyleneaminooxy)ethanol

10(a) 2-Phenyl-5-pyridinecarboxaldehyde oxime O-2-(tetrahydropyran-2-yloxy)ethyl ether Following a procedure similar to that described in Preparation 1(a), but using 1.58 g of 2-(2-bromoethoxy)tetrahydropyran, 500 mg of 2-phenyl-5-pyridinecarboxaldehyde oxime and 2.09 g of potassium carbonate, 734 mg of the title compound were obtained as a syrup.

10(b) 2-(2-Phenyl-5-pyridylmethyleneaminooxy)ethanol

Following a procedure similar to that described in Preparation 1(b), but using 727 mg of 2-phenyl-5-pyridinecarboxaldehyde oxime O-2-(tetrahydropyran-2-yloxy)ethyl ether |prepared as described in step (a) above| and 466 mg of p-toluenesulfonic acid monohydrate, 404 mg of the title compound, melting at 100°–101° C., were obtained.

$^1$H Nuclear Magnetic Resonance Spectrum (CDCl$_3$, 270 MHz, using tetramethylsilane as the internal standard), δ ppm:

2.20 (1H, triplet, J=5 Hz);
3.93–3.97 (2H, multiplet);
4.32–4.36 (2H, multiplet);
7.41–7.53 (3H, multiplet);
7.76 (1H, doublet, J=8.5 Hz);
8.00–8.05 (3H, multiplet);
8.19 (1H, singlet);
8.78 (1H, doublet, J=2 Hz).

PREPARATION 11

2-(3-Phenyl-5-pyridylmethyleneaminooxy)ethanol

11(a) 3-Phenyl-5-pyridinecarboxaldehyde oxime O-2-(tetrahydropyran-2-yloxy)ethyl ether Following a procedure similar to that described in Preparation 1(a), but using 1.80 g of 2-(2-bromoethoxy)tetrahydropyran, 600 mg of 3-phenyl-5-pyridinecarboxaldehyde oxime and 2.50 g of potassium carbonate, 809 mg of the title compound were obtained as a syrup.

11(b) 2-(3-Phenyl-5-pryridylmethyleneaminooxy)ethanol

Following a procedure similar to that described in Preparation 1(b), but using 809 mg of 3-phenyl-5-pyridinecarboxaldehyde oxime O-2-(tetrahydropyran-2-yloxy)ethyl ether |prepared as described in step (a) above| and 750 mg of p-toluenesulfonic acid monohydrate, 529 mg of the title compound, melting at 102°–104° C., were obtained.

$^1$H Nuclear Magnetic Resonance Spectrum (CDCl$_3$, 270 MHz, using tetramethylsilane as the internal standard), δ ppm:

2.26 (1H, broad singlet);
3.98–4.02 (2H, multiplet);
4.33–4.37 (2H, multiplet);
7.40–7.53 (3H, multiplet);
7.59–7.62 (2H, multiplet);
8.13 (1H, triplet, J=2 Hz);
8.21 (1H, singlet);
8.69 (1H, doublet, J=2 Hz);
8.84 (1H, doublet, J=2 Hz).

PREPARATION 12

2-(2-Ethoxy-5-pyridylmethyleneaminooxy)ethanol
12(a) 2-Ethoxy-5-pyridinecarboxaldehyde oxime O-2-(tetrahydropyran-2-yloxy)ethyl ether Following a procedure similar to that described in Preparation 1(a), but using 2.00 g of 2-(2-bromoethoxy) tetrahydropyran, 1.00 g of 2-ethoxy-5-pyridinecarboxaldehyde oxime and 2.50 g of potassium carbonate, 1.76 g of the title compound were obtained as a syrup.

12(b) 2-(2-Ethoxy-5-pyridylmethyleneaminooxy)ethanol

Following a procedure similar to that described in Preparation 1(b), but using 1.76 g of 2-ethoxy-5-pyridinecarboxaldehyde oxime O-2-(tetrahydropyran-2-yloxy)ethyl ether [prepared as described in step (a) above] and 1.60 g of p-toluenesulfonic acid monohydrate, 0.73 g of the title compound, melting at 52°–54° C., was obtained.

$^1$H Nuclear Magnetic Resonance Spectrum (CDCl$_3$, 270 MHz, using tetramethylsilane as the internal standard), δ ppm:

1.40 (3H, triplet, J=7 Hz);
2.20 (1H, triplet, J=6 Hz);
3.90–3.95 (2H, multiplet);
4.26–4.29 (2H, multiplet);
4.39 (2H, quartet, J=7 Hz);
6.74 (1H, doublet, J=8.5 Hz);
7.90 (1H, doublet of doublets, J=2 & 8.5 Hz);
8.08 (1H, singlet);
8.18 (1H, doublet, J=2 Hz).

PREPARATION 13

2-[1-(2-Naphthyl)ethylideneaminooxy)ethanol
13(a) 2-Acetonaphthone oxime O-2-(tetrahydropyran-2-yloxy)ethyl ether Following a procedure similar to that described in Preparation 1(a) (except that the time required for the reaction was 20 hours), but using 4.52 g of 2-(2-bromoethoxy) tetrahydropyran, 2.00 g of 2-acetonaphtone oxime and 5.97 g of potassium carbonate, 3.32 g of the title compound were obtained as a syrup.

13(b) 2-[1-(2-Naphthyl)ethylideneaminooxy]ethanol

Following a procedure similar to that described in Preparation 1(b), but using 3.32 g of 2-acetonaphthone oxime O-2-(tetrahydropyran-2-yloxy)ethyl ether [prepared as described in step (a) above] and 0.30 g of p-toluenesulfonic acid monohydrate, 1.31 g of the title compound, melting at 94°–96° C., were obtained.

$^1$H Nuclear Magnetic Resonance Spectrum (CDCl$_3$, 270 MHz, using tetramethylsilane as the internal standard), δ ppm:

2.39 (3H, singlet);
2.58 (1H, broad singlet);
3.97–4.00 (2H, multiplet);
4.36–4.39 (2H, multiplet);
7.47–7.53 (2H, multiplet);
7.79–7.88 (4H, multiplet);
8.00 (1H, singlet).

PREPARATION 14

2-[1-(2-Quinolyl)ethylideneaminooxy]ethanol
14(a) 2-Acetylquinoline oxime O-2-(tetrahydropyran-2-yloxy)ethyl ether Following a procedure similar to that described in Preparation 1(a) (except that the time required for the reaction was 20 hours), but using 2.09 g of 2-(2-bromoethoxy) tetrahydropyran, 930 mg of 2-acetylquinoline oxime and 2.76 g of potassium carbonate, 1.51 g of the title compound were obtained as a syrup.

14(b) 2-[1-(2-Quinolyl)ethylideneaminooxy]ethanol

Following a procedure similar to that described in Preparation 1(b), but using 1.51 g of 2-acetylquinoline oxime O-2-(tetrahydropyran-2-yloxy)ethyl ether [prepared as described in step (a) above], 0.85 g of the title compound, melting at 89° C., was obtained.

$^1$H Nuclear Magnetic Resonance Spectrum (CDCl$_3$, 270 MHz, using tetramethylsilane as the internal standard), δ ppm:

2.44 (1H, triplet, J=6 Hz);
2.51 (3H, singlet);
3.96–4.02 (2H, multiplet);
4.40–4.43 (2H, multiplet);
7.54 (1H, triplet, J=9.5 Hz);
7.71 (1H, triplet, J=7.5 Hz);
7.80 (1H, doublet, J=8 Hz);
8.01 (1H, doublet, J=8.5 Hz);
8.08–8.11 (2H, multiplet).

PREPARATION 15

2-[1-(4-Biphenylyl)ethylideneaminooxy]ethanol
15(a) 2-Acetylbiphenyl oxime O-2-(tetrahydropyran-2-yloxy)ethyl ether Following a procedure similar to that described in Preparation 1(a) (except that the time required for the reaction was 16 hours), but using 15.8 g of 2-(2-bromoethoxy) tetrahydropyran, 6.40 g of 4-acetylbiphenyl oxime and 20.9 g of potassium carbonate, 10.2 g of the title compound were obtained as a syrup.

15(b) 2-[1-(4-Biphenylyl)ethylideneaminooxy]ethanol

Following a procedure similar to that described in Preparation 1(b), but using 10.2 g of 4-acetylbiphenyl oxime O-2-(tetrahydropyran-2-yloxy)ethyl ether [prepared as described in step (a) above], 6.53 g of the title compound, melting at 128°–130° C., were obtained.

$^1$H Nuclear Magnetic Resonance Spectrum (CDCl$_3$, 270 MHz, using tetramethylsilane as the internal standard), δ ppm:

2.30 (3H, singlet);
2.58 (1H, broad singlet);
3.95–3.99 (2H, multiplet);
4.32–4.36 (2H, multiplet);
7.36–7.48 (3H, multiplet);
7.59–7.62 (4H, multiplet);
7.71 (2H, doublet, J=8.5 Hz).

PREPARATION 16

2-[1-(3-Biphenylyl)ethylideneaminooxy]ethanol
16(a) 3-Acetylbiphenyl oxime O-2- (tetrahydropyran-2-yloxy)ethyl ether Following a procedure similar to that described in Preparation 1(a) (except that the time required for the reaction was 16 hours), but using 4.16 g of 2-(2-bromoethoxy) tetrahydropyran, 1.68 g of 3-acetylbiphenyl oxime and 5.50 g of potassium carbonate, 2.69 g of the title compound were obtained as a syrup.

16(b) 2-|1-(3-Biphenylyl)ethylideneaminooxy|ethanol

Following a procedure similar to that described in Preparation 1(b), but using 2.69 g of 3-acetylbiphenyl oxime O-2-(tetrahydropyran-2-yloxy)ethyl ether |prepared as described in step (a) above| and 0.15 g of toluenesulfonic acid monohydrate, 1.45 g of the title compound were obtained as a syrup.

$^1$H Nuclear Magnetic Resonance Spectrum (CDCl$_3$, 270 MHz, using tetramethylsilane as the internal standard), δ ppm:

2.32 (3H, singlet);

2.58 (1H, broad singlet);

3.94–3.98 (2H, multiplet);

4.32–4.36 (2H, multiplet);

7.34–7.48 (4H, multiplet);

7.59–7.62 (4H, multiplet);

7.83 (H, doublet, J=1.5 Hz).

PREPARATION 17

2-|1-(2-Phenyl-5-pyridyl)ethylideneaminooxy| ethanol

17(a) 5-Acetyl-2-phenylpyridine oxime O-2-(tetrahdropyran-2-yloxy)ethyl ether

Following a procedure similar to that described in Preparation 1(a) (except that the time required for the reaction was 16 hours), but using 1.48 g of 2-(2-bromoethoxy) tetrahydropyran, 600 mg of 5-acetyl-2-phenylpyridine oxime and 2.30 g of potassium carbonate, 886 mg of the title compound were obtained as a syrup.

17(b) 2-|1-(2-Phenyl-5-pyridyl)ethylideneaminooxy| ethanol

Following a procedure similar to that described in Preparation 1(b), but using 882 mg of 5-acetyl-2-phenylpyridine oxime O-2-(tetrahydropyran-2-yloxy)ethyl ether |prepared as described in step (a) above| and 542 mg of p-toluenesulfonic acid monohydrate, 519 mg of the title compound, melting at 76° C., were obtained.

$^1$H Nuclear Magnetic Resonance Spectrum (CDCl$_3$, 270 MHz, using tetramethylsilane as the internal standard), δ ppm:

2.32 (3H, singlet);

2.42 (1H, broad singlet);

3.96–3.99 (2H, multiplet);

4.35–4.38 (2H, multiplet);

7.44–7.53 (3H, multiplet);

7.75 (1H, doublet, J=8 Hz);

8.00–8.04 (3H, multiplet);

8.93 (1H, doublet of doublets, J=2 & 5 Hz).

PREPARATION 18

2-|1-(3-Phenyl-5-pyridyl)ethylideneaminooxy| ethanol

18(a) 5-Acetyl-3-phenylpyridine oxime O-2-(tetrahydropyran-2-yloxy)ethyl ether

Following a procedure similar to that described in Preparation 1(a) (except that the time required for the reaction was 16 hours), but using 985 mg of 2-(2-bromoethoxy) tetrahydropyran, 500 mg of 5-acetyl-3-phenylpyridine oxide and 1.30 g of potassium carbonate, 641 mg of the title compound were obtained as a syrup.

18(b) 2-|1-(3-Phenyl-5-pyridyl)ethylideneaminooxy| ethanol

Following a procedure similar to that described in Preparation 1(b), but using 641 mg of 5-acetyl-3-phenylpyridine oxime O-2-(tetrahydropyran-2-yloxy)ethyl ether |prepared as described in step (a) above| and 419 mg of p-toluenesulfonic acid monohydrate, 419 mg of the title compound were obtained as a syrup.

$^1$H Nuclear Magnetic Resonance Spectrum (CDCl$_3$, 270 MHz, using tetramethylsilane as the internal standard), δ ppm:

2.34 (3H, singlet);

2.40 (1H, broad singlet);

3.95–3.99 (2H, multiplet);

4.35–4.39 (2H, multiplet);

7.43–7.52 (3H, multiplet);

7.59–7.62 (2H, multiplet);

8.11 (1H, triplet, J=2 Hz);

8.82 (1H, doublet, J=2 Hz);

8.83 (1H, doublet, J=2 Hz).

PREPARATION 19

2-|1-(2-ethoxy-5-pyridyl)ethylideneaminooxy| ethanol

19(a) 5-Acetyl-2-ethoxypyridine oxime O-2-(tetrahdropyran-2-yloxy)ethyl ether

Following a procedure similar to that described in Preparation 1(a) (except that the time required for the reaction was 18 hours), but using 1.16 g of 2-(2-bromoethoxy) tetrahydropyran, 500 mg of 5-acetyl-2-ethoxypyridine oxime and 1.53 g of potassium carbonate, 850 mg of the title compound were obtained as a syrup.

19(b) 2-|1-(2-Ethoxy-5-pyridyl)ethlideneaminooxy|ethanol

Following a procedure similar to that described in Preparation 1(b), but using 903 mg of 5-acetyl-2-ethoxypyridine oxime O-2-(tetrahydropyran-2-yloxy)ethyl ether |prepared as described in step (a) above| and 580 mg of p-toluenesulfonic acid monohydrate, 548 mg of the title compound were obtained as a syrup.

$^1$H Nuclear Magnetic Resonance Spectrum (CDCl$_3$, 270 MHz, using tetramethylsilane as the internal standard), δ ppm:

1.40 (3H, triplet, J=7 Hz);

2.24 (3H, singlet);

2.49 (1H, triplet, J=5.5 Hz);

3.91–3.96 (2H, multiplet);

4.29–4.32 (2H, multiplet);

4.38 (2H, quartet, J=7 Hz);

6.72 (1H, doublet, J=9 Hz);

7.89 (1H, doublet of doublets, J=2.5 & 9 Hz);

8.35 (1H, doublet, J=2.5 Hz).

PREPARATION 20

2-|1-(4-1'-Imidazolylphenyl)ethylideneaminooxy| ethanol

20(a) 4'-(Imidazol-1-yl)acetophenone oxime O-2-(tetrahydropyran-2-yloxy)ethyl ether Following a procedure similar to that described in Preparation 1(a) (except that the time required for the reaction was 16 hours), but using 2.01 g of 2-(2-bromoethoxy) tetrahydropyran, 1.00 g of 4'-(imidazol-1-yl)acetophenone oxime and 2.50 g of potassium carbonate, 1.14 g of the title compound were obtained as a syrup.

20(b) 2-[1-(4-1'-Imidazolylphenyl)ethylideneaminooxy] ethanol

Following a procedure similar to that described in Preparation 1(b), but using 1.14 g of 4'-(imidazol-1-yl) acetophenone oxime O-2-(tetrahydropyran-2-yloxy)ethyl ether [prepared as described in step (a) above] and 1.59 g of p-toluenesulfonic acid monohydrate, 562 mg of the title compound, melting at 127°-129° C., were obtained.

¹H Nuclear Magnetic Resonance Spectrum (hexadeuterated dimethyl sulfoxide, 270 MHz, using tetramethylsilane as the internal standard), δ ppm:

2.23 (3H, singlet);

3.68 (2H, quartet, J=5.5 Hz);

4.17 (2H, triplet, J=5.5 Hz);

4.73 (1H, triplet, J=5.5 Hz);

7.13 (1H, singlet);

7.70 (2H, doublet, J=8.5 Hz);

7.79 (2H, doublet, J=8.5 Hz);

7.80 (1H, singlet);

8.33 (1H, singlet).

PREPARATION 21

2-[1-(4-2'-Pyridylphenyl)ethylideneaminooxy] ethanol

21(a) 4'-(2-Pyridyl)acetophenone oxime O-2-(tetrahydropyran-2-yloxy)ethyl ether

Following a procedure similar to that described in Preparation 1(a) (except that the time required for the reaction was 16 hours), but using 3.20 g of 2-(2-bromoethoxy) tetrahydropyran, 1.30 g of 4'-(2-pyridyl)acetophenone oxime and 6.00 g of potassium carbonate, 2.01 g of the title compound were obtained as a syrup.

21(b) 2-[1-(4-2'-Pyridylphenyl)ethylideneaminooxy]ethanol

Following a procedure similar to that described in Preparation 1(b), but using 2.01 g of 4'-(2-pyridyl)acetophenone oxime O-2-(tetrahydropyran-2-yloxy)ethyl ether [prepared as described in step (a) above] and 1.30 g of p-toluenesulfonic acid monohydrate, 1.35 g of the title compound, melting at 74°-76° C., were obtained.

¹H Nuclear Magnetic Resonance Spectrum (CDCl₃, 270 MHz, using tetramethylsilane as the internal standard), δ ppm:

2.31 (3H, singlet);

2.57 (1H, triplet, J=6 Hz);

3.95-3.99 (2H, multiplet);

4.34-4.36 (2H, multiplet);

7.24-7.27 (1H, multiplet);

7.74-7.77 (4H, multiplet);

8.02 (2H, doublet, J=8.5 Hz);

8.71 (1H, doublet of doublets, J=1.5 & 5 Hz).

PREPARATION 22

2-[1-(4-3'-Pyridylphenyl)ethylideneaminooxy] ethanol

22(a) 4'-(3-Pyridyl)acetophenone oxime O-2-(tetrahydropyran-2-yloxy)ethyl ether

Following a procedure similar to that described in Preparation 1(a) (except that the time required for the reaction was 16 hours), but using 9.20 g of 2-(2-bromoethoxy) tetrahydropyran, 3.76 g of 4'-(3-pyridyl)acetophenone oxime and 17.4 g of potassium carbonate, 2.60 g of the title compound were obtained as a syrup.

22(b) 2-[1-(4-3'-Pyridylphenyl)ethylideneaminooxy]ethanol

Following a procedure similar to that described in Preparation 1(b), but using 2.60 g of 4'-(3-pyridyl)acetophenone oxime O-2-(tetrahydropyran-2-yloxy)ethyl ether [prepared as described in step (a) above] and 1.70 g of p-toluenesulfonic acid monohydrate, 1.69 g of the title compound, melting at 69°-70° C., were obtained.

¹H Nuclear Magnetic Resonance Spectrum (CDCl₃, 270 MHz, using tetramethylsilane as the internal standard), δ ppm:

2.31 (3H, singlet);

2.58 (1H, triplet, J=6 Hz);

3.95-4.00 (2H, multiplet);

4.34-4.37 (2H, multiplet);

7.39 (1H, doublet of doublets, J=4.5 & 8 Hz);

7.60 (2H, doublet, J=8.5 Hz);

7.75 (2H, doublet, J=8.5 Hz);

7.87-7.92 (1H, multiplet);

8.61 (1H, doublet of doublets, J=1.5 & 4.5 Hz);

8.87 (1H, doublet, J=2 Hz).

PREPARATION 23

2-[1-(4-4'-Pyridylphenyl)ethylideneaminooxy] ethanol

23(a) 4'-(4-Pyridyl)acetophenone oxime O-2-(tetrahydropyran-2-yloxy)ethyl ether

A mixture of 2.30 g of 2-(2-bromoethoxy) tetrahydropyran, 1.00 g of 4'-(4-pyridyl)acetophenone oxime and 4.00 g of potassium carbonate in 20 ml of 2-butanone was stirred whilst being heated under reflux for 4 hours. At the end of this time, the reaction mixture was diluted with ethyl acetate, after which it was washed with an aqueous solution of sodium chloride. It was then dried over anhydrous magnesium sulfate, and the solvent was removed by distillation under reduced pressure. The resulting residue was purified by column chromatography through silica gel, using a gradient elution method, with mixtures of methylene chloride and methanol in ratios ranging from 98:2 to 95:5 by volume as the eluent, to give 1.58 g of the title compound as a syrup.

23(b) 2-[1-(4-4'-Pyridylphenyl)ethylideneaminooxy]ethanol

Following a procedure similar to that described in Preparation 1(b), but using 1.58 g of 4'-(4-pyridyl)acetophenone oxime O-2-(tetrahydropyran-2-yloxy)ethyl ether [prepared as described in step (a) above] and 1.44 g of p-toluenesulfonic acid monohydrate, 1.01 g of the title compound, melting at 133° C., were obtained.

¹H Nuclear Magnetic Resonance Spectrum (CDCl₃, 270 MHz, using tetramethylsilane as the internal standard), δ ppm:

2.31 (3H, singlet);

2.53 (1H, triplet, J=6 Hz);

3.95-3.98 (2H, multiplet);

4.34-4.37 (2H, multiplet);

7.52 (2H, doublet of doublets, J=1.5 & 5 Hz);

7.65 (2H, doublet, J=8.5 Hz);

7.76 (2H, doublet, J=8.5 Hz);

8.68 (2H, doublet of doublets, J=1.5 & 5 Hz).

PREPARATION 24

2-(1,4-Dimethyl-2-phenylimidazol-5-ylmethyleneaminooxy)ethanol

24(a) 1,4-Dimethyl-2-phenylimidazole-5-carboxaldehyde oxime O-2-(tetrahydropyran-2-yloxy)ethyl ether Following a procedure similar to that described in Preparation 1(a) (except that the time required for the reaction was 5 hours), but using 1.46 g of 2-(2-bromoethoxy) tetrahydropyran, 500 mg of 1,4-dimethyl-2-phenylimidazole-5-carboxaldehyde oxime and 1.93 g of potassium carbonate, 716 mg of the title compound were obtained as a syrup.

24(b) 2-(1,4-Dimethyl-2-phenylimidazol-5-ylmethyleneaminooxy)ethanol

Following a procedure similar to that described in Preparation 1(b), but using 713 mg of 1,4-dimethyl-2-phenylimidazole-5-carboxaldehyde oxime O-2-(tetrahydropyran-2-yloxy)ethyl ether [prepared as described in step (a) above] and 434 mg of p-toluenesulfonic acid monohydrate, 454 mg of the title compound, melting at 95°–97° C., were obtained.

$^1$H Nuclear Magnetic Resonance Spectrum (CDCl$_3$, 270 MHz, using tetramethylsilane as the internal standard), δ ppm:

2.34 (3H, singlet);
3.82 (3H, singlet);
3.91–3.95 (2H, multiplet);
4.25–4.28 (2H, multiplet);
7.43–7.51 (3H, multiplet);
7.59–7.62 (2H, multiplet);
8.21 (1H, singlet).

PREPARATION 25

2-[1-(1-Methyl-2-phenylimidazol-4-yl)ethylideneaminooxy]ethanol

25(a) 4-Acetyl-1-methyl-2-phenylimidazole oxime O-2-(tetrahydropyran-2-yloxy)ethyl ether Following a procedure similar to that described in Preparation 1(a) (except that the time required for the reaction was 16 hours), but using 1.40 g of 2-(2-bromoethoxy) tetrahydropyran, 673 mg of 4-acetyl-1-methyl-2-phenylimidazole oxime and 2.00 g of potassium carbonate, 0.78 g of the title compound was obtained as a syrup.

25(b) 2-[1-(1-Methyl-2-phenylimidazol-4-yl)ethylideneaminooxy]ethanol

Following a procedure similar to that described in Preparation 1(b), but using 0.78 g of 4-acetyl-1-methyl-2-phenylimidazole oxime O-2-(tetrahydropyran-2-yloxy)ethyl ether [prepared as described in step (a) above] and 0.50 g of p-toluenesulfonic acid monohydrate, 0.42 g of the title compound, melting at 133°–135° C., was obtained.

$^1$H Nuclear Magnetic Resonance Spectrum (CDCl$_3$, 270 MHz, using tetramethylsilane as the internal standard), δ ppm:

2.30 (3H, singlet);
2.75 (1H, broad singlet);
3.73 (3H, singlet);
3.92–3.94 (2H, multiplet);
4.28–4.30 (2H, multiplet);
7.27 (1H, singlet);
7.40–7.48 (3H, multiplet);
7.60–7.63 (2H, multiplet).

PREPARATION 26

2-[1-(4'-Methylbiphenyl-4-yl)ethylideneaminooxy]ethanol

26(a) 4'-(4-Methylphenyl)acetophenone oxime O-2-(tetrahydropyran-2-yloxy)ethyl ether Following a procedure similar to that described in Preparation 1(a) (except that the time required for the reaction was 16 hours), but using 2.78 g of 2-(2-bromoethoxy) tetrahydropyran, 1.20 g of 4'-(4-methylphenyl) acetophenone oxime and 3.68 g of potassium carbonate, 1.84 g of the title compound were obtained as a syrup.

26(b) 2-[1-(4'-Methylbiphenyl-4-yl)ethylideneaminooxy]ethanol

Following a procedure similar to that described in Preparation 1(b), but using 1.84 g of 4'-(4-methylphenyl) acetophenone oxime O-2-(tetrahydropyran-2-yloxy)ethyl ether [prepared as described in step (a) above] and 0.10 g of p-toluenesulfonic acid monohydrate, 1.12 g of the title compound, melting at 142°–144° C., were obtained.

$^1$H Nuclear Magnetic Resonance Spectrum (CDCl$_3$, 270 MHz, using tetramethylsilane as the internal standard), δ ppm:

2.30 (3H, singlet);
2.40 (3H, singlet);
2.59 (1H, triplet, J=6 Hz);
3.93–3.99 (2H, multiplet);
4.32–4.40 (2H, multiplet);
7.26 (2H, doublet, J=8 Hz);
7.50 (2H, doublet, J=8 Hz);
7.59 (2H, doublet, J=8.5 Hz);
7.68 (2H, doublet, J=8.5 Hz).

PREPARATION 27

2-[1-(4'-Fluorobiphenyl-4-yl)ethylideneaminooxy]ethanol

27(a) 4'-(4-Fluorophenyl)acetophenone oxime O-2-(tetrahydropyran-2-yloxy)ethyl ether Following a procedure similar to that described in Preparation 1(a) (except that the time required for the reaction was 20 hours), but using 3.42 g of 2-(2-bromoethoxy) tetrahydropyran, 1.50 g of 4'-(4-fluorophenyl)acetophenone oxime and 4.52 g of potassium carbonate, 2.33 g of the title compound were obtained as a syrup.

27(b) 2-[1-(4'-Fluorobiphenyl-4-yl)ethylideneaminooxy]ethanol

Following a procedure similar to that described in Preparation 1(b), but using 2.33 g of 4'-(4-fluorophenyl) acetophenone oxime O-2 -(tetrahydropyran-2-yloxy)ethyl ether [prepared as described in step (a) above] and 0.12 g of p-toluenesulfonic acid monohydrate, 1.42 g of the title compound, melting at 133°–134° C., were obtained.

$^1$H Nuclear Magnetic Resonance Spectrum (CDCl$_3$, 270 MHz, using tetramethylsilane as the internal standard), δ ppm:

2.30 (3H, singlet);
2.57 (1H, triplet, J=5.5 Hz);
3.94–3.99 (2H, multiplet);
4.33–4.36 (2H, multiplet);
7.14 (2H, triplet, J=8.5 Hz);
7.53–7.59 (4H, multiplet);
7.70 (2H, doublet, J=8.5 Hz).

PREPARATION 28

2-[1-(4'-Trifluoromethylbiphenyl-4-yl)ethylideneaminooxy]ethanol

28(a) 4'-(4-Trifluoromethylphenyl)acetophenone oxime O-2-(tetrahydropyran-2-yloxy)ethyl ether Following a procedure similar to that described in Preparation 1(a) (except that the time required for the reaction was 24 hours), but using 1.50 g of 2-(2-bromoethoxy) tetrahydropyran, 800 mg of 4'-(4-trifluoromethylphenyl) acetophenone oxime and 1.98 g of potassium carbonate, 1.16 g of the title compound were obtained as a syrup.

28(b) 2-|1-(4'-Trifluoromethylbiphenyl-4-yl) ethylideneaminooxy|ethanol

Following a procedure similar to that described in Preparation 1(b), but using 1.16 g of 4'-(4-trifluoromethylphenyl) acetophenone oxime O-2-(tetrahydropyran-2-yloxy)ethyl ether |prepared as described in step (a) above| and 55 mg of p-toluenesulfonic acid monohydrate, 772 mg of the title compound, melting at 108°–111° C., were obtained.

$^1$H Nuclear Magnetic Resonance Spectrum (CDCl$_3$, 270 MHz, using tetramethylsilane as the internal standard). δ ppm:

2.31 (3H, singlet);
2.52 (1H, triplet, J=6 Hz);
3.94–3.97 (2H, multiplet);
4.33–4.37 (2H, multiplet);
7.61 (2H, doublet, J=8.5 Hz);
7.70 (4H, singlet);
7.74 (2H, doublet, J=8.5 Hz).

PREPARATION 29

2-|1-(4-Ethoxyphenyl)ethylideneaminooxy|ethanol

29(a) 4'-Ethoxyacetophenone oxime O-2-(tetrahydropyran-2-yloxy)ethyl ether

Following a procedure similar to that described in Preparation 1(a) (except that the time required for the reaction was 20 hours), but using 6.42 g of 2-(2-bromoethxoy) tetrahydropyran, 2.20 g of 4'-ethoxyacetophenone oxime and 8.48 g of potassium carbonate, 3.77 g of the title compound were obtained as a syrup.

29(b) 2-|1-(4-Ethoxyphenyl)ethylideneaminooxy|ethanol

Following a procedure similar to that described in Preparation 1(b), but using 3.77 g of 4'-ethoxyacetophenone oxime O-2-(tetrahydropyran-2-yloxy)ethyl ether [prepared as described in step (a) above] and 0.23 g of p-toluenesulfonic acid monohydrate, 1.88 g of the title compound, melting at 51°–54° C., were obtained.

$^1$H Nuclear Magnetic Resonance Spectrum (CDCl$_3$, 270 MHz, using tetramethylsilane as the internal standard). δ ppm:

1.42 (3H, triplet, J=7 Hz);
2.24 (3H, singlet);
2.69 (1H, triplet, J=5.5 Hz);
3.91–3.95 (2H, multiplet);
4.05 (2H, quartet, J=7 Hz);
4.28–4.31 (2H, multiplet);
6.88 (2H, doublet, J=9 Hz);
7.56 (2H, doublet, J=9 Hz).

PREPARATION 30

2-|1-(3',4'-Methylenedioxybiphenyl-4-yl) ethylideneaminooxy|ethanol

30(a) 3',4'-Methylenedioxyacetophenone oxime O-2-(tetrahydropyran-2-yloxy)ethyl ether Following a procedure similar to that described in Preparation 1(a) (except that the time required for the reaction was 6 hours), but using 1.75 g of 2-(2-bromoethoxy) tetrahydropyran, 0.80 g of 3',4'-methylenedioxyacetophenone oxime and 3.40 g of potassium carbonate, 1.12 g of the title compound were obtained as a syrup.

30(b) 2-|1-(3',4'-Methylenedioxybiphenyl-4-yl) ethylideneaminooxy|ethanol

Following a procedure similar to that described in Preparation 1(b), but using 1.12 g of 3',4'-methylenedioxyacetophenone oxime O-2-(tetrahydropyran-2-yloxy)ethyl ether |prepared as described in step (a) above| and 0.03 g of p-toluenesulfonic acid monohydrate, 740 mg of the title compound, melting at 132°–134° C., were obtained.

$^1$H Nuclear Magnetic Resonance Spectrum (CDCl$_3$, 270 MHz, using tetramethylsilane as the internal standard). δ ppm:

2.29 (3H, singlet);
2.59 (1H, triplet, J=6 Hz);
3.94–3.98 (2H, multiplet);
4.32–4.35 (2H, multiplet);
6.01 (2H, singlet);
6.89 (1H, doublet, J=8.5 Hz);
7.07–7.09 (2H, multiplet);
7.52 (2H, doublet, J=8.5 Hz);
7.67 (2H, doublet, J=8.5 Hz).

PREPARATION 31

2-|1-(2-Methoxy-5-pyridyl)ethylideneaminooxy| ethanol

31(a) 5-Acetyl-2-methoxypyridine oxime O-2-(tetrahydropyran-2-yloxy)ethyl ether

Following a procedure similar to that described in Preparation 1(a) (except that the time required for the reaction was 20 hours), but using 1.01 g of 2-(2-bromoethoxy) tetrahydropyran, 321 mg of 5-acetyl-2-methoxypyridine oxime and 1.33 g of potassium carbonate, 560 mg of the title compound were obtained as a syrup.

31(b) 2-|1-(2-Methoxy-5-pyridyl)ethylideneaminooxy| ethanol

Following a procedure similar to that described in Preparation 1(b), but using 560 mg of 5-acetyl-2-methoxypyridine oxime O-2-(tetrahydropyran-2-yloxy)ethyl ether |prepared as described in step (a) above| and 398 mg of p-toluenesulfonic acid monohydrate, 346 mg of the title compound were obtained as a syrup.

$^1$H Nuclear Magnetic Resonance Spectrum (CDCl$_3$, 270 MHz, using tetramethylsilane as the internal standard). δ ppm:

2.25 (3H, singlet);
2.45 (1H, triplet, J=5.5 Hz);
3.92–3.96 (2H, multiplet);
3.96 (3H, singlet);
4.29–4.32 (2H, multiplet);
6.74 (1H, doublet, J=9 Hz);
7.90 (1H, doublet of doublets, J=2 & 9 Hz);
8.37 (1H, doublet, J=2 Hz).

PREPARATION 32

2-|1-(2-Isopropoxy-5-pyridyl)ethylideneaminooxy| ethanol

32(a) 5-Acetyl-2-isopropoxypyridine oxime O-2-(tetrahydropyran-2-yloxy)ethyl ether Following a procedure similar to that described in Preparation 1(a) (except that the time required for the reaction was 15 hours), but using 3.23 g of 2-(2-bromoethoxy) tetrahydropyran, 1.20 g of 5-acetyl-2-isopropoxypyridine oxime and 4.27 g of potassium carbonate, 1.99 g of the title compound were obtained as a syrup.

32(b) 2-|1-(2-Isopropoxy-5-pyridyl)ethylideneaminooxy| ethanol

Following a procedure similar to that described in Preparation 1(b), but using 1.99 g of 5-acetyl-2-isopropoxypyridine oxime O-2-(tetrahydropyran-2-yloxy) ethyl ether |prepared as described in step (a) above| and 1.29 g of p-toluenesulfonic acid monohydrate, 1.02 g of the title compound were obtained as a syrup.

$^1$H Nuclear Magnetic Resonance Spectrum (CDCl$_3$, 270 MHz, using tetramethylsilane as the internal standard), δ ppm:

1.35 (6H, doublet, J=6 Hz);
2.24 (3H, singlet);
2.48 (1H, triplet, J=6 Hz);
3.91–3.96 (2H, multiplet);
4.28–4.32 (2H, multiplet);
5.32 (1H, septet, J=6 Hz);
6.67 (1H, doublet, J=9 Hz);
7.87 (1H, doublet of doublets, J=2.5 & 9 Hz);
8.35 (1H, doublet, J=2.5 Hz).

PREPARATION 33

2-|1-(2-Phenylsulfonyl-5-pyridyl) ethylideneaminooxy|ethanol

33(a) 5-Acetyl-2-(phenylsulfonyl)pyridine oxime O-2-(tetrahydropyan-2-yloxy)ethyl ether Following a procedure similar to that described in Preparation 1(a), but using 1.60 g of 2-(2-bromoethoxy) tetrahydropyran, 0.80 g of 5-acetyl-2-(phenylsulfonyl) pyridine oxime and 3.20 g of potassium carbonate, 0.97 g of the title compound was obtained as a syrup.

33(b) 2-|1-(2-Phenylsulfonyl-5-pyridyl) ethylideneaminooxy|ethanol

Following a procedure similar to that described in Preparation 1(b), but using 0.97 g of 5-acetyl-2-(phenylsulfonyl) pyridine oxime O-2-(tetrahydropyran-2-yloxy)ethyl ether |prepared as described in step (a) above| and 0.40 g of 2-toluenesulfonic acid monohydrate, 0.72 g of the title compound, melting at 77°–78° C., was obtained.

$^1$H Nuclear Magnetic Resonance Spectrum (CDCl$_3$, 270 MHz, using tetramethylsilane as the internal standard), δ ppm:

2.01 (1H, triplet, J=6 Hz);
2.27 (3H, singlet);
3.91–3.95 (2H, multiplet);
4.34–4.36 (2H, multiplet);
7.52–7.56 (2H, multiplet);
7.60–7.64 (1H, multiplet);
8.06–8.08 (2H, multiplet);
8.13 (1H, doublet of doublets, J=2 & 8.5 Hz);
8.19 (1H, doublet, J=8.5 Hz);
8.91 (1H, doublet, J=2 Hz).

PREPARATION 34

2-(1-{2-|N-(4-Methylphenylsulfonyl)-N-methylamino|pyridin-5-yl}ethylideneaminooxy) ethanol 34(a) 5-Acetyl-2-[N-(4-methylphenylsulfonyl)-N-methylamino|pyridine oxime O-2- (tetrahydropyran-2-yloxy)ethyl ether Following a procedure similar to that described in Preparation 1(a) (except that the time required for the reaction was 14 hours), but using 2.61 g of 2-(2-bromoethoxy) tetrahydropyran, 1.50 g of 5-acetyl-2-|N-(4-methylphenylsulfonyl)-N-methylamino|pyridine oxime and 5.20 g of potassium carbonate, 1.93 g of the title compound were obtained as a syrup.

34(b) 2-(1-{2-|N-(4-Methylphenylsulfonyl)-N-methylamino|pyridin-5-yl}ethylideneaminooxy)ethanol Following a procedure similar to that described in Preparation 1(b), but using 1.22 g of 5-acetyl-2-|N-(4-methylphenylsulfonyl)-N-methylamino|pyridine oxime O-2-(tetrahydropyran-2 -yloxy)ethyl ether |prepared as described in step (a) above| and 1.00 g of p-toluenesulfonic acid monohydrate, 1.22 g of the title compound were obtained as a syrup.

$^1$H Nuclear Magnetic Resonance Spectrum (CDCl$_3$, 270 MHz, using tetramethylsilane as the internal standard), δ ppm:

2.25 (3H, singlet);
2.39 (3H, singlet);
3.29 (3H, singlet);
3.91–3.96 (2H, multiplet);
4.31–4.34 (2H, multiplet);
7.23 (2H, doublet, J=8.5 Hz);
7.49 (2H, doublet, J=8.5 Hz);
7.72 (1H, doublet, J=8.5 Hz);
7.95 (1H, doublet of doublets, J=2.5 & 8.5 Hz);
8.51 (1H, doublet, J=2.5 Hz).

PREPARATION 35

2-|1-(4-Phenylsulfonlphenyl)ethylideneaminooxy| ethanol

35(a) 4'-(Phenylsulfonyl)acetophenone oxime O-2-(tetrahydropyran-2-yloxy)ethyl ether Following a procedure similar to that described in Preparation 1(a) (except that the time required for the reaction was 7 hours), but using 4.46 g of 2-(2-bromoethoxy) tetrahydropyran, 2.35 g of 4'-(phenylsulfonyl)acetophenone oxime and 5.90 g of potassium carbonate, 2.55 g of the title compound were obtained as a syrup.

35(b) 2-[1-(4-Phenylsulfonylphenyl)ethylideneaminooxy] ethanol

Following a procedure similar to that described in Preparation 1(b), but using 2.55 g of 4'-(phenylsulfonyl) acetophenone oxime O-2-(tetrahydropyran-2-yloxy)ethyl ether |prepared as described in step (a) above| and 0.20 g of p-toluenesulfonic acid monohydrate, 1.72 g of the title compound, melting at 87°–88° C., were obtained.

$^1$H Nuclear Magnetic Resonance Spectrum (CDCl$_3$, 270 MHz, using tetramethylsilane as the internal standard), δ ppm:

2.20 (1H, triplet, J=6 Hz);
2.25 (3H, singlet);
3.90–3.95 (2H, multiplet);
4.31–4.35 (2H, multiplet);
7.47–7.60 (3H, multiplet);
7.75 (2H, doublet, J=8.5 Hz);
7.92–7.98 (4H, multiplet).

PREPARATION 36

2-|1-(4-Phenylthiophenyl)ethylideneaminooxy| ethanol

36(a) 4'-(Phenylthio)acetophenone oxime O-2-(tetrahydropyran-2-yloxy)ethyl ether Following a procedure similar to that described in Preparation 1(a) (except that the time required for the reaction was 16 hours), but using 4.51 g of 2-(2-bromoethoxy) tetrahydropyran, 2.10 g of 4'-(phenylthio)acetophenone oxime and 5.96 g of potassium carbonate, 3.20 g of the title compound were obtained as a syrup.

36(b) 2-[1-(4-Phenylthiophenyl)ethylideneaminooxy] ethanol

Following a procedure similar to that described in Preparation 1(b), but using 3.20 g of 4'-(phenylthio)acetophenone oxime O-2-(tetrahyropyran-2-yloxy)ethyl ether [prepared as described in step (a) above] and 0.17 g of p-toluenesulfonic acid monohydrate, 1.69 g of the title compound, melting at 56° C., were obtained.

$^1$H Nuclear Magnetic Resonance Spectrum (CDCl$_3$, 270 MHz, using tetramethylsilane as the internal standard), δ ppm:

2.24 (3H, singlet);
3.91–3.96 (2H, multiplet);
4.29–4.32 (2H, multiplet);
7.26–7.41 (7H, multiplet);
7.54 (2H, doublet, J=8.5 Hz).

PREPARATION 37

2-(1-{4-[N-(Phenylsulfonyl)-N-methylamino] phenyl}ethylideneaminooxy)ethanol

37(a) 4'-[(N-Phenylsulfonyl)-N-methylamino]acetophenone oxime O-2-(tetrahydropyran-2-yloxy)ethyl ether Following a procedure similar to that described in Preparation 1(a) (except that the time required for the reaction was 16 hours), but using 2.78 g of 2-(2-bromoethoxy) tetrahydropyran, 1.62 g of 4'-[(N-phenylsulfonyl)-N-methylamino]acetophenone oxime and 2.20 g of potassium carbonate, 2.15 g of the title compound were obtained as a syrup.

37(b) 2-(1-{4-[N-(Phenylsulfonyl)-N-methylamino] phenyl}ethylideneaminooxy)ethanol Following a procedure similar to that described in Preparation 1(b), but using 2.15 g of 4'-[(N-phenylsulfonyl)-N-methylamino]acetophenone oxime O-2-(tetrahydropyan-2-yloxy)ethyl ether [prepared as described in step (a) above] and 0.30 g of p-toluenesulfonic acid monohydrate, 1.50 g of the title compound, melting at 76°–77° C., were obtained.

$^1$H Nuclear Magnetic Resonance Spectrum (CDCl$_3$, 270 MHz, using tetramethylsilane as the internal standard), δ ppm:

2.26 (3H, singlet);
3.18 (3H, singlet);
3.91–3.97 (2H, multiplet);
4.30–4.34 (2H, multiplet);
7.11 (2H, doublet, J=8.5 Hz);
7.46 (2H, triplet, J=8 Hz);
7.55–7.59 (5H, multiplet).

PREPARATION 38

2-[1-(4-Biphenylyl)propylideneaminooxy]ethanol

38(a) 4-Propionylbiphenyl oxime O-2-(tetrahydropyran-2-yloxy)ethyl ether

Following a procedure similar to that described in Preparation 1(a) (except that the time required for the reaction was 24 hours), but using 3.25 g of 2-(2-bromoethoxy) tetrahydropyran, 1.40 g of 4-propionylbiphenyl oxime and 2.57 g of potassium carbonate, 2.20 g of the title compound were obtained as a syrup.

38(b) 2-[1-(4-Biphenylyl)propylideneaminooxy]ethanol

Following a procedure similar to that described in Preparation 1(b), but using 2.20 g of 4-propionylbiphenyl oxime O-2-(tetrahydropyran-2-yloxy)ethyl ether [prepared as described in step (a) above] and 0.15 g of p-toluenesulfonic acid monohydrate, 0.77 g of the title compound, melting at 76° C., was obtained.

$^1$H Nuclear Magnetic Resonance Spectrum (CDCl$_3$, 270 MHz, using tetramethylsilane as the internal standard), δ ppm:

1.19 (3H, triplet, J=7.5 Hz);
2.59 (1H, triplet, J=6 Hz);
2.82 (2H, quartet, J=7.5 Hz);
3.93–3.98 (2H, multiplet);
4.31–4.34 (2H, multiplet);
7.36 (1H, triplet, J=7 Hz);
7.45 (2H, triplet, J=7 Hz);
7.61 (4H, doublet, J=8 Hz);
7.70 (2H, doublet, J=8.5 Hz).

PREPARATION 39

2-[1-(5-Phenyl-2-pyridyl)ethylideneaminooxy] ethanol

39(a) 2-Acetyl-5-phenylpyridine oxime O-2-(tetrahydropyran-2-yloxy)ethyl ether

Following a procedure similar to that described in Preparation 1(a) (except that the time required for the reaction was 16 hours), but using 4.29 g of 2-(2-bromoethoxy) tetrahydropyran, 1.74 g of 2-acetyl-5-phenylpyridine oxime and 2.27 g of potassium carbonate, 2.21 g of the title compound were obtained as a syrup.

39(b) 2-[1-(5-Phenyl-2-pyridyl)ethylideneaminooxy] ethanol

Following a procedure similar to that described in Preparation 1(b), but using 2.21 g of 2-acetyl-5-phenylpyridine oxime O-2-(tetrahydropyran-2-yloxy)ethyl ether [prepared as described in step (a) above] and 1.23 g of p-toluenesulfonic acid monohydrate, 1.41 g of the title compound, melting at 66°–68° C., were obtained.

$^1$H Nuclear Magnetic Resonance Spectrum (CDCl$_3$, 270 MHz, using tetramethylsilane as the internal standard), δ ppm:

2.41 (3H, singlet);
2.46 (1H, triplet, J=6 Hz);
3.95–4.00 (2H, multiplet);
4.37–4.40 (2H, multiplet);
7.39–7.52 (3H, multiplet);
7.61 (2H, doublet of doublets, J=1.5 & 8.5 Hz);
7.85–7.92 (2H, multiplet);
8.84 (1H, doublet, J=2 Hz).

FORMULATION 1

Capsules

The following powders were thoroughly mixed:

| | |
|---|---|
| Compound of Example 21(b) | 10 mg |
| Lactose | 110 mg |
| Corn starch | 58 mg |
| Magnesium stearate | 2 mg |
| | 180 mg |

The mixture was then filtered through a 60 mesh (Tyler standard) sieve. 180 mg of the mixture was weighed out and packed into a No. 3 gelatin capsule to prepare capsules.

FORMULATION 2

Tablets

The following powders were thoroughly mixed:

| | |
|---|---|
| Compound of Example 15 | 10 mg |
| Lactose | 85 mg |
| Corn starch | 34 mg |
| Microcrystalline cellulose | 20 mg |
| Magnesium stearate | 1 mg |
| | 150 mg |

The mixture was then compressed to form tablets, each weighing 150 mg. If desired, these tablets may be coated with sugar or a suitable film.

FORMULATION 3

Granules

The following powders were thoroughly mixed:

| | |
|---|---|
| Compound of Example 35 | 10 mg |
| Lactose | 839 mg |
| Corn starch | 150 mg |
| Hydroxypropyl cellulose | 1 mg |
| | 1000 mg |

The mixture was then moistened with purified water, granulated with a basket granulator and dried, to provide granules.

BIOLOGICAL ACTIVITY

The biological activity of the compounds of the present invention is illustrated by the following Experiments.

Experiment 1

Hypoglycemic activity

The test animals used were hyperglycemic male mice of the KK strain, each having a body weight of at least 40 g. The compounds under test were mixed with a 1:1 by volume mixture of polyethylene glycol 400 and a 0.5% w/v solution of carboxymethylcellulose in physiological saline. Each animal was orally administered a test compound in an amount of 1 mg/kg and then allowed to feed freely for 18 hours. At the end of this time, blood was collected from the tail veins without anesthesia. The blood glucose level (BGL) was determined by means of a glucose analyzer (GL-101, manufactured by Mitsubishi Chemical Industries, Ltd.).

The hypoglycemic effect was calculated by the following equation:

Hypoglycemic effect (%)=|($BGL_s$-$BGL_t$)/$BGL_s$|×100 where:

$BGL_s$ is the blood glucose level in the group administered a solvent only, but no active compound; and $BGL_t$ is the blood glucose level in the group administered a test compound.

The results are shown in the following Table 27, in which each compound of the present invention is identified by the number of one of the following Examples in which its preparation is illustrated.

TABLE 27

| Cpd. of Example No. | Hypoglycemic effect (%) |
|---|---|
| 2 | 22.1 |
| 5 | 20.8 |
| 8 | 25.1 |
| 9 | 27.0 |
| 14 | 19.3 |
| 15 | 26.7 |
| 18 | 23.5 |
| 19 | 28.7 |
| 21 | 16.6 |
| 23 | 16.5 |
| 26 | 27.0 |
| 31 | 49.3* |
| 32 | 42.2 |
| 33 | 19.2 |
| 35 | 25.0 |
| 36 | 43.2 |
| 37 | 15.5 |
| 38 | 27.7 |
| 40 | 27.0 |
| 47 | 18.7 |
| 48 | 17.9 |
| 50 | 38.1 |
| 51 | 26.4* |
| 55 | 34.1 |

*: This value is the hypoglycemic effect 3 hours after administration of the test compound.

As is apparent from Table 27, the compounds of the present invention exhibited excellent activity.

We claim:

1. A compound of formula (I):

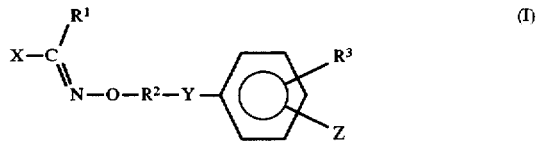

wherein:

$R^1$ represents a hydrogen atom or an alkyl group having from 1 to 6 carbon atoms;

$R^2$ represents an alkylene group having from 2 to 6 carbon atoms;

$R^3$ represents a hydrogen atom, an alkyl group having from 1 to 6 carbon atoms, an alkoxy group having from 1 to 4 carbon atoms, an alkylthio group having from 1 to 4 carbon atoms, a halogen atom, a nitro group, an amino group, a monoalkylamino group having from 1 to 4 carbon atoms, a dialkylamino group whose alkyl groups are the same or different and each has from 1 to 4 carbon atoms, an aryl group having from 6 to 10 carbon atoms in a carbocyclic ring which is unsubstituted or is substituted by at least one of the following substituents α, or an aralkyl group in which an alkyl group having from 1 to 4 carbon atoms is substituted by an aryl group as defined above;

X represents an aryl group having from 6 to 10 carbon atoms in a carbocyclic ring which is unsubstituted or is substituted by at least one of the following substituents α, said substituents α are selected from the group consisting of:

alkyl groups having from 1 to 6 carbon atoms;

halogenated alkyl groups having from 1 to 4 carbon atoms;

hydroxy groups;

acyloxy groups having from 1 to 4 carbon atoms;

alkoxy groups having from 1 to 4 carbon atoms;

alkylenedioxy groups having from 1 to 4 carbon atoms;

aralkyloxy groups in which an alkoxy group having from 1 to 4 carbon atoms is substituted by an aryl group having from 6 to 10 carbon atoms in a carbocyclic ring which is unsubstituted or is substituted by at least one of the following substituents β;

alkylthio groups having from 1 to 4 carbon atoms;

alkylsulfonyl groups having from 1 to 4 carbon atoms;

halogen atoms;

nitro groups;

amino groups;

monoalkylamino groups having from 1 to 4 carbon atoms;

dialkylamino groups, whose alkyl groups are the same or different and each is an alkyl group having from 1 to 4 carbon atoms;

aralkyl groups in which an alkyl group having from 1 to 4 carbon atoms is substituted by an aryl group having from 6 to 10 carbon atoms in a carbocyclic ring which is unsubstituted or is substituted by at least one of the following substituents β;

aryl groups having from 6 to 10 carbon atoms in a carbocyclic ring which is unsubstituted or is substituted by at least one of the following substituents β;

aryloxy groups in which the aryl part has from 6 to 10 carbon atoms in a carbocyclic ring which is unsubstituted or is substituted by at least one of the following substituents β;

arylthio groups in which the aryl part has from 6 to 10 carbon atoms in a carbocyclic ring which is unsubstituted or is substituted by at least one of the following substituents β;

arylsulfonyl groups in which the aryl part has from 6 to 10 carbon atoms in a carbocyclic ring which is unsubstituted or is substituted by at least one of the following substituents β;

arylsulfonylamino groups in which the aryl part has from 6 to 10 carbon atoms in a carbocyclic ring which is unsubstituted or is substituted by at least one of the following substituents β, and in which the nitrogen atom is unsubstituted or is substituted by an alkyl group having from 1 to 6 carbon atoms;

said substituents β are selected from the group consisting of alkyl groups having from 1 to 6 carbon atoms, halogenated alkyl groups having from 1 to 4 carbon atoms, alkoxy groups having from 1 to 4 carbon atoms, halogen atoms, and alkylenedioxy groups having from 1 to 4 carbon atoms;

Y represents an oxygen atom, a sulfur atom or a group of formula >N—R⁴, in which R⁴ represents a hydrogen atom, an alkyl group having from 1 to 6 carbon atoms or an acyl group having from 1 to 8 carbon atoms; and Z represents a group of formula (Za), (Zb), (Zc) or (Zd):

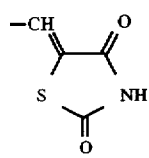 (Za)

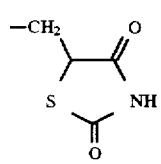 (Zb)

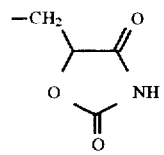 (Zc)

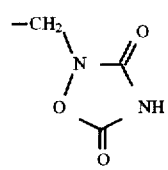 (Zd)

and salts thereof.

2. The compound of claim 1, wherein $R^1$ represents a hydrogen atom or an alkyl group having from 1 to 4 carbon atoms.

3. The compound of claim 1, wherein $R^1$ represents a hydrogen atom or an alkyl group having from 1 to 3 carbon atoms.

4. The compound of claim 1, wherein $R^1$ represents a hydrogen atom, a methyl or ethyl group.

5. The compound of claim 1, wherein $R^1$ represents a methyl or ethyl group.

6. The compound of claim 1, wherein $R^2$ represents an alkylene group having from 2 to 5 carbon atoms.

7. The compound of claim 1, wherein $R^2$ represents an alkylene group having 2 or 3 carbon atoms.

8. The compound of claim 1, wherein $R^2$ represents an ethylene, trimethylene or methylethylene group.

9. The compound of claim 1, wherein $R^2$ represents an ethylene group.

10. The compound of claim 1, wherein $R^3$ represents a hydrogen atom, an alkyl group having from 1 to 4 carbon atoms, an alkoxy group having 1 or 2 carbon atoms, an alkylthio group having 1 or 2 carbon atoms or a halogen atom.

11. The compound of claim 1, wherein $R^3$ represents a hydrogen atom.

12. The compound of claim 1, wherein X represents: an aryl group, which has from 6 to 10 ring carbon atoms and is unsubstituted or is substituted by from 1 to 3 substituents selected from the group consisting of substituents $\alpha^1$, defined below;

said substituents $\alpha^1$ being selected from the group consisting of:

alkyl groups having from 1 to 6 carbon atoms, halogenated alkyl groups having from 1 to 4 carbon atoms, hydroxy groups, acyloxy groups having from 1 to 4 carbon atoms, alkoxy groups having from 1 to 4 carbon atoms, alkylenedioxy groups having from 1 to 4 carbon atoms, aralkyloxy groups having a total of from 7 to 12 carbon atoms, alkylthio groups having from 1 to 4 carbon atoms, alkylsulfonyl groups having from 1 to 4 carbon atoms, halogen atoms, aralkyl groups having a total of from 7 to 12 carbon atoms, phenyl groups which are unsubstituted or are substituted by from 1 to 3 of substituents $\beta^1$, defined below, phenoxy groups which are unsubstituted or are substituted by from 1 to 3 of substituents $\beta^1$, defined below, phenylthio groups which are unsubstituted or are substituted by from 1 to 3 of substituents $\beta^1$, defined below, phenylsulfonyl groups which are unsubstituted or are substituted by from 1 to 3 of substituents $\beta^1$, defined below, phenylsulfonylamino groups in which the phenyl group is unsubstituted or is substituted by from 1 to 3 of substituents $\beta^1$, defined below, and the nitrogen atom is unsubstituted or is substituted by an alkyl group having from 1 to 6 carbon atoms, said substituents $\beta^1$ being selected from the group consisting of alkyl groups having from 1 to 6 carbon atoms, halogenated alkyl groups having from 1 to 4 carbon atoms, alkoxy groups having from 1 to 4 carbon atoms, halogen atoms and alkylenedioxy groups having from 1 to 4 carbon atoms.

13. The compound of claim 1, wherein X represents: an aryl group, which has from 6 to 10 ring carbon atoms and is unsubstituted or is substituted by from 1 to 3 substituents selected from the group consisting of substituents $\alpha^2$, defined below;

said substituents $\alpha^2$ being selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, alkylenedioxy groups having from 1 to 4 carbon atoms, aralkyloxy groups having a total of from 7 to 12 carbon atoms, alkylthio groups having from 1 to 4 carbon atoms, alkylsulfonyl groups having from 1 to 4 carbon atoms, fluorine atoms, chlorine atoms and bromine atoms, aralkyl groups having a total of from 7 to 12 carbon atoms, phenyl groups which are unsubstituted or are substituted by from 1 to 3 of substituents $\beta^1$, defined below, phenoxy groups which are unsubstituted or are substituted by from 1 to 3 of substituents $\beta^1$, defined below, phenylthio groups which are unsubstituted or are substituted by from 1 to 3 of substituents $\beta^1$, defined below, phenylsulfonyl groups which are unsubstituted or are substituted by from 1 to 3 of substituents $\beta^1$, defined below, phenylsulfonylamino groups in which the phenyl group is unsubstituted or is substituted by from 1 to 3 of substituents $\beta^1$, defined below, and the nitrogen atom is unsubstituted or is substituted by an alkyl group having from 1 to 6 carbon atoms, said substituents $\beta^1$ being selected from the group consisting of alkyl groups having from 1 to 6 carbon atoms, halogenated alkyl groups having from 1 to 4 carbon atoms, alkoxy groups having from 1 to 4 carbon atoms, halogen atoms and alkylenedioxy groups having from 1 to 4 carbon atoms.

14. The compound of claim 1, wherein X represents a phenyl or naphthyl group, each of which is unsubstituted or is substituted by from 1 to 3 substituents selected from the group consisting of substituents $\alpha^3$, defined below;

said substituents $\alpha^3$ are selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, the methylenedioxy group, aralkyloxy groups having a total of from 7 to 12 carbon atoms, alkylthio groups having from 1 to 4 carbon atoms, alkylsulfonyl groups having from 1 to 4 carbon atoms, fluorine, chlorine and bromine atoms, aralkyl groups having a total of from 7 to 12 carbon atoms, phenyl groups which are unsubstituted or are substituted by from 1 to 3 of substituents $\beta^2$, defined below, phenoxy groups which are unsubstituted or are substituted by from 1 to 3 of substituents $\beta^2$, defined below, phenylthio groups which are unsubstituted or are substituted by from 1 to 3 of substituents $\beta^2$, defined below, phenylsulfonyl groups which are unsubstituted or are substituted by from 1 to 3 of substituents $\beta^2$, defined below, phenylsulfonylamino groups in which the phenyl group is unsubstituted or is substituted by from 1 to 3 of substituents $\beta^2$, defined below, and the nitrogen atom is unsubstituted or is substituted by an alkyl group having from 1 to 6 carbon atoms, said substituents $\beta^2$ are selected from the group consisting of methyl groups, trifluoromethyl groups, methoxy groups, fluorine atoms and methylenedioxy groups.

15. The compound of claim 1, wherein X represents a phenyl or naphthyl group, each of which is unsubstituted or is substituted by from 1 to 3 substituents selected from the group consisting of substituents $\alpha^4$, defined below;

said substituents $\alpha^4$ are selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, methylenedioxy, benzyloxy, phenethyloxy and naphthylmethyloxy groups, alkylthio groups having from 1 to 4 carbon atoms, alkylsulfonyl groups having from 1 to 4 carbon atoms, fluorine, chlorine and bromine atoms, the benzyl group, phenyl groups which are unsubstituted or are substituted by from 1 to 3 of substituents $\beta^2$, defined below, phenoxy groups which are unsubstituted or are substituted by from 1 to 3 of substituents $\beta^2$, defined below, the phenylthio, phenylsulfonyl, phenylsulfonylamino, and N-methylphenylsulfonylamino groups.

16. The compound of claim 1, wherein X represents a phenyl or naphthyl group, each of which is unsubstituted or is substituted by from 1 to 3 substituents selected from the group consisting of substituents $\alpha^5$, defined below;

said substituents $\alpha^5$ are selected from the group consisting of:

alkyl groups having from 1 to 3 carbon atoms,
the trifluoromethyl, difluoromethyl, fluoromethyl, hydroxy, formyloxy and acetoxy groups,
alkoxy groups having from 1 to 3 carbon atoms,
the methylenedioxy, benzyloxy, methylthio, ethylthio, methylsulfonyl and ethylsulfonyl groups,
the fluorine, chlorine and bromine atoms, and
the benzyl, phenyl 4-methylphenyl 4-trifluoromethylphenyl, 4-methoxyphenyl, 4-fluorophenyl, 3,4-methylenedioxyphenyl, phenoxy, phenylthio, phenylsulfonyl, phenylsulfonylamino or N-methylphenylsulfonylamino groups.

17. The compound of claim 1, wherein X represents a phenyl or naphthyl group, each of which is unsubstituted or is substituted by from 1 to 3 substituents selected from the group consisting of substituents $\alpha^6$, defined below;

said substituents $\alpha^6$ are selected from the group consisting of: methyl, ethyl, isopropyl, trifluoromethyl, hydroxy, acetoxy, methoxy, ethoxy, isopropoxy, methylenedioxy, benzyloxy, methylthio, ethylthio, methylsulfonyl, ethylsulfonyl, benzyl, phenyl, phenoxy, phenylthio, phenylsulfonyl, phenylsulfonylamino, N-methylphenylsulfonylamino groups, and chlorine atoms.

18. The compound of claim 1, wherein X represents a phenyl group which is unsubstituted or is substituted by from 1 to 3 substituents selected from the group consisting of substituents $\alpha^7$, defined below;

said substituents $\alpha^7$ are selected from the group consisting of: methyl, hydroxy, acetoxy, benzyl, phenyl, phenoxy, phenylthio, phenylsulfonyl, phenylsulfonylamino, N-methylphenylsulfonylamino groups, and chlorine atoms.

19. The compound of claim 1, wherein Y represents an oxygen atom, a sulfur atom or a group of formula >N—R$^4$, in which R$^4$ represents a hydrogen atom, an alkyl group having from 1 to 3 carbon atoms or an alkanoyl group having from 2 to 5 carbon atoms.

20. The compound of claim 1, wherein Y represents an oxygen atom.

21. The compound of claim 1, wherein Z represents a 2,4-dioxothiazolidin-5-ylmethyl, 2,4-dioxooxazolidin-5-ylmethyl or 3,5-dioxooxadiazolidin-2 -ylmethyl group.

22. The compound of claim 1, wherein Z represents a 2,4-dioxothiazolidin-5-ylmethyl or 2,4-dioxooxazolidin-5-ylmethyl group.

23. The compound of claim 1, wherein Z represents a 2,4-dioxothiazolidin-5-ylmethyl group.

24. The compound of claim 1, wherein:

R$^1$ represents a hydrogen atom or an alkyl group having from 1 to 4 carbon atoms;

R$^2$ represents an alkylene group having from 2 to 5 carbon atoms;

R$^3$ represents a hydrogen atom, an alkyl group having from 1 to 4 carbon atoms, an alkoxy group having 1 or 2 carbon atoms, an alkylthio group having 1 or 2 carbon atoms or a halogen atom;

X represents: an aryl group, which has from 6 to 10 ring carbon atoms and is unsubstituted or is substituted by from 1 to 3 substituents selected from the group consisting of substituents $\alpha^1$, defined below;

said substituents $\alpha^1$ being selected from the group consisting of:

alkyl groups having from 1 to 6 carbon atoms,
halogenated alkyl groups having from 1 to 4 carbon atoms,
hydroxy groups,
acyloxy groups having from 1 to 4 carbon atoms,
alkoxy groups having from 1 to 4 carbon atoms,
alkylenedioxy groups having from 1 to 4 carbon atoms,
aralkyloxy groups having a total of from 7 to 12 carbon atoms,
alkylthio groups having from 1 to 4 carbon atoms,
alkylsulfonyl groups having from 1 to 4 carbon atoms,
halogen atoms,
aralkyl groups having a total of from 7 to 12 carbon atoms,
phenyl groups which are unsubstituted or are substituted by from 1 to 3 of substituents $\beta^1$, defined below,
phenoxy groups which are unsubstituted or are substituted by from 1 to 3 of substituents $\beta^1$, defined below,
phenylthio groups which are unsubstituted or are substituted by from 1 to 3 of substituents $\beta^1$, defined below,
phenylsulfonyl groups which are unsubstituted or are substituted by from 1 to 3 of substituents $\beta^1$, defined below,
phenylsulfonylamino groups in which the phenyl group is unsubstituted or is substituted by from 1 to 3 of substituents $\beta^1$, defined below, and the nitrogen atom is unsubstituted or is substituted by an alkyl group having from 1 to 6 carbon atoms,
said substituents $\beta^1$ being selected from the group consisting of alkyl groups having from 1 to 6 carbon atoms, halogenated alkyl groups having from 1 to 4 carbon atoms, alkoxy groups having from 1 to 4 carbon atoms, halogen atoms and alkylenedioxy groups having from 1 to 4 carbon atoms;

Y represents an oxygen atom, a sulfur atom or a group of formula >N—R$^4$, in which R$^4$ represents a hydrogen atom, an alkyl group having from 1 to 3 carbon atoms or an alkanoyl group having from 2 to 5 carbon atoms; and Z represents a 2,4-dioxothiazolidin-5-ylmethyl, 2,4-dioxooxazolidin-5-ylmethyl or 3,5-dioxooxadiazolidin-2-ylmethyl group.

25. The compound of claim 1, wherein:

R$^1$ represents a hydrogen atom or an alkyl group having from 1 to 4 carbon atoms;

R$^2$ represents an alkylene group having from 2 to 5 carbon atoms;

R$^3$ represents a hydrogen atom;

X represents: an aryl group, which has from 6 to 10 ring carbon atoms and is unsubstituted or is substituted by from 1 to 3 substituents selected from the group consisting of substituents $\alpha^2$, defined below;

said substituents $\alpha^2$ being selected from the group consisting of:

alkyl groups having from 1 to 6 carbon atoms,
halogenated alkyl groups having from 1 to 4 carbon atoms,
hydroxy groups,
alkanoyloxy groups having from 1 to 4 carbon atoms,
alkoxy groups having from 1 to 4 carbon atoms,
alkylenedioxy groups having from 1 to 4 carbon atoms,
aralkyloxy groups having a total of from 7 to 12 carbon atoms,
alkylthio groups having from 1 to 4 carbon atoms,
alkylsulfonyl groups having from 1 to 4 carbon atoms,
fluorine atoms, chlorine atoms and bromine atoms,
aralkyl groups having a total of from 7 to 12 carbon atoms, phenyl groups which are unsubstituted or are substituted by from 1 to 3 of substituents $\beta^1$, defined below, phenoxy groups which are unsubstituted or are substituted by from 1 to 3 of substituents $\beta^1$, defined below, phenylthio groups which are unsubstituted or are substituted by from 1 to 3 of substituents $\beta^1$, defined below, phenylsulfonyl groups which are unsubstituted or are substituted by from 1 to 3 of substituents $\beta^1$, defined below, phenylsulfonylamino groups in which the phenyl group is unsubstituted or is substituted by from 1 to 3 of substituents $\beta^1$, defined below, and the nitrogen atom is unsubstituted or is substituted by an alkyl group having from 1 to 6 carbon atoms, said substituents $\beta^1$ being selected from the group consisting of alkyl groups having from 1 to 6 carbon atoms, halogenated alkyl groups having from 1 to 4 carbon atoms, alkoxy groups having from 1 to 4 carbon atoms, halogen atoms and alkylenedioxy groups having from 1 to 4 carbon atoms;

Y represents an oxygen atom; and

Z represents a 2,4-dioxothiazolidin-5-ylmethyl or 2,4-dioxooxazolidin-5-ylmethyl group.

26. The compound of claim 1, wherein:

$R^1$ represents a hydrogen atom or an alkyl group having from 1 to 3 carbon atoms;

$R^2$ represents an alkylene group having 2 or 3 carbon atoms;

$R^3$ represents a hydrogen atom;

X represents a phenyl or naphthyl group, each of which is unsubstituted or is substituted by from 1 to 3 substituents selected from the group consisting of substituents $\alpha^3$, defined below;

said substituents $\alpha^3$ are selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, the methylenedioxy group, aralkyloxy groups having a total of from 7 to 12 carbon atoms, alkylthio groups having from 1 to 4 carbon atoms, alkylsulfonyl groups having from 1 to 4 carbon atoms, fluorine, chlorine and bromine atoms, aralkyl groups having a total of from 7 to 12 carbon atoms, phenyl groups which are unsubstituted or are substituted by from 1 to 3 of substituents $\beta^2$, defined below, phenoxy groups which are unsubstituted or are substituted by from 1 to 3 of substituents $\beta^2$, defined below, phenylthio groups which are unsubstituted or are substituted by from 1 to 3 of substituents $\beta^2$, defined below, phenylsulfonyl groups which are unsubstituted or are substituted by from 1 to 3 of substituents $\beta^2$, defined below, phenylsulfonylamino groups in which the phenyl group is unsubstituted or is substituted by from 1 to 3 of substituents $\beta^2$, defined below, and the nitrogen atom is unsubstituted or is substituted by an alkyl group having from 1 to 6 carbon atoms, said substituents $\beta^2$ are selected from the group consisting of methyl groups, trifluoromethyl groups, methoxy groups, fluorine atoms and methylenedioxy groups;

Y represents an oxygen atom; and

Z represents a 2,4-dioxothiazolidin-5-ylmethyl group.

27. The compound of claim 1, wherein:

$R^1$ represents a hydrogen atom, a methyl or ethyl group;

$R^2$ represents an ethylene, trimethylene or methylethylene group;

$R^3$ represents a hydrogen atom;

X represents a phenyl or naphthyl group, each of which is unsubstituted or is substituted by from 1 to 3 substituents selected from the group consisting of substituents $\alpha^4$, defined below;

said substituents $\alpha^4$ are selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, methylenedioxy, benzyloxy, phenethyloxy and naphthylmethyloxy groups, alkylthio groups having from 1 to 4 carbon atoms, alkylsulfonyl groups having from 1 to 4 carbon atoms, fluorine, chlorine and bromine atoms, the benzyl group, phenyl groups which are unsubstituted or are substituted by from 1 to 3 of substituents $\beta^2$, defined below, phenoxy groups which are unsubstituted or are substituted by from 1 to 3 of substituents $\beta^2$, defined below, the phenylthio, phenylsulfonyl phenylsulfonylamino and N-methylphenylsulfonylamino groups;

Y represents an oxygen atom; and

Z represents a 2,4-dioxothiazolidin-5-ylmethyl group.

28. The compound of claim 1, wherein:

$R^1$ represents a hydrogen atom, a methyl or ethyl group;

$R^2$ represents an ethylene, trimethylene or methylethylene group;

$R^3$ represents a hydrogen atom;

X represents a phenyl or naphthyl group, each of which is unsubstituted or is substituted by from 1 to 3 substituents selected from the group consisting of substituents $\alpha^5$, defined below;

said substituents $\alpha^5$ are selected from the group consisting of:

alkyl groups having from 1 to 3 carbon atoms, the trifluoromethyl, difluoromethyl, fluoromethyl, hydroxy, formyloxy and acetoxy groups, alkoxy groups having from 1 to 3 carbon atoms, the methylenedioxy, benzyloxy, methylthio, ethylthio, methylsulfonyl and ethylsulfonyl groups, the fluorine, chlorine and bromine atoms, and the benzyl, phenyl, 4-methylphenyl, 4-trifluoromethylphenyl, 4-methoxyphenyl, 4-fluorophenyl, 3,4-methylenedioxyphenyl, phenoxy, phenylthio, phenylsulfonyl, phenylsulfonylamino and/or N-methylphenylsulfonylamino groups;

Y represents an oxygen atom; and

Z represents a 2,4-dioxothiazolidin-5-ylmethyl group.

29. The compound of claim 1, wherein:

$R^1$ represents a hydrogen atom, a methyl or ethyl group;

$R^2$ represents an ethylene group;

$R^3$ represents a hydrogen atom;

X represents a phenyl or naphthyl group, each of which is unsubstituted or is substituted by from 1 to 3 substituents selected from the group consisting of substituents $\alpha^6$, defined below;

145 said substituents α⁶ are selected from the group consisting of: methyl, ethyl, isopropyl, trifluoromethyl, hydroxy, acetoxy, methoxy, ethoxy, isopropoxy, methylenedioxy, benzyloxy, methylthio, ethylthio, methylsulfonyl, ethylsulfonyl, benzyl, phenyl, phenoxy, phenylthio, phenylsulfonyl, phenylsulfonylamino and N-methylphenylsulfonylamino groups and chlorine atoms;

Y represents an oxygen atom; and

Z represents a 2,4-dioxothiazolidin-5-ylmethyl group.

30. The compound of claim 1, wherein:

$R^1$ represents a methyl or ethyl group;

$R^2$ represents an ethylene group;

$R^3$ represents a hydrogen atom;

X represents a phenyl group which is unsubstituted or is substituted by from 1 to 3 substituents selected from the group consisting of substituents α⁷, defined below;

said substituents α⁷ are selected from the group consisting of: methyl, hydroxy, acetoxy, benzyl, phenyl, phenoxy, phenylthio, phenylsulfonyl, phenylsulfonylamino and N-methylphenylsulfonylamino groups and chlorine atoms;

Y represents an oxygen atom; and

Z represents a 2,4-dioxothiazolidin-5-ylmethyl group.

31. The compound of claim 1, selected from the group consisting of 5-(4-{2-[1-(4-biphenylyl)ethylideneaminooxy]ethoxy}benzyl)thiazolidine-2,4-dione and pharmaceutically acceptable salts thereof.

32. The compound of claim 1, selected from the group consisting of 5-(4-{2-[1-(4-phenylsulfonylphenyl)ethylideneaminooxy]ethoxy}benzyl)thiazolidine-2,4-dione and pharmaceutically acceptable salts thereof.

33. A pharmaceutical composition for the treatment or prophylaxis of diabetes and hyperglycemia which composition comprises an effective amount of an active compound in admixture with a pharmaceutically acceptable carrier or diluent, wherein said active compound is selected from the group consisting of compounds of formula (I), as claimed in claim 1, and salts thereof.

34. The composition of claim 33, wherein:

$R^1$ represents a hydrogen atom or an alkyl group having from 1 to 4 carbon atoms;

$R^2$ represents an alkylene group having from 2 to 5 carbon atoms;

$R^3$ represents a hydrogen atom, an alkyl group having from 1 to 4 carbon atoms, an alkoxy group having 1 or 2 carbon atoms, an alkylthio group having 1 or 2 carbon atoms or a halogen atom;

X represents: an aryl group, which has from 6 to 10 ring carbon atoms and is unsubstituted or is substituted by from 1 to 3 substituents selected from the group consisting of substituents α¹, defined below;

said substituents α¹ being selected from the group consisting of:

alkyl groups having from 1 to 6 carbon atoms, halogenated alkyl groups having from 1 to 4 carbon atoms, hydroxy groups, acyloxy groups having from 1 to 4 carbon atoms, alkoxy groups having from 1 to 4 carbon atoms, alkylenedioxy groups having from 1 to 4 carbon atoms, aralkyloxy groups having a total of from 7 to 12 carbon atoms, alkylthio groups having from 1 to 4 carbon atoms, alkylsulfonyl groups having from 1 to 4 carbon atoms,

146 halogen atoms, aralkyl groups having a total of from 7 to 12 carbon atoms, phenyl groups which are unsubstituted or are substituted by from 1 to 3 of substituents β¹, defined below, phenoxy groups which are unsubstituted or are substituted by from 1 to 3 of substituents β¹, defined below, phenylthio groups which are unsubstituted or are substituted by from 1 to 3 of substituents β¹, defined below, phenylsulfonyl groups which are unsubstituted or are substituted by from 1 to 3 of substituents β¹, defined below, phenylsulfonylamino groups in which the phenyl group is unsubstituted or is substituted by from 1 to 3 of substituents β¹, defined below, and the nitrogen atom is unsubstituted or is substituted by an alkyl group having from 1 to 6 carbon atoms, said substituents β¹ being selected from the group consisting of alkyl groups having from 1 to 6 carbon atoms, halogenated alkyl groups having from 1 to 4 carbon atoms, alkoxy groups having from 1 to 4 carbon atoms, halogen atoms and alkylenedioxy groups having from 1 to 4 carbon atoms;

Y represents an oxygen atom, a sulfur atom or a group of formula >N—$R^4$, in which $R^4$ represents a hydrogen atom, an alkyl group having from 1 to 3 carbon atoms or an alkanoyl group having from 2 to 5 carbon atoms; and Z represents a 2,4-dioxothiazolidin-5-ylmethyl, 2,4-dioxooxazolidin-5-ylmethyl or 3,5-dioxooxadiazolidin-2-ylmethyl group.

35. The composition of claim 33, wherein:

$R^1$ represents a hydrogen atom or an alkyl group having from 1 to 4 carbon atoms;

$R^2$ represents an alkylene group having from 2 to 5 carbon atoms;

$R^3$ represents a hydrogen atom;

X represents: an aryl group, which has from 6 to 10 ring carbon atoms and is unsubstituted or is substituted by from 1 to 3 substituents selected from the group consisting of substituents α², defined below;

said substituents α² being selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, alkylenedioxy groups having from 1 to 4 carbon atoms, aralkyloxy groups having a total of from 7 to 12 carbon atoms, alkylthio groups having from 1 to 4 carbon atoms, alkylsulfonyl groups having from 1 to 4 carbon atoms, fluorine atoms, chlorine atoms and bromine atoms, aralkyl groups having a total of from 7 to 12 carbon atoms, phenyl groups which are unsubstituted or are substituted by from 1 to 3 of substituents β¹, defined below, phenoxy groups which are unsubstituted or are substituted by from 1 to 3 of substituents β¹, defined below, phenylthio groups which are unsubstituted or are substituted by from 1 to 3 of substituents β¹, defined below, phenylsulfonyl groups which are unsubstituted or are substituted by from 1 to 3 of substituents β¹, defined below,

147 phenylsulfonylamino groups in which the phenyl group is unsubstituted or is substituted by from 1 to 3 of substituents $\beta^1$, defined below, and the nitrogen atom is unsubstituted or is substituted by an alkyl group having from 1 to 6 carbon atoms, said substituents $\beta^1$ being selected from the group consisting of alkyl groups having from 1 to 6 carbon atoms, halogenated alkyl groups having from 1 to 4 carbon atoms, alkoxy groups having from 1 to 4 carbon atoms, halogen atoms and alkylenedioxy groups having from 1 to 4 carbon atoms;

Y represents an oxygen atom; and

Z represents a 2,4-dioxothiazolidin-5-ylmethyl or 2,4-dioxooxazolidin-5-ylmethyl group.

36. The composition of claim 33, wherein:

$R^1$ represents a hydrogen atom or an alkyl group having from 1 to 3 carbon atoms;

$R^2$ represents an alkylene group having 2 or 3 carbon atoms;

$R^3$ represents a hydrogen atom;

X represents a phenyl or naphthyl group, each of which is unsubstituted or is substituted by from 1 to 3 substituents selected from the group consisting of substituents $\alpha^3$, defined below;

said substituents $\alpha^3$ are selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, the methylenedioxy group, aralkyloxy groups having a total of from 7 to 12 carbon atoms, alkylthio groups having from 1 to 4 carbon atoms, alkylsulfonyl groups having from 1 to 4 carbon atoms, fluorine, chlorine and bromine atoms, aralkyl groups having a total of from 7 to 12 carbon atoms, phenyl groups which are unsubstituted or are substituted by from 1 to 3 of substituents $\beta^2$, defined below, phenoxy groups which are unsubstituted or are substituted by from 1 to 3 of substituents $\beta^2$, defined below, phenylthio groups which are unsubstituted or are substituted by from 1 to 3 of substituents $\beta^2$, defined below, phenylsulfonyl groups which are unsubstituted or are substituted by from 1 to 3 of substituents $\beta^2$, defined below, phenylsulfonylamino groups in which the phenyl group is unsubstituted or is substituted by from 1 to 3 of substituents $\beta^2$, defined below, and the nitrogen atom is unsubstituted or is substituted by an alkyl group having from 1 to 6 carbon atoms, said substituents $\beta^2$ are selected from the group consisting of methyl groups, trifluoromethyl groups, methoxy groups, fluorine atoms and methylenedioxy groups;

Y represents an oxygen atom; and

Z represents a 2,4-dioxothiazolidin-5-ylmethyl group.

37. The composition of claim 33, wherein:

$R^1$ represents a hydrogen atom, a methyl or ethyl group;

$R^2$ represents an ethylene, trimethylene or methylethylene group;

$R^3$ represents a hydrogen atom;

148

X represents a phenyl or naphthyl group, each of which is unsubstituted or is substituted by from 1 to 3 substituents selected from the group consisting of substituents $\alpha^4$, defined below:

said substituents $\alpha^4$ are selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, methylenedioxy, benzyloxy, phenethyloxy and naphthylmethyloxy groups, alkylthio groups having from 1 to 4 carbon atoms, alkylsulfonyl groups having from 1 to 4 carbon atoms, fluorine, chlorine and bromine atoms, the benzyl group, phenyl groups which are unsubstituted or are substituted by from 1 to 3 of substituents $\beta^2$, defined below, phenoxy groups which are unsubstituted or are substituted by from 1 to 3 of substituents $\beta^2$, defined below, the phenylthio phenylsulfonyl phenylsulfonylamino and N-methylphenylsulfonylamino groups;

Y represents an oxygen atom; and

Z represents a 2,4-dioxothiazolidin-5-ylmethyl group.

38. The composition of claim 33, wherein:

$R^1$ represents a hydrogen atom, a methyl or ethyl group;

$R^2$ represents an ethylene, trimethylene or methylethylene group;

$R^3$ represents a hydrogen atom;

X represents a phenyl or naphthyl group, each of which is unsubstituted or is substituted by from 1 to 3 substituents selected from the group consisting of substituents $\alpha^5$, defined below;

said substituents $\alpha^5$ are selected from the group consisting of:

alkyl groups having from 1 to 3 carbon atoms, the trifluoromethyl, difluoromethyl, fluoromethyl, hydroxy, formyloxy and acetoxy groups, alkoxy groups having from 1 to 3 carbon atoms, the methylenedioxy, benzyloxy, methylthio, ethylthio, methylsulfonyl and ethylsulfonyl groups, the fluorine, chlorine and bromine atoms, and the benzyl, phenyl, 4-methylphenyl, 4-trifluoromethylphenyl, 4-methoxyphenyl, 4-fluorophenyl, 3,4-methylenedioxyphenyl, phenoxy, phenylthio, phenylsulfonyl, phenylsulfonylamino and/or N-methylphenylsulfonylamino groups;

Y represents an oxygen atom; and

Z represents a 2,4-dioxothiazolidin-5-ylmethyl group.

39. The composition of claim 33, wherein:

$R^1$ represents a hydrogen atom, a methyl or ethyl group;

$R^2$ represents an ethylene group;

$R^3$ represents a hydrogen atom;

X represents a phenyl or naphthyl group, each of which is unsubstituted or is substituted by from 1 to 3 substituents selected from the group consisting of substituents $\alpha^6$, defined below;

said substituents $\alpha^6$ are selected from the group consisting of: methyl, ethyl, isopropyl, trifluoromethyl, hydroxy, acetoxy, methoxy, ethoxy, isopropoxy, methylenedioxy, benzyloxy, methylthio, ethylthio, methylsulfonyl, ethylsulfonyl, benzyl, phenyl, phenoxy, phenylthio,

149 phenylsulfonyl phenylsulfonylamino and N-methylphenylsulfonylamino groups and chlorine atoms;

Y represents an oxygen atom; and

Z represents a 2,4-dioxothiazolidin-5-ylmethyl group.

40. The composition of claim 33, wherein:

$R^1$ represents a methyl or ethyl group;

$R^2$ represents an ethylene group;

$R^3$ represents a hydrogen atom;

X represents a phenyl group which is unsubstituted or is substituted by from 1 to 3 substituents selected from the group consisting of substituents $\alpha^7$, defined below;

said substituents $\alpha^7$ are selected from the group consisting of: methyl, hydroxy, acetoxy, benzyl, phenyl, phenoxy, phenylthio, phenylsulfonyl, phenylsulfonylamino and N-methylphenylsulfonylamino groups and chlorine atoms;

Y represents an oxygen atom; and

Z represents a 2,4-dioxothiazolidin-5-ylmethyl group.

41. The composition of claim 33, wherein said active compound is selected from the group consisting of:

5-(4-{2-[1-(4-biphenylyl)ethylideneaminooxy]ethoxy}benzyl)thiazolidine-2,4-dione;

5-(4-{2-[1-(4-phenylsulfonylphenyl)ethylideneaminooxy]ethoxy}benzyl)thiazolidine-2,4-dione; and pharmaceutically acceptable salts thereof.

42. A method for the treatment or prophylaxis of diabetes and hyperglycemia, which method comprises administering to a mammal an effective amount of an active compound, wherein said active compound is selected from the group consisting of compounds of formula (I), as claimed in claim 1, and salts thereof.

43. The method of claim 42, wherein:

$R^1$ represents a hydrogen atom or an alkyl group having from 1 to 4 carbon atoms;

$R^2$ represents an alkylene group having from 2 to 5 carbon atoms;

$R^3$ represents a hydrogen atom, an alkyl group having from 1 to 4 carbon atoms, an alkoxy group having 1 or 2 carbon atoms, an alkylthio group having 1 or 2 carbon atoms or a halogen atom;

X represents: an aryl group, which has from 6 to 10 ring carbon atoms and is unsubstituted or is substituted by from 1 to 3 substituents selected from the group consisting of substituents $\alpha^1$, defined below;

said substituents $\alpha^1$ being selected from the group consisting of:

alkyl groups having from 1 to 6 carbon atoms, halogenated alkyl groups having from 1 to 4 carbon atoms, hydroxy groups, acyloxy groups having from 1 to 4 carbon atoms, alkoxy groups having from 1 to 4 carbon atoms, alkylenedioxy groups having from 1 to 4 carbon atoms, aralkyloxy groups having a total of from 7 to 12 carbon atoms, alkylthio groups having from 1 to 4 carbon atoms, alkylsulfonyl groups having from 1 to 4 carbon atoms, halogen atoms, aralkyl groups having a total of from 7 to 12 carbon atoms, phenyl groups which are unsubstituted or are substituted by from 1 to 3 of substituents $\beta^1$, defined below, phenoxy groups which are unsubstituted or are substituted by from 1 to 3 of substituents $\beta^1$, defined below,

150 phenylthio groups which are unsubstituted or are substituted by from 1 to 3 of substituents $\beta^1$, defined below, phenylsulfonyl groups which are unsubstituted or are substituted by from 1 to 3 of substituents $\beta^1$, defined below, phenylsulfonylamino groups in which the phenyl group is unsubstituted or is substituted by from 1 to 3 of substituents $\beta^1$, defined below, and the nitrogen atom is unsubstituted or is substituted by an alkyl group having from 1 to 6 carbon atoms, said substituents $\beta^1$ being selected from the group consisting of alkyl groups having from 1 to 6 carbon atoms, halogenated alkyl groups having from 1 to 4 carbon atoms, alkoxy groups having from 1 to 4 carbon atoms, halogen atoms and alkylenedioxy groups having from 1 to 4 carbon atoms;

Y represents an oxygen atom, a sulfur atom or a group of formula >N—$R^4$, in which $R^4$ represents a hydrogen atom, an alkyl group having from 1 to 3 carbon atoms or an alkanoyl group having from 2 to 5 carbon atoms; and Z represents a 2,4-dioxothiazolidin-5-ylmethyl, 2,4-dioxooxazolidin-5-ylmethyl or 3,5-dioxooxadiazolidin-2-ylmethyl group.

44. The method of claim 42, wherein:

$R^1$ represents a hydrogen atom or an alkyl group having from 1 to 4 carbon atoms;

$R^2$ represents an alkylene group having from 2 to 5 carbon atoms;

$R^3$ represents a hydrogen atom;

X represents: an aryl group, which has from 6 to 10 ring carbon atoms and is unsubstituted or is substituted by from 1 to 3 substituents selected from the group consisting of substituents $\alpha^2$, defined below;

said substituents $\alpha^2$ being selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, alkylenedioxy groups having from 1 to 4 carbon atoms, aralkyloxy groups having a total of from 7 to 12 carbon atoms, alkylthio groups having from 1 to 4 carbon atoms, alkylsulfonyl groups having from 1 to 4 carbon atoms, fluorine atoms, chlorine atoms and bromine atoms, aralkyl groups having a total of from 7 to 12 carbon atoms, phenyl groups which are unsubstituted or are substituted by from 1 to 3 of substituents $\beta^1$, defined below, phenoxy groups which are unsubstituted or are substituted by from 1 to 3 of substituents $\beta^1$, defined below, phenylthio groups which are unsubstituted or are substituted by from 1 to 3 of substituents $\beta^1$, defined below, phenylsulfonyl groups which are unsubstituted or are substituted by from 1 to 3 of substituents $\beta^1$, defined below, phenylsulfonylamino groups in which the phenyl group is unsubstituted or is substituted by from 1 to 3 of substituents $\beta^1$, defined below, and the nitrogen atom is unsubstituted or is substituted by an alkyl group having from 1 to 6 carbon atoms, said substituents $\beta^1$ being selected from the group consisting of alkyl groups having from 1 to 6 carbon atoms, halogenated alkyl groups having from 1 to 4 carbon atoms, alkoxy groups having from 1 to 4 carbon atoms, halogen atoms and alkylenedioxy groups having from 1 to 4 carbon atoms;

Y represents an oxygen atom; and

Z represents a 2,4-dioxothiazolidin-5-ylmethyl or 2,4-dioxooxazolidin-5-ylmethyl group.

45. The method of claim 42, wherein:

$R^1$ represents a hydrogen atom or an alkyl group having from 1 to 3 carbon atoms;

$R^2$ represents an alkylene group having 2 or 3 carbon atoms;

$R^3$ represents a hydrogen atom;

X represents a phenyl or naphthyl group, each of which is unsubstituted or is substituted by from 1 to 3 substituents selected from the group consisting of substituents $\alpha^3$, defined below;

said substituents $\alpha^3$ are selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, the methylenedioxy group, aralkyloxy groups having a total of from 7 to 12 carbon atoms, alkylthio groups having from 1 to 4 carbon atoms, alkylsulfonyl groups having from 1 to 4 carbon atoms, fluorine, chlorine and bromine atoms, aralkyl groups having a total of from 7 to 12 carbon atoms, phenyl groups which are unsubstituted or are substituted by from 1 to 3 of substituents $\beta^2$, defined below, phenoxy groups which are unsubstituted or are substituted by from 1 to 3 of substituents $\beta^2$, defined below, phenylthio groups which are unsubstituted or are substituted by from 1 to 3 of substituents $\beta^2$, defined below, phenylsulfonyl groups which are unsubstituted or are substituted by from 1 to 3 of substituents $\beta^2$, defined below, phenylsulfonylamino groups in which the phenyl group is unsubstituted or is substituted by from 1 to 3 of substituents $\beta^2$, defined below, and the nitrogen atom is unsubstituted or is substituted by an alkyl group having from 1 to 6 carbon atoms, said substituents $\beta^2$ are selected from the group consisting of methyl groups, trifluoromethyl groups, methoxy groups, fluorine atoms and methylenedioxy groups;

Y represents an oxygen atom; and

Z represents a 2,4-dioxothiazolidin-5-ylmethyl group.

46. The method of claim 42, wherein:

$R^1$ represents a hydrogen atom, a methyl or ethyl group;

$R^2$ represents an ethylene, trimethylene or methylethylene group;

$R^3$ represents a hydrogen atom;

X represents a phenyl or naphthyl group, each of which is unsubstituted or is substituted by from 1 to 3 substituents selected from the group consisting of substituents $\alpha^4$, defined below;

said substituents $\alpha^4$ are selected from the group consisting of:

alkyl groups having from 1 to 6 carbon atoms, halogenated alkyl groups having from 1 to 4 carbon atoms, hydroxy groups, alkanoyloxy groups having from 1 to 4 carbon atoms, alkoxy groups having from 1 to 4 carbon atoms, methylenedioxy, benzyloxy, phenethyloxy and naphthylmethyloxy groups, alkylthio groups having from 1 to 4 carbon atoms, alkylsulfonyl groups having from 1 to 4 carbon atoms, fluorine, chlorine and bromine atoms, the benzyl group, phenyl groups which are unsubstituted or are substituted by from 1 to 3 of substituents $\beta^2$, defined below, phenoxy groups which are unsubstituted or are substituted by from 1 to 3 of substituents $\beta^2$, defined below, the phenylthio, phenylsulfonyl, phenylsulfonylamino and N-methylphenylsulfonylamino groups;

Y represents an oxygen atom; and

Z represents a 2,4-dioxothiazolidin-5-ylmethyl group.

47. The method of claim 42, wherein:

$R^1$ represents a hydrogen atom, a methyl or ethyl group;

$R^2$ represents an ethylene, trimethylene or methylethylene group;

$R^3$ represents a hydrogen atom;

X represents a phenyl or naphthyl group, each of which is unsubstituted or is substituted by from 1 to 3 substituents selected from the group consisting of substituents $\alpha^5$, defined below;

said substituents $\alpha^5$ are selected from the group consisting of:

alkyl groups having from 1 to 3 carbon atoms, the trifluoromethyl, difluoromethyl, fluoromethyl, hydroxy, formyloxy and acetoxy groups, alkoxy groups having from 1 to 3 carbon atoms, the methylenedioxy, benzyloxy, methylthio, ethylthio, methylsulfonyl and ethylsulfonyl groups, the fluorine, chlorine and bromine atoms, and the benzyl, phenyl, 4-methylphenyl, 4-trifluoromethylphenyl, 4-methoxyphenyl, 4-fluorophenyl, 3,4-methylenedioxyphenyl, phenoxy, phenylthio, phenylsulfonyl, phenylsulfonylamino and/or N-methylphenylsulfonylamino groups;

Y represents an oxygen atom; and

Z represents a 2,4-dioxothiazolidin-5-ylmethyl group.

48. The method of claim 42, wherein:

$R^1$ represents a hydrogen atom, a methyl or ethyl group;

$R^2$ represents an ethylene group;

$R^3$ represents a hydrogen atom;

X represents a phenyl or naphthyl group, each of which is unsubstituted or is substituted by from 1 to 3 substituents selected from the group consisting of substituents $\alpha^6$, defined below;

said substituents $\alpha^6$ are selected from the group consisting of: methyl, ethyl, isopropyl, trifluoromethyl, hydroxy, acetoxy, methoxy, ethoxy, isopropoxy, methylenedioxy, benzyloxy, methylthio, ethylthio, methylsulfonyl, ethylsulfonyl, benzyl, phenyl, phenoxy, phenylthio, phenylsulfonyl, phenylsulfonylamino and N-methylphenylsulfonylamino groups and chlorine atoms;

Y represents an oxygen atom; and

Z represents a 2,4-dioxothiazolidin-5-ylmethyl group.

49. The method of claim 42, wherein:

$R^1$ represents a methyl or ethyl group;

$R^2$ represents an ethylene group;

$R^3$ represents a hydrogen atom;

X represents a phenyl group which is unsubstituted or is substituted by from 1 to 3 substituents selected from the group consisting of substituents $\alpha^7$, defined below;

said substituents $\alpha^7$ are selected from the group consisting of: methyl, hydroxy, acetoxy, benzyl, phenyl, phenoxy, phenylthio, phenylsulfonyl, phenylsulfonylamino and N-methylphenylsulfonylamino groups and chlorine atoms;

Y represents an oxygen atom; and

Z represents a 2,4-dioxothiazolidin-5-ylmethyl group.

50. The method of claim 42, wherein said active compound is selected from the group consisting of:

5-(4-{2-[1-(4-biphenylyl)ethylideneaminooxy]ethoxy}benzyl)thiazolidine-2,4-dione;

5-(4-{2-[1-(4-phenylsulfonylphenyl)ethylideneaminooxy]ethoxy}benzyl)thiazolidine-2,4-dione; and pharmaceutically acceptable salts thereof.

* * * * *

UNITED STATES PATENT AND TRADEMARK OFFICE
CERTIFICATE OF CORRECTION

PATENT NO. : 5,780,490
DATED : July 14, 1998
INVENTOR(S) : YANAGISAWA et al

It is certified that error appears in the above-identified patent and that said Letters Patent is hereby corrected as shown below:

Column 3, line 4, delete "p" and insert --$\beta$--.

Column 7, line 25, after "substituent" delete "a" and insert --$\alpha$--.

Column 7, line 35, after "substituent" delete "a" and insert --$\alpha$--.

Column 7, line 45, after "substituent" delete "a" and insert --$\alpha$--.

Column 7, line 57, after "substituent" delete "c" and insert --$\alpha$--.

Column 7, line 65, after "substituent" delete "a" and insert --$\alpha$--.

Column 8, line 30, after "substituent" delete "a" and insert --$\alpha$--.

UNITED STATES PATENT AND TRADEMARK OFFICE
CERTIFICATE OF CORRECTION

PATENT NO. : 5,780,490
DATED : July 14, 1998
INVENTOR(S) : YANAGISAWA et al

It is certified that error appears in the above-identified patent and that said Letters Patent is hereby corrected as shown below:

Column 9, line 33, after "substituent" delete "a" and insert --α--.

Column 9, line 39, after "substituent" delete "a" and insert --α--.

Column 9, line 53, after "substituent" delete "a" and insert --α--.

Signed and Sealed this

First Day of May, 2001

Attest:

NICHOLAS P. GODICI

Attesting Officer     Acting Director of the United States Patent and Trademark Office